United States Patent
Hawryluk et al.

(10) Patent No.: US 11,578,372 B2
(45) Date of Patent: Feb. 14, 2023

(54) NTRK1 FUSION MOLECULES AND USES THEREOF

(71) Applicant: FOUNDATION MEDICINE, INC., Cambridge, MA (US)

(72) Inventors: Matthew J. Hawryluk, Watertown, MA (US); Doron Lipson, Cambridge, MA (US); Vincent A. Miller, West Orange, NJ (US); Philip James Stephens, Lexington, MA (US)

(73) Assignee: Foundation Medicine, Inc., Cambridge, MA (US)

( * ) Notice: Subject to any disclaimer, the term of this patent is extended or adjusted under 35 U.S.C. 154(b) by 189 days.

(21) Appl. No.: 16/683,575

(22) Filed: Nov. 14, 2019

(65) Prior Publication Data
US 2020/0299775 A1 Sep. 24, 2020

Related U.S. Application Data

(63) Continuation of application No. 14/473,508, filed on Aug. 29, 2014, now abandoned, which is a continuation of application No. PCT/US2013/068457, filed on Nov. 5, 2013.

(60) Provisional application No. 61/872,559, filed on Aug. 30, 2013, provisional application No. 61/763,442, filed on Feb. 11, 2013, provisional application No. 61/722,533, filed on Nov. 5, 2012.

(51) Int. Cl.
| | |
|---|---|
| C12Q 1/6886 | (2018.01) |
| C12N 15/113 | (2010.01) |
| C12N 9/12 | (2006.01) |
| C07K 14/47 | (2006.01) |
| A61K 31/519 | (2006.01) |
| A61K 31/553 | (2006.01) |
| A61K 45/06 | (2006.01) |

(52) U.S. Cl.
CPC .......... *C12Q 1/6886* (2013.01); *A61K 31/519* (2013.01); *A61K 31/553* (2013.01); *A61K 45/06* (2013.01); *C07K 14/47* (2013.01); *C12N 9/12* (2013.01); *C12N 15/1138* (2013.01); *C12N 2310/14* (2013.01); *C12Q 2600/106* (2013.01); *C12Q 2600/136* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 3,773,919 A | 11/1973 | Boswell et al. |
| 4,366,241 A | 12/1982 | Tom et al. |
| 4,376,110 A | 3/1983 | David et al. |
| 4,458,066 A | 7/1984 | Caruthers et al. |
| 4,469,863 A | 9/1984 | Ts'o et al. |
| 4,476,301 A | 10/1984 | Imbach et al. |
| 4,517,288 A | 5/1985 | Giegel et al. |
| 4,676,980 A | 6/1987 | Segal et al. |
| 4,816,567 A | 3/1989 | Cabilly et al. |
| 4,837,168 A | 6/1989 | de Jaeger et al. |
| 4,845,205 A | 7/1989 | Dinh et al. |
| 4,868,103 A | 9/1989 | Stavrianopoulos et al. |
| 4,873,316 A | 10/1989 | Meade et al. |
| 4,981,957 A | 1/1991 | Lebleu et al. |
| 4,987,071 A | 1/1991 | Cech et al. |
| 5,023,243 A | 6/1991 | Tullis |
| 5,034,506 A | 7/1991 | Summerton et al. |
| 5,093,246 A | 3/1992 | Cech et al. |
| 5,116,742 A | 5/1992 | Cech et al. |
| 5,118,800 A | 6/1992 | Smith et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,195 A | 1/1993 | Gregory et al. |
| 5,185,444 A | 2/1993 | Summerton et al. |
| 5,188,897 A | 2/1993 | Suhadolnik et al. |
| 5,214,134 A | 5/1993 | Weis et al. |
| 5,216,141 A | 6/1993 | Benner |
| 5,223,409 A | 6/1993 | Ladner et al. |
| 5,225,539 A | 7/1993 | Winter |
| 5,235,033 A | 8/1993 | Summerton et al. |
| 5,264,423 A | 11/1993 | Cohen et al. |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann et al. |

(Continued)

FOREIGN PATENT DOCUMENTS

| | | |
|---|---|---|
| CA | 2880013 A1 | 1/2014 |
| CN | 113186287 A | 7/2021 |

(Continued)

OTHER PUBLICATIONS

Muller-Tidow et al., Identification of Metastasis-Associated Receptor Tyrosine Kinases in Non-Small Cell Lung Cancer, 2005, Cancer Res., vol. 65, No. 5, pp. 1778-1782 (Year: 2006).*

Thress et al., Identification and precliinical characterization of AZ-23, a novel, selective, and orally bioavailable inhibitor of the Trk kinase pathway, 2009, Mol. Cancer Ther., vol. 8, No. 7, pp. 1818-1827 (Year: 2009).*

(Continued)

*Primary Examiner* — Jeffrey S Lundgren
*Assistant Examiner* — Michael J Schmitt
(74) *Attorney, Agent, or Firm* — Morrison & Foerster LLP

(57) ABSTRACT

Novel NTRK1 fusion molecules, detection reagents, and uses and kits for evaluating, identifying, assessing and/or treating a subject having a cancer are disclosed.

23 Claims, 39 Drawing Sheets

Specification includes a Sequence Listing.

(56) References Cited

U.S. PATENT DOCUMENTS

| | | |
|---|---|---|
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann et al. |
| 5,399,676 A | 3/1995 | Froehler |
| 5,405,938 A | 4/1995 | Summerton et al. |
| 5,405,939 A | 4/1995 | Suhadolnik et al. |
| 5,432,272 A | 7/1995 | Benner |
| 5,434,257 A | 7/1995 | Matteucci et al. |
| 5,446,137 A | 8/1995 | Maag et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,489,677 A | 2/1996 | Sanghvi et al. |
| 5,491,224 A | 2/1996 | Bittner et al. |
| 5,500,362 A | 3/1996 | Robinson et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,536,821 A | 7/1996 | Agrawal et al. |
| 5,539,082 A | 7/1996 | Nielsen et al. |
| 5,541,307 A | 7/1996 | Cook et al. |
| 5,541,316 A | 7/1996 | Engelskirchen et al. |
| 5,545,806 A | 8/1996 | Lonberg et al. |
| 5,547,835 A | 8/1996 | Koster |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,567,811 A | 10/1996 | Misiura et al. |
| 5,569,825 A | 10/1996 | Lonberg et al. |
| 5,571,799 A | 11/1996 | Tkachuk et al. |
| 5,571,894 A | 11/1996 | Wels et al. |
| 5,576,427 A | 11/1996 | Cook et al. |
| 5,587,361 A | 12/1996 | Cook et al. |
| 5,587,458 A | 12/1996 | King et al. |
| 5,587,469 A | 12/1996 | Cook et al. |
| 5,591,722 A | 1/1997 | Montgomery et al. |
| 5,594,121 A | 1/1997 | Froehler et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,605,798 A | 2/1997 | Koster |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,070 A | 4/1997 | Cook et al. |
| 5,624,821 A | 4/1997 | Winter et al. |
| 5,625,050 A | 4/1997 | Beaton et al. |
| 5,625,126 A | 4/1997 | Lonberg et al. |
| 5,627,053 A | 5/1997 | Usman et al. |
| 5,631,169 A | 5/1997 | Lakowicz et al. |
| 5,633,360 A | 5/1997 | Bischofberger et al. |
| 5,633,425 A | 5/1997 | Lonberg et al. |
| 5,639,873 A | 6/1997 | Barascut et al. |
| 5,646,265 A | 7/1997 | McGee |
| 5,648,260 A | 7/1997 | Winter et al. |
| 5,658,873 A | 8/1997 | Bertsch-Frank et al. |
| 5,661,016 A | 8/1997 | Lonberg et al. |
| 5,663,312 A | 9/1997 | Chaturvedula |
| 5,670,633 A | 9/1997 | Cook et al. |
| 5,677,437 A | 10/1997 | Teng et al. |
| 5,677,439 A | 10/1997 | Weis et al. |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,731,168 A | 3/1998 | Carter et al. |
| 5,750,373 A | 5/1998 | Garrard et al. |
| 5,750,692 A | 5/1998 | Cook et al. |
| 5,770,429 A | 6/1998 | Lonberg et al. |
| 5,776,688 A | 7/1998 | Bittner et al. |
| 5,821,337 A | 10/1998 | Carter et al. |
| 5,869,046 A | 2/1999 | Presta et al. |
| 5,876,930 A | 3/1999 | Livak et al. |
| 6,015,886 A | 1/2000 | Dale et al. |
| 6,028,188 A | 2/2000 | Arnold et al. |
| 6,075,181 A | 6/2000 | Kucherlapati et al. |
| 6,124,445 A | 9/2000 | Imbach et al. |
| 6,147,200 A | 11/2000 | Manoharan et al. |
| 6,150,584 A | 11/2000 | Kucherlapati et al. |
| 6,160,109 A | 12/2000 | Just et al. |
| 6,166,197 A | 12/2000 | Cook et al. |
| 6,169,170 B1 | 1/2001 | Gryaznov et al. |
| 6,172,209 B1 | 1/2001 | Manoharan et al. |
| 6,194,551 B1 | 2/2001 | Idusogie et al. |
| 6,222,025 B1 | 4/2001 | Cook et al. |
| 6,235,887 B1 | 5/2001 | Froehler et al. |
| 6,239,265 B1 | 5/2001 | Cook |
| 6,248,516 B1 | 6/2001 | Winter et al. |
| 6,268,490 B1 | 7/2001 | Imanishi et al. |
| 6,277,569 B1 | 8/2001 | Bittner et al. |
| 6,277,603 B1 | 8/2001 | Cook |
| 6,326,199 B1 | 12/2001 | Cook et al. |
| 6,346,614 B1 | 2/2002 | Metelev et al. |
| 6,380,368 B1 | 4/2002 | Froehler et al. |
| 6,444,423 B1 | 9/2002 | Meade et al. |
| 6,455,258 B2 | 9/2002 | Bastian et al. |
| 6,528,640 B1 | 3/2003 | Beigelman et al. |
| 6,531,590 B1 | 3/2003 | Manoharan et al. |
| 6,534,639 B1 | 3/2003 | Manoharan et al. |
| 6,602,684 B1 | 8/2003 | Umaña et al. |
| 6,608,035 B1 | 8/2003 | Agrawal et al. |
| 6,617,438 B1 | 9/2003 | Beigelman et al. |
| 6,639,062 B2 | 10/2003 | Manoharan et al. |
| 6,670,461 B1 | 12/2003 | Wengel et al. |
| 6,683,167 B2 | 1/2004 | Metelev et al. |
| 6,737,056 B1 | 5/2004 | Presta |
| 6,794,499 B2 | 9/2004 | Wengel et al. |
| 6,858,715 B2 | 2/2005 | Ravikumar et al. |
| 6,867,294 B1 | 3/2005 | Sanghvi et al. |
| 6,878,805 B2 | 4/2005 | Manoharan et al. |
| 6,982,321 B2 | 1/2006 | Winter |
| 6,998,484 B2 | 2/2006 | Koch et al. |
| 7,015,315 B1 | 3/2006 | Cook et al. |
| 7,041,816 B2 | 5/2006 | Ravikumar et al. |
| 7,041,870 B2 | 5/2006 | Tomizuka et al. |
| 7,045,610 B2 | 5/2006 | Dempcy et al. |
| 7,053,207 B2 | 5/2006 | Wengel |
| 7,084,125 B2 | 8/2006 | Wengel |
| 7,087,409 B2 | 8/2006 | Barbas et al. |
| RE39,464 E | 1/2007 | Cook et al. |
| 7,189,826 B2 | 3/2007 | Rodman |
| 7,244,567 B2 | 7/2007 | Chen et al. |
| 7,273,933 B1 | 9/2007 | Krotz et al. |
| 7,321,029 B2 | 1/2008 | Gryaznov et al. |
| 7,332,581 B2 | 2/2008 | Presta |
| 7,371,826 B2 | 5/2008 | Presta |
| 7,399,845 B2 | 7/2008 | Seth et al. |
| 7,427,672 B2 | 9/2008 | Imanishi et al. |
| 7,495,088 B1 | 2/2009 | Brakel et al. |
| 7,521,541 B2 | 4/2009 | Eigenbrot et al. |
| 7,527,791 B2 | 5/2009 | Adams et al. |
| 8,377,921 B2 | 2/2013 | Michellys et al. |
| 10,000,814 B2 | 6/2018 | Cronin et al. |
| 10,980,804 B2 | 4/2021 | Ali et al. |
| 11,098,368 B2 | 8/2021 | Cronin et al. |
| 11,230,589 B2 | 1/2022 | Lipson et al. |
| 2002/0164328 A1 | 11/2002 | Shinkawa et al. |
| 2002/0197679 A1 | 12/2002 | Tang et al. |
| 2003/0115614 A1 | 6/2003 | Kanda et al. |
| 2003/0143204 A1 | 7/2003 | Lewis et al. |
| 2003/0157108 A1 | 8/2003 | Presta |

(56) References Cited

U.S. PATENT DOCUMENTS

| | | |
|---|---|---|
| 2003/0166282 A1 | 9/2003 | Brown et al. |
| 2003/0224432 A1 | 12/2003 | Myers et al. |
| 2004/0038278 A1 | 2/2004 | Tzertzinis et al. |
| 2004/0086884 A1 | 5/2004 | Beach et al. |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0079574 A1 | 4/2005 | Bond |
| 2005/0119455 A1 | 6/2005 | Fuh et al. |
| 2005/0123546 A1 | 6/2005 | Umana et al. |
| 2005/0266000 A1 | 12/2005 | Bond et al. |
| 2005/0287541 A1 | 12/2005 | Nakagawara et al. |
| 2006/0025576 A1 | 2/2006 | Miller et al. |
| 2006/0246497 A1 | 11/2006 | Huang et al. |
| 2006/0275779 A1 | 12/2006 | Li et al. |
| 2007/0010657 A1 | 1/2007 | Klocke et al. |
| 2007/0059710 A1 | 3/2007 | Luke et al. |
| 2007/0061900 A1 | 3/2007 | Murphy et al. |
| 2007/0087362 A1 | 4/2007 | Church et al. |
| 2007/0117126 A1 | 5/2007 | Sidhu et al. |
| 2007/0160598 A1 | 7/2007 | Dennis et al. |
| 2007/0194225 A1 | 8/2007 | Zorn |
| 2007/0237764 A1 | 10/2007 | Birtalan et al. |
| 2007/0248605 A1 | 10/2007 | Hestir et al. |
| 2007/0292936 A1 | 12/2007 | Barthelemy et al. |
| 2008/0051462 A1 | 2/2008 | Fritz et al. |
| 2008/0069820 A1 | 3/2008 | Fuh et al. |
| 2008/0131375 A1 | 6/2008 | Gordon et al. |
| 2008/0171689 A1 | 7/2008 | Williams |
| 2008/0226664 A1 | 9/2008 | Old et al. |
| 2009/0002360 A1 | 1/2009 | Chen et al. |
| 2009/0130101 A1 | 5/2009 | Cohen |
| 2009/0156475 A1 | 6/2009 | Rikova et al. |
| 2009/0209496 A1 | 8/2009 | Chaplin et al. |
| 2010/0029498 A1 | 2/2010 | Gnirke et al. |
| 2011/0118298 A1 | 5/2011 | Fritz et al. |
| 2011/0150893 A1 | 6/2011 | Cho et al. |
| 2011/0183924 A1 | 7/2011 | Mintz et al. |
| 2012/0039805 A1 | 2/2012 | Lisanti et al. |
| 2012/0208706 A1 | 8/2012 | Downing et al. |
| 2013/0034559 A1 | 2/2013 | Queva et al. |
| 2013/0096021 A1 | 4/2013 | Chinnaiyan et al. |
| 2014/0336236 A1 | 11/2014 | Cronin et al. |
| 2015/0073036 A1 | 3/2015 | Hawryluk et al. |
| 2015/0366866 A1 | 12/2015 | Ali et al. |
| 2016/0009785 A1 | 1/2016 | Lipson et al. |
| 2016/0010068 A1 | 1/2016 | Bastian et al. |
| 2016/0272725 A1 | 9/2016 | Stransky et al. |
| 2018/0030548 A1 | 2/2018 | Nanda et al. |
| 2018/0045727 A1 | 2/2018 | Spetzler et al. |
| 2018/0346992 A1 | 12/2018 | Cronin et al. |
| 2021/0283134 A1 | 9/2021 | Ali et al. |
| 2022/0002818 A1 | 1/2022 | Cronin et al. |
| 2022/0169703 A1 | 6/2022 | Lipson et al. |

FOREIGN PATENT DOCUMENTS

| | | |
|---|---|---|
| EP | 171496 A2 | 2/1986 |
| EP | 173494 A2 | 3/1986 |
| EP | 184187 A2 | 6/1986 |
| EP | 264166 A1 | 4/1988 |
| EP | 404097 A2 | 12/1990 |
| EP | 125023 B1 | 6/1991 |
| EP | 430402 A2 | 6/1991 |
| EP | 698096 B1 | 2/1996 |
| EP | 2057465 A2 | 5/2009 |
| EP | 2877854 A1 | 6/2015 |
| WO | WO-1986001533 A1 | 3/1986 |
| WO | WO-1987002671 A1 | 10/1987 |
| WO | WO-1988009810 A1 | 12/1988 |
| WO | WO-1989010134 A1 | 11/1989 |
| WO | WO-1990002809 A1 | 3/1990 |
| WO | WO-1992001047 A1 | 7/1991 |
| WO | WO-1991017271 A1 | 11/1991 |
| WO | WO-1992009690 A2 | 6/1992 |
| WO | WO-1992015679 A1 | 9/1992 |
| WO | WO-1992018619 A1 | 10/1992 |
| WO | WO-1992020791 A1 | 11/1992 |
| WO | WO-1993001161 A1 | 1/1993 |
| WO | WO-1993001288 A1 | 1/1993 |
| WO | WO-1993008829 A1 | 5/1993 |
| WO | WO-1993016185 A2 | 8/1993 |
| WO | WO-1994016101 A2 | 7/1994 |
| WO | WO-1994021822 A1 | 9/1994 |
| WO | WO-1994026889 A2 | 11/1994 |
| WO | WO-1994029351 A2 | 12/1994 |
| WO | WO-1996029431 A2 | 9/1996 |
| WO | WO-1997030087 A1 | 8/1997 |
| WO | WO-1998058964 A1 | 12/1998 |
| WO | WO-1999022764 A1 | 5/1999 |
| WO | WO-1999051642 A1 | 10/1999 |
| WO | WO-2000061739 A1 | 10/2000 |
| WO | WO-2001027407 A1 | 4/2001 |
| WO | WO-2001029246 A1 | 4/2001 |
| WO | WO-2002031140 A1 | 4/2002 |
| WO | WO-2003011878 A2 | 2/2003 |
| WO | WO-2003031568 A2 | 4/2003 |
| WO | WO-2003084570 A1 | 10/2003 |
| WO | WO-2003085107 A1 | 10/2003 |
| WO | WO-2003085119 A1 | 10/2003 |
| WO | WO-2004013099 A1 | 2/2004 |
| WO | WO-2004056312 A2 | 7/2004 |
| WO | WO-2005035586 A1 | 4/2005 |
| WO | WO-2005035778 A1 | 4/2005 |
| WO | WO-2005053742 A1 | 6/2005 |
| WO | WO-2005100402 A1 | 10/2005 |
| WO | WO-2006000121 A1 | 1/2006 |
| WO | WO-2006029879 A2 | 3/2006 |
| WO | WO-2007005874 A2 | 1/2007 |
| WO | WO-2007060402 A1 | 5/2007 |
| WO | WO-2008021290 A2 | 2/2008 |
| WO | WO-2008077546 A1 | 7/2008 |
| WO | WO-2009089004 A1 | 7/2009 |
| WO | WO-2009101611 A1 | 8/2009 |
| WO | WO-2009114335 A2 | 9/2009 |
| WO | WO-2010027827 A2 | 3/2010 |
| WO | WO-2010077634 A1 | 7/2010 |
| WO | WO-2010081817 A1 | 7/2010 |
| WO | WO-2011005861 A1 | 1/2011 |
| WO | WO-2011066342 A2 | 6/2011 |
| WO | WO-2011066389 A1 | 6/2011 |
| WO | WO-2011135376 A1 | 11/2011 |
| WO | WO-2012092426 A1 | 7/2012 |
| WO | WO-2013059740 A1 | 4/2013 |
| WO | WO-2013076186 A1 | 5/2013 |
| WO | WO-2013087716 A2 | 6/2013 |
| WO | WO-2014018673 A2 | 1/2014 |
| WO | WO-2014036387 A2 | 3/2014 |
| WO | WO-2014071358 A2 | 5/2014 |
| WO | WO-2014071419 A2 | 5/2014 |
| WO | WO-2014113729 A2 | 7/2014 |
| WO | WO-2014130975 A1 | 8/2014 |
| WO | WO-2016196671 A1 | 12/2016 |
| WO | WO-2019158512 A1 | 8/2019 |

OTHER PUBLICATIONS

Ardini et al., (2014). "The TPM3-NTRK1 rearrangement is a recurring event in colorectal carcinoma and is associated with tumor sensitivity to TRKA kinase inhibition," Mol Oncol., 8:1495-507.

Bender et al., (2019). "Refractory and metastatic infantile fibrosarcoma harboring LMNA-NTRK1 fusion shows complete and durable response to crizotinib," Cold Spring Harb Mol Case Stud., 5:a00376, 9 pages.

Cocco et al., (2018). "NTRK fusion-positive cancers and TRK inhibitor therapy," Nat Rev Clin Oncol., 15:731-747, 34 pages.

Deinhardt et al., (2014). "Trk receptors," Handb Exp Pharmacol., 220:103-19.

(56) References Cited

OTHER PUBLICATIONS

Fang et al., (2016). "Detection of a novel RET gene fusion in a non-small cell lung cancer patient using AMP chemistry," J Thoracic Oncol., 11:S21-S22.
Fang et al., (2019). "MPRIP-ALK, a Novel ALK Rearrangement That Responds to ALK Inhibition in NSCLC," J Thorac Oncol., 14:e148-e151.
Gainor et al., (2013). "Novel targets in non-small cell lung cancer: ROS1 and RET fusions," Oncologist, 18:865-75.
Gosenca et al., (2014). "Identification and functional characterization of imatinib-sensitive DTD1-PDGFRB and CCDC88C-PDGFRB fusion genes in eosinophilia-associated myeloid/lymphoid neoplasms," Genes Chromosomes Cancer, 53:411-21.
Greco et al., (1998). "Role of the TFG N-terminus and coiled-coil domain in the transforming activity of the thyroid TRK-T3 oncogene," Oncogene, 16:809-16.
Griono et al., (2019). "A Simple RNA Target Capture NGS Strategy for Fusion Genes Assessment in the Diagnostics of Pediatric B-cell Acute Lymphoblastic Leukemia," Hemasphere, 3:e250, 9 pages.
Hirai et al., (2020). "Large-scale metabarcoding analysis of epipelagic and mesopelagic copepods in the Pacific," PLOS One, 15:e0233189, 24 pages.
International Search Report for International Application No. PCT/US2020/034421 dated Dec. 11, 2020, 12 pages.
Kheder et al., (2018). "Emerging Targeted Therapy for Tumors with NTRK Fusion Proteins," Clin. Cancer Res, 24(23):5807-5814.
Naumann et al., (2015). "Fusion of PDGFRB to MPRIP, CPSF6, and GOLGB1 in three patients with eosinophilia-associated myeloproliferative neoplasms," Genes Chromosomes Cancer, 54:762-70.
Shu et al., (2020). "Identification of a Novel MPRIP-ROS1 Fusion and Clinical Efficacy of Crizotinib in an Advanced Lung Adenocarcinoma Patient: A Case Report," Onco Targets Ther., 13:10387-10391.
Tuysuz et al., (2008). "Novel NTRK1 mutations cause hereditary sensory and autonomic neuropathy type IV: demonstration of a founder mutation in the Turkish population," Neurogenetics, 9:119-125.
Vendrell et al., (2017). "Detection of known and novel ALK fusion transcripts in lung cancer patients using next-generation sequencing approaches," Sci. Rep., 7(12510):1-11.
Zhang et al., (2010). "Fusion of EML4 and ALK is associated with development of lung adenocarcinomas lacking EGFR and KRAS mutations and is correlated with ALK expression," Mol Cancer, 9:188, 12 pages.
Albanese, C. et al., "Dual targeting of CDK and tropomyosin receptor kinase families by the oral inhibitor PHA-848125, an agent with broad-spectrum antitumor efficacy", Mol Cancer Ther 9(8):2243-54, Aug. 3, 2010.
Amatu et al. "NTRK gene fusions as novel targets of cancer therapy across multiple tumour types" ESMO Open (2016) vol. 1, e000023, pp. 1-9.
Bai et al. "GP369, an FGFR2-IIIb-Specific Antibody, Exhibits Potent antitumor Activity against Human Cancers Driven by Activated FGFR2 Signaling" Cancer Research (2010), 70(19):7630-39.
Brave et al. "Assessing the Activity of Cediranib, a VEGFR-2/3 Tyrosine Kinase Inhibitor, against VEGFR-1 and Members of the Structurally Related PDGFR Family" Molecular Cancer Therapeutics (2011) vol. 10 No. 5 pp. 861-873.
Byron et al. "Inhibition of Activated Fibroblast Growth Factor Receptor 2 in Endometrial Cancer Cells Induces Cell Death Despite PTEN Abrogation" Cancer Research (2008), 68(17):6902-10005.
Camidge et al. Optimizing the detection of lung cancer patients harboring anaplastic lymphoma kinase (ALK) gene rearrangements potentially suitable for ALK inhibitor treatment. Clin Cancer Res Nov. 14, 2010 vol. 16 No. 22 pp. 5581-5590. Especially p. 5586 col. 2 para 2-3.
Chiorean et al., "Imatinib Mesylate (STI-571), a c-Abl Kinase Inhibitor, Indirectly Blocks Receptor Tyrosine Kinase Activation and Induces Apoptosis in a Human Cholangiocarcinoma Cell Line" Gastroenterology (2003) 124(4):1.
Cho et al. "Enhanced Expression of Keratinocyte Growth Factor and Its Receptor Correlates with Venous Invasion in Pancreatic Cancer" The American Journal of Pathology (2007), 170(6):1964-74.
ClinicalTrials.Gov Identifier No. NCT02568267, "Basket Study of Entrectinib (RXDX-101) for the Treatment of Patients With Solid Tumors Harboring NTRK 1/2/3/ (Trk A/B/C), ROS1, or ALK Gene Rearrangements (Fusions) (STARTRK-2)" First Received: Oct. 2, 2016; Last Updated : Jan. 3, 2017 https://clinicaltrials.gov/ct2/show/NCT02568267?term=NTRK1+fusion+lung&rank=1 Retrieved Jan. 4, 2017, 5 pages.
ClinicalTrials.Gov Identifier No. NCT0257643.1, "Study of LOXO-101 in Subjects With NTRK Fusion Positive Solid Tumors (NAVIGATE)" First Received: Oct. 12, 2015; Last Updated: Nov. 16, 2016 https://clinicaltrials.gov/ct2/show/NCT02576431 ?term=NTRK1+fusion+lung&rank=2 Retrieved Jan. 4, 2017, 4 pages.
Cohen, Roger B. et al., "A phase I dose-escalation study of danusertib (PHA-739358) administered as a 24-hour infusion with and without granulocyte colony-stimulating factor in a 14-day cycle in patients with advanced solid tumors", Clin Cancer Res 15(21):6694-701, ePub Oct. 13, 2009, Nov. 1, 2009.
Cole et al. "Inhibition of FGFR2 and FGFR1 increases cisplatin sensitivity in ovarian cancer" Cancer Biology & Therapy (2010) vol. 10 No. 5 pp. 495-504.
Cortes et al. "A Pivotal PhaM 2 Trial of Ponatinib in Patients with Chronic Myeloid Leukemia (CML) and Philadelphia Chromosome-Positive Acute Lymphoblastic Leukemia (Ph+ALL) Reslltllnt or Intole111nt to Dasatlnlb or Nilotinib, or with the T315l BCR-ABL Mutation: 1Z-Month Follow-up of the PACE Trial" ASH Annual Meeting and Exposition (Dec. 9, 2012) Abstract No. 163, 2 pages.
Degrassi, A et al., "Efficacy of PHA-848125, a cyclin-dependent kinase inhibitor, on the K-Ras(G12D) LA2 lung adenocarcinoma transgenic mouse model: evaluation by multimodality imaging", Mol Cancer Ther 9(3):673-81, Mar. 9, 2010.
Doebele et al. "An Oncogenic NTRK Fusion in a Patient with Soft-Tissue Sarcoma with Response to the Tropomyosin-Related Kinase Inhibitor LOXO-101" Cancer Discovery (2015) vol. 5, pp. 1049-1057.
Doebele et al., "NTRK1 Gene Fusions as a Novel Oncogene Target in Lung Cancer", 2013 ASCO Annual Meeting; Abstract No. 8023; Abstract only (May 31-Jun. 4, 2013), 2 pages.
Doebele et al., "NTRK1 Gene Fusions as a Novel Oncogene Target in Lung Cancer", 2013 ASCO Annual Meeting; Abstract No. 8023; Poster (May 31-Jun. 4, 2013), 1 page.
Farago et al., "Durable Clinical Response to Entrectinib in NTRK1-Rearranged Non-Small Cell Lung Cancer" Journal of Thoracic Oncology (2015) vol. 10, No. 12, pp. 1670-1674.
Garcia-Mayoral et al. "The Structure of the C-Terminal KH Domains of KSRP Reveals a Noncanonical Motif Important for mRNA Degradation" Structure (2007) vol. 15 pp. 485-498.
Gartside et al. "Loss-of-Function Fibroblast Growth Factor Receptor-2 Mutations in Melanoma" Molecular Cancer Research (2009) vol. 7 No. 1 pp. 41-54.
GenBank Accession No. NM_000141 accessed Nov. 19, 2015 from <http://www.ncbi.nlm.nih.gov/nuccore/189083823>, 8 pages.
GenBank Accession No. NM_001012331 accessed Nov. 19, 2015 from <http://www.ncbi.nlm.nih.gov/nuccore/NM_001012331.1>, 6 pages.
Genbank Accession No. NM_001080512 accessed Nov. 19, 2015 from <http://www.ncbi.nlm.nih.gov/nuccore/NM_001080512.2>, 6 pages.
GenBank Accession No. NM_001127211 accessed Nov. 19, 2015 from <http://www.ncbi.nlm.nih.gov/nuccore/385198090>, 6 pages.
GenBank Accession No. NM_001144915 accessed on Nov. 17, 2015 from <http://www.ncbi.nlm.nih.gov/nuccore/NM_001144915.1>, 6 pages.
GenBank Accession No. NM_003787 accessed Nov. 19, 2015 from <http://www.ncbi.nlm.nih.gov/nuccore/NM_003787>, 4 pages.
GenBank Accession No. NM_004562 accessed Nov. 19, 2015 from <http://www.ncbi.nlm.nih.gov/nuccore/NM_004562.2>, 5 pages.

(56) References Cited

OTHER PUBLICATIONS

GenBank Accession No. NM_006342 accessed Nov. 19, 2015 from <http://www.ncbi.nlm.nih.gov/nuccore/NM_006342>, 6 pages.
GenBank Accession No. NM_022494 accessed Nov. 19, 2015 from <http://www.ncbi.nlm.nih.gov/nuccore/NM_022494.2>, 3 pages.
GenBank Accession No. NP_001012331 accessed Nov. 19, 2015 from <http://www.ncbi.nlm.nih.gov/protein/59889558>, 5 pages.
Greco A, et al. "Characterization of the NTRK1 genomic region involved in chromosomal rearrangements generating TRK oncogenes." Genomics (1993) 18(2):397-400.
Greco A, et al. "TRK-T1 is a novel oncogene formed by the fusion of TPR and TRK genes in human papillary thyroid carcinomas." Oncogene (1992) 7(2):237-42.
Greco et al. Rearrangements of NTRK1 gene in papillary thyroid carcinoma. Mol Cell Endocrinol May 28, 2010 vol. 321 No. 1 pp. 44-49. Especially p. 46 col. 2 para 3.
Greco, A. et al., "The DNA rearrangement that generates the TRK-T3 oncogene involves a novel gene on chromosome 3 whose product has a potential coiled-coil domain", Mol Cell Biol 15(11):6118-27, Nov. 1995.
Han, Sy et al., "Evaluation of a multi-kinase inhibitor KRC-108 as an anti-tumor agent in vitro and in vivo", Invest New Drugs 30(2):518-23, ePub Nov. 16, 2010, Apr. 2012.
Huehne K, et al. "Novel missense, insertion and deletion mutations in the neurotrophic tyrosine kinase receptor type 1 gene (NTRK1) associated with congenital insensitivity to pain with anhidrosis." Neuromuscul Disord (2008) 18(2):159-66.
Huether et al.: "Sorafenib alone or as combination therapy for growth control of cholangiocarcinoma", Biochemical Pharmacology, Elsevier, US, vol. 73, No. 9, Mar. 24, 2007 (Mar. 24, 2007), pp. 1308-1317.
Hyman et al. "The efficacy of larotrectinib (LOXO-101), a selective tropomyosin receptor kinase (TRK) inhibitor, in adult and pediatric TRK fusion cancers" Presentation from the ASCO Annual Meeting 2017, 1-24 pages.
Indo Y, et al. "Structure and organization of the human TRKA gene encoding a high affinity receptor for nerve growth factor." Jpn J Hum Genet (1997) 42(2):343-51.
International Preliminary Report on Patentability and Written Opinion for International Application No. PCT/US2012/061211 dated Apr. 22, 2014, 8 pages.
International Preliminary Report on Patentability for International Application No. PCT/US2013/068604 dated May 5, 2015, 9 pages.
International Preliminary Reporton Patentability from PCT/US14/12136 dated Mar. 18, 2015, 18 pages.
International Search Report and Written Opinion for International Application No. PCT/US2013/068457 dated Jul. 11, 2014, 15 pages.
International Search Report and Written Opinion for PCT/US2014/012136 dated Jul. 16, 2014, 20 pages.
International Search Report for International Application No. PCT/US2012/061211 dated Feb. 5, 2013, 4 pages.
International Search Report for International Application No. PCT/US2013/068604 dated Nov. 7, 2014, 16 pages.
Iyer, R. et al., "Lestaurtinib enhances the antitumor efficacy of chemotherapy in murine xenograft models of neuroblastoma", Clin Cancer Res 16(5):1478-85, ePub Feb. 23, 2010, Mar. 1, 2010.
Kelleher et al. The emerging pathogenic and therapeutic importance of the anaplastic Tymphoma kinase gene. Eur J Cancer Sep. 2010 vol. 46 No. 13 pp. 2357-2368. Especially p. 2365 table 6.
Ko et al. "Phase II study of telatinib (T) in combination with capecitabine (X) and cisplatin (P) as first-line treatment in patients (pts) with advanced cancer of the stomach (G) or gastro-esophageal junction (GEJ)." Journal of Clinical Oncology ASCO Annual Meeting Abstracts, vol. 28 No. 15; May 20 supplement (2010), 1 page.
Landis et al. "Cancer Statistics, 1998" Ca Cancer J Clin (1998) vol. 48 No. 1 pp. 6-29.
Lih et al. "N of 2 Responders With LMNA-NTRK1" J Natl Cancer Inst (2016) vol. 108, No. 1, djv376, pp. 1-2.

Lin et al., "Exon Array Profiling Detects EML4-ALK Fusion in Breast, Colorectal, and Non-Small Cell Lung Cancers" Mol Cancer Research (2009) vol. 7, No. 9, pp. 1466-1476.
Lorenzi et al. "FRAG1, a gene that potently activates fibroblast growth factor receptor by C-terminal fusion through chromosomal rearrangement" Proc. Natl. Acad. Sci. USA (1996) vol. 93 pp. 8956-8961.
Lorenzi et al. "Ligand-independent activation of fibroblast growth factor receptor-2 by carboxl terminal alterations" Oncogene (1997) vol. 15 pp. 817-826.
Marchetti et al., "Frequent Mutations in the Neurotrophic Tyrosine Receptor Kinase Gene Family in Large Cell Neuroendocrine Carcinoma of the Lung" Human Mutation (2008) vol. 29, No. 5, pp. 609-616.
Mardy et al., Congenital insensitivity to pain with anhidrosis: Novel mutations in the TRKA (NTRK1) gene encoding a high-affinity receptor for nerve growth factor, 1999, Am. J. Hum. Genet., 64, pp. 1570-1579.
Martin-Zanca D, et al. "A human oncogene formed by the fusion of truncated tropomyosin and protein tyrosine kinase sequences." Nature (1986) 319(6056):743-8.
Matsumoto et al. "FGFR2 gene amplification and clinicopathological features in gastric cancer" British Journal of Cancer (2012) vol. 106 No. 4 pp. 727-732.
McKay et al. "PP58 Novel potential therapeutic targets for cholangiocarcinoma identified by array comparitive hybridization" European Journal of Cancer (2009) vol. 7 No. 4, 1 page.
Meulenbeld, Hielke J. et al., "Danusertib, an aurora kinase inhibitor," Expert Opinion Investigative Drugs. Mar. 2012, 21(3), pp. 383-393.
Miura Y, et al. "Mutation and polymorphism analysis of the TRKA (NTRK1) gene encoding a high-affinity receptor for nerve growth factor in congenital insensitivity to pain with anhidrosis (CIPA) families." Hum Genet (2000) 106(1):116-24.
Muller-Tidow et al., Identification of Metastasis-Associated Receptor Tyrosine Kinases in Non-Small Cell Lung Cancer, 2005, Cancer Res., vol. 65, No. 5 pp. 1778-1782.
Narong and Leelawat "Basic fibroblast growth factor induces cholangiocarcinoma cell migration via activation of the MEK1/2 pathway" Oncology Letters (2011) pp. 821-825.
Patel et al. "Cholangiocarcinoma—controversies and challenges" Nat Rev Gastroenterol Hepatol (2011), 8(4):1-25.
Patel et al. "Worldwide trends in mortality from biliary tract malignancies" BMC Cancer (2002), 2(10):1-5.
Perez-Pinera P, et al. "The Trk tyrosine kinase inhibitor K252a regulates growth of lung adenocarcinomas." Mol Cell Biochem (2007) 295(1-2):19-26.
Powers et al. "Fibroblast growth factors, their receptors and signaling" Endocrine-Related Cancer (2000) vol. 7 pp. 165-197.
Rao, R. et al., "Heat shock protein 90 inhibition depletes TrkA levels and signaling in human acute leukemia cells", Mol Cancer Ther 9(8):2232-42, ePub Jul. 27, 2010, Aug. 2010.
Sartore-Bianchi et al. "Sensitivity to Entrectinib Associated With a Novel LMNA-NTRK1 Gene Fusion in Metastatic Colorectal Cancer" J Natl Cancer Inst (2016) vol. 108, No. 1, djv306, pp. 1-4.
Schneider et al., "The transforming acidic coiled coil 3 protein is essential for spindle-dependent chromosome alignment and mitotic survival" The Journal of Biological Chemistry, 282(40):29273-29283 (2007).
Singh et al. "Transforming Fusions of FGFR and TACC Genes in Human Glioblastoma" Science (2012) vol. 337(6099) pp. 1231-1235.
Tacconelli, A. et al. , "TrkA alternative splicing: a regulated tumor-promoting switch in human neuroblastoma", Cancer Cell 6(4):347-60, Oct. 2004.
Takeuchi et al. Multiplex reverse transcription-PCR screening for EML4-ALK fusion transcripts. Clin Cancer Res Oct. 15, 2008 vol. 14 No. 20 pp. 6618-6624. Especially p. 6619 col. 1 para.
Teixeira et al., "Recurrent Fusion Oncogenes in Carcinomas" Critical Reviews in Oncogenesis, 12(3-4):257-271 (2006).

(56) References Cited

OTHER PUBLICATIONS

Thress, K. et al., "Identification and preclinical characterization of AZ-23, a novel, selective, and orally bioavailable inhibitor of the Trk kinase pathway", Mol Cancer Ther 8(7):1818-27, ePub Jun. 9, 2009, Jul. 2009.
Toyokawa et al. "Co-expression of keratinocyte growth factor and K-sam is an independent prognostic factor in gastric carcinoma" Oncology Reports (2009) vol. 21 pp. 875-880.
Turner et al. "Fibroblast growth factor signalling: from development to cancer" Nature (2010) vol. 10, pp. 116-129.
Turner et al. "Integrative molecular profiling of triple negative breast cancers identifies amplicon drivers and potential therapeutic targets" Oncogene (2010) vol. 8 No. 29 pp. 2013-2023.
Undevia, SD et al., "Phase I clinical trial of CEP-2563 dihydrochloride, a receptor tyrosine kinase inhibitor, in patients with refractory solid tumors", Invest New Drugs 22(4):449-58, Nov. 2004.
University of Colorado Denver; "NTRK1: A new oncogene and target in lung cancer". Press Release, Public release date: Jun. 3, 2013, 2 pages.
Vaishnavi, Aria et al., "Oncogenic and drug-sensitive NTRK1 rearrangements in lung cancer", Nature Medicine, vol. 19, No. 11, pp. 1469-1472, ePub Oct. 27, 2013, Nov. 2013.
Wang et al. "Mutations in Isocitrate Dehydrogenase 1 and 2 Occur Frequently in Intrahepatic Cholangiocarcinomas and Share Hypermethylation Targets with Glioblastomas" Oncogene (2013), 23(25):1-22.
Wang et al. Fusion of dynactin 1 to anaplastic lymphoma kinase in inflammatory myofibroblastic tumor. Hum Pathol ePub Jun. 1, 2012 vol. 43 No. 11 pp. 2047-2052. Especially abstract.
Weiss, GJ et al., "Phase I study of the safety, tolerability and pharmacokinetics of PHA-848125AC, a dual tropomyosin receptor kinase A and cyclin-dependent kinase inhibitor, in patients with advanced solid malignancies", Invest New Drugs, 30(6):2334-2343 ePub Dec. 2011, Dec. 2012.
Williams et al., "Oncogenic FGFR3 gene fusions in bladder cancer" Human Molecular Genetics, 22(4):795-803 (2013).
Wong et al. "Evaluation of a Congenital Infantile Fibrosarcoma by Comprehensive Genomic Profiling Reveals an LMNA NTRK1 Gene Fusion Responsive to Crizotinib" J Natl Cancer Inst (2016) vol. 108, No. 1, djv307, pp. 1-3.
Written Opinion for International Application No. PCT/US2013/068604 dated May 5, 2015, 8 pages.
Wu et al. "Identification of Targetable FGFR Gene Fusions in Diverse Cancers" Cancer Discovery (Jun. 2013) pp. 636-647.
Yoon et al. "Enhanced epidermal growth factor receptor activation in human cholangiocarcinoma cells" Journal of Hepatology (2004) pp. 808-814.
[No Author Listed] National Center for Biotechnology Information PubChem Database. Ceritinib, CID=57379345, pubchem.ncbi.nim.nih.gov/compund/Ceritinib, created 2012, accessed on Jul. 21, 2019, 42 pages.
Altorki et al. "Phase II Proof-of-Concept Study of Pazopanib Monotherapy in Treatment-Naive Patience With State I/II Resectable Non-Small-Cell Lung Cancer" Journal of Clinical Oncology (2010) vol. 28, No. 19, pp. 3131-3137.
Avet-Loiseau et al. "High Incidence of Translocations t(11;14)(q13;q32) and t(4;14)(p16;q32) in Patients with Plasma Cell Malignancies" Cancer Research (1998) vol. 58, pp. 5640-5645.
Brambilla et al., "The new World Health Organization classification of lung tumours," Eur Respir J (2001) vol. 18, pp. 1059-1068.
Caneiro et al. "FGFR3-TACC3: A novel gene fusion in cervical cancer" Gynecologic Oncology Reports (2015), vol. 13, pp. 53-56.
Capelletti et al. "Identification of Recurrent FGFR3-TACC3 Fusion Oncogenes from Lung Adenocarcinoma" Clin Cancer Res (2014) vol. 20, pp. 6551-6558.
Cappellen et al., "Frequent activating mutations of FGFR3 in human bladder and cervix carcinomas," Nature Genetics (1999) vol. 23, pp. 18-20.
Chen et al. "FGFR3 as a therapeutic target of the small molecule inhibitor PKC412 in hematopoietic malignancies" Oncogene (2005) vol. 24, pp. 8259-8267.
Costa et al. "FGFR3-TACC3 fusion in solid tumors: mini review" Oncotarget (2016) vol. 7, No. 34, pp. 55924-55938.
Dhami et al., "Comprehensive genomic profiling aids in treatment of metastatic endometrial cancer," Cold Spring Harb Mol Case Stud (2018) vol. 4, Article a002089, 14 pages.
Gergely et al. "The TACC domain identifies a family of centrosomal proteins that can interact with microtubules" Proc Natl Acad Sci. (2000) vol. 97, pp. 14352-14357.
Giamas et al., (2007). "Protein kinases as targets for cancer treatment," Pharmacogenomics, 8(8); 1005-1016.
Gozgit et al. "Ponatinib (AP24534), a Multitargeted Pan-FGFR Inhibitor with Activity in Multiple FGFR-Amplified or Mutated Cancer Models" Molecular Cancer Therapeutics (2012) vol. 11 No. 3 pp. 690-699.
Guagnano et al., "FGFR Genetic Alterations Predict for Sensitivity to NVP-BGJ398, a Selective Pan-FGFR Inhibitor," Cancer Discovery (2012) vol. 2, pp. 1118-1133.
Javle et al., "Biliary Cancer: Utility of Next-Generation Sequencing for Clinical Management," Cancer (2016) vol. 122, pp. 3838-3847.
Jiao et al., "Exome sequencing identifies frequest inactivating mutations in BAP1, ARID1A and PBRM in intrahepatic cholangiocarcinomas," Nature Genetics (2013) vol. 45, No. 12, 53 pages, and Supplementary Information.
Kang et al., "microRNA-99b acts as a tumor suppressor in non-small cell lung cancer by directly targeting fibroblast growth factor receptor 3," Experimental and Therapeutic Medicine (2012) vol. 3, pp. 149-153.
Keats et al. "In multiple myeloma, t(4;14)(p16;q32) is an adverse prognostic factor irrespective of FGFR3 expression" Blood (2003) vol. 101, No. 4, pp. 1520-1529.
Keegan et al. "Isolation of an additional member of the fibroblast growth factor receptor family, FGFR-3" Proc Natl Acad Sci. (1991) vol. 88, No. 4, pp. 1095-1099.
Lam et al., "Expression profiling in lung adenocarcinomas with or without epidermal growth factor receptor (EGFR) gene mutation at exons 18-21 reveals expression signatures related to the EGFR pathway," Proc Amer Assoc Cancer Res (2005) vol. 46, Abstract 883, 2 pages.
Lee et al., "The potential role of comprehensive genomic profiling to guide targeted therapy for patients with biliary cancer," Ther Adv Gastroenterol (2017) vol. 10, No. 6, pp. 507-520.
Monk et al. "Phase II, Open-Label Study of Pazopanib or Lapatinib Monotherapy Compared With Pazopanib Plus Lapatinib Combination Therapy in Patients With Advanced and Recurrent Cervical Cancer" Journal of Clinical Oncology (2010) vol. 28, No. 22, pp. 3562-3569.
Notification of Transmittal of the International Search Report and Written Opinion of the International Searching Authority from corresponding PCT/US2013/068457 dated Jul. 11, 2014, 1 page.
Notification of Transmittal of the International Search Report and Written Opinion of the International Searching Authority from corresponding PCT/US2013/068604 dated Jul. 11, 2014, 1 page.
Ou et al., "Emergence of FGFR3-TACC3 fusions as a potential by-pass resistance mechanism to EGFR tyrosine kinase inhibitors in EGFR mutated NSCLC patients," Lung Cancer (2017) vol. 111, pp. 61-67.
Reck et al. "A phase II double-blind study to investigate efficacy and safety of two doses of the triple angiokinase inhibitor BIBF 1120 in patients with relapsed advanced nonsmall-cell lung cancer" Annals of Oncology (2011) vol. 22, pp. 1374-1381.
Richelda et al. "A Novel Chromosomal Translocation t(4; 14)(p16.3; q32) in Multiple Myeloma Involves the Fibroblast Growth Factor Receptor 3 Gene" Blood (1997) vol. 90, No. 10, pp. 4062-4070.
Santra et al. "A subset of multiple myeloma harboring the t(4;14)(p16;q32) translocation lacks FGFR3 expression but maintains an IGH/MMSET fusion transcript" Blood (2003) vol. 101, No. 6, pp. 2374-2376.
Stewart et al. "Correlation of TACC3, FGFR3, MMSET and p21 expression with the t(4;14)(p16.3;q32) in multiple myeloma" British Journal of Haematology (2004) vol. 126, pp. 72-76.

(56) References Cited

OTHER PUBLICATIONS

Ware et al. "Rapidly Acquired Resistance to EGFR Tyrosine Kinase Inhibitors in NSCLC Cell Lines through De-Repression of FGFR2 and FGFR3 Expression" PLOS One (2010) vol. 5, No. 11, 9 pages.
Wiesner et al., "Kinase fusions are frequent in Spitz tumours and spitzoid melanomas," Nature Communications (2014) vol. 5, Article 3116, 9 pages.
Woenckhaus et al., "Prognostic value of FHIT, CTNNB1, and MUC1 expression in non-small cell lung cancer," Human Pathology (2008) vol. 39, pp. 126-136.
Extended European Search Report received for European Patent Application No. 21179077.9 dated Dec. 10, 2021, 7 pages.
Miki et al., (1992). "Determination of ligand-binding specificity by alternative splicing: two distinct growth factor receptors encoded by a single gene," PNAS USA, 89(1):246-250.
PubChem, (2012). "Ceritinib, CID=57379345," Available online at <https://pubchem.ncbi.nlm.nih.gov/compound/Ceritinib>, 50 pages.
Werner et al., (2020). "Genomics based personalized oncology of cancer of unknown primary," Cancer Research, 80(16), 1 page.
Wessley et al., (2001). "Gene Expression Pattern: Identification and expression of the mammalian homologue of Bicaudal-C," Mech. Dev. 101, 267-270.
Albertson (1984). "Localization of the ribosomal genes in Caenorhabditis elegans chromosomes by in situ hybridization using biotin-labeled probes," EMBO J., 3:1227-1234.
Almagro et al., (2008). "Humanization of antibodies," Front. Biosci., 13:1619-1633.
Altschul et al., (1990). "Basic local alignment search tool," J. Mol Biol., 215:403-410.
Altschul et al., (1997). "Gapped BLAST and PSI-BLAST: a new generation of protein database search programs," Nucleic Acids Res., 25(17):3389-3402.
Arbitrario et al., (2010). "SNS-314, a pan-Aurora kinase inhibitor, shows potent anti-tumor activity and dosing flexibility in vivo," Cancer Chemother Pharmacol., 65(4):707-717.
Baca et al., (1997). "Antibody humanization using monovalent phage display," J. Biol. Chem., 272(16):10678-10684.
Banerji et al., (1983). "A lymphocyte-specific cellular enhancer is located downstream of the joining region in immunoglobulin heavy chain genes," Cell, 33(3):729-740.
Barringer et al., (1990). "Blunt-end and single-strand ligations by *Escherichia coli* ligase: influence on an in vitro amplification scheme," Gene, 89(1):117-122.
Bartel et al., (1993). "Isolation of new ribozymes from a large pool of random sequences," Science, 261(5127):1411-1418.
Beaucage et al., (1981). "Deoxynucleoside phosphoramidites—A new class of key intermediates for deoxypolynucleotide synthesis," Tetrahedron Letters, 22(20):1859-1862.
Beidler et al., (1988). "Cloning and high level expression of a chimeric antibody with specificity for human carcinoembryonic antigen," J. Immunol., 141(11):4053-4060.
Better et al. (1988). "*Escherichia coli* secretion of an active chimeric antibody fragment," Science, 240(4855):1041-1043.
Bhatia et al., (2011). "Immunobiology of Merkel cell carcinoma: implications for immunotherapy of a polyomavirus-associated cancer," Curr. Oncol. Rep., 13(6):488-497.
Billy et al., (2001). "Specific interference with gene expression induced by long, double-stranded RNA in mouse embryonal teratocarcinoma cell lines," Proc. Natl. Sci. USA, 98(25):14428-14433.
Boerner et al., (1991). "Production of antigen-specific human monoclonal antibodies from in vitro-primed human splenocytes," J. Immunol., 147(1):86-95.
Branton et al., (2008). "The potential and challenges of nanopore sequencing," Nat Biotechnol., 26(10):1146-1153.
Brennan et al., (1985). "Preparation of bispecific antibodies by chemical recombination of monoclonal immunoglobulin G1 fragments," Science, 229(4708):81-83.
Bruggemann et al., (1987). "Comparison of the effector functions of human immunoglobulins using a matched set of chimeric antibodies," J. Exp. Meet., 166(5):1351-1361.
Butler et al., (2008). "ALLPATHS: de novo assembly of whole-genome shotgun microreads," Genome Res., 18(5):810-820.
Byrne et al., (1989). "Multiplex gene regulation: a two-tiered approach to transgene regulation in transgenic mice," Proc. Natl. Acad. Sci. USA, 86(14):5473-5477.
Calame et al., (1988). "Transcriptional controlling elements in the immunoglobulin and T cell receptor loci," Adv. Immunol., 43:235-275.
Camper et al., (1989). "Postnatal repression of the alpha-fetoprotein gene is enhancer independent," Genes Dev., 3(4):537-546.
Carboni et al., (2009). "BMS-754807, a small molecule inhibitor of insulin-like growth factor-1R/IR," Mol Cancer Ther., 8(12):3341-3349.
Carell et al., (1994). "A Solution-Phase Screening Procedure for the Isolation of Active Compounds from a Library of Molecules," Angew. Chem. Int. Ed. Engl., 33(20):2061-2064.
Carrell et al., (1994). "A Novel Procedure for the Synthesis of Libraries Containing Small Organic Molecules," Angew. Chem. Int. Ed. Engl., 33(20):2059-2061.
Carter et al., (1992). "Humanization of an anti-p185HER2 antibody for human cancer therapy," Proc. Natl. Acad. Sci. USA, 89(10):4285-4289.
Chen et al., (1999). "Selection and analysis of an optimized anti-VEGF antibody: crystal structure of an affinity-matured Fab in complex with antigen," J Mol Biol., 293(4):865-881.
Chi et al., (2012). "ETV6-NTRK3 as a therapeutic target of small molecule inhibitor PKC412," Biochem Biophys Res Commun., 429(1-2):87-92.
Cho et al., (1993). "An unnatural biopolymer," Science, 261 (5126):1303-1305.
Chowdhury (2008). "Engineering hot spots for affinity enhancement of antibodies," Methods Mol. Biol., 207:179-196.
Chu et al., (2008). "Potent RNAi by short RNA triggers," RNA, 14(9):1714-1719.
Clackson et al., (1991). "Making antibody fragments using phage display libraries," Nature, 352(6336):624-628.
Clemens et al., (2000). "Use of double-stranded RNA interference in *Drosophila* cell lines to dissect signal transduction pathways," Proc. Natl. Acad. Sci. USA, 97(12):6499-6503.
Clynes et al., (1998). "Fc receptors are required in passive and active immunity to melanoma," Proc. Nat'l Acad. Sci. USA, 95:652-656.
Cocco et al., (2019). "Resistance to TRK inhibition mediated by convergent MAPK pathway activation," Nat Med., 25(9):1422-1427.
Cohen et al., (1996). "Emerging technologies for sequencing antisense oligonucleotides: capillary electrophoresis and mass spectrometry," Adv Chromatogr., 36:127-162.
Cragg et al., (2003). "Complement-mediated lysis by anti-CD20 mAb correlates with segregation into lipid rafts," Blood, 101 (3):1045-1052.
Cronin et al. (2004). "Measurement of gene expression in archival paraffin-embedded tissues: development and performance of a 92-gene reverse transcriptase-polymerase chain reaction assay," Am J Pathol., 164(1):35-42.
Cull et al., (1992). "Screening for receptor ligands using large libraries of peptides linked to the C terminus of the lac repressor," Proc Natl Acad Sci USA, 89(5):1865-1869.
Cunningham et al., (1989). "High-resolution epitope mapping of hGH-receptor interactions by alanine-scanning mutagenesis," Science, 244(4908):1081-1085.
Cwirla et al., (1990). "Peptides on phage: a vast library of peptides for identifying ligands," Proc. Natl. Acad. Sci., 87(16):6378-6382.
Dall'Acqua et al., (2005). "Antibody humanization by framework shuffling," Methods, 36(1):43-60.
Demetri et al., (2018). "Efficacy and safety of entrectinib in patients with NTRK fusion-positive (NTRK-fp) Tumors: Pooled analysis of STARTRK-2, STARTRK-1 and ALKA-372-001," ESMO, 29(S8), 1 page.

(56) References Cited

OTHER PUBLICATIONS

Devlin et al., (1990). "Random peptide libraries: a source of specific protein binding molecules," Science, 249(4967):404-406.
DeWitt et al., (1993). "'Diversomers': an approach to nonpeptide, nonoligomeric chemical diversity," Proc. Natl. Acad Sci. U.S.A., 90(15):6909-6913.
Doebele et al., (2018). "Efficacy and Safety of Entrectinib in Locally Advanced or Metastatic ROS1-Positive Non-Small Cell Lung Cancer (NSCLC)," IASLC 19th World Conference on Lung Cancer; Abstract No. 0A02.01, 2 pages.
Doebele et al., (2019). "Time-to-treatment discontinuation (TTD) and real-world progression-free survival (rwPFS) as endpoints for comparative efficacy analysis between entrectinib trial and crizotinib real-world ROS1 fusion-positive (ROS1+) NSCLC patients," 2019 ASCO Annual Meeting I; ASCO Abstract 9070, 2 pages.
Drilon et al., (2017). "Safety and Antitumor Activity of the Multitargeted Pan-TRK, ROS1, and ALK Inhibitor Entrectinib: Combined Results from Two Phase I Trials (ALKA-372-001 and STARTRK-1)," Cancer Discov., 7(4):400-409.
Drilon et al., (2018). "Efficacy of Larotrectinib in TRK Fusion-Positive Cancers in Adults and Children," N Engl J Med., 378(8):731-739.
Duncan et al., (1988). "The binding site for C1q on IgG," Nature, 322(6166):738-740.
Edlund et al., (1985). "Cell-specific expression of the rat insulin gene: evidence for role of two distinct 5' flanking elements," Science, 230(4728):912-916.
Edwards et al., "Mass-spectrometry DNA sequencing," Mut. Res., 573(1-2):3-12. Abstract only, 1 page.
Elbashir et al., (2001). "Duplexes of 21-nucleotide RNAs mediate RNA interference in cultured mammalian cells," Nature, 411(6836):494-498.
Elbashir et al., (2001). "Functional anatomy of siRNAs for mediating efficient RNAi in *Drosophila* melanogaster embryo lysate," EMBO, 20(23):6877-6888.
Elmen et al., (2005). "Locked nucleic acid (LNA) mediated improvements in siRNA stability and functionality," Nucleic Acids Research, 33(1):439-447.
Erb et al., (1994). "Recursive deconvolution of combinatorial chemical libraries," Proc. Natl. Acad Sci. USA, 91 (24): 11422-11426.
Faria et al., (2001). "Phosphoramidate oligonucleotides as potent antisense molecules in cells and in vivo," Nature Biotech., 19(1):40-44.
Felici et al., (1991). "Selection of antibody ligands from a large library of oligopeptides expressed on a multivalent exposition vector," J. Mol. Biol., 222(2):301-310.
Fellouse et al., (2004). "Synthetic antibodies from a four-amino-acid code: a dominant role for tyrosine in antigen recognition," Proc. Natl. Acad. Sci. USA, 101 (34):12467-12472.
Fletcher et al., (2011). "ENMD-2076 is an orally active kinase inhibitor with antiangiogenic and antiproliferative mechanisms of action," Mol Cancer Ther., 10(1):126-137.
Fodor et al., (1993). "Multiplexed biochemical assays with biological chips," Nature, 364(6437):555-556.
Fuchs et al., (1991). "Targeting Recombinant Antibodies to the Surface of *Escherichia coli*: Fusion to a Peptidoglycan Associated Lipoprotein," Nature Biotechnology, 9:1370-1372.
Fuse et al., (2017). "Mechanisms of Resistance to NTRK Inhibitors and Therapeutic Strategies in NTRK1-Rearranged Cancers," Molecular Cancer Therapeutics, 16(10):2130-2143.
Gallop et al., (1994). "Applications of combinatorial technologies to drug discovery. 1. Background and peptide combinatorial libraries," J. Med. Chem., 37(9):1233-1251.
Gautier et al., (1987). "Alpha-DNA. IV: Alpha-anomeric and beta-anomeric tetrathymidylates covalently linked to intercalating oxazolopyridocarbazole. Synthesis, physicochemical properties and poly (rA) binding," Nucleic Acids. Res., 15(16):6625-6641.

Gazzano-Santoro et al., (1996). "A non-radioactive complement-dependent cytotoxicity assay for anti-CD20 monoclonal antibody," J. Immunol. Methods, 202(2):163-171.
Ginzinger et al., (2000). "Measurement of DNA copy number at microsatellite loci using quantitative PCR analysis," Cancer Research, 60(19):5405-5409.
Gluzman (1981). "SV40-transformed simian cells support the replication of early SV40 mutants," Cell, 23(1):175-182.
Gossen et al., (1992). "Tight control of gene expression in mammalian cells by tetracycline-responsive promoters," Proc. Natl. Acad Sci. USA, 89(12):5547-5551.
Griffin et al., (1993). "DNA sequencing. Recent innovations and future trends," Appl Biochem Biotechnol., 38(1-2):147-159.
Griffiths et al., (1993). "Human anti-self antibodies with high specificity from phage display libraries," EMBO J., 12(2):725-734.
Gruber et al., (1994). "Efficient tumor cell lysis mediated by a bispecific single chain antibody expressed in *Escherichia coli*," J. Immunol., 152(11):5368-5374.
Grunweller et al., (2003). "Comparison of different antisense strategies in mammalian cells using locked nucleic acids, 2'-O-methyl RNA, phosphorothioates and small interfering RNA," Nucleic Acids Research, 31(12):3185-3193.
Guatelli et al. (1990). "Isothermal, in vitro amplification of nucleic acids by a multienzyme reaction modeled after retroviral replication," Proc. Nat. Acad. Sci. USA, 87(5):1874-1878.
Gudernova et al., (2017). "Inhibitor repurposing reveals ALK, LTK, FGFR, RET and TRK kinases as the targets of AZD1480," Oncotarget, 8(65):109319-109331.
Guyer et al., (1976). "Immunoglobulin binding by mouse intestinal epithelial cell receptors," J. Immunol., 117(2):587-593.
Hanna et al., (2000). "Comparison of sequencing by hybridization and cycle sequencing for genotyping of human immunodeficiency virus type 1 reverse transcriptase," J. Clin. Microbiol., 38(7):2715-2721.
Hara et al., (1998). "Amplification of c-myc, K-sam, and c-met in gastric cancers: detection by fluorescence in situ hybridization," Lab Invest, 78(9):1143-53.
Haselhoff et al., (1988). "Simple RNA enzymes with new and highly specific endoribonuclease activities," Nature, 334(6183):585-591.
Hay et al., (1992). "Bacteriophage cloning and *Escherichia coli* expression of a human IgM Fab," Hum. Antibod. Hybridomas, 3(2):81-85.
Helene (1991). "The anti-gene strategy: control of gene expression by triplex-forming-oligonucleotides," Anticancer Drug Des., 6(6):569-584.
Helene et al., (1992). "Control of gene expression by triple helix-forming oligonucleotides. The antigene strategy," Ann. N.Y. Acad. Sci., 660:27-36.
Hellstrom et al., (1985). "Strong antitumor activities of IgG3 antibodies to a human melanoma-associated ganglioside," Proc. Nat'l Acad. Sci. USA, 82(5):1499-1502.
Hellstrom et al., (1986). "Antitumor effects of L6, an IgG2a antibody that reacts with most human carcinomas," Proc. Nat'l Acad. Sci. USA, 83(18):7059-7063.
Holliger et al., (1993). "'Diabodies': small bivalent and bispecific antibody fragments," Proc. Natl. Acad. Sci. USA, 90(14):6444-6448.
Hoogenboom et al., (1992). "By-passing immunisation. Human antibodies from synthetic repertoires of germline VH gene segments rearranged in vitro," J Mol Biol., 227(2):381-388.
Hoogenboom et al., (2002). "Overview of antibody phage-display technology and its applications," Methods in Molecular Biology, 178:1-37.
Houghten et al., (1992). "The use of synthetic peptide combinatorial libraries for the identification of bioactive peptides," Biotechniques, 13(3):412-421.
Hudson et al., (2003). "Engineered antibodies," Nat. Med., 9(1):129-134.
Huse et al., (1989). "Generation of a large combinatorial library of the immunoglobulin repertoire in phage lambda," Science, 246(4935):1275-1281.

(56) References Cited

OTHER PUBLICATIONS

Hyman et al., (2019). "445PD—Durability of response with larotrectinib in adult and pediatric patients with TRK fusion cancer," Annals of Oncology, 30(S5):v162-v163.

Hyrup et al., (1996). "Peptide nucleic acids (PNA): synthesis, properties and potential applications," Bioorganic & Medicinal Chemistry, 4(1):5-23.

Idusogie et al., (2000). "Mapping of the C1q binding site on rituxan, a chimeric antibody with a human IgG1 Fc," J. Immunol., 164(8):4178-4184.

Imanishi et al., (2002). "BNAs: novel nucleic acid analogs with a bridged sugar moiety," Chem. Commun., 16:1653-1659.

Inoue et al., (1987). "Sequence-dependent hydrolysis of RNA using modified oligonucleotide splints and RNase H," FEBS Lett., 215(2):327-330.

Inoue et al., (1987). "Synthesis and hybridization studies on two complementary nona(2'-O-methyl)ribonucleotides," Nucleic Acids Res., 15(15):6131-6148.

Jani et al., (2010). "PF-03814735, an orally bioavailable small molecule aurora kinase inhibitor for cancer therapy," Mol Cancer Ther., 9(4):883-894.

Jepson et al., (2004). "Locked nucleic acid: a potent nucleic acid analog in therapeutics and biotechnology," Oligonucleotides, 14(2):130-146. Abstract only, 1 page.

Jones et al., (1986). "Replacing the complementarity-determining regions in a human antibody with those from a mouse," Nature, 321(6069):552-525.

Kalampokas et al., (2017). "Primary Vaginal Melanoma, A Rare and Aggressive Entity. A Case Report and Review of the Literature," In Vivo, 31(1):133-140.

Kallioniemi et al., (1992). "ERBB2 amplification in breast cancer analyzed by fluorescence in situ hybridization," Proc. Natl Acad Sci USA, 89(12):5321-5325.

Kam et al., (2005). "Carbon nanotubes as multifunctional biological transporters and near-infrared agents for selective cancer cell destruction," Proc. Natl. Acad. Sci. USA, 102(33):11600-11605.

Kanda et al., (2006). "Comparison of cell lines for stable production of fucose-negative antibodies with enhanced ADCC," Biotechnol. Bioeng., 94(4):680-688.

Karlin et al., (1990). "Methods for assessing the statistical significance of molecular sequence features by using general scoring schemes," Proc. Natl. Acad. Sci. USA, 87(6):2264-2268.

Karlin et al., (1993). "Applications and statistics for multiple high-scoring segments in molecular sequences," Proc. Natl. Acad. Sci. USA, 90(12):5873-5877.

Kashmiri et al., (2005). "SDR grafting—a new approach to antibody humanization," Methods, 36(1):25-34.

Kessel et al., (1990). "Murine developmental control genes," Science, 249(4967):374-379.

Khotskaya et al., (2017). "Targeting TRK family proteins in cancer," Pharmacol Ther., 173:58-66. Abstract only, 1 page.

Kim et al., (1994). "Localization of the site of the murine IgG1 molecule that is involved in binding to the murine intestinal Fc receptor," Eur J Immunol., 24(10):2429-2434. Abstract only, 1 page.

Kim et al., (2005). "Synthetic dsRNA Dicer substrates enhance RNAi potency and efficacy," Nat Biotech., 23(2):222-226.

Klimka et al., (2000). "Human anti-CD30 recombinant antibodies by guided phage antibody selection using cell panning," Br. J. Cancer, 83(2):252-260.

Kohler et al., (1975). "Continuous cultures of fused cells secreting antibody of predefined specificity," Nature, 256(5517):495-497.

Kostelny et al., (1992). "Formation of a bispecific antibody by the use of leucine zippers," J. Immunol., 148(5):1547-1553.

Kozbor et al., (1983). "The production of monoclonal antibodies from human Tymphocytes," Immunol. Today, 4(3):72-79.

Kozbor et al., (1984). "A human hybrid myeloma for production of human monoclonal antibodies," J Immunol., 133(6):3001-3005.

Krishnakumar et al., (2008). "A comprehensive assay for targeted multiplex amplification of human DNA sequences," Proc. Natl. Acad. Sci. USA, 105(27):9296-9310.

Kwoh et al., (1989). "Transcription-based amplification system and detection of amplified human immunodeficiency virus type 1 with a bead-based sandwich hybridization format," Proc. Nail. Acad. Sci. USA, 86(4):1173-1177.

Lam (1997). "Application of combinatorial library methods in cancer research and drug discovery," Anticancer Drug Des., 12(3):145-167.

Lam et al., (1991). "A new type of synthetic peptide library for identifying ligand-binding activity," Nature, 354(6348):82-84.

Landegren et al., (1988). "A ligase-mediated gene detection technique," Science, 241(4869):1077-1080.

Lassen et al., (2018). "Abstract 409O: Larotrectinib efficacy and safety in TRK fusion cancer: an expanded clinical dataset showing consistency in an age and tumor agnostic approach," Annals of Oncology 29 (Supplement 8): viii133-viii148, 1 page.

Lee et al., (2004). "Bivalent antibody phage display mimics natural immunoglobulin," J. Immunol. Methods, 284(1-2):119-132.

Lee et al., (2004). "High-affinity human antibodies from phage-displayed synthetic Fab libraries with a single framework scaffold," J. Mol. Biol., 340(5):1073-1093.

Lemaitre et al., (1987). "Specific antiviral activity of a poly(L-lysine)-conjugated oligodeoxyribonucleotide sequence complementary to vesicular stomatitis virus N protein mRNA initiation site," Proc. Natl. Acad. Sci. USA, 84(3):648-652.

Letsinger et al., (1989). "Cholesteryl-conjugated oligonucleotides: synthesis, properties, and activity as inhibitors of replication of human immunodeficiency virus in cell culture," Proc. Natl. Acad Sci. USA, 86(17):6553-6556.

Li et al., (2006). "Human antibodies for immunotherapy development generated via a human B cell hybridoma technology," Proc. Natl. Acad. Sci. USA, 103(10):3557-3562.

Liu et al., (1987). "Chimeric mouse-human IgG1 antibody that can mediate lysis of cancer cells," Proc. Natl. Acad. Sci. USA, 84(10):3439-3443.

Liu et al., (1987). "Production of a mouse-human chimeric monoclonal antibody to CD20 with potent Fc-dependent biologic activity," J Immunol. 139(10):3521-3526.

Lonberg (2005). "Human antibodies from transgenic animals," Nat. Biotech., 23(9):1117-1125.

Lonberg (2008). "Fully human antibodies from transgenic mouse and phage display platforms," Curr. Opin. Immunol., 20(4):450-459.

Lonberg et al., (1995). "Human antibodies from transgenic mice," Int. Rev. Immunol., 13(1):65-93.

Maher (1992). "DNA triple-helix formation: an approach to artificial gene repressors?" Bioassays, 14(12):807-815.

Marks et al., (1992). "By-passing immunization. Human antibodies from V-gene libraries displayed on phage," J Mot Biol., 222(3):581-597.

Marks et al., (2004). "Selection of human antibodies from phage display libraries," Methods in Molecular Biology, 248:161-176.

Martin (1995). "Ein neuer Zugang zu 2'-O-Alkylribonucleosiden und Eigenschaften deren Oligonucleotide," Helvetica, 78(2):486-504. English abstract.

Masuda et al., (1999). "Analysis of chemical modification of RNA from formalin-fixed samples and optimization of molecular biology applications for such samples," Nucleic Acids Res., 27(22):4436-4443.

McCafferty et al., (1990). "Phage antibodies: filamentous phage displaying antibody variable domains," Nature, 348(6301):552-554.

Meric-Bernstam et al., (2018). "Activity of larotrectinib, a highly selective inhibitor of tropomyosin receptor kinase, in TRK fusion breast cancers", SABCS Abstract P6-20-02, 2 pages.

Metzker (2010). "Sequencing technologies—the next generation," Nature Biotechnology Reviews, 11(1):31-46.

Milstein et al., (1983). "Hybrid hybridomas and their use in immunohistochemistry," Nature, 305(5934):537-540.

Mody et al., (2015). "Integrative Clinical Sequencing in the Management of Refractory or Relapsed Cancer in Youth," JAMA, 314(9):913-925.

Mook et al., (2007). "Evaluation of locked nucleic acid-modified small interfering RNA in vitro and in vivo," Mol Cancer Ther., 6(3):833-843.

(56) References Cited

OTHER PUBLICATIONS

Morrison (1985). "Transfectomas provide novel chimeric antibodies," Science, 229(4719):1202-1207.
Morrison et al., (1984). "Chimeric human antibody molecules: mouse antigen-binding domains with human constant region domains," Proc. Natl. Acad. Sci. USA, 81(21):6851-6855.
Myers et al., (1988). "Optimal alignments in linear space," Comput Appl Biosci, 4(1):11-17.
Nath et al., (1998). "Fluorescence in situ hybridization (FISH): DNA probe production and hybridization criteria," Biotechnic Histochem., 73(1):6-22.
Ni (2006). "Research progress and future perspectives in antibodomics and antibodomic Drugs," J. General Review, 26(4):265-268. Abstract only, 3 pages.
Nielsen et al., (1991). "Sequence-selective recognition of DNA by strand displacement with a thymine-substituted polyamide," Science, 254(5037):1497-1500.
Nishimura et al., (1987). "Recombinant human-mouse chimeric monoclonal antibody specific for common acute lymphocytic leukemia antigen," Cancer Res., 47(4):999-1005.
Nishiyama et al., (2018). "Foretinib Overcomes Entrectinib Resistance Associated with the NTRK1 G667C Mutation in NTRK1 Fusion-Positive Tumor Cells in a Brain Metastasis Model," Clin Cancer Res., 24(10):2357-2369.
Oi et al., (1986). "Chimeric antibodies," BioTechniques, 4(3), 214-221.
Okamura et al., (2018). "Analysis of NTRK Alterations in Pan-Cancer Adult and Pediatric Malignancies: Implications for NTRK-Targeted Therapeutics," JCO Precis Oncol., PO.18.00183, 20 pages.
Okazaki et al., (2004). "Fucose depletion from human IgG1 oligosaccharide enhances binding enthalpy and association rate between IgG1 and FcgammaRIIIa," J. Mol. Biol., 336(5):1239-1249.
Osbourn et al., (2005). "From rodent reagents to human therapeutics using antibody guided selection," Methods, 36(1):61-68.
Padlan (1991). "A possible procedure for reducing the immunogenicity of antibody variable domains while preserving their ligand-binding properties," Mol. Immunol., 28(4-5):489-498.
Paillard (1989). "'Tet-on': a gene switch for the exogenous regulation of transgene expression," Human Gene Therapy, 9(7):983-985.
Park et al., (2016). "NTRK1 fusions for the therapeutic intervention of Korean patients with colon cancer," Oncotarget, 7(7):8399-8412.
Pearson et al., (1988). "Improved tools for biological sequence comparison," Proc. Natl. Acad. Sci. USA, 85(8):2444-2448.
Penault-Llorca et al., (2019). "Testing algorithm for identification of patients with TRK fusion cancer," J Clin Pathol., 72(7):460-467.
Perry-O'Keefe et al., (1996). "Peptide nucleic acid pre-gel hybridization: an alternative to southern hybridization," Proc. Natl. Acad. Sci., 93(25):14670-14675.
Petkova et al., (2006). "Enhanced half-life of genetically engineered human IgG1 antibodies in a humanized FcRn mouse model: potential application in humorally mediated autoimmune disease," Intl. Immunol., 18(12):1759-1769.
Pinkel et al., (1988). "Fluorescence in situ hybridization with human chromosome-specific libraries: detection of trisomy 21 and translocations of chromosome 4," Proc. Natl. Acad. Sci. USA, 85(23):9138-9142.
Pinkel et al., (1998). "High resolution analysis of DNA copy number variation using comparative genomic hybridization to microarrays," Nature Genetics, 20(2):207-211.
Pinkert et al., (1987). "An albumin enhancer located 10 kb upstream functions along with its promoter to direct efficient, liver-specific expression in transgenic mice," Genes Dev., 1(3):268-277.
Porreca et al., (2007). "Multiplex amplification of large sets of human exons," Nature Methods, 4(11):931-936.
Presta et al., (1993). "Humanization of an antibody directed against IgE," J. Immunol, 151(5):2623-2632.
Presta et al., (1997). "Humanization of an anti-vascular endothelial growth factor monoclonal antibody for the therapy of solid tumors and other disorders," Cancer Res., 57(20):4593-4599.
Queen et al., (1983). "Immunoglobulin gene transcription is activated by downstream sequence elements," Cell, 33(3):741-748.
Queen et al., (1989). "A humanized antibody that binds to the interleukin 2 receptor," Proc. Nat'l Acad. Sci. USA, 86(24):10029-10033.
Ravetch et al., (1991). "Fc receptors," Annu. Rev. Immunol., 9:457-492.
Riechmann et al., (1988). "Reshaping human antibodies for therapy," Nature, 332(6162):323-329.
Ripka et al., (1986). "Two Chinese hamster ovary glycosylation mutants affected in the conversion of GDP-mannose to GDP-fucose," Arch. Biochem. Biophys., 249(2):533-545.
Robinson et al., (2019). "Phase 1/1B trial to assess the activity of entrectinib in children and adolescents with recurrent or refractory solid tumors including central nervous system (CNS) tumors," 2019 ASCO Annual Meeting I, ASCO Abstract 10009, 3 pages.
Rosok et al., (1996). "A combinatorial library strategy for the rapid humanization of anticarcinoma BR96 Fab," J. Biol. Chem., 271 (37):22611-22618.
Sanger et al., (1977). "DNA sequencing with chain-terminating inhibitors," Proc. Nat. Acad. Sci, 74(12):5463-5467.
Schram et al., (2017). "Potential role of larotrectinib (LOXO-101), a selective pan-TRK inhibitor, in NTRK fusion-positive recurrent glioblastoma," AACR Annual Meeting 2017, AACR abstract LB-302, 1 page.
Scott et al., (1990). "Searching for peptide ligands with an epitope library," Science, 249(4967):386-390.
Shaw et al., (1988). "Mouse/human chimeric antibodies to a tumor-associated antigen: biologic activity of the four human IgG subclasses," J. Natl. Cancer Inst. 80(19):1553-1559.
Shields et al., (2001). "High resolution mapping of the binding site on human IgG1 for Fc gamma RI, Fc gamma RII, Fc gamma RIII, and FcRn and design of IgG1 variants with improved binding to the Fc gamma R," J. Biol. Chem., 9(2):6591-6604.
Shimomura et al., (2010). "MK-5108, a highly selective Aurora-A kinase inhibitor, shows antitumor activity alone and in combination with docetaxel," Mol Cancer Ther., 9(1):157-166.
Sidhu et al., (2004). "Phage-displayed antibody libraries of synthetic heavy chain complementarity determining regions," J Mot Biol., 338(2):299-310.
Siena et al., (2019). "Efficacy of entrectinib in patients (pts) with solid tumors and central nervous system (CNS) metastases: Integrated analysis from three clinical trials," 2019 ASCO Annual Meeting I, ASCO Abstract 3017, 3 pages.
Sims et al., (1993). "A humanized CD18 antibody can block function without cell destruction," J. Immunol., 151(4):2296-2308.
Siolas et al., (2005). "Synthetic shRNAs as potent RNAi triggers," Nat. Biotechnol., 23(2):227-231.
Sjolander et al., (1991). "Integrated fluid handling system for biomolecular interaction analysis," Anal. Chem., 63(20):2338-2345.
Smith et al., (1988). "Single-step purification of polypeptides expressed in *Escherichia coli* as fusions with glutathione S-transferase," Gene, 67(1):31-40.
Smith et al., (2018). "Antitumor Activity of Entrectinib, a Pan-TRK, ROS1, and ALK Inhibitor, in ETV6-NTRK3-Positive Acute Myeloid Leukemia," Mol Cancer Ther., 17(2):455-463.
Specht et al., (2001). "Quantitative gene expression analysis in microdissected archival formalin-fixed and paraffin-embedded tumor tissue," Am J Pathol., 158(2):419-429.
Sun et al., (1987). "Chimeric antibody with human constant regions and mouse variable regions directed against carcinoma-associated antigen 17-1A," Proc. Natl. Acad. Sci. USA, 84(1):214-218.
Szabo et al., (1995). "Surface plasmon resonance and its use in biomolecular interaction analysis (BIA)," Curr. Opin. Struct. Biol., 5(5):699-705.
Tewhey et al., (2009). "Microdroplet-based PCR enrichment for large-scale targeted sequencing," Nature Biotech., 27(11):1025-1031, 25 pages.
Trapnell et al., (2009). "How to map billions of short reads onto genomes," Nature Biotech., 27(5):455-457.

(56) References Cited

OTHER PUBLICATIONS

Traunecker et al., (1991). "Bispecific single chain molecules (Janusins) target cytotoxic lymphocytes on HIV infected cells," EMBO J., 10(12):3655-3659.
Turner et al., (2009). "Massively parallel exon capture and library-free resequencing across 16 genomes," Nature Methods, 6(5):315-316.
Tutt et al., (1991). "Trispecific F(ab')3 derivatives that use cooperative signaling via the TCR/CD3 complex and CD2 to activate and redirect resting cytotoxic T cells," J. Immunol., 147(1):60-69.
van Dijk et al., (2001). "Human antibodies as next generation therapeutics," Curr. Opin. Pharmacol., 5(4):368-374.
Verhoeyen et al., (1988). "Reshaping human antibodies: grafting an antilysozyme activity," Science, 239(4847):1534-1536.
Vollmers et al., (2005). "Death by stress: natural IgM-induced apoptosis," Methods and Findings in Experimental and Clinical Pharmacology, 27(3):185-191.
Vollmers et al., (2005). "The 'early birds': natural IgM antibodies and immune surveillance," Histology and Histopathology, 20(3):927-937.
Wada et al., (1992). "Codon usage tabulated from the GenBank genetic sequence data," Nucleic Acids Res., 20:2111-2118.
Wang et al., (2019). "Durable Clinical Response to Crizotinib in IRF2BP2-NTRK1 Non-small-cell Lung Cancer," Clin Lung Cancer, 20(3):e233-e237.
Warren et al., (2007). "Assembling millions of short DNA sequences using SSAKE," Bioinformatics, 23(4):500-501.
Wheeless et al., (1994). "Bladder irrigation specimens assayed by fluorescence in situ hybridization to interphase nuclei," Cytometry, 17(4):319-326.
Winoto et al., (1989). "A novel, inducible and T cell-specific enhancer located at the 3' end of the T cell receptor alpha locus," EMBO J., 8(3):729-733.
Winter et al., (1994). "Making antibodies by phage display technology," Ann. Rev. Immunol., 12:433-455.
Wood et al., (1985). "The synthesis and in vivo assembly of functional antibodies in yeast," Nature, 314(6010):446-449.
Wright et al., (1997). "Effect of glycosylation on antibody function: implications for genetic engineering," Trends Biotechnol., 15(1):26-32.
Yamane-Ohnuki et al., (2004). "Establishment of FUT8 knockout Chinese hamster ovary cells: an ideal host cell line for producing completely defucosylated antibodies with enhanced antibody-dependent cellular cytotoxicity," Biotechnol Bioeng., 87(5):614-622.
Yang et al., (2002). "Short RNA duplexes produced by hydrolysis with *Escherichia coli* RNase III mediate effective RNA interference in mammalian cells," Proc. Natl. Acad. Sci. USA, 99(15):9942-9947.
Zerbino et al., (2008). "Velvet: algorithms for de novo short read assembly using de Bruijn graphs," Genome Res., 18(5):821-829.
Zhou et al., (2018). "A primary undifferentiated pleomorphic sarcoma of the lumbosacral region harboring a LMNA-NTRK1 gene fusion with durable clinical response to crizotinib: a case report," BMC Cancer, 18(1):842.
Ziegler et al., (2018). "Brief Report: Potent clinical and radiological response to Tarotrectinib in TRK fusion-driven high-grade glioma," Br J Cancer, 119(6):693-696.
Zon (1988). "Oligonucleotide analogues as potential chemotherapeutic agents," Pharm. Res., 5(9):539-549.
Zuckermann et al., (1994). "Discovery of nanomolar ligands for 7-transmembrane G-protein-coupled receptors from a diverse N-(substituted)glycine peptoid library," J Med Chem., 37(17):2678-2685.
Adnane et al., (1991). "BEK and FLG, two receptors to members of the FGF family, are amplified in subsets of human breast cancers," Oncogene, 6(4):659-63.
Akslen et al., (2005). "BRAF and NRAS mutations are frequent in nodular melanoma but are not associated with tumor cell proliferation or patient survival," J Invest Dermatol, 125(2):312-7.

Al-Ahmadie et al., (2011). "Somatic mutation of fibroblast growth factor receptor-3 (FGFR3) defines a 20 distinct morphological subtype of high-grade urothelial carcinoma," J Pathol, 224(2):270-9, 20 pages.
Alazzouzi et al., (2005). "SMAD4 as a prognostic marker in colorectal cancer," Clinical cancer research, 11(7):2606-11.
Andoniou et al., (1994). "Tumour induction by activated abl involves tyrosine phosphorylation of the product of the cbl oncogene," EMBO J, 13(19):4515-23.
Bacher et al., (2010). "Mutations of the TET2 and CBL 20 genes: novel molecular markers in myeloid malignancies," Ann Hematol, 89(7):643-52.
Baraniskin et al., (2011). "A Prognostic value of reduced SMAD4 expression in patients with metastatic colorectal cancer under oxaliplatin-containing chemotherapy: a translational study of the AIO colorectal study group," Clinical colorectal cancer, 10(1):24-9.
Beimfohr et al., (1999). "NTRK1 re-arrangement in papillary thyroid carcinomas of children after the Chernobyl reactor accident," Int J Cancer, 80(6):842-7.
Bernt et al., (2011). "A role for DOT1L in MLL-rearranged leukemias," Epigenomics, 3(6):667-70.
Bernt et al., (2011). "MLL-rearranged leukemia is dependent on aberrant H3K79 methylation by DOT1L," Cancer Cell, 20(1):66-78.
Birch et al., (2011). "Chromosome 3 Anomalies Investigated by Genome Wide SNP Analysis of Benign, Low Malignant Potential and Low Grade Ovarian Serous Tumours," PLoS One, 6:e28250, 20 pages.
Bown, (2001). "Neuroblastoma tumour genetics: clinical and biological aspects," J Clin Pathol, 54(12):897-910.
Brenner et al., (2011). "Mechanistic rationale for inhibition of poly(ADP-ribose) polymerase in ETS gene fusion-positive prostate cancer," Cancer Cell, 19(5):664-78.
Brodeur et al., (2009). "Trk receptor expression and inhibition in neuroblastomas," Clin Cancer Res, 15(10):3244-50.
Carrillo de Santa Pau et al., (2009). "Prognostic significance of the expression of vascular endothelial growth factors A, B, C, and D and their receptors R1, R2, and R3 in patients with nonsmall cell lung cancer," Cancer, 115(8):1701-1712.
Carver et al., (2009). "Aberrant ERG expression cooperates with loss of PTEN to promote cancer progression in the prostate," Nat Genet, 41(5):619-24, 14 pages.
Chase et al., (2012). "Ponatinib as targeted therapy for FGFR1 fusions associated with the 8p11 myeloproliferative syndrome," Haematologica, 98:103-6.
Daigle et al., (2011). "Selective killing of mixed lineage leukemia cells by a potent small-molecule DOT1L inhibitor," Cancer Cell, 20(1):53-65.
Daugrois et al., (2021). "Gene Expression Signature Associated with Clinical Outcome in ALK-Positive Anaplastic Large Cell Lymphoma," Cancers, 13(21):5523.
Davies et al., (2012). "Identifying and targeting ROS1 gene fusions in non-small cell lung cancer," Clin Cancer Res., 18(17):4570-4579.
De Braekeleer et al., (2012). "MLL-ELL fusion gene 15 in two infants with acute monoblastic leukemia and myeloid sarcoma," Leukemia Lymphoma, 53(6):1222-4.
di Martino et al., (2012). "A Decade of FGF Receptor Research in Bladder Cancer: Past, Present, and Future Challenges," Adv Urol, 2012:429213, 10 pages.
Diep et al., (2012). "Down-regulation of Yes Associated Protein 1 expression reduces cell proliferation and clonogenicity of pancreatic cancer cells," PloS one, 7(3):e32783, 9 pages.
Doebele et al., (2012). "Mechanisms of resistance to crizotinib in patients with ALK gene rearranged non-small cell lung cancer," Clin Cancer Res, 18:1472-1482.
Duijkers et al., (2012). "High anaplastic 25 lymphoma kinase immunohistochemical staining in neuroblastoma and ganglioneuroblastoma is an independent predictor of poor outcome," Am J Pathol, 180(3):1223-31.
Edgar, (2006). "From cell structure to transcription: Hippo forges a new path," Cell, 124(2):267-73.

(56) References Cited

OTHER PUBLICATIONS

El-Osta et al., (2011). "BRAF mutations in advanced cancers: clinical 5 characteristics and outcomes," PLoS One, 6(10):e25806, 13 pages.
Eswarakumar et al., (2005). "Cellular signaling by fibroblast growth factor receptors," Cytokine Growth Factor Rev, 16(2):139-49.
Falk et al., (2011). "An efficient high-throughput screening method for MYST family acetyltransferases, a new class of epigenetic drug targets," J Biomol Screen, 16(10):1196-205.
Feng et al., (2002). "Methylation of H3-lysine 79 is mediated by a new family of HMTases without a SET domain," Curr Biol., 12(12):1052-8.
Fountzilas et al., (2008). "Gemcitabine combined with gefitinib in patients with inoperable or metastatic pancreatic cancer: a phase II Study of the Hellenic Cooperative Oncology Group with biomarker evaluation," Cancer Invest, 26(8):784-93.
Fu et al., (2011). "Novel functions of endocytic player clathrin in mitosis," Cell research, 21:1655-1661.
Fuehrer et al., (2012). "ALK-1 protein expression and ALK gene rearrangements aid in the diagnosis of inflammatory myofibroblastic tumors of the female genital tract," Arch Pathol Lab Med, 136(6):623-6.
George et al., (1999). "Sustained in Vivo Regression of Dunning H Rat Prostate Cancers Treated with Combinations of Androgen Ablation and Trk Tyrosine Kinase Inhibitors, CEP-751 (KT-6587) or CEP-701 (KT-5555)," Cancer Res, 59(10):2395-2401, 21 pages.
Gnirke et al., (2009). "Solution hybrid selection with ultra-long oligonucleotides for massively parallel targeted sequencing," Nat Biotechnol., 27(2):182-189, 24 pages.
Grande et al., (2011). "Targeting oncogenic ALK: a promising strategy for cancer treatment," Mol Cancer Ther, 10(4):569-79.
Gu et al., (2011). "Survey of Tyrosine Kinase Signaling Reveals ROS Kinase Fusions in Human Cholangiocarcinoma," PLoS One, 6:e15640, 9 pages.
Harper et al., (2008). "Chromosomal rearrangements leading to MLL gene fusions clinical and biological aspects," Cancer research, 68(24):10024-7, 7 pages.
Hatzivassiliou et al., (2010). "RAF inhibitors prime wild-type RAF to activate the MAPK pathway and enhance growth," Nature, 464(7287):431-5.
Heiskanen et al., (2001). "CGH, cDNA and tissue microarray analyses implicate FGFR2 amplification in a small subset of breast tumors," Anal Cell Pathol, 22(4):229-34.
Hermans et al., (2009). "Overexpression of prostate-specific TMPRSS2(exon 0)-ERG fusion transcripts corresponds with favorable prognosis of 5 prostate cancer," Clin Cancer Res, 15(20):6398-403.
Herquel et al., (2011). "Transcription cofactors TRIM24, TRIM28, and TRIM33 associate to form regulatory complexes that suppress murine hepatocellular carcinoma," Proc Natl Acad Sci USA, 108(20):8212-7.
International Search Report for International Application No. PCT/US2021/65561 dated Jun. 7, 2022, 13 pages.
Isaksson-Mettavainio et al., (2011). "High SMAD4 levels appear in microsatellite instability and hypermethylated colon cancers, and indicate a better prognosis. International journal of cancer," Int J Cancer, 131:779-88.
Jain et al., (2011). "Association of overexpression of TIF1 ? with colorectal carcinogenesis and advanced colorectal 5 adenocarcinoma," World journal of gastroenterology, 17(35):3994-4000.
Jones et al., (2009). "Oncogenic RAF1 rearrangement and a novel BRAF mutation as alternatives to KIAA1549:BRAF fusion in activating the MAPK pathway in pilocytic astrocytoma," Oncogene, 28(20):2119-23, 8 pages.
Ju et al., (2012). "A transforming KIF5B and RET gene fusion in lung adenocarcinoma Yevealed from whole-genome and transcriptome sequencing," Genome Res, 22(3):436-45.
Kim et al., (2012). "The ubiquitin-specific protease USP2a enhances tumor progression by targeting cyclin AI in bladder cancer," Cell Cycle, 11 (6):1123-30.

King et al., (2009). "Cooperativity of TMPRSS2-ERG with PI3-kinase pathway activation in prostate oncogenesis," Nat Genet, 41(5):524-6, 8 pages.
Klein et al., (1991). "The trk proto-oncogene encodes a receptor for nerve growth factor," Cell, 65(1):189-97.
Klezovitch et al., (2008). "A causal role for ERG in neoplastic transformation of prostate epithelium," Proc Natl Acad Sci USA, 105(6):2105-10.
Kohno et al., (2012). "KIF5B-RET fusions in lung adenocarcinoma," Nat Med, 18(3):375-7, 7 pages.
Krivtsov et al., (2008). "H3K79 methylation profiles define murine and human MLL-AF4 leukemias," Cancer Cell, 14(5):355-68.
Kwak et al., (2010). "Anaplastic lymphoma kinase inhibition in non-small-cell lung cancer," N Engl J Med., 363(18):1693-1703.
Lapointe et al., (2007). "A variant TMPRSS2 isoform and ERG fusion product in prostate cancer with implications for molecular diagnosis," Mod Pathol, 20(4):467-73.
Lasken (2007). "Single-cell genomic sequencing using Multiple Displacement Amplification," Curr Opin Microbiol., 10(5):510-516.
Le Douarin et al., (1995). "The N-terminal partof TIF1, a putative mediator of the ligand-dependent activation function (AF-2) of nuclear receptors, is fused to B-raf in the oncogenic protein T18," EMBO J, 14(9):2020-33.
Lipson et al., (2012). "Identification of new ALK and RET gene fusions from colorectal and lung cancer biopsies," Nat Med, 18(3):382-4, 7 pages.
Liu et al., (2011). "FOXO1-FGFR1 fusion and amplification in a solid variant of alveolar rhabdomyosarcoma," Mod Pathol, 24(10):1327-35.
Lucas et al., (2008). "The androgen-regulated type II serine protease TMPRSS2 is differentially expressed and mislocalized in prostate adenocarcinoma," J Pathol, 215(2):118-25.
Malkoski et al., (2012). "Two sides of the story? Smad4 loss in 20 pancreatic cancer versus head-and-neck cancer," FEBS letters, 586:1984-92.
Marschalek, (2011). "Mechanisms of leukemogenesis by MLL fusion proteins," British journal of haematology, 152:141-54.
Massague, (2008). "TGFbeta in Cancer," Cell, 34(2):215-30.
Maurer et al., (2011). "Raf kinases in cancer-roles and therapeutic opportunities," Oncogene, 30(32):3477-88.
Maxam et al., (1977). "A new method for sequencing DNA," Proc. Natl Acad Sci USA, 74(2):560-564.
Mayer et al., (1993). "The prognostic significance of proliferating cell nuclear antigen, epidermal growth factor receptor, and mdr gene expression in colorectal cancer," Cancer, 71(8):2454-60.
Mesker et al., (2009). "Presence of a high amount of stroma and downregulation of SMAD4 predict for worse survival for stage I-II colon cancer patients," Cellular oncology, 31(3):169-78.
Minturn et al., (2011). "Phase I trial of lestaurtinib for children with refractory neuroblastoma: a new approaches to neuroblastoma therapy consortium study," Cancer Chemother Pharmacol, 68(4):1057-65, 18 pages.
Miyaki et al., (1999). "Higher frequency of Smad4 gene mutation in human colorectal cancer with distant metastasis," Oncogene, 18(20):3098-103.
Mizukawa et al., (2011). "Inhibition of Rac GTPase signaling and downstream prosurvival Bcl-2 proteins as combination targeted therapy in MLL-AF9 leukemia," Blood, 118(19):5235-45.
Mok et al., (2009). "Gefitinib or Carboplatin-Paclitaxel in Pulmonary Adenocarcinoma," N Engl J Med, 361:947-957.
Murati et al., (2009). "Genome profiling of acute myelomonocytic leukemia: alteration of the MYB locus in MYST3-linked cases," Leukemia, 23(1):85-94.
Nacu et al., (2011). "Deep RNA sequencing analysis of readthrough gene fusions in human prostate adenocarcinoma and reference samples," BMC Med Genomics, 4:11.
Naeve et al., (1995). "Accuracy of automated DNA sequencing: a multi-laboratory comparison of sequencing results," Biotechniques, 19(3):448-453.
Nakashima et al., (2007). "RET oncogene 10 amplification in thyroid cancer: correlations with radiation—associated and high-grade malignancy," Hum Pathol, 38(4):621-8, 8 pages.

(56) References Cited

OTHER PUBLICATIONS

Natale et al., (2011). "Phase III trial of vandetanib compared with erlotinib in patients with previously treated advanced non-small-cell lung cancer," J Clin Oncol, 29(8):1059-66.
Nikiforov, (2008). "Thyroid carcinoma: molecular pathways and therapeutic targets," Mod Pathol, 21 (Suppl 2):S37-43.
Okada et al., (2005). "hDOT1L links histone methylation to leukemogenesis," Cell, 121(2):167-78.
Ono et al., (2009). "Mixed-lineage—leukemia (MLL) fusion protein collaborates with Ras to induce acute leukemia through aberrant Hox expression and Raf activation," Leukemia, 23(12):2197-209.
Overholtzer et al., (2006). "Transforming properties of YAP, a candidate oncogene on the chromosome 11q22 amplicon," PNAS USA, 103(33):12405-10.
Palanisamy et al., (2010). "Rearrangements of the RAF kinase pathway in prostate cancer, gastric cancer and melanoma," Nature medicine, 16(7):793-8, 6 pages.
Papageorgis et al., (2011). "Smad4 inactivation promotes malignancy and drug resistance of colon cancer," Cancer research, 71(3):998-1008.
Peifer et al., (2012). "Integrative genome analyses identify key somatic driver mutations of small-cell lung cancer," Nat Genet 44, 1104-1110, 22 pages.
Perner et al., (2006). "TMPRSS2:ERG fusion-associated deletions provide insight into the heterogeneity of prostate cancer," Cancer Res, 66(17):8337-41.
Peset et al., (2008). "The TACC proteins: TACC-ling microtubule dynamics and centrosome function," Trends in cell biology, 18.8:379-388.
Phay et al., (2010). "Targeting RET receptor tyrosine kinase activation in cancer," Clin Cancer Res, 16(24):5936-41.
Qiu et al., (2008). "Mechanism of activation and inhibition of the HER4/ErbB4 kinase," Structure, 16(3):460-7.
Reindl et al., (2009). "CBL exon 8/9 mutants activate the FLT3 pathway and cluster in core binding factor/11q deletion acute myeloid leukemia/myelodysplastic syndrome subtypes," Clin Cancer Res, 15(7):2238-47.
Ren et al., (2011). "Src activation plays an important key role in lymphomagenesis induced by FGFR1 fusion kinases," Cancer Res, 71(23):7312-22.
Roland et al., (2011). "Rab GTPase-Myo5B complexes control membrane recycling and epithelial polarization," PNAS, 108(7):2789-94.
Roongjang et al., (2007). "Inhibition of bcl-xLexpression by antisense oligonucleotides containing various bridged nucleic acids (BNAs)," Nucleic Acids Symp Ser, 51:113-114.
Royle, (2011). "Mitotic moonlighting functions for membrane trafficking proteins," Traffic, 12:791-798.
Sameer et al., (2010). "SMAD4—molecular gladiator of the TGF-beta signaling is trampled upon by mutational insufficiency in colorectal carcinoma of Kashmiri population: an analysis with relation to KRAS proto-oncogene," BMC cancer, 10:300, 11 pages.
Sasaki et al., (2011). "A novel ALK secondary mutation and EGFR signaling cause resistance to ALK kinase inhibitors," Cancer Res, 71:6051-6060.
Scheble et al., (2010). "ERG rearrangement is specific to prostate cancer and does not occur in any of her common tumor," Mod Pathol, 23(8):1061-7.
Shi et al., (2011). "Ubiquitin-specific cysteine protease 2a (USP2a) regulates the stability of Aurora-A," J Biol Chem, 286(45):38960-8.
Si et al., (2012). "Prevalence of BRAF V600E mutation in Chinese melanoma patients: large scale analysis of BRAF and NRAS mutations in a 432-case cohort," Eur J Cancer, 48(1):94-100.
Socinski, (2011). "Multitargeted receptor tyrosine kinase inhibition: an antiangiogenic strategy in non-small cell lung cancer," Cancer Treat Rev, 37(8):611-7.
Soda et al., (2007). "Identification of the transforming EML4-ALK fusion gene in nonsmall-cell lung cancer," Nature, 448:561-566.

Spigel et al., (2011). "Randomized, double-blind, placebo-controlled, phase II trial of sorafenib and erlotinib or erlotinib alone in previously treated advanced non-small-cell lung cancer," J Clin Oncol, 29(18):2582-9.
Stanton et al., (1989). "Definition of the human raf amino-30 terminal regulatory region by deletion mutagenesis," Molecular and cellular biology, 9(2):639-47.
Stephens et al., (1994). "Trk receptors use redundant signal transduction pathways involving SHC and PLC-gamma 1 to mediate NGF responses," Neuron, 12(3):691-705.
Sukov et al., (2007). "Utility of ALK-1 protein expression and ALK rearrangements in distinguishing inflammatory myofibroblastic tumor from malignant spindle cell lesions of the urinary bladder," Mod Pathol, 20(5):592-603.
Sukov et al., (2012). "ALK alterations in adult renal cell carcinoma: frequency, clinicopathologic features and outcome in a large series of consecutively treated patients," Mod Pathol, 25(11):1516-25.
Surks et al., (2003). "Myosin phosphatase-Rho interacting protein. A new member of the myosin phosphatase complex that directly binds RhoA," J Biol Chem, 278:51484-51493.
Szperl et al., (2011). "Functional characterization of mutations in the myosin Vb gene associate d with microvillus inclusion disease," Journal of pediatric gastroenterology and nutrition, 52(3):307-13.
Takeda et al., (2012). "Clinical outcome for EML4-ALK-positive patients 20 with advanced non-small-cell lung cancer treated with first-line platinum-based chemotherapy," Ann Oncol, 23(11):2931-6.
Takeuchi et al., (2012). "RET, ROS1 and ALK fusions in lung cancer," Nat Med, 18:378-381.
Thien et al., (1997). "EGF receptor binding and transformation by v-cbl is ablated by the introduction of a loss-of-function mutation from the Caenorhabditis elegans sli-1 gene," Oncogene, 14(18):2239-49.
Tomlins et al., (2005). "Recurrent fusion of TMPRSS2 and 15 ETS transcription factor genes in prostate cancer," Science, 310(5748):644-8.
Tomlins et al., (2008). "Role of the TMPRSS2-ERG gene fusion in prostate cancer," Neoplasia, 10(2):177-88.
Tomlinson et al., (2009). "Fibroblast growth factor receptor 1 promotes proliferation and survival via activation of the mitogen-activated protein kinase pathway in bladder cancer," Cancer Res, 69(11):4613-20.
Tomlinson et al., (2012). "FGFR1-induced epithelial to mesenchymal transition through MAPK/PLC/COX-2-mediated mechanisms," PLoS One, 7(6):e38972, 10 pages.
van der Krol et al., (1988). "Modulation of eukaryotic gene expression by complementary RNA or DNA sequences," Biotechniques, 6(10):958-976.
van Hattem et al., (2011). "Histologic variations in juvenile polyp phenotype correlate with genetic defect underlying juvenile polyposis," Am J Surg Path, 35(4):530-6, 16 pages.
Wan et al., (2004). "Mechanism of activation of the RAF-ERK signaling pathway by oncogenic mutations of B- Raf," Cell, 116(6):855-67.
Wasag et al., (2011). "The kinase inhibitor TKI258 is active against the novel CUX1-FGFR1 fusion detected in a patient with T-lymphoblastic leukemia/lymphoma and t(7;8)(q22;p 11)," Haematologica, 96(6):922-6.
Wells et al., (2010). "Abstract 5503: Vandetanib (VAN) in locally advanced or metastatic medullary thyroid cancer (MTC): A randomized, double-blind phase III trial (ZETA)," J Clinical Oncology, 28(15 Suppl), 3 pages.
Werynska et al., (2009). "Role of lymphangiogenesis in lung cancer," Folia Histochem Cytobiol, 47(3):333-42.
Wooten et al., (2001). "The atypical protein kinase C-interacting protein p62 is a scaffold for NF- kappaB activation by nerve growth factor," J Biol Chem, 276(11):7709-12.
Wu et al., (1989). "The ligation amplification reaction (LAR)—amplification of specific DNA sequences using sequential rounds of template-dependent ligation," Genomics, 4(4):560-569.
Wu, (2005). "Urothelial tumorigenesis: a tale of divergent pathways," Nat Rev Cancer, 5(9):713-25.

(56) References Cited

OTHER PUBLICATIONS

Yuan et al., (2008). "Yes-associated protein (YAP) functions as a tumor suppressor in breast," Cell death and differentiation, 15(11):1752-9.
Zhan et al., (2009). "Prognostic value of vascular endothelial growth factor expression in patients with lung cancer: a systematic review with meta-analysis," J Thorac Oncol., 4(9):1094-103.
Zhang et al., (2009). "Oncogenic Adenomatous polyposis coli mutants impair the mitotic checkpoint through direct interaction with Mad2," Molecular biology of the cell, 20(9):2381-8.
Zhou et al., (2009). "Novel mutant-selective EGFR kinase inhibitors against EGFR T790M," Nature, 462:1070-1074, 12 pages.
Bouhana et al., (2012). "Abstract 1798: Identification of pan-Trk inhibitors for the treatment of Trk-driven cancers," Cancer Res, 72(8 Suppl):1798, 2 pages.
Shaw et al., (2012). "LBA1_PR—Phase III Study of Crizotinib Versus Pemetrexed or Docetaxel Chemotherapy in Patients with Advanced Alk-Positive Non-Small Cell Lung Cancer (NSCLC) (Profile 1007)," Annals of Oncology, 23(9):ixe21, 1 page.
Alberti et al., (2003). "RET and NTRK1 proto-oncogenes in human diseases," J Cell Physiol, 195:168-186.
Borrow et al., (1996). "The translocation t(8;16)(p11;p13) of acute myeloid leukaemia fuses a putative 25 acetyltransferase to the CREB-binding protein," Nat Genet, 14(1):33-41.
Butti et al., (1995). "A sequence 10 analysis of the genomic regions involved in the Yearrangements between TPM3 and NTRK1 genes producing TRK oncogenes in papillary thyroid carcinomas," Genomics, 28(1):15-24.
Chan et al., (2008). "A phase I trial of CEP-701 + gemcitabine in patients with advanced adenocarcinoma of the pancreas," Invest New Drugs, 26(3):241-7.
Clark et al., (2007). "Diversity of TMPRSS2-ERG fusion transcripts in the human prostate," Oncogene, 26(18):2667-73.
Clark et al., (2009). "ETS gene fusions in prostate cancer," Nat Rev Urol., 6(8):429-39.
Cui et al., (2011). "Structure Based Drug Design of Crizotinib (PF-02341066), a Potent and Selective Dual Inhibitor of Mesenchymal—Epithelial Transition Factor (c-MET) Kinase and Anaplastic Lymphoma Kinase (ALK)," J Med Chem, 54:6342-6363.
Curran et al., (2012). "Crizotinib: in locally advanced or metastatic non-small cell lung cancer," Drugs, 72(1):99-107.
Dong et al., (2012). "Inactivation of MYO5B Promotes Invasion and Motility in Gastric Cancer Cells," Digestive diseases and sciences, 57:1247-52.
Donnem et al., (2011). "Prognostic impact of angiogenic markers in non-small-cell lung cancer is related to tumor size," Clin Lung Cancer, 12:106-15.
Feng et al., (2011). "RNAi-mediated silencing of VEGF-C inhibits non-small cell lung cancer progression by simultaneously down-regulating the CXCR4, CCR7, VEGFR-2 and VEGFR-3-dependent axes-induced ERK, p38 and AKT signalling pathways," Eur J Cancer, 47:2353-63.
Gervais et al., (2011). "Phase II study of sunitinib as maintenance therapy in patients with locally advanced or metastatic non-small cell lung cancer," Lung Cancer, 74(3):474-80.
Gollob et al., (2006). "Role of Raf kinase in cancer: therapeutic 15 potential of targeting the Raf/MEK/ERK signal transduction pathway," Semin Oncol, 33(4):392-406.

Harvey et al., (2007). "The Salvador-Warts-Hippo 20 pathway—an emerging tumour-suppressor network," Nature reviews Cancer, 7(3):182-91.
Helias-Rodzewicz et al., (2010). "YAP1 and VGLL3, encoding two cofactors of TEAD transcription factors, are amplified and overexpressed in a subset of soft tissue sarcomas," Genes, chromosomes cancer, 49(12):1161-71.
Hess, (2004). "MLL: a histone methyltransferase disrupted in leukemia," Trends in molecular medicine, 10(10):500-7.
Jin et al., (2011). "The driver of malignancy in KG-1a leukemic cells, FGFR1OP2-FGFR1, encodes an HSP90 addicted oncoprotein," Cell Signal, 23(11):1758-66.
Khramova et al., (2012). "Downregulation of VEGF-C expression in lung and colon cancer cells decelerates tumor growth and inhibits metastasis via multiple mechanisms," Oncogene, 31(11):1389-97.
Leng et al., (2009). "Smad4/Smad7 balance: a role of tumorigenesis in gastric cancer," Experimental and molecular pathology, 87(1):48-53.
Li et al., (2011). "Roles of VEGF-C and Smad4 in the lymphangiogenesis, lymphatic metastasis, and prognosis in colon cancer," Journal of gastrointestinal surgery, 15(11):2001-10.
Loughran et al., (2008). "The transcription factor Erg is essential for definitive hematopoiesis and the function of adult hematopoietic stem cells," Nat Immunol, 9(7):810-9.
Marshall et al., (2005). "Phase I trial of orally administered CEP-701, a novel neurotrophin receptor-linked tyrosine kinase inhibitor," Invest New Drugs, 23(1):31-7.
Mayr et al., (2006). "KRAS and BRAF mutations in ovarian tumors: a comprehensive study of invasive carcinomas, borderline tumors and extraovarian implants," Gynecol Oncol, 103(3):883-7.
Mulligan et al., (1994). "Specific mutations of the RET proto-oncogene are related to disease phenotype in MEN 2A and FMTC," Nat Genet, 6(1):70-4.
Nakagawara, (2001). "Trk receptor tyrosine kinases: a bridge between cancer and neural development," Cancer Lett, 169(2):107-14.
Necchi et al., (2012). "Pazopanib in advanced and platinum-resistant urothelial cancer: an open-label, single group, phase 2 trial," Lancet Oncol, 13(8):810-6.
Pontes et al., (2010). "Immunoexpression of Ki67, proliferative cell nuclear antigen, and Bcl-2 proteins in a case of ameloblastic fibrosarcoma," Annals of diagnostic pathology, 14(6):447-52.
Takahashi et al., (1985). "Activation of a novel human transforming gene, ret, by DNA rearrangement," Cell, 42(2):581-8.
Thien et al., (1997). "Tyrosine kinase activity of the EGF receptor is enhanced by the expression of oncogenic 70Z-Cbl," Oncogene, 15(24):2909-19.
Toulme, (2001). "New candidates fortrue antisense," Nature Biotech., 19:17-18.
van Oers et al., (2009). "FGFR3 mutations indicate better survival in invasive upper urinary tract and bladder tumours," Eur Urol, 55(3):650-7.
Yamayoshi et al., (2004). "Expression of keratinocyte growth factor/fibroblast growth factor-7 and its receptor in human lung cancer: correlation with tumour proliferative activity and patient prognosis," J Pathol, 204(1):110-8.
Zhong et al., (1999). "A RA-dependent, tumour-growth suppressive transcription complex is the target of the PML-RARalpha and T18 oncoproteins," Nat Genet, 23(3):287-95.
Safran et al., (2008). "Lapatinib/gemcitabine and lapatinib/gemcitabine/oxaliplatin: a phase I study for advanced pancreaticobiliary cancer," Am J Clin Oncol, 31(2):140-4.

\* cited by examiner

| Fusion | Disease | Breakpoint 1 | Breakpoint 2 | Rearrangement |
|---|---|---|---|---|
| MPRIP-NTRK1 | Lung adenocarcinoma | chr1:156,845,212 | chr17:17,080,829 | chr1:17 translocation |

Fig. 1A

| Fusion | 5' Transcript ID | Last exon of 5' transcript | 3' Transcript ID | First exon of 3' transcript |
|---|---|---|---|---|
| MPRIP-NTRK1 | NM_015134 | exon 21 | NM_002529 | exon 12 |

Fig. 1B

| FUSION /COMPONENT | Type of Sequence | SEQ ID | FIGURE |
|---|---|---|---|
| MPRIP-NTRK1 | | | |
| 5' partner | Nt | 1 | 2 |
| 5' partner | Aa | 2 | 3 |
| 3' partner | Nt | 3 | 4 |
| 3' partner | Aa | 4 | 5 |

Fig. 1C

```
TGCAGCTGGG AGCGCACAGA CGGCTGCCCC GCCTGAGCGA GGCGGGCGCC    50
GCCGCGATGC TGCGAGGCGG ACGGCGCGGG CAGCTTGGCT GGCACAGCTG   100
GGCTGCGGGG CCGGGCAGCC TGCTGGCTTG GCTGATACTG GCATCTGCGG   150
GCGCCGCACC CTGCCCCGAT GCCTGCTGCC CCACGGCTC CTCGGGACTG    200
CGATGCACCC GGGATGGGGC CTGGATAGCC CTCCACCACC TGCCCGGCGC   250
AGAGAACCTG ACTGAGCTCT ACATCGAGAA CCAGCAGCAT CTGCAGCATC   300
TGGAGCTCCG TGATCTGAGG GGCCTGGGGG AGCTGAGAAA CCTCACCATC   350
GTGAAGAGTG GTCTCCGTTT CGTGGCGCCA GATGCCTTCC ATTTCACTCC   400
TCGGCTCAGT CGCCTGAATC TCTCCTTCAA CGCTCTGGAG TCTCTCTCCT   450
GGAAAACTGT GCAGGGCCTC TCCTTACAGG AACTGGTCCT GTCGGGGAAC   500
CCTCTGCACT GTTCTTGTGC CCTGCGCTGG CTACAGCGCT GGGAGGAGGA   550
GGGACTGGGC GGAGTGCCTG AACAGAAGCT GCAGTGTCAT GGGCAAGGGC   600
CCCTGGCCCA CATGCCCAAT GCCAGCTGTG GTGTGCCCAC GCTGAAGGTC   650
CAGGTGCCCA ATGCCTCGGT GGATGTGGGG GACGACGTGC TGCTGCGGTG   700
CCAGGTGGAG GGGCGGGGCC TGGAGCAGGC CGGCTGGATC CTCACAGAGC   750
TGGAGCAGTC AGCCACGGTG ATGAAATCTG GGGTCTGCC ATCCCTGGGG    800
CTGACCCTGG CCAATGTCAC CAGTGACCTC AACAGGAAGA ACGTGACGTG   850
CTGGCAGAG AACGATGTGG GCCGGGCAGA GGTCTCTGTT CAGGTCAACG    900
YCYCCTTCCC GGCCAGTGTG CAGCTGCACA CGGCGGTGGA GATGCACCAC   950
TGGTGCATCC CCTTCTCTGT GGATGGGCAG CCGGCACCGT CTCTGCGCTG  1000
GCTCTTCAAT GGCTCCGTGC TCAATGAGAC CAGCTTCATC TTCACTGAGT  1050
TCCTGGAGCC GGCAGCCAAT GAGACCGTGC GGCACGGGTG TCTGCGCCTC  1100
AACCAGCCCA CCCACGTCAA CAACGGCAAC TACACGCTGC TGGCTGCCAA  1150
CCCCTTCGGC CAGGCCTCCG CCTCCATCAT GGCTGCCTTC ATGGACAACC  1200
CTTTCGAGTT CAACCCCGAG GACCCCATCC CTGTCTCCTT CTCGCCGGTG  1250
GACACTAACA GCACATCTGG AGACCCGGTG GAGAAGAAGG ACGAAACACC  1300
TTTTGGGGTC TCGGTGGCTG TGGGCCTGGC CGTCTTTGCC TGCCTCTTCC  1350
TTTCTACGCT GCTCCTTGTG CTCAACAAAT GTGGACGGAG AAACAAGTTT  1400
GGGATCAACC GCCCGGCTGT GCTGGCTCCA GAGGATGGGC TGGCCATGTC  1450
CCTGCATTTC ATGACATTGG GTGGCAGCTC CCTGTCCCCC ACCGAGGGCA  1500
AAGGCTCTGG GCTCCAAGGC CACATCATCG AGAACCCACA ATACTTCAGT  1550
GATGCCTGTG TTCACCACAT CAAGCGCCGG GACATCGTGC TCAAGTGGGA  1600
GCTGGGGGAG GGCGCCTTTG GAAGGTCTT CCTTGCTGAG TGCCACAACC   1650
TCCTGCCTGA GCAGGACAAG ATGCTGGTGG CTGTCAAGGC ACTGAAGGAG  1700
GCGTCCGAGA GTGCTCGGCA GGACTTCCAG CGTGAGGCTG AGCTGCTCAC  1750
CATGCTGCAG CACCAGCACA TCGTGCGCTT CTTCGGCGTC TGCACCGAGG  1800
GCCGCCCCCT GCTCATGGTC TTTGAGTATA TGCGGCACGG GGACCTCAAC  1850
CGCTTCCTCC GATCCCATGG ACCTGATGCC AAGCTGCTGG CTGGTGGGA   1900
GGATGTGGCT CCAGGCCCCC TGGGTCTGGG GCAGCTGCT GCCGTGGCTA   1950
GCCAGGTCGC TGCGGGATG GTGTACCTGG CGGGTCTGCA TTTTGTGCAC  2000
CGGGACCTGG CCACACGCAA CTGTCTAGTG GGCCAGGGAC TGGTGGTCAA  2050
GATTGGTGAT TTTGGCATGA GCAGGGATAT CTACAGCACC GACTATTACC  2100
GTGTGGGAGG CCGCACCATG CTGCCCATTC GCTGGATGCC GCCCGAGAGC  2150
ATCCTGTACC GTAAGTTCAC CACCGAGAGC GACGTGTGGA GCTTCGGCGT  2200
GGTGCTCTGG GAGATCTTCA CCTACGGCAA GCAGCCCTGG TACCAGCTCT  2250
CCAACACGGA GGCAATCGAC TGCATCACGC AGGGACGTGA GTTGGAGCGG  2300
CCACGTGCCT GCCCACCAGA GGTCTACGCC ATCATGCGGG GCTGCTGGCA  2350
GCGGGAGCCC CAGCAACGCC ACAGCATCAA GGATGTGCAC GCCCGGCTGC  2400
AAGCCCTGGC CCAGGCACCT CCTGTCTACC TGGATGTCCT GGGCTAGGGG  2450
GCCGGCCCAG GGGCTGGGAG TGGTTAGCCG GAATACTGGG GCCTGCCCTC  2500
AGCATCCCCC ATAGCTCCCA GCAGCCCCAG GGTGATCTCA AGTATCTAA   2550
TTCACCCTCA GCATGTGGGA AGGGACAGGT GGGGCTGGG AGTAGAGGAT   2600
GTTCCTGCTT CTCTAGGCAA GGTCCCGTCA TAGCAATTAT ATTTATTATC  2650
CCTTGaaaaa aaa (SEQ ID NO: 1)
```

Fig. 2

MLRGGRRGQLGWHSWAAGPGSLLAWLILASAGAAPCPDACCPHGSSGLRCTRDGALDSLH
HLPGAENLTELYIENQQHLQHLELRDLRGLGELRNLTIVKSGLRFVAPDAFHFTPRLSRL
NLSFNALESLSWKTVQGLSLQELVLSGNPLHCSCALRWLQRWEEEGLGGVPEQKLQCHGQ
GPLAHMPNASCGVPTLKVQVPNASVDVGDDVLLRCQVEGRGLEQAGWILTELEQSATVMK
SGGLPSLGLTLANVTSDLNRKNVTCWAENDVGRAEVSVQVNVSFPASVQLHTAVEMHHWC
IPFSVDGQPAPSLRWLFNGSVLNETSFIFTEFLEPAANETVRHGCLRLNQPTHVNNGNYT
LLAANPFGQASASIMAAFMDNPFEFNPEDPIPVSFSPVDTNSTSGDPVEKKDETPFGVSV
AVGLAVFACLFLSTLLLVLNKCGRRNKFGINRPAVLAPEDGLAMSLHFMTLGGSSLSPTE
GKGSGLQGHIIENPQYFSDACVHHIKRRDIVLKWELGEGAFGKVFLAECHNLLPEQDKML
VAVKALKEASESARQDFQREAELLTMLQHQHIVRFFGVCTEGRPLLMVFEYMRHGDLNRF
LRSHGPDAKLLAGGEDVAPGPLGLGQLLAVASQVAAGMVYLAGLHFVHRDLATRNCLVGQ
GLVVKIGDFGMSRDIYSTDYYRVGGRTMLPIRWMPPESILYRKFTTESDVWSFGVVLWEI
FTYGKQPWYQLSNTEAIDCITQGRELERPRACPPEVYAIMRGCWQREPQQRHSIKDVHAR
LQALAQAPPVYLDVLG- (SEQ ID NO: 2)

Fig. 3

| | | | | | |
|---|---|---|---|---|---|
| GCGGCCGCGC | TGAGCCCCTA | GCCCGCCGGG | AGCGCCAGGC | CGGCCAGGCC | 50 |
| TGCGCCGCCG | CCGCCGCCGC | CGTCGCCGCC | GCGCCGACCA | TGTCGGCAGC | 100 |
| CAAGGAGAAC | CCGTGCAGGA | AATTCCAGGC | CAACATCTTC | AACAAGAGCA | 150 |
| AGTGTCAGAA | CTGCTTCAAG | CCCCGCGAGT | CGCATCTGCT | CAACGACGAG | 200 |
| GACCTGACGC | AGGCAAAACC | CATTTATGGC | GGTTGGCTGC | TCCTGGCTCC | 250 |
| AGATGGGACC | GACTTTGACA | ACCCAGTGCA | CCGGTCTCGG | AAATGGCAGC | 300 |
| GACGGTTCTT | CATCCTTTAC | GAGCACGGCC | TCTTGCGCTA | CGCCCTGGAT | 350 |
| GAGATGCCCA | CGACCCTTCC | TCAGGGCACC | ATCAACATGA | CCAGTGCAC | 400 |
| AGATGTGGTG | GATGGGGAGG | GCCGCACGGG | CCAGAAGTTC | TCCCTGTGTA | 450 |
| TTCTGACGCC | TGAGAAGGAG | CATTTCATCC | GGGCGGAGAC | CAAGGAGATC | 500 |
| GTCAGTGGGT | GGCTGGAGAT | GCTCATGGTC | TATCCCCGGA | CCAACAAGCA | 550 |
| GAATCAGAAG | AAGAAACGGA | AAGTGGAGCC | CCCCACACCA | CAGGAGCCTG | 600 |
| GGCCTGCCAA | GGTGGCTGTT | ACCAGCAGCA | GCAGCAGCAG | CAGCAGCAGC | 650 |
| AGCAGCATCC | CCAGTGCTGA | GAAAGTCCCC | ACCACCAAGT | CCACACTCTG | 700 |
| GCAGGAAGAA | ATGAGGACCA | AGGACCAGCC | AGATGGCAGC | AGCCTGAGTC | 750 |
| CAGCTCAGAG | TCCAGCCAG | AGCCAGCCTC | CTGCTGCCAG | CTCCCTGCGG | 800 |
| GAACCTGGGC | TAGAGAGCAA | AGAAGAGGAG | AGCGCCATGA | GTAGCGACCG | 850 |
| CATGGACTGT | GGCCGCAAAG | TCCGGGTGGA | GAGCGGCTAC | TTCTCTCTGG | 900 |
| AGAAGACCAA | ACAGGACTTG | AAGGCTGAAG | AACAGCAGCT | GCCCCGCCG | 950 |
| CTCTCCCCTC | CCAGCCCCAG | CACCCCCAAC | CACAGGAGGT | CCCAGGTGAT | 1000 |
| TGAAAAGTTT | GAGGCCTTGG | ACATTGAGAA | GGCAGAGCAC | ATGGAGACCA | 1050 |
| ATGCAGTGGG | GCCCTCACCA | TCCAGCGACA | CACGCCAGGG | CCGCAGCGAG | 1100 |
| AAGAGGGCGT | TCCCTAGGAA | GCGGGACTTC | ACCAATGAAG | CCCCCCAGC | 1150 |
| TCCTCTCCCA | GACGCCTCGG | CTTCCCCCCT | GTCTCCACAC | CGAAGAGCCA | 1200 |
| AGTCACTGGA | CAGGAGGTCC | ACGGAGCCCT | CCGTGACGCC | CGACCTGCTG | 1250 |
| AATTTCAAGA | AAGGCTGGCT | GACTAAGCAG | TATGAGGACG | GCCAGTGGAA | 1300 |
| GAAACACTGG | TTTGTCCTCG | CCGATCAAAG | CCTGAGATAC | TACAGGGATT | 1350 |
| CAGTGGCTGA | GGAGGCAGCC | GACTTGGATG | GAGAAATTGA | CTTGTCCGCA | 1400 |
| TGTTACGATG | TCACAGAGTA | TCCAGTTCAG | AGAAACTATG | GCTTCCAGAT | 1450 |
| ACATACAAAG | GAGGGCGAGT | TTACCCTGTC | GGCCATGACA | TCTGGGATTC | 1500 |
| GGCGGAACTG | GATCCAGACC | ATCATGAAGC | ACGTGCACCC | GACCACTGCC | 1550 |
| CCGGATGTGA | CCAGCTCGTT | GCCAGAGGAA | AAAACAAGA | GCAGCTGCTC | 1600 |
| TTTTGAGACC | TGCCCGAGGC | CTACTGAGAA | GCAAGAGGCA | GAGCTGGGGG | 1650 |
| AGCCGGACCC | TGAGCAGAAG | AGGAGCCGCG | CACGGGAGCG | GAGGCGAGAG | 1700 |
| GGCCGCTCCA | AGACCTTTGA | CTGGGCTGAG | TTCCGTCCCA | TCCAGCAGGC | 1750 |
| CCTGGCTCAG | GAGCGGGTGG | GCGGCGTGGG | GCCTGCTGAC | ACCCACGAGC | 1800 |
| CCCTGCGCCC | TGAGGCGGAG | CCTGGGGAGC | TGGAGCGGGA | GCGTGCACGG | 1850 |
| AGGCGGGAGG | AGCGCCGCAA | GCGCTTCGGG | ATGCTCGACG | CCACAGACGG | 1900 |
| GCCAGGCACT | GAGGATGCAG | CCCTGCGCAT | GGAGGTGGAC | CGGAGCCCAG | 1950 |
| GGCTGCCTAT | GAGCGACCTC | AAAACGCATA | ACGTCCACGT | GGAGATTGAG | 2000 |
| CAGCGGTGGC | ATCAGGTGGA | GACCACACCT | CTCCGGGAAG | AGAAGCAGGT | 2050 |
| GCCCATCGCC | CCCGTCCACC | TGTCTTCTGA | AGATGGGGGT | GACCGGCTCT | 2100 |
| CCACACACGA | GCTGACCTCT | CTGCTCGAGA | AGGAGCTGGA | GCAGAGCCAG | 2150 |
| AAGGAGGCCT | CAGACCTTCT | GGAGCAGAAC | CGGCTCCTGC | AGGACCAGCT | 2200 |
| GAGGGTGGCC | CTGGGCCGGG | AGCAGAGCGC | CCGTGAGGGC | TACGTGCTGC | 2250 |
| AGGCCACGTG | CGAGCGAGGG | TTTGCAGCAA | TGGAAGAAAC | GCACCAGAAG | 2300 |
| AAGATTGAAG | ATCTCCAGAG | GCAGCACCAG | CGGGAGCTAG | AGAAACTTCG | 2350 |
| AGAAGAGAAA | GACCGCCTCC | TAGCCGAGGA | GACAGCGGCC | ACCATCTCAG | 2400 |
| CCATCGAAGC | CATGAAGAAC | GCCCACCGGG | AGGAAATGGA | GCGGGAGCTG | 2450 |
| GAGAAGAGCC | AGCGGTCCCA | GATCAGCAGC | GTCAACTCGG | ATGTTGAGGC | 2500 |
| CCTGCGGCGC | CAGTACCTGG | AGGAGCTGCA | GTCGGTGCAG | CGGGAACTGG | 2550 |

Fig. 4

```
AGGTCCTCTC GGAGCAGTAC TCGCAGAAGT GCCTGGAGAA TGCCCATCTG 2600
GCCCAGGCGC TGGAGGCCGA GCGGCAGGCC CTGCGGCAGT GCCAGCGTGA 2650
GAACCAGGAG CTCAATGCCC ACAACCAGGA GCTGAACAAC CGCCTGGCTG 2700
CAGAGATCAC ACGGTTGCGG ACGCTGCTGA CTGGGGACGG CGGTGGGGAG 2750
GCCACTGGGT CACCCCTTGC ACAGGGCAAG GATGCCTATG AACTAGAGGT 2800
CTTATTGCGG GTAAAGGAAT CGGAAATACA GTACCTGAAA CAGGAGATTA 2850
GCTCCCTCAA GGATGAGCTG CAGACGGCAC TGCGGGACAA GAAGTACGCA 2900
AGTGACAAGT ACAAGACAT CTACACAGAG CTCAGCATCG CGAAGGCTAA 2950
GGCTGACTGT GACATCAGCA GGTTGAAGGA GCAGCTCAAG GCTGCAACGG 3000
AAGCACTGGG GGAGAAGTCC CCTGACAGTG CCACGGTGTC CGGATATGAT 3050
ATAATGAAAT CTAAAAGCAA CCCTGACTTC TTGAAGAAAG ACAGATCCTG 3100
TGTCACCCGG CAACTCAGAA ACATCAGGTC CAAGAGTCTG AAGGAAGGCC 3150
TGACGGTGCA AGAACGGTTG AAGCTCTTTG AATCCAGGGA CTTGAAGAAA 3200
GACTAGGTGT GTCCCATCCA AGTTGAGCAC GCGCCTTCCC CAGCTTGCAG 3250
CAGCACACCC CAAGCGCTGC TTTTCACCTG TACCTTTGTT TTATTATTAT 3300
TATTATTATT GCTGTTGTTG TCATCGTTAA CTGTGGGCAT GGAATGCGTG 3350
AGGCTGGCTT CTGGGTTGTC CACACCACTC TCTGCTGTGT TGACTTCCTG 3400
TTGTCTTCAT CAAAGCTTTT TTCCGTGGTA TTCTAAAATT AGGCCAGCAG 3450
TGGGGGCTGG GAGGGCATCT GTGTTAGTCC TTTCCTGGCT GTGACCCGCC 3500
ACACTCACTG TCAGTATTAA GGCCCAGCAG CCTGTTGATA AGCTACCCTG 3550
TCTCACCATG TGCTGGTGTG GAAACGGGGC CCAGCCAGCA CGCCTCAAGG 3600
TAGATGGAAT CCCCACTGGT CAGAGAAAAA GCTATGCGGA CACTCCAGCT 3650
TGGCCTGGGT CACAGCACTG ACTCCTCACC CGCTAGTCTG GCTGTTAAGA 3700
GGAGAAAGTG CACTGCCTTC CAGCCCAGGA GGAGGACAGC ATTTTGTATT 3750
TGTTCCACTG ATGCAGCTTA GAACCACACC CCTGAGAGTC GTGGCAAACC 3800
TTTCACAACC TGGAAAATGT TGAAAGCAAC CATTCCTATT TTTGTTTGTT 3850
TTTTATTAAA TCTTGCACAA AATCCCCGGC CCCTCTCCTT CCTTCCTTCC 3900
TTCCTTCCTC CGCTCGTTCC TTTCTTGGTC TCCAGTAACC CTGGTCTTTT 3950
CATAACTGCT CGAGATTGTT GACCTGCAGC CCAGGTTTCA GACTCTGATT 4000
GCAAAAAACA AATGAATTCC CCCCAGGAAT CATTCAAAAT GGGGGAAGGT 4050
TTGGGGGTTT GGGTTTTTTT TTTACCTTTT GGAAAAGAAA CCGTCACATT 4100
GCTTTGGAAA AGGTTGAGAG GAGACCCCTG TTAAGTCAAG AAGAAAGTAC 4150
AGAGGATGTC AGAATCTGAT GAGAACAGCA CATTAGTGTT TATTGAGACT 4200
CCGATCTTAA CTCTCATTTA ATTAATCTGA GCTCTGAAAA CCTATCTTGC 4250
AGCATTTATC TTTAAAAGAG CCTGGTTAAA GTAAACCTAT ACTAACAATT 4300
TTGCTTTTTC TAACAGTTTG AGGAAGACCT TTTAACCAC CACAAAACAT 4350
TCTATGGCAA TTCTTGAAAA TCTCTTAAAT TGGAGTCTAT TATGGCCCCA 4400
TGAAAACCAT TAATCCCATT AAGATAGGGA GTATAAACCC CTGGCTGGTG 4450
GAACAGGTTC TGCTACTTTA GGAGCAAGGT GGGGTGTGAG TAGATGGTTT 4500
TCATGCCAAG AACATGCTTT CACTTTGTAT TCATGCTTGT GTTGGTGTGA 4550
TGGTCTCTGT GGGTGGGTGG ATGCTTTGGG CGTTGAAATC TAGAAATCCT 4600
GTTGCTCAGT TTCTAGATGA AGTCATGAGC AAGGCCATCA GTGGAGCTCT 4650
GGCCCCGCCC CCAATGTGCA GAAGGGCCGG GAGCAAGGCC TGGAGTTTTC 4700
ATGTGTTTTC AGACCCAGGT TTAGGTGCTC TCTTCTCACT GAAATAACTA 4750
AGTGCTCTCC ACTGGCATCG AGCCCTTTCC ACAAGTTTTT AAGGCTCTTA 4800
ACCCACACTT TCACTCCTCT GCTACTAGTC TTCAGTGTTG TTAACAGCAA 4850
GAGAAAATTG GGTTTGTTTA AAAATCTACT TCTCTGAGGT GGCACAGTTG 4900
CGTAGCTGTA GTCCAGCTA CTCAGGAGGC TGAGGTAGTA GGATTGCTTG 4950
AGCCCGGGAG GTCGAGGCTG CAATCAGTCA TGATCGTGTC ACTGCACTCC 5000
AGCCTGGGTG ACAAAGCAAG GCCCCATATC AGATATAGAT ATACTTATCA 5050
GACCCCCCCT GACCATTTAG ATTGGCAGTG CTTTGAGAAA TGCACTATGA 5100
```

```
CCTTTCTGTG TCAATGGGAA TATACAGAAG GAACATTCGG GACCCCGCTG 5150
TCCCCCACAG CCTCATTGTT GTCTCCAGGA CACTGCTGGG TCACACGAAT 5200
GCTCCAGGAC AGACAGGGAC CTGGAGTGCA TCAGGATCTG ACCAGATAGG 5250
AGTTTTTGCC TCGTGTCTGG GTGCTACGAT TTTGTGCCGT TCTCTGAGGT 5300
CCACCACCTG CCCTTCCTGG CATGGTTTCC TTCGTGACCA TCCCTGCTGC 5350
CCCTGGGGGT GGACCCCACT GGCCCTTCTG CAGACAGCTC CCTGCCTTCT 5400
GCCCTCCAGG GGGTTCTGGC CAGAGTCCAT GCTTGGAGAC AGGATCATCT 5450
GCCTTCAGCC CTCACAGTGC TTTAAATTAA AGCAAGTTTG CCCATAGGAC 5500
AAAAGAGCAT TTGATTCCCT TTTTTCTGTC ACATATCCCT GAGGCTGGA 5550
CTTCAGGAAT CCTGGAAAAT TAATATGAGT GCAGCATGTG AGGGGTCAGA 5600
GACAGGCCAG CAGGGCGTCT GCATTCCTCC CTGCCACAGG TCTCTCCCA 5650
GAGGCTGGTT TAGTGTAGGG TATTGCCAGG AAACGGACTG AGGCTGCTTT 5700
GCTAAGAGCT CCTGAAAATG CCCTGGGCCT GTCCTGGCGT TTCTGAAGAG 5750
CCCTCATACA GGACAGCCA CCATCTGGGT CAAGGAAGTC TGGGTTCCCT 5800
GCTGGTGGGC TCCATCCTGC GATGGAGTGA ACCAGGCGAG AAAGGATGAC 5850
GATGTTCTTC ATGTTGCACC TGGACATGCC CCAGGAACAG AGACTTGCCC 5900
AGTGGCAAC ACTGGCACAG ATGTTGACGG CTGCCCAACT GGTGCCACAC 5950
TGAGCAGGGA GCCTTGTGCT GCACAGGGCT GGGCCCTCTC TCCAGTTTCC 6000
TTCCTGCAGG CATCCAAATA CCCTGGAAGG GATTAACCC CTGAATTCCA 6050
GAGGGAAGAA AGAAGAACAG TGAAGAAGTA GAACTGGTTT CTGTATGGGG 6100
AGAGGAAAGT CTTAGGGACA GCTGCAGGCG GGGTCTCAGG CTGCTCCTTG 6150
GCACCAGCTA CACAGTAGTG AGCTTTCCCA GCTTTACCGA TGAGGAAGAA 6200
GTTCAAATAG ATAGACTTCA GCATTTAAT TATTTTCCTA TAAATGTATT 6250
TATGTGTAGT ATGCTAGCAC CAGCCAGTAA GCTGTGCCAC ACATATGAAT 6300
GGGAAAGCGA GGCAGTTGTG CTCGTGTGAG TTTCTGCAGG CTTGTGGGTA 6350
ATTACCTTGT GTGCACGCCT GCACGTGCAG AATAGTCACT TTCTGCTGGT 6400
CAGTTTCTTT ATCCACCCAT GGTGCCCCAG CCCCAGGCAG GTGTGGAGAC 6450
CAGCATTTCA GAGGACGCGC TGTCCACAGC CTCCCGGGTC TGAGTGGATC 6500
ATTGGGCAGG GGTGGAGACA GTGCGCTGCC CTCTGAGCTG GAAGCCTGTG 6550
CTTCAGGGAG TCATAATGGG CCTGTGCTAA GTGGGTGATG CAGTGGACAT 6600
CCCAGGGCGA CTAGAGGTGG CAGTATCGCG AATTTGCAGG TTTATTGAAC 6650
AAGAGGTAAC ATCGGAGAGG ATCTTGCCTT CGGATTCAGC AAGTATGAAG 6700
GCAGAAGAGC ATGGAGAGCA AGGCCCCACA GCCTGCTTAG TGAGTTGGAA 6750
GGCCCAGCAA GAACCTGTTT CTGCAGCAGC CACCAGCTCC CATCACCCCT 6800
TGACCCTCCA GCTCATGCTG GAGAAGAGGG AATTTTGGCT GTTTAAAGAA 6850
CACAGTTGTG AATCTCAGAA TGTGCCTGAA AGGAATACTG ACAGATAAGG 6900
CCGGAAACAA AACTGATGGC TTGAAAAACA TTTTTATGGA ATGTATTTAC 6950
TATCATTTTG TTTTACTATA GAGGTAGATG GGACTCTTAA CTTTTGGGTA 7000
CATGGAAACA TGCTGAAAAC TGAACACAAT CCTGATCATC ACTCCTGCCT 7050
GGCTGTCTCC TGGGAGGCTG CCGGGTGCCA CGGAGCTGGG ACACAGCAGA 7100
GCCCGCTAGG TGTTGCAGGG CCCTGGAGGC CAAGGCCACC CTGTGTGGGG 7150
TCCCTGTTGG CAGCCAGGTC CCTACACAAA CAAGTAATCC TGTTTGGCCT 7200
CCTAGGTTTT GCATATGACC TGCAGCCTAA TTTGGGGTGT AGGGGAAGCT 7250
CTGCTGGCCC CTGCTCCTTT GTATGTTGGG TGACTTTAAT GGCTGGCCAC 7300
ATACCCCTTT CTCCCAGCTA CTCATTCACT GACTTGGGTA AGTTCTAAGA 7350
CAGTTCGCAC TTAGAAAAGA ATGTGACACA TCAACATTAA CTTTTCCTGA 7400
AAAGAAGAGT TTGCCTAACA TGGTCCTAAA GAAGCTTGGA ATTTATAAGA 7450
CTTTCCTTTA TAAGATATAG TGGGGGTTTT TTTGGGTGGA GGGGGTTGT 7500
TTTTTGTTTT TTGTTTTCAA GACAGAGTCT CGCTCTGTTG TCCAGGCTGG 7550
AGTGTAGTGG CATGATCTCG GCTCACTGCA ACCTCTGCCT CCCAGGTTCA 7600
TGCCATTCTC CTGCCTCAGC CTCCCGAGTA GCTGGGACTA CAGGTGTCTG 7650
```

Fig. 4 Continued

```
CCGCCACGCC TGGCTAATTT TTTTGTATTT TTAGTAGAGA CGGGGTTTCA 7700
CCATGTTGGT CAGGATGGTC TCGATTTCCT GACCTCGTGA TCCGCCTGTC 7750
TCGGCCTCCC AAAGTGCTGG GATTACAGGC GTGAGCCACC ACGCCTGGCC 7800
TATAAGATAC GGTAAAAAAA AAAAACTGTG ACCCCTTTGT CACTAAGGGA 7850
GAAAGAAATT AAGTATTGTC AAAGTTCTAT AAAGAATGGA AATGTATGAT 7900
ATTATACTTC AAAGGAATTT GATGTTGAAA TTTTAAAGAA AATTTGTCAT 7950
GTTGATGAGA AGCTTCACTT TCCTGGGAAC TTCATTCGTT TTAGGGCATG 8000
AGATAAAAGT CCTGGCTAGG GGAGCCATAG GTCTGTTGTA CAAGGAATTT 8050
GCTTTCTAAA CAAGTTGTAA CTTGCCCTAA GGTCCTGTT GGAGCACTAA 8100
GAGGTGACAC AGGCCAGAGA CAACGTTTCG TTTCCCCTTC CCTGCAAGCT 8150
GGGATCAGCC CTGTGTTTTC TCCTTTCAGC TGAAGTGAGC GAAGGTTCTC 8200
AGTGCTGGCA AAAGAGCCCA CTTTCTAAAA GGACTTGGGA AGAAAGCTGC 8250
TGGGAACTTG CTTATTAAAA AGTTCCTTAG AATTAAGGTA TCTACCCACT 8300
GTTTTCGCAC CTTTCACCTT CCTGGGCTTT CCTGCCCTCC AGCATTCTTC 8350
TCTAGAGAGG TTCCTAGCCC GCTCAGCGCG AGCGTCTCCA GTAGGTAATA 8400
GCAGCTGAAC GTGGGTTTTC CACGGACTTC AGGCTTGGAG GTGCCATATA 8450
CAAGCACACT TCTTCCTTCC CCTGGCTTCT CCATGCCACC ACCCACTTTA 8500
AAGATGTAAA CTCAGTAGAT TTTTCATCCA GTGAACGGTC ATCTTCACAT 8550
CGAAAGGTGA AGGCCACCAC TGTTCTCAAT GCCAAGCAAC AGAACGTTCT 8600
GAGATGGCCG TTCTTCCTTG CACAGCAGCT ACGGCAGGTT GTTCTGCAGC 8650
CACCCCTTAG AGGGGGCTCT TCGTTTTACC TTTGTACAGT TCTTGTGTTT 8700
ACACATTTGG GCCAAACAGC TTTCAGCAAG GGCATGTGTC CACAGCTGAT 8750
GGGCAGTTAA GAACCAGCCT GAGCTGAAGG CTAGTAATAC CGTGCTGTAG 8800
GCTCTTTAAA AGGAAAGCCT GGCATAAACC CAGCATGGAA AGGAACATTA 8850
TCAGTTATCT CAAATTTTGT CTGCCAGGGA CAAGACCCTG TTCATTCTTT 8900
TGCCCTTTTC AGAACTGTGA GCTTCAAGTA TTCTTGCTTC TCTGTAAAGG 8950
GAAGACATCT CCCTTCTCTG AAATCCTTCA ACAAAAGAAA AGGCTCTTGG 9000
CAGGGTAGGG GAGTCAGTAG CTCAACACTA GATCATCCCT AGAGATGGGG 9050
CAAGTTTCTG TCTGAACACG TCTTGGGTCC GAGTCCTTAG GTGTTCGGAT 9100
GCAGTACTTT GTGAATACTT AAGCTACTGC ATGCTTGGTG TAGCTTGCAA 9150
TTTCTCTGTA TTTAAAAGCA GCTGTGTTTA TTTTCTTCAA AATAACCTGT 9200
ATATTATTTA GAGCAAGCAA TGTAAATATT ACTGAGAAGT TACTGCAGGG 9250
ATTTTTGTGA CAGAGTTTGT ATGGGTTTTT AAAAAAATCT TAGACACCCC 9300
TTTTTAAGAT GGGGAGAACA GGGTTGACTG CACCGTTGAA GCCCGCCCAG 9350
CATTATAAGG AAATGTTTTT AATGACTGCT GCATCTTTGT AAAACGTTTG 9400
GTCATCTAAC AGATGGTTTT AAAGTGTACA ATATCCAAAA TAACGATAGC 9450
CCTGTATCCA TACATTGTTT CATTGAAAGA ATTCTCTATT GCCTCTTCTT 9500
GGTAGAGCCA GAGTCCTTAA GGAAAATCAG GAAAATTAAG AAAATGATGG 9550
TGCCATCTTG ACCAGACTTC TGCACAGTAA TTTAACGCTA TCCTAGGGAG 9600
ACTTGGTTGA AGGCACAGTT CTGGGATCAG GGTCTAAATG TGCAGTTTCT 9650
GAGAACCTTC AAGACCACTC ACTGGGCAGG GCTCTGTGGA GCACTGGAGC 9700
TGTTTGGATT CCCCAGCCCT TTGGTCATAT CCTGGAATTC CGTGGAGGCT 9750
GCAGAACTTA GATGCAGCTG TTTTTACAG CACCTATTTT TGTCAGATTG 9800
GTAAGGAAAC ACTGAGTCAC AGAATACTTA AGAATTGGAG ACTCCAGTAA 9850
TGTAGGATGG CCTGAGAGGA CGTCCAAGTC CAAGGGGTG GACACGGCAT 9900
GTTCCTCGGG CACAGCCTCA GTGGGGCCT TCCCCAGGCG CAGCTCGGCC 9950
ACCTGAGGAA AGGGTGTTTC GGAGGCGCAG CCACACACAC AGCGCTGGCA 10000
GCCTCACGGT CACGCCCATC ACTCCCTGCC CCCACTGCC CTTGAGAAGT 10050
TAGTGGTGTC ACATCCTTAG TTTTATAGAC AGCTAGGAAT AGATTGTGAA 10100
GAACACTCAG TTCACTACTG TGTTACATTT ATATCACAAG CTTCAATTAA 10150
AATGGATTTT AAAGGATTTT AGGATTTACC TTTAGTATTA ACAACGTATC 10200
```

Fig. 4 Continued

```
TACTGACATA CTGTTAGGAT TCAAAACCAG TTAAGTATAA GAATTACTTC    10250
ATGTGGTTTT CCTAGGGTAC AATTTATAAA AGGTAGAAAG CATCCAAGTG    10300
GCTCCTCAAC AATTACAATT CTTAATGATT TTTCTCACAG CTGTGCCCTT    10350
CTGTCAGGGT CAGTGTCAAA ATTCGTTATC AAAGGCAAAA CCTACTGTGC    10400
CAAGCTGGGG CGCTATATGT GAACGGAGTG GAAATGCTTC AGTCACCTCT    10450
GCCGCAGCTT GTGATTCCAG CAGTTCTCAC AAACGTTCTG TCACATGATG    10500
AAAAGAAGCA GCTTGTATAA TTCCAACTGG TGTTTCATTT CTGTTCTAAT    10550
GCTAAGTGGT AACGCTTAAC AAACAGACTA AAGCTGTGT GCAGAAGAAA     10600
GGGCTGAATG AGTACCGCCT CCCTAGGTTC CAGCACAGCG CTCGGGTCTA    10650
AGAAGTAGAG CCCCGGGTA GGGTGGGCCA TCCACTGTCA GGCCAGTGTC     10700
TCAAGAAAGC CTGACCAGCT GAGCTGCTGC TTTTTTTTTG GGGGGGGGG     10750
GGGGAGGGGC GTCTTGAGGC TTTTTTTTTT TTTACAAAGT TAGTTTGTGA    10800
TCAACGATTC ACTACAATTG AAGTGTTACT TTGTCAGAAT ATTTATTCCT    10850
TTGTGTGACA TGCTAGATTC CCTGGATGTA GCTGATGATT TTTATTTTGT    10900
AAATATTACC TAACTTTACA TAAACTATAT CATAATAAAC TATTTTGCA     10950
TCACCCTTTG (SEQ ID NO: 3)
```

Fig. 4 Continued

MSAAKENPCRKFQANIFNKSKCQNCFKPRESHLLNDEDLTQAKPIYGGWLLLAPDGTDFD
NPNHRSRKWQRRFFILYEHGLLRYALDEMPTTLPQGTINMNQCTDVVDGEGRTGQKFSLC
ILTPEKEHFIRAETKEIVSGWLEMLMVYPRTNKQNQKKKRKVEPPTPQEPGPAKVAVTSS
SSSSSSSSSIPSAEKVPTTKSTLWQEEMRTKDQPDGSSLSPAQSPSQSQPPAASSLREPG
LESKEEESAMAADRMDCGRKVRVESGYFSLEKTKQDLKAEEQQLPPPLSPPSPSTPNHRR
SQVIEKFEALDIEKAEHMETNAVGPAPAADTRQGRSEKRAFPKRDFTNEAPPAPLPDAS
ASPLSPHRRAKSLDRRSTEPSVTPDLLNFKKGWLTKQYEDGQWKKHWFVLADQSLRYYRD
SVAEEAADLDGEIDLSACYDVTEYPVQRNYGFQIHTKEGEFTLSAMTSGIRRNWIQTIMK
HVHPTTAPDVTSSLPEEKNKSSCSFETCPRPTEKQEAELGEPDPEQKRSRARERRREGRS
KTFDWAEFRPIQQALAQERVGGVGPADTHEPLRPEAEPGELERERARRREERRKRFGMLD
ATDGPGTEDAALRMEVDRSPGLPMSDLKTHNVHVEIEQRWHQVETTPLREEKQVPIAPVH
LSSEDGGDRLSTHELTSLLEKELEQSQKEASDLLEQNRLLQDQLRVQLGREQSAREGYVL
QATCERGFAAMEETHQKKIEDLQRQHQRELEKLREEKDRLLAEETAATISAIEAMKNAHR
EEMERELEKSQRSQISSVNSDVEALRRQYLEELQSVQRELEVLSEQYSQKCLENAHLAQA
LEAERQALRQCQRENQELNAHNQELNNRLAAEITRLRTLLTGDGGGEATGSPLAQGKDAY
ELEVLLRVKESEIQYLKQEISSLKDELQTALRDKKYASDKYKDIYTELSIAKAKADCDIS
RLKEQLKAATEALGEKSPDSATVSGYDIMKSKSNPDFLKKDRSCVTRQLRNIRSKSLKEG
LTVQERLKLFESRDLKKD- (SEQ ID NO: 4)

Fig. 5

*MPRIP-NTRK1 cDNA sequence* gcggccgcgctgagcccctagcgcgggagccggagccgccaggccgctcgccgccgccgtcgccgccgccgacCATGTCGGCAGCCAAGGAGAACCCGTCGCAGGAAAT
TCCAGGCCAACATCTTCAACAAGAGCAAGTCTCAGAACTGCTGCTTCAAGCCCCGCCAGTGCCAGGACCTGACGCGCAGGCAAAACCCATTTATGCGCGGTTGGCTCCTGG
CTCCAGATGGACCGACTTTGACAACCAGTGCACAGTGCACAGACGTTGGAAATGCAGGGCCGCGTCCAGCGACCACGGCCTTGCCTGCCGGGCCCTTTGAGCAGAGATGCCCACGACCCTC
CTCAGGGCCACCATCAACATGAACCAGTGCAGCAGCAGGCCGCACAGATGTGGCACAGATGCTCATGGTCATCCCCGGACCAACCAGAATCAGAGAAGTTCCTGTGTATTCTGAGAAGGAGCATTTCATCCGGCGGAGACCA
AGGAGATCGTCAGTGGCTGGTGGTAGCAGCAGCAGCAGCAGCAGTCCAGAGTCCCAGTGCTGAGAAGAATGGAGAACTCTGGCAGGAAGAAATGAGGACCAAGGACCAGGCAGATGCA
CTGTTACCAGCAGCAGCAGCAGCAGCAGCATCCCAGTTGCTGAGCAGTCCCTGCGGAACTGGGCTGAGAACAGCAGTTGAAGCTGGAGAACAGCAGTTGAAGCTGGAGAACAGAGAGCGCCATGAGTAGCCGACCTGAGCAGGACCAGCCGCATGAGTAGCCGACCTGTG
GCAGCTGAGTCCAGTTCAGTCGAGTCCCAGAGTCCGGGTGAGAGGCTACTTCTCTGAGATGGAGAAGGAGGATGAAGGGAAACAGACTTGAAGACTGTGAAGCATGCCCCCTCCCCAGCCCCGACCACCCCAACCACA
GCCGCAAAGTCCCGGTGGAGAGCGGCTACTTCTCTGAGACTCGCTGAATTTGAGGCATTGAGAGAGTCCAGTGGGGCCTCAGCGACACGGCACACGAGCCAGGGCCCAGCGAGAAGAGGG
GGAGGTCCCAGGTGATTGAAAGTTGAGGCTTGGGCCCTTGGGACATTGAGAGGCAGACCAATGCAGTGGGAGACATGCAGTGGGAGACATGCAGTGGAGCCCAGGCCCGACACGCCAGCGACACAGAAGAGCAGTCCAGATACATACAAAAGAAACAAGACCAGGGCCAGTTTACCC
CGTTCCCTAGGAAGCGGGACTTCACCAATGAAGCCCCAGAGAGCTCCTCCCAGAGAGCAGCCAAGTCACTGGTTGTCTCGCCGATCAAAGCCTGAGATACTACAGGGATTTCAG
CCGTGACGCCGAACTGCTGCTGAATTCAAGAAAGAAGGCTGACTAAGCAGCTATATGAGGACGGCCAGTGACGCCAGGCGTCAGCGACCCCTGCGCCCCCTGCGCCCAGGATCGCAGTGAGGAGGCTGAAGGTACACGAAGGCCCCTGCCCCCTGCCCCTTGAAGACTGTGCT
TGGCTGAGGAGGCAGCCGACTTGGATGGAGAAATTTCCAGAAAGGCTTCAGTTGACAATGTCCCATGTTACCATGCAGGCGCGATCAGTGAGGCAGGACGGCACAGAGATGAGGACGGCAGTGATCAGGAGAAAACACTGGTTTGCTCGCCGATCAAGCCATGAGATACAAAGAGAGAAAAACAAGAGCAGTCCT
TGTCGGCCATGACATCTGGGATTCGGGGAGCCATGACCTGCAGAGACCATGACATCTGGGATTCGGGGGAGCCCCTGAGACCTGCTACAGAGATGAAGACCATCATGATGAAGACCATCATGATGAAGACCATCATGATGAAGACCTCGCCCATGGACATCTGGGGCCCCTGAGGATGCTTCTGTTCTGTCTCTTCTGAAGATGGGGGTG
CTTTTGAGACCTGCCTCACGTGGAGATTGAGCAGGAGCCAGCAGCAGCAGCAGCAGCAGCAGCAGATGTAGCTGAGCCTGGAGTGGGGCCCTGAGGCTGAGGCTGAGCTGGAGCCTGAGCTGGAGCTGGTG
GGGCTGAGTTCCGTCCATCCAGCAGCGCCAGGAGCGCTTGGACACGTGGGGGGCTGGGCATCAGGAGCAGCGGGGTGCATCAGGAGCAGCGGGGTGCATCAGGAGGAGCTGGCATCAGTTGGGGCATCAGGAGGAGCTGGCATCAGGCTGTGGACCAGCAGTGACCACCTCCCCCGTCCTCTCTGCCCCAGCCAGCGACCGGTG
CACGGAGCAGAGCGCCGTGCAGGAGACGCGCCCTTCCTAGCCGAGCCGGAGACACAGCGGCGGCCCATCGAGCCTCAGCCCATCGAGCCTCAGCCCATCGAGCCTCAGCCCATCGAGCCTCAGCCCATCGAGCCTCAGCCCATCCAGCCCATGAAGGAAAATGGAGCGGAGCTGGAGAAGAGCC
GCCGGGAGCAGAGCGCCGCCATCGACCCCGCCGTGCGGAAGCGCCATCGACCGGAACGGCACCACACGCACCGGAACGGCACCACACGCACCGGAACGGCACCACACGCACCACCACCACCACCACCACCACCACCACCACCACCACCACCACCACCACCACCATCCAGCCACCCCGCGCACCCAACCCGCAACCCCGACCCGGAACGGCACCCAGGGCCCAGGGCCCAGGGCCCAGGGCCCAGGGCCCAGGGCCCCATCCAGCCCGCCGCCACCAACCACCACCACCACCACCACCACCACCACCACCACCACCACCAGGTCAGGTCCCTGCCTGAGTCTACAGGCTGAGAGATGGAAATGGAGCCCAGAGA
TAGAGAAACTTCGAGAAGAGCAAAGAACGCCGCCATCCTTAGCCAGGATGAGCATCTCAGCCATCGAGACGCTGAGAATGGAGCCGGAGCTGGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGAAGTCGAGCAGCAGTACTACGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGCAGTACTACGCCTGGCTGCTCTTGAAGATGGGGTG
AGCGGCTGGACAACAGGACCAGCAGCGGTCAACTGGACACTCGGATGTTGAGGCCGTCGGAGGCGGCGGCGGCGTCGGAGGCGGCGGCGGCGTCGGAGGCGGCGGCGGCGTCGGAGGCGGCGGCGGCGTCGGAGGCGGCGGCGGCGTCAGCAGCATCTCAGGGAACTGGAGGTCCTCTCGGAGCAGTACTACTGGCAGAAGTGCC
TGGAGAATGCCCAGATCGCCATCTGGGCTGAGCGGCTGAGCGTGAGCGCAGCCTGGGCAGCGTCCAAGTGGCCAGCGTGAGAAGTCCTGAACGCATCAATGCCTATCAGCCAAAGGATGCCAAGGTCTTATTGCGGGTAAAGGAATCGGAAGGCTAAGG
TGGAGAAGGCAGTGGAGAATTGACATTGGGCTGCAGCAGCAGCAGCAGTGGAGCGTCGAAGCACTGAGCAGCATCAATGCCTATCAGCCAAAGGATGCCAAGGTCTTATTGCGGGTAAAGGAATCGGAAGGCTAAGG
AGTACCTGAAACAGGAGAGATTAGCTCCCCTGAGATTGAGCTCAAGGATGAGCTGGTGAAGGTCTTCCTTGCTGAACTGACCTGAGCTGCCTGAGCTGTGACTGACTGACAGGTCCCTGAGTCCACTGGGCAGGAGAGCCCTAAGCCGAAGGCTAAGG
CTGACTGTGACATGGCATGCCTGCATTTCATGACATTGGATGCTGGTGCAGCAGCAGTTGGGCGGCAGCTCCTCAAGGATGAGCTCAAGGATGAGCTGGTGACCTGAGTCCACTGAGTCCACAGGTCCCTGAGTCCACTGAAGATGCTGGCTG
GGCTGGCCATGCTGGCCATGCTGGCCAGGCTGTGAGGCTGTCAAGTGGTGCAGCTCCCCACAAGGCGGCGCCCTTGGGAAGGCGCTTCCCTTGCTGAGACTGAGACTGAGGACACAAGAATCGCAAGGCTAAGG
TTCAAGCTGCCCGGGCGCGGGGACATCGTGCTCAAGTGGGAGCTGGGAGAGGCACCCCTGCACAACCTCCCCTCCTGCTGCTGCTGAGCTGAGCTGAGCTGAGCTGAGCTGAGCTGAGCTGAGCTGAGCTGAGCTGAGCTGCAGGTAAGCCATCGCTGGCTGCTGGCTGTGGCTG
TCAAGGCACTGAAGGAGCTCGGGAGAGTGCTCGGCAGGACTTCGCGGAGAAGCAGGCTCTGCCGGTCTCATCTGAGGTGCTCCAGCGTGAGGCTGCCAGCGTGAGGCTGAAGGCTGGCTGGCTGCTCTGTGCCTG

Fig. 11A

CCCTGCTCATGGTCTTTGAGTATATGGGCACGGGGACCTCAACCGCTTCCTCTCCGATCCCATGGACCTCAAGCTGCTGGCTGTGGGAGGATGTGGCTCCAGGCCCCCTGGGTCTGG
GGCAGCTGCTGGCCGTGGCTAGCCAGGTCGCTGCGGGGATGCTGCGGTGTACCTGGCCATTTGCACACGGGTGCCACTGCTCTAGTGGGCCAGGGACTGGTGCTCAAGA
TTGGTGATTTTGGCCATGACGCAGGATATCTACAGCACCGACTATTACCGTGTGGGAGCCCGCACCATGCCCGAGAGCATCCTGTACCGTAAGTTCACCACCG
AGAGCGACGTGCGGAGCTTCGGCGTGCTGCTCTGGGAGATCTTCACCTTACGGCAAGCAATCGACTTCCTGTACCAGCAGCAGCAAGCCGCCATCGCATCACCGCAGGACGTGAGTTGGAGC
GGCCACGTGCCTGCCGCCAGAGAGTTCATGCGGCCATCATGCGGGGTGCTGGCAGCGGAGCCCCAGCGGCAACGCCAAGATGTGCACGCCCGGCTGCAAGCCCTGGCCCAGGGACCTC
CTGTCTACCTGGGATGTCCTGGGCTAGgggggccggcagggctgggagtggttagccggaatactggggcctgcctgcccatagctccccagtcccagccccaggtgatctcaaagt
atctaattcacctcagcatgtgtggaaggggacaggtgggggctggggctggggagtagaggattgttcctgcttctctagcaaggtccgtcatagcaattatattttattccttgaaaaaa
(SEQ ID NO: 5)

Fig. 11A
Continued

```
GCGGCCGCGC TGAGCCCCTA GCCCGCCGGG AGCGCCAGGC CGGCCAGGCC    50
TGCGCCGCCG CCGCCGCCGC CGTCGCCGCC GCGCCGACCA TGTCGGCAGC   100
CAAGGAGAAC CCGTGCAGGA AATTCCAGGC CAACATCTTC AACAAGAGCA   150
AGTGTCAGAA CTGCTTCAAG CCCCGCGAGT CGCATCTGCT CAACGACGAG   200
GACCTGACGC AGGCAAAACC CATTTATGGC GGTTGGCTGC TCCTGGCTCC   250
AGATGGGACC GACTTTGACA ACCCAGTGCA CCGGTCTCGG AAATGGCAGC   300
GACGGTTCTT CATCCTTTAC GAGCACGGCC TCTTGCGCTA CGCCCTGGAT   350
GAGATGCCCA CGACCCTTCC TCAGGGCACC ATCAACATGA CCAGTGCAC    400
AGATGTGGTG GATGGGGAGG GCCGCACGGG CCAGAAGTTC TCCCTGTGTA   450
TTCTGACGCC TGAGAAGGAG CATTTCATCC GGGCGGAGAC CAAGGAGATC   500
GTCAGTGGGT GGCTGGAGAT GCTCATGGTC TATCCCCGGA CCAACAAGCA   550
GAATCAGAAG AAGAAACGGA AGTGGAGCC CCCACACCA CAGGAGCCTG    600
GGCCTGCCAA GGTGGCTGTT ACCAGCAGCA GCAGCAGCAG CAGCAGCAGC   650
AGCAGCATCC CCAGTGCTGA GAAAGTCCCC ACCACCAAGT CCACACTCTG   700
GCAGGAAGAA ATGAGGACCA AGGACCAGCC AGATGGCAGC AGCCTGAGTC   750
CAGCTCAGAG TCCCAGCCAG AGCCAGCCTC CTGCTGCCAG CTCCCTGCGG   800
GAACCTGGGC TAGAGAGCAA AGAAGAGGAG AGCGCCATGA GTAGCGACCG   850
CATGGACTGT GGCCGCAAAG TCCGGGTGGA GAGCGGCTAC TTCTCTCTGG   900
AGAAGACCAA ACAGGACTTG AAGGCTGAAG AACAGCAGCT GCCCCCGCCG   950
CTCTCCCCTC CCAGCCCCAG CACCCCCAAC CACAGGAGGT CCCAGGTGAT  1000
TGAAAAGTTT GAGGCCTTGG ACATTGAGAA GGCAGAGCAC ATGGAGACCA  1050
ATGCAGTGGG GCCCTCACCA TCCAGCGACA CACGCCAGGG CCGCAGCGAG  1100
AAGAGGGCGT TCCCTAGGAA GCGGGACTTC ACCAATGAAG CCCCCCCAGC  1150
TCCTCTCCCA GACGCCTCGG CTTCCCCCCT GTCTCCACAC CGAAGAGCCA  1200
AGTCACTGGA CAGGAGGTCC ACGGAGCCCT CCGTGACGCC CGACCTGCTG  1250
AATTTCAAGA AAGGCTGGCT GACTAAGCAG TATGAGGACG GCCAGTGGAA  1300
GAAACACTGG TTTGTCCTCG CCGATCAAAG CCTGAGATAC TACAGGGATT  1350
CAGTGGCTGA GGAGGCAGCC GACTTGGATG GAGAAATTGA CTTGTCCGCA  1400
TGTTACGATG TCACAGAGTA TCCAGTTCAG AGAAACTATG GCTTCCAGAT  1450
ACATACAAAG GAGGGCGAGT TTACCCTGTC GGCCATGACA TCTGGGATTC  1500
GGCGGAACTG GATCCAGACC ATCATGAAGC ACGTGCACCC GACCACTGCC  1550
CCGGATGTGA CCAGCTCGTT GCCAGAGGAA AAAACAAGA GCAGCTGCTC   1600
TTTTGAGACC TGCCCGAGGC CTACTGAGAA GCAAGAGGCA GAGCTGGGGG  1650
AGCCGGACCC TGAGCAGAAG AGGAGCCGCG CACGGGAGCG GAGGCGAGAG  1700
GGCCGCTCCA AGACCTTTGA CTGGGCTGAG TTCCGTCCCA TCCAGCAGGC  1750
CCTGGCTCAG GAGCGGGTGG GCGGCGTGGG GCCTGCTGAC ACCCACGAGC  1800
CCCTGCGCCC TGAGGCGGAG CCTGGGGAGC TGGAGCGGGA GCGTGCACGG  1850
AGGCGGGAGG AGCGCCGCAA GCGCTTCGGG ATGCTCGACG CCACAGACGG  1900
GCCAGGCACT GAGGATGCAG CCCTGCGCAT GGAGGTGGAC CGGAGCCCAG  1950
GGCTGCCTAT GAGCGACCTC AAAACGCATA ACGTCCACGT GGAGATTGAG  2000
CAGCGGTGGC ATCAGGTGGA GACCACACCT CTCCGGGAAG AGAAGCAGGT  2050
GCCCATCGCC CCCGTCCACC TGTCTTCTGA AGATGGGGGT GACCGGCTCT  2100
CCACACACGA GCTGACCTCT CTGCTCGAGA AGGAGCTGGA GCAGAGCCAG  2150
AAGGAGGCCT CAGACCTTCT GGAGCAGAAC CGGCTCCTGC AGGACCAGCT  2200
GAGGGTGGCC CTGGGCCGGG AGCAGAGCGC CGTGAGGGC TACGTGCTGC    2250
AGGCCACGTG CGAGCGAGGG TTTGCAGCAA TGGAAGAAAC GCACCAGAAG  2300
AAGATTGAAG ATCTCCAGAG GCAGCACCAG CGGGAGCTAG AGAAACTTCG  2350
AGAAGAGAAA GACCGCCTCC TAGCCGAGGA GACAGCGGCC ACCATCTCAG  2400
CCATCGAAGC CATGAAGAAC GCCACCGGG AGGAAATGGA GCGGGAGCTG    2450
GAGAAGAGCC AGCGGTCCCA GATCAGCAGC GTCAACTCGG ATGTTGAGGC  2500
```

Fig. 11B

```
CCTGCGGCGC CAGTACCTGG AGGAGCTGCA GTCGGTGCAG CGGGAACTGG  2550
AGGTCCTCTC GGAGCAGTAC TCGCAGAAGT GCCTGGAGAA TGCCCATCTG  2600
GCCCAGGCGC TGGAGGCCGA GCGGCAGGCC CTGCGGCAGT GCCAGCGTGA  2650
GAACCAGGAG CTCAATGCCC ACAACCAGGA GCTGAACAAC CGCCTGGCTG  2700
CAGAGATCAC ACGGTTGCGG ACGCTGCTGA CTGGGACGG  CGGTGGGGAG  2750
GCCACTGGGT CACCCCTTGC ACAGGGCAAG GATGCCTATG AACTAGAGGT  2800
CTTATTGCGG GTAAAGGAAT CGGAAATACA GTACCTGAAA CAGGAGATTA  2850
GCTCCCTCAA GGATGAGCTG CAGACGGCAC TGCGGGACAA GAAGTACGCA  2900
AGTGACAAGT ACAAAGACAT CTACACAGAG CTCAGCATCG CGAAGGCTAA  2950
GGCTGACTGT GACATCAGCA GGTTGAAGGA GCAGCTCAAG GCTGCAACGG  3000
AAGCACTGGG GGAGAAGTCC CCTGACAGTG CCACGGTGTC CGGATATGGC  3050
CCGGCTGTGC TGGCTCCAGA GGATGGGCTG GCCATGTCCC TGCATTTCAT  3100
GACATTGGGT GGCAGCTCCC TGTCCCCCAC CGAGGGCAAA GGCTCTGGGC  3150
TCCAAGGCCA CATCATCGAG AACCCACAAT ACTTCAGTGA TGCCTGTGTT  3200
CACCACATCA AGCGCCGGGA CATCGTGCTC AAGTGGGAGC TGGGGGAGGG  3250
CGCCTTTGGG AAGGTCTTCC TTGCTGAGTG CCACAACCTC CTGCCTGAGC  3300
AGGACAAGAT GCTGGTGGCT GTCAAGGCAC TGAAGGAGGC GTCCGAGAGT  3350
GCTCGGCAGG ACTTCCAGCG TGAGGCTGAG CTGCTCACCA TGCTGCAGCA  3400
CCAGCACATC GTGCGCTTCT TCGGCGTCTG CACCGAGGGC CGCCCCCTGC  3450
TCATGGTCTT TGAGTATATG CGGCACGGGG ACCTCAACCG CTTCCTCCGA  3500
TCCCATGGAC CTGATGCCAA GCTGCTGGCT GGTGGGGAGG ATGTGGCTCC  3550
AGGCCCCCTG GGTCTGGGGC AGCTGCTGGC CGTGGCTAGC CAGGTCGCTG  3600
CGGGGATGGT GTACCTGGCG GGTCTGCATT TTGTGCACCG GGACCTGGCC  3650
ACACGCAACT GTCTAGTGGG CCAGGGACTG GTGGTCAAGA TTGGTGATTT  3700
TGGCATGAGC AGGGATATCT ACAGCACCGA CTATTACCGT GTGGGAGGCC  3750
GCACCATGCT GCCCATTCGC TGGATGCCGC CCGAGAGCAT CCTGTACCGT  3800
AAGTTCACCA CCGAGAGCGA CGTGTGGAGC TTCGGCGTGG TGCTCTGGGA  3850
GATCTTCACC TACGGCAAGC AGCCCTGGTA CCAGCTCTCC AACACGGAGG  3900
CAATCGACTG CATCACGCAG GGACGTGAGT TGGAGCGGCC ACGTGCCTGC  3950
CCACCAGAGG TCTACGCCAT CATGCGGGGC TGCTGGCAGC GGGAGCCCCA  4000
GCAACGCCAC AGCATCAAGG ATGTGCACGC CCGGCTGCAA GCCCTGGCCC  4050
AGGCACCTCC TGTCTACCTG GATGTCCTGG GCTAGGGGGC CGGCCCAGGG  4100
GCTGGGAGTG GTTAGCCGGA ATACTGGGGC CTGCCCTCAG CATCCCCCAT  4150
AGCTCCCAGC AGCCCCAGGG TGATCTCAAA GTATCTAATT CACCCTCAGC  4200
ATGTGGGAAG GGACAGGTGG GGGCTGGGAG TAGAGGATGT TCCTGCTTCT  4250
CTAGGCAAGG TCCCGTCATA GCAATTATAT TTATTATCCC TTGaaaaaaa  4300
a (SEQ ID NO: 6)
```

Fig. 11B Continued

MSAAKENPCRKFQANIFNKSKCQNCFKPRESHLLNDEDLTQAKPIYGGWLLLAPDGTDFD
NPVHRSRKWQRRFFILYEHGLLRYALDEMPTTLPQGTINMNQCTDVVDGEGRTGQKFSLC
ILTPEKEHFIRAETKEIVSGWLEMLMVYPRTNKQNQKKKRKVEPPTPQEPGPAKVAVTSS
SSSSSSSSSIPSAEKVPTTKSTLWQEEMRTKDQPDGSSLSPAQSPSQSQPPAASSLREPG
LESKEEESAMSSDRMDCGRKVRVESGYFSLEKTKQDLKAEEQQLPPPLSPPSPSTPNHRR
SQVIEKFEALDIEKAEHMETNAVGPSPSSDTRQGRSEKRAFPRKRDFTNEAPPAPLPDAS
ASPLSPHRRAKSLDRRSTEPSVTPDLLNFKKGWLTKQYEDGQWKKHWFVLADQSLRYYRD
SVAEEAADLDGEIDLSACYDVTEYPVQRNYGFQIHTKEGEFTLSAMTSGIRRNWIQTIMK
HVHPTTAPDVTSSLPEEKNKSSCSFETCPRPTEKQEAELGEPDPEQKRSRSRERRREGRS
KTFDWAEFRPIQQALAQERVGGVGPADTHEPLRPEAEPGELERERARRREERRKRFGMLD
ATDGPGTEDAALRMEVDRSPGLPMSDLKTHNVHVEIEQRWHQVETTPLREEKQVPIAPVH
LSSEDGGDRLSTHELTSLLEKELEQSQKEASDLLEQNRLLQDQLRVALGREQSAREGYVL
QATCERGFAAMEETHQKKIEDLQRQHQRELEKLREEKDRLLAEETAATISAIEAMKNAHR
EEMERELEKSQRSQISSVNSDVEALRRQYLEELQSVQRELEVLSEQYSQKCLENAHLAQA
LEAERQALRQCQRENQELNAHNQELNNRLAAEITRLRTLLTGDGGGEATGSPLAQGKDAY
ELEVLLRVKESEIQYLKQEISSLKDELQTALRDKKYASDKYKDIYTELSIAKAKADCDIS
RLKEQLKAATEALGEKSPDSATVSGYGPAVLAPEDGLAMSLHFMTLGGSSLSPTEGKGSG
LQGHIIENPQYFSDACVHHIKRRDIVLKWELGEGAFGKVFLAECHNLLPEQDKMLVAVKA
LKEASESARQDFQREAELLTMLQHQHIVRFFGVCTEGRPLLMVFEYMRHGDLNRFLRSHG
PDAKLLAGGEDVAPGPLGLGQLLAVASQVAAGMVYLAGLHFVHRDLATRNCLVGQGLVVK
IGDFGMSRDIYSTDYYRVGGRTMLPIRWMPPESILYRKFTTESDVWSFGVVLWEIFTYGK
QPWYQLSNTEAIDCITQGRELERPRACPPEVYAIMRGCWQREPQQRHSIKDVHARLQALA
QAPPVYLDVLG—(SEQ ID NO: 7)

Fig. 11C

ARRY-470

*(S)-N-(5-((R)-2-(2,5-difluorophenyl)pyrrolidin-1-yl)pyrazolo[1,5-a]pyrimidin-3-yl)-3-hydroxypyrrolidine-1-carboxamide*

| Characteristic | Total Number | NTRK1+ |
|---|---|---|
| Total | 35 | 2 |
| Histology | | |
| Adenocarcinoma | 32 | 2 |
| Squamous | 1 | 0 |
| Other | 1 | 0 |
| NA | 1 | 0 |
| Molecular Status* | | |
| *EGFR* mutation negative | 35 | 2 |
| *KRAS* mutation negative | 35 | 2 |
| *ALK* fusion negative | 35 | 2 |
| *ROS1* fusion negative | 34 | 2 |
| *RET* fusion negative | 5 | 1* |
| Smoking history | | |
| Never | | |
| Current/former | | |
| NA | | |
| Sex | | |
| Male | 9 | 0 |
| Female | 25 | 2 |
| NA | 1 | 0 |
| Median age, years (range)§ | 60 (31-83) | NA |
| Pathologic stage at diagnosis | | |
| I | 9 | 0 |
| II | 5 | 1 |
| III | 4 | 0 |
| IV | 4 | 1 |
| NA | 13 | 0 |

*All patients tested for each of the molecular markers were negative for that oncogene, one patient was *MET* FISH positive §age data was missing on 13 patients, median age not calculated for *NTRK1* FISH positive patients

Fig. 21

| Characteristic | Total Number | NTRK1+ |
|---|---|---|
| Total | 56 | 1 |
| Histology | | |
|   Adenocarcinoma | 52 | 1 |
|   Squamous | 0 | 0 |
|   Other | 4 | 0 |
| Molecular Status | | |
|   EGFR mutation negative | 56 | 1 |
|   KRAS mutation negative | 55 | 1 |
|   ALK fusion negative | 56 | 1 |
|   ROS1 fusion negative | 56 | 1 |
|   RET fusion negative | 56 | 1 |
| Smoking history | | |
|   Never | 30 | 0 |
|   Current/former | 26 | 1 |
| Sex | | |
|   Male | 32 | 0 |
|   Female | 24 | 1 |
| Median age, years (range) | 63 (23-87) | NA |
| Pathologic stage | | |
|   I | 8 | 1 |
|   II | 6 | 0 |
|   III | 15 | 0 |
|   IV | 27 | 0 |

Fig. 22

Kinase Selectivity Analysis of ARRY-470 at 1 μM (100 fold Trk enzyme IC₅₀)

ArrayTrkA enzyme (500 μM ATP) IC₅₀ = 10 nM
Upstate panel run at 100 μM ATP or less

| Kinase | POC | Kinase | POC | Kinase | POC | Kinase | POC | Kinase | POC |
|---|---|---|---|---|---|---|---|---|---|
| Abl | 96 | CLK2 | 104 | Flt4 | 94 | MAPKAP-K3 | 96 | PAK4 | 104 | ROCK-II | 103 |
| Abl2 | 96 | CLK3 | 96 | Fms | 99 | MAPKAP-K5 | 100 | PAK5 | 96 | Ron | 102 |
| AKT1 | 101 | c-RAF | 104 | Fyn | 92 | MARK1 | 94 | PAK6 | 105 | Ros | 98 |
| AKT2 | 116 | CSK | 99 | GRK5 | 101 | MEK1 | 102 | PAR-1Salpha | 102 | Rse | 102 |
| AKT3 | 101 | DAPK1 | 101 | GRK6 | 97 | MELK | 113 | PASK | 92 | Rsk1 | 115 |
| ALK | 100 | DAPK2 | 96 | GRK7 | 99 | Mer | 94 | PDGFRalpha | 103 | Rsk2 | 106 |
| ALK4 | 100 | DAPK3 | 114 | GSK3alpha | 105 | Met | 83 | PDGFRbeta | 103 | Rsk3 | 101 |
| AMPK_r | 91 | DCAMKL2 | 110 | GSK3beta | 106 | MINK | 104 | PDK1 | 106 | Rsk4 | 135 |
| ARK5 | 95 | DDR2 | 105 | Haspin | 93 | MKK4 | 98 | PhKgamma2 | 105 | SGK1 | 106 |
| AURKA | 111 | DMPK | 101 | Hck | 98 | MKK6 | 98 | Pim-1 | 92 | SGK2 | 110 |
| Axl | 116 | DRAK1 | 94 | HIPK2 | 104 | MKK7beta | 89 | Pim-1 | 103 | SGK3 | 99 |
| BLK_m | 116 | DYRK2 | 110 | HIPK3 | 101 | MKNK2 | 101 | Pim-3 | 103 | SIK | 96 |
| Bmx | 79 | eEF-2K | 97 | IGF-1R | 97 | MLK1 | 96 | PKAC-alpha | 100 | SRC | 100 |
| BrSK1 | 91 | EGFR | 90 | IGF-1R Activated | 97 | MRCKalpha | 101 | PKCalpha | 94 | SRPK1 | 94 |
| BrSK2 | 106 | EphA1 | 100 | IKKalpha | 99 | MRCKbeta | 96 | PKCbeta1 | 98 | SRPK2 | 91 |
| BTK | 138 | EphA2 | 99 | IKKbeta | 93 | MSK1 | 92 | PKCbetaII | 98 | STK33 | 102 |
| CAMK1 | 97 | EphA3 | 99 | IR | 94 | MSK2 | 104 | PKCdelta | 92 | Syk | 101 |
| CAMK1d | 98 | EphA4 | 102 | IR Activated | 104 | MSSK1 | 109 | PKCepsilon | 99 | TAK1 | 95 |
| CAMK2b | 99 | EphA5 | 127 | IRAK1 | 99 | MST1 | 97 | PKCeta | 92 | TAO1 | 103 |
| CAMK2d | 93 | EphA7 | 94 | IRAK4 | 97 | MST2 | 104 | PKCgamma | 96 | TAO2 | 97 |
| CAMK2g | 89 | EphA8 | 96 | IRR | 103 | MST3 | 103 | PKCiota | 100 | TAO3 | 97 |
| CAMK4 | 93 | EphB1 | 90 | ITK | 106 | mTOR | 101 | PKCmu | 102 | TBK1 | 98 |
| CDK1/cyclinB | 112 | EphB2 | 96 | JAK2 | 147 | mTOR/FKBP12 | 101 | PKCtheta | 104 | TEC Activated | 96 |
| CDK2/cyclinA | 109 | EphB3 | 110 | JAK3 | 91 | MuSK | 76 | PKCzeta | 110 | Tie2 | 106 |
| CDK2/cyclinE | 95 | EphB4 | 99 | JNK1alpha1 | 88 | MYLK | 99 | PKD2 | 101 | TLK2 | 96 |
| CDK3/cyclinE | 109 | ErbB4 | 103 | JNK2alpha2 | 103 | NEK11 | 102 | Pk1 | 100 | TNK2 | 38 |
| CDK5/p25 | 94 | ERK1 | 105 | JNK3 | 100 | NEK2 | 121 | Pk2 | 89 | TrkA | 0 |
| CDK5/p35 | 104 | ERK2 | 101 | KDR | 110 | NEK3 | 96 | Pk3 | 100 | TrkB | 0 |
| CDK7/cyclinH/MAT1 | 98 | FAK | 101 | KIT | 100 | NEK6 | 104 | PRK2 | 87 | TSSK1 | 67 |
| CDK9/cyclinT1 | 113 | Fer | 92 | Lck | 106 | NEK7 | 94 | PRKG1alpha | 89 | TSSK2 | 96 |
| CHK1 | 101 | Fes | 114 | LIMK1 | 97 | NLK | 101 | PRKG1beta | 99 | Txk | 78 |
| CHK2 | 102 | FGFR1 | 102 | LKB1 | 81 | p38alpha | 96 | PrKX | 100 | ULK2 | 107 |
| CK1_Y | 97 | FGFR2 | 101 | LOK | 101 | p38beta | 100 | PTK5 | 111 | ULK3 | 97 |
| CK1delta | 107 | FGFR3 | 96 | Lyn | 97 | p38delta | 100 | PTK6 | 107 | VFK2 | 106 |
| CK1gamma1 | 100 | FGFR4 | 113 | MAP3K5 | 110 | p38gamma | 100 | Pyk2 | 95 | WNK2 | 78 |
| CK1gamma2 | 97 | Fgr | 97 | MAP4K2 | 97 | p70S6K | 100 | Ret | 97 | WNK3 | 106 |
| CK1gamma3 | 84 | Flt1 | 94 | MAPKAP-K2 | 104 | PAK2 | 105 | RIPK2 | 98 | Yes | 99 |
| CK2 | 99 | Flt3 | 107 | | | PAK3 | 103 | ROCK-I | 102 | ZAP-70 | 103 |
| CK2alpha2 | 92.7 | | | | | | | | | | |

Fig. 23

| Primer Name | Primer Sequence (5'->3') |
|---|---|
| MPRIPStart | ACCATGTCGGCAGCCAAGGAGAACCCGTGC (SEQ ID NO: 9) |
| MPRIP CC1F1 | ACACACGAGCTGACCTCTCTGC (SEQ ID NO: 10) |
| MPRIP CC3F1 | GCGAAGGCTAAGGCTGACTGTG (SEQ ID NO: 11) |
| MPRIP XhoR1 | CCATTGCTGCAAACCCTCGCTC (SEQ ID NO: 12) |
| EcoRI MPRIP Kozak ATG | GAATTCGCCGCGGCCGCCATGTCGG (SEQ ID NO: 13) |
| NTRK1Y490R1 | CGGCGCTTGATGTGGTGAAC (SEQ ID NO: 14) |
| NTRK1stopR1 | TATTCCGGCTAACCACTCCCAG (SEQ ID NO: 15) |
| NTRK1stopR2 | CCTAGCCCAGGACATCCAGG (SEQ ID NO: 16) |
| NTRK1 HAstop Not1 | CGCGGCCGCTTAAGCGTAGTCTGGGACGTCGTATGGGTAGCCCAGGACATCCAGG (SEQ ID NO: 17) |

Fig. 24

TRKA inhibitors used in this study

| Drug | Company | Cell IC$_{50}$ (nM) | | | Phase of Clinical Development | Other Known Targets |
| --- | --- | --- | --- | --- | --- | --- |
| | | TRKA | TRKB | TRKC | | |
| ARRY-470 | Array | 9.5 | 24 | 24 | pre-clinical | None at 1 μM* |
| ARRY-523 | Array | 10 | 8.1 | 10 | pre-clinical | None at 1 μM* |
| ARRY-772 | Array | 2 | 2.1 | 2.3 | pre-clinical | None at 1 μM* |
| PF-02341066 (crizotinib) | Pfizer | 580 | 399 | NA | Approved§ | ALK, ROS1, MET |
| CEP-701 (lestaurtinib) | Cephalon | 8.3 | 14 | 14 | III | FLT-3, RET, STAT5, JAK2 |

*Array Biopharma data on file
§Approved for ALK FISH positive NSCLC

Fig. 25

CUTO-3 cells derived from index patient

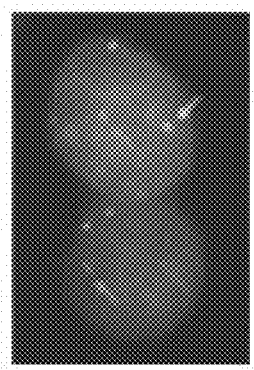

CUTO-3 cells, a short-term culture derived from a
pleural effusion, harbor the *MPRIP-NTRK1* gene fusion.
*NTRK1* FISH analysis of CUTO-3 cells

Fig. 27A

CUTO-3 cells derived from index patient

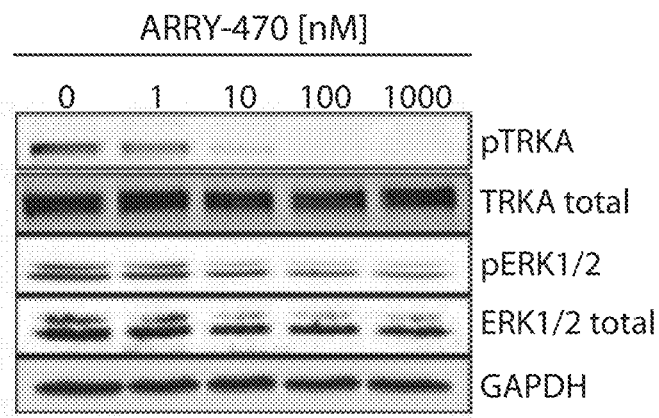

CUTO-3 cells, a short-term culture derived from a
pleural effusion, harbor the *MPRIP-NTRK1* gene fusion.
Immunoblot analysis of CUTO-3 cells demonstrating inhibition
of pTRKA and pERK by the pan-TRK inhibitor, ARRY-470

Fig. 27B

NTRK1 FUSION MOLECULES AND USES THEREOF

The present application is a continuation of U.S. application Ser. No. 14/473,508, filed Aug. 29, 2014, which is a continuation application of PCT International Application No. PCT/US2013/068457 (published on May 8, 2013, as PCT publication no. WO2014071358), filed Nov. 5, 2013, which claims the benefit of U.S. Provisional Application No. 61/872,559, filed Aug. 30, 2013; U.S. Provisional Application No. 61/763,442, filed Feb. 11, 2013; and U.S. Provisional Application No. 61/722,533, filed Nov. 5, 2012. The contents of all of which are hereby incorporated by reference in their entirety.

SEQUENCE LISTING

The instant application contains a Sequence Listing which has been submitted electronically in ASCII format and is hereby incorporated by reference in its entirety. Said ASCII copy, created on Aug. 29, 2014, is named "Sequence_Listing_ST25.txt" and is 59 KB in size.

BACKGROUND

Cancer represents the phenotypic end-point of multiple genetic lesions that endow cells with a full range of biological properties required for tumorigenesis. Indeed, a hallmark genomic feature of many cancers, including, for example, B cell cancer, lung cancer, breast cancer, ovarian cancer, pancreatic cancer, and colon cancer, is the presence of numerous complex chromosome structural aberrations, including translocations, intra-chromosomal inversions, point mutations, deletions, gene copy number changes, gene expression level changes, and germline mutations, among others.

The need still exists for identifying novel genetic lesions associated with cancer. Such genetic lesions can be an effective approach to develop compositions, methods and assays for evaluating and treating cancer patients.

SUMMARY

The invention is based, at least in part, on the discovery of novel NTRK1 rearrangements that give rise to fusion molecules that include all or part of MPRIP (Myosin phosphatase Rho-interacting protein) and all or part of NTRK1 (Neurotrophic tyrosine kinase receptor type 1), referred to herein as "MPRIP-NTRK1 fusion molecules." In one embodiment, all or part of MPRIP is fused in-frame to the C-terminal portion of NTRK1, e.g., the C-terminal portion of NTRK1 which includes the full NTRK1 tyrosine kinase domain. For example, a fragment of the MPRIP gene is fused to a fragment of a NTRK1 gene, e.g., a fusion that includes a 5'-exon and a 3'-exon as summarized in FIGS. 1A-1C (e.g., said fragments correspond to exons 1-21 from MPRIP and exons 12-17 of NTRK, which include the full NTRK1 tyrosine kinase domain encoded by exons 13-17). Applicants further provide that the MPRIP-NTRK1 fusion molecules disclosed herein have constitutive TRKA kinase activity, and are oncogenic (e.g., capable of transforming cell lines in vitro (e.g., Ba/F3 and NIH3T3 cells), which cells are tumorigenic when injected in vivo). Further disclosed herein are experiments demonstrating that tyrosine kinase inhibitors, including TRK- or TRKA-specific inhibitors reduce and/or inhibit the activity of the MPRIP-NTRK1 fusion molecules by e.g., reducing and/or inhibiting downstream signaling and/or cellular proliferation. Further embodiments disclosed herein show that a human subject with lung cancer (e.g., lung adenocarcinoma) treated with crizotinib, a weak TRKA-inhibitor, showed tumor shrinkage consistent with the level of in vitro inhibition and predicted patient drug levels. Other embodiments disclosed herein identified the MPRIP-NTRK1 fusion molecules in approximately 3.3% of lung adenocarcinomas that did not harbor other oncogenic alterations tested.

Accordingly, the invention provides, at least in part, the following: methods for identifying, assessing or detecting an MPRIP-NTRK1 fusion molecule as described herein; methods for identifying, assessing, evaluating, and/or treating a subject having a cancer, e.g., a cancer having an MPRIP-NTRK1 fusion molecule as described herein; isolated MPRIP-NTRK1 fusion nucleic acid molecules, nucleic acid constructs, host cells containing the nucleic acid molecules; purified fusion polypeptides and binding agents; detection reagents (e.g., probes, primers, antibodies, kits, capable, e.g., of specific detection of a fusion nucleic acid or protein); screening assays for identifying molecules that interact with, e.g., inhibit, the fusions, e.g., novel kinase inhibitors; as well as assays and kits for evaluating, identifying, assessing and/or treating a subject having a cancer, e.g., a cancer having a fusion. The compositions and methods identified herein can be used, for example, to identify new inhibitors; to evaluate, identify or select a subject, e.g., a patient, having a cancer; and to treat or prevent a cancer. In one embodiment, the cancer is a lung cancer, e.g., a lung adenocarcinoma.

MPRIP-NTRK1 Fusions

Disclosed herein are fusion molecules that comprise all or part of MPRIP and all or part of NTRK1. The term "fusion" or "fusion molecule" is used generically herein, and includes any fusion molecule (e.g., gene, gene product (e.g., cDNA, mRNA, or polypeptide), and variant thereof) that includes a fragment of first gene and a fragment of second gene described herein, including, e.g., an MPRIP-NTRK1 as summarized in FIGS. 1A-1C. Expression of the fusion molecules was detected in cancer tissues, thus suggesting an association with cancer, e.g., lung cancer, e.g., a lung adenocarcinoma. The MPRIP-NTRK1 fusion molecules disclosed herein have constitutive TRKA kinase activity, are oncogenic, and can be inhibited with TRK- or TRKA-specific inhibitors.

In one embodiment, a fusion molecule includes an in-frame fusion of an exon of MPRIP, e.g., one more exons of MPRIP (e.g., one or more of exons 1-21 of MPRIP) or a fragment thereof, and an exon of NTRK1, e.g., one or more exons of a NTRK1 (e.g., one or more of exons 12-17 of NTRK1 of FIG. 4 (SEQ ID NO:3), or one or more of exons 13-17 encoding the kinase domain, or exons 14-19 of NTRK1 of FIG. 6) or a fragment thereof. In another embodiment, the fusion molecule includes open reading frame of the nucleotide sequence of SEQ ID NO:5 (FIG. 11A) or a nucleotide sequence substantially identical thereto. In one embodiment, the fusion molecule includes the nucleotide sequence of SEQ ID NO:6 (FIG. 11B) or a nucleotide sequence substantially identical thereto; or encodes the amino acid sequence SEQ ID NO:7 (FIG. 11C), or an amino acid sequence substantially identical thereto. For example, the MPRIP-NTRK1 fusion can include an in-frame fusion within an intron of MPRIP (e.g., intron 21) or a fragment thereof, with an intron of NTRK1 (e.g., intron 11 or intron 13) or a fragment thereof. In one embodiment, the fusion of the MPRIP-NTRK1 fusion comprises the nucleotide sequence of: chromosome 1 at one or more of nucleotide 156,845,212 (plus or minus 10, 20, 30, 50, 60, 70, 80, 100 or more nucleotides) and chromosome 17 at one or more of nucleotide 17,080,829 (plus or minus 10, 20, 30, 50, 60, 70, 80, 100 or more nucleotides). In one embodiment, the MPRIP-NTRK1 fusion is a translocation, e.g., a translocation of a portion of chromosome 1 and a portion of chromosome 17.

In certain embodiments, the MPRIP-NTRK1 fusion is in a 5'-MPRIP to 3'-NTRK1 configuration (also referred to herein as "5'-MPRIP-NTRK1-3')." The term "fusion" or "fusion molecule" can refer to a polypeptide or a nucleic acid fusion, depending on the context. It may include a full-length sequence of a fusion or a fragment thereof, e.g., a fusion junction (e.g., a fragment including a portion of MPRIP and a portion of NTRK1, e.g., a portion of the MPRIP-NTRK1 fusion described herein). In one embodiment, the MPRIP-NTRK1 fusion polypeptide includes a fragment of the amino acid sequence shown in FIG. 5 (SEQ ID NO:4) and a fragment of the amino acid sequence shown in FIG. 3 (SEQ ID NO:2), or an amino acid sequence substantially identical thereto. In another embodiment, the MPRIP-NTRK1 fusion polypeptide includes the amino acid sequence of SEQ ID NO:7 shown in FIG. 11C, or an amino acid sequence substantially identical thereto.

In another embodiment, the MPRIP-NTRK1 fusion nucleic acid includes a fragment of the nucleotide sequence shown in FIG. 4 (SEQ ID NO:3) and a fragment of the nucleotide sequence shown in FIG. 2 (SEQ ID NO: 1), or a nucleotide sequence substantially identical thereto. In another embodiment, the fusion molecule includes open reading frame of the nucleotide sequence of SEQ ID NO:5 (FIG. 11A) or a nucleotide sequence substantially identical thereto. In one embodiment, the fusion molecule includes the nucleotide sequence of SEQ ID NO:6 (FIG. 11B) or a nucleotide sequence substantially identical thereto; or encodes the amino acid sequence SEQ ID NO:7 (FIG. 11C), or an amino acid sequence substantially identical thereto.

In one embodiment, the MPRIP-NTRK1 fusion polypeptide comprises sufficient MPRIP and sufficient NTRK1 sequence such that the 5' MPRIP-3' NTRK1 fusion has kinase activity, e.g., has elevated (e.g., constitutive) activity, e.g., NTRK1 tyrosine kinase activity, as compared with wild type NTRK1, e.g., in a cell of a cancer referred to herein (e.g., adenocarcinoma, e.g., lung adenocarcinoma).

In certain embodiments, the MPRIP-NTRK1 fusion comprises one or more (or all of) exons (or corresponding amino acid encoded exons) 1-21 from MPRIP of SEQ ID NOs: 1-2 or FIGS. 2-3, respectively, and one or more (or all of) exons (or corresponding amino acid encoded exons) 12-17 of NTRK1 of FIG. 4-5 (SEQ ID NO:3-4, respectively), or one or more of exons (or corresponding amino acid encoded exons) 13-17 encoding the kinase domain, or exons (or corresponding amino acid encoded exons) 14-19 of NTRK1 of FIG. 6. In another embodiment, the MPRIP-NTRK1 fusion comprises one or more (or all of) exons 1-21 of MPRIP and one or more (or all of) exons 12-17 or exons 14-19 of NTRK1. In certain embodiments, the MPRIP-NTRK1 fusion comprises at least 1, 2, 3, 4, 5, 6, 7, 8, 9, 10, 11, 12, 13, 14, 15, 16, 17, 18, 19, 20, 21 or more exons (or encoded exons) from MPRIP and at least 1, 2, 3, 4, 5, 6 or more exons (or encoded exons) from NTRK1 (e.g., from the MPRIP and NTRK1 sequences shown in FIG. 4 and FIG. 5 (SEQ ID NO:3 and 4) and FIG. 2 and FIG. 3 (SEQ ID NOs:1 and 2).

In certain embodiments, the MPRIP-NTRK1 fusion comprises exon 21 or a fragment thereof from MPRIP, and exon 12 or exon 14 or a fragment thereof from NTRK1 (e.g., as shown in FIG. 5 (SEQ ID NO:4) and FIG. 3 (SEQ ID NO:2)). In one embodiment, the MPRIP-NTRK1 fusion comprises at least 5, 10, 15, 20, 30, 40, 50 or more amino acids from exon 21 of MPRIP (e.g., from the amino acid sequence of MPRIP as shown in FIG. 5 (SEQ ID NO:4) (e.g., from the amino acid sequence of MPRIP preceding the fusion junction with NTRK1, and at least 5, 10, 15, 20, 30, 40, 50 or more amino acids from exon 12 or exon 14 of NTRK1 (e.g., from the amino acid sequence of NTRK1 as shown in FIG. 3 (SEQ ID NO:2)). In another embodiment, the MPRIP-NTRK1 fusion comprises at least 6, 12, 15, 20, 25, 50, 75, 100 or more nucleotides from exon 21 of MPRIP (e.g., from the nucleotide sequence of MPRIP as shown in FIG. 4 (SEQ ID NO:3) (e.g., from the nucleotide sequence of MPRIP preceding the fusion junction with NTRK1); and at least 6, 12, 15, 20, 25, 50, 75, 100 or more nucleotides from exon 12 or exon 14 of NTRK1 (e.g., from the nucleotide sequence of NTRK1 as shown in FIG. 2 (SEQ ID NO: 1)).

MPRIP-NTRK1 Nucleic Acid Molecules

In one aspect, the invention features a nucleic acid molecule (e.g., an isolated or purified) nucleic acid molecule that includes a fragment of a MPRIP gene and a fragment of a NTRK1 gene. In one embodiment, the nucleotide sequence encodes a MPRIP-NTRK1 fusion polypeptide that includes a NTRK1 tyrosine kinase domain or a functional fragment thereof. In another embodiment, the nucleotide sequence encodes a fragment of the NTRK1 polypeptide including the amino acid sequence of SEQ ID NO:2 or a fragment thereof, or a sequence substantially identical thereto. In other embodiments, the nucleic acid molecule includes a fragment of the MPRIP gene encoding the amino acid sequence of SEQ ID NO:4 or a fragment thereof, or a sequence substantially identical thereto. In yet other embodiments, the nucleic acid molecule includes a nucleotide sequence encoding the amino acid sequence shown in FIG. 4 (SEQ ID NO:3), or a fragment thereof, and the amino acid sequence shown in FIG. 2 (SEQ ID NO: 1) or a fragment thereof, or a sequence substantially identical thereto.

In one embodiment, the nucleic acid molecule includes a fusion, e.g., an in-frame fusion, between an intron of MPRIP (e.g., intron 21, or a fragment thereof), and an intron of NTRK1 (e.g., intron 11 or intron 13, or a fragment thereof). The MPRIP-NTRK1 fusion can comprise a fusion of the nucleotide sequence of: chromosome 1 at one or more of nucleotide 156,845,212 (plus or minus 10, 20, 30, 50, 60, 70, 80, 100 nucleotides) and chromosome 17 at one or more of nucleotide 17,080,829 (plus or minus 10, 20, 30, 50, 60, 70, 80, 100 nucleotides), or a fragment thereof. In one embodiment, the MPRIP-NTRK1 fusion comprises a fusion of the nucleotide sequence of: chromosome 1 at one or more of nucleotide 156,845,212 (plus or minus 10, 20, 30, 50, 60, 70, 80, 100 nucleotides) and chromosome 17 at one or more of nucleotide 17,080,829 (plus or minus 10, 20, 30, 50, 60, 70, 80, 100 nucleotides), or a fragment thereof.

In another embodiment, the MPRIP-NTRK1 fusion comprises a nucleotide sequence (e.g., a fragment of a nucleotide sequence) shown in FIG. 4 (SEQ ID NO:3) and a nucleotide sequence (e.g., a fragment of a nucleotide sequence) shown in FIG. 2 (SEQ ID NO: 1), or a fragment of the fusion. In one embodiment, the MPRIP-NTRK1 fusion comprises a nucleotide sequence substantially identical to the nucleotide sequence (e.g., a fragment of a nucleotide sequence) shown in FIG. 4 (SEQ ID NO:3) and the nucleotide sequence (e.g., a fragment of a nucleotide sequence) shown FIG. 2 (SEQ ID NO: 1), or a fragment of the fusion. In one embodiment, the MPRIP-NTRK1 fusion comprises a nucleotide sequence at least 70%, at least 75%, at least 80%, at least 85%, at least 90%, at least 95%, at least 99%, at least 99.5 or greater, identical to the nucleotide sequence (e.g., a fragment of a nucleotide sequence) shown in FIG. 4 (SEQ ID NO:3) and to the nucleotide sequence (e.g., a fragment of a nucleotide sequence) shown in FIG. 2 (SEQ ID NO: 1). In yet other embodiments, the MPRIP-NTRK1 fusion comprises the nucleotide sequence of the open reading frame of SEQ ID NO:5 (FIG. 11A), or the nucleotide sequence of SEQ ID NO:6 (FIG. 11B), or a nucleotide sequence substantially identical thereto (e.g., at least 70%, at least 75%, at least 80%, at least 85%, at least 90%, at least 95%, at least 99%, at least 99.5 or greater, identical to the nucleotide sequence, or a fragment of a nucleotide sequence).

In one embodiment, the MPRIP-NTRK1 fusion comprises a nucleotide sequence containing at least 25, 50, 100, 150, 200, 500, 1000, 1500, 2000, 2500, 3000, or more nucleotides of the nucleotide sequence shown in FIG. 4 (SEQ ID NO:3) and a nucleotide sequence containing at least 25, 50, 100, 150, 200, 500, 1000, 1500, 2000, 2500, 3000, or more nucleotides of the nucleotide sequence shown in FIG. 2 (SEQ ID NO: 1). In one embodiment, the MPRIP-NTRK1 fusion comprises a nucleotide sequence containing at least 25, 50, 100, 150, 200, 500, 1000, 1500, 2000, 2500, 3000, or more contiguous nucleotides of the nucleotide sequence shown in FIG. 4 (SEQ ID NO:3) and a nucleotide sequence containing at least 25, 50, 100, 150, 200, 500, 1000, 1500, 2000, 2500, 3000, or more nucleotides of the nucleotide sequence shown in FIG. 2 (SEQ ID NO:1).

In another embodiment, the nucleic acid molecule includes a fusion, e.g., an in-frame fusion, of at least exon 21 of MPRIP or a fragment thereof (e.g., one or more of exons 1-21 of MPRIP or a fragment thereof), and at least exon 12 or exon 14 or a fragment thereof (e.g., one or more of exons 12-17 of SEQ ID NO:3, or exons 14-19 of NTRK1 or a fragment thereof). In yet other embodiments, the nucleic acid molecule includes a fragment the nucleotide sequence shown in FIG. 4 (SEQ ID NO:3) and a fragment of the nucleotide sequence shown in FIG. 2 (SEQ ID NO: 1) or a fragment of the fusion, or a sequence substantially identical thereto.

In one embodiment, the nucleic acid molecule is complementary to at least a portion of a nucleotide sequence disclosed herein, e.g., is capable of hybridizing under a stringency condition described herein to SEQ ID NO:3 and/or SEQ ID NO:1, or SEQ ID NO:5 or SEQ ID NO:6, or a fragment of any of the aforesaid sequences. In yet another embodiment, the nucleic acid molecule hybridizes to a nucleotide sequence that is complementary to at least a portion of a nucleotide sequence disclosed herein, e.g., is capable of hybridizing under a stringency condition to a nucleotide sequence complementary to SEQ ID NO:3 and/or SEQ ID NO: 1, or SEQ ID NO:5 or SEQ ID NO:6, or a fragment thereof. The nucleotide sequence of a cDNA encoding an exemplary 5' MPRIP-3' NTRK1 fusion is shown in at least exon 21 (e.g., exons 1-21) of SEQ ID NO:3 and at least exon 12 (e.g., exons 12-17) of SEQ ID NO:1; or the open reading frame of SEQ ID NO:5, or the nucleotide sequence of SEQ ID NO:6, and the predicted amino acid sequence is shown in the corresponding encoded exons of SEQ ID NO:4 and the corresponding encoded exons of SEQ ID NO:2, respectively; or the amino acid sequence of SEQ ID NO:7.

In an embodiment the MPRIP-NTRK1 nucleic acid molecule comprises sufficient MPRIP and sufficient NTRK1 sequence such that the encoded 5' MPRIP-3' NTRK1 fusion has kinase activity, e.g., has elevated activity, e.g., NTRK1 kinase activity, as compared with wild type NTRK1, e.g., in a cell of a cancer referred to herein. In certain embodiments, the 5' MPRIP-3' NTRK1 fusion comprises exons 1-21 from MPRIP and exons 12-17 from NTRK1. In certain embodiments, the MPRIP-NTRK1 fusion comprises at least 1, 2, 3, 4, 5, 6, 7, 8, 9, 10, 11, 12, 13, 14, 15, 16, 17, 18, 19, 20, 21 or more exons from MPRIP and at least 1, 2, 3, 4, 5, 6 or more, exons from NTRK1. In certain embodiments, the MPRIP-NTRK1 fusion comprises a fusion of exon 21 from MPRIP and exon 12 from NTRK1. In another embodiment, the MPRIP-NTRK1 fusion comprises at least 1, 2, 3, 4, 5, 6, 7, 8, 9, 10, 11, 12, 13, 14, 15, 16, 17, 18, 19, 20, 21 exons from MPRIP; and at least 1, 2, 3, 4, 5 or 6, exons from NTRK1.

In one embodiment, the nucleic acid molecule includes a nucleotide sequence that has an in-frame fusion of intron 21 of MPRIP (e.g., NM_015134) with intron 11 or intron 13 of NTRK1 (e.g., NM_002529). In another embodiment, the nucleic acid molecule includes a nucleotide sequence that includes a breakpoint. For example, the nucleic acid molecule includes a nucleotide sequence that includes the fusion junction between the MPRIP gene and the NTRK1 gene, e.g., the breakpoint between intron 21 of MPRIP and intron 11 or intron 13 of NTRK1. In other embodiments, the nucleic acid molecules includes a nucleotide sequence of one or more of nucleotide 156,845,212 of chromosome 1 coupled to (e.g., directly or indirectly juxtaposed to) one or more of nucleotide 17,080,829 of chromosome 17. In one embodiment, the nucleic acid molecule includes the nucleotide sequence of: chromosome 1 at one or more of nucleotide 156,845,212 plus or minus 10, 20, 30, 40, 50, 60, 80, 100, 150 nucleotides and chromosome 17 at one or more of nucleotide 17,080,829 plus or minus 10, 20, 30, 40, 50, 60, 80, 100, 150 nucleotides (corresponding to the breakpoint of a MPRIP-NTRK1 fusion), or a fragment thereof, or a sequence substantially identical thereto. In one embodiment, the nucleic acid molecule is complementary to at least a portion of a nucleotide sequence disclosed herein, e.g., is capable of hybridizing under a stringency condition described herein to SEQ ID NO:3 and/or SEQ ID NO: 1 or a fragment thereof. In yet other embodiment, the nucleic acid molecule hybridizes to a nucleotide sequence that is complementary to at least a portion of a nucleotide sequence disclosed herein, e.g., is capable of hybridizing under a stringency condition described herein to a nucleotide sequence complementary to SEQ ID NO:3 or 1, 5 or 6 or a fragment thereof.

In another embodiment, the MPRIP-NTRK1 fusion nucleic acid comprises at least 6, 12, 15, 20, 25, 50, 75, 100 or more nucleotides from exon 21 of MPRIP (e.g., from the nucleotide sequence of MPRIP preceding the fusion junction with NTRK1, e.g., of the MPRIP sequence shown in FIG. 4 (SEQ ID NO:3)), and at least 6, 12, 15, 20, 25, 50, 75, 100 or more nucleotides from exon 12 or exon 14 of NTRK1 (e.g., from the nucleotide sequence of NTRK1 following the fusion junction with MPRIP, e.g., of the NTRK1 sequence shown in FIG. 2 (SEQ ID NO:1)).

In other embodiments, the nucleic acid molecule includes a nucleotide sequence encoding a MPRIP-NTRK1 fusion polypeptide that includes a fragment of a MPRIP gene and a fragment of an NTRK1 gene. In one embodiment, the nucleotide sequence encodes a MPRIP-NTRK1 fusion polypeptide that includes e.g., an NTRK1 tyrosine kinase domain or a functional fragment thereof. In yet other embodiments, the nucleic acid molecule includes a nucleotide sequence encoding the amino acid sequence (e.g., a fragment of the amino acid sequence) shown in FIG. 5 (e.g., SEQ ID NO:4) and a nucleotide sequence encoding the amino acid sequence (e.g., a fragment of the amino acid sequence) shown in FIG. 3 (e.g., SEQ ID NO:2), or a fragment of the fusion, or a sequence substantially identical thereto. In yet other embodiments, the nucleic acid includes a nucleotide sequence encoding the amino acid sequence of SEQ ID NO:7, or a fragment thereof (or a sequence substantially identical thereto). In one embodiment, the encoded MPRIP-NTRK1 fusion polypeptide includes an NTRK1 tyrosine kinase domain (e.g., one or more of exons 13-17 of SEQ ID NO:3, or a functional fragment thereof.

In a related aspect, the invention features nucleic acid constructs that include the MPRIP-NTRK1 nucleic acid molecules described herein. In certain embodiments, the nucleic acid molecules are operatively linked to a native or a heterologous regulatory sequence. Also included are vectors and host cells that include the MPRIP-NTRK1 nucleic acid molecules described herein, e.g., vectors and host cells suitable for producing the nucleic acid molecules and polypeptides described herein.

In a related aspect, methods of producing the nucleic acid molecules and polypeptides described herein are also described.

In another aspect, the invention features nucleic acid molecules that reduce or inhibit the expression of a nucleic acid molecule that encodes a MPRIP-NTRK1 fusion described herein. Examples of such nucleic acid molecules include, for example, antisense molecules, ribozymes, RNAi, triple helix molecules that hybridize to a nucleic acid encoding MPRIP-NTRK1, or a transcription regulatory region of MPRIP-NTRK1, and blocks or reduces mRNA expression of MPRIP-NTRK1.

Nucleic Acid Detection and Capturing Reagents

The invention also features a nucleic acid molecule, e.g., nucleic acid fragment, suitable as probe, primer, bait or library member that includes, flanks, hybridizes to, which are useful for identifying, or are otherwise based on, the MPRIP-NTRK1 fusions described herein. In certain embodiments, the probe, primer or bait molecule is an oligonucleotide that allows capture, detection or isolation of a MPRIP-NTRK1 fusion nucleic acid molecule described herein. The oligonucleotide can comprise a nucleotide sequence substantially complementary to a fragment of the MPRIP-NTRK1 fusion nucleic acid molecules described herein. The sequence identity between the nucleic acid fragment, e.g., the oligonucleotide, and the target MPRIP-NTRK1 sequence need not be exact, so long as the sequences are sufficiently complementary to allow the capture, detection or isolation of the target sequence. In one embodiment, the nucleic acid fragment is a probe or primer that includes an oligonucleotide between about 5 and 25, e.g., between 10 and 20, or 10 and 15 nucleotides in length. In other embodiments, the nucleic acid fragment is a bait that includes an oligonucleotide between about 100 to 300 nucleotides, 130 and 230 nucleotides, or 150 and 200 nucleotides, in length.

In one embodiment, the nucleic acid fragment can be used to identify or capture, e.g., by hybridization, a MPRIP-NTRK1 fusion. For example, the nucleic acid fragment can be a probe, a primer, or a bait, for use in identifying or capturing, e.g., by hybridization, a MPRIP-NTRK1 fusion described herein. In one embodiment, the nucleic acid fragment can be useful for identifying or capturing a MPRIP-NTRK1 breakpoint, e.g., the nucleotide sequence of: chromosome 1 at nucleotide 156,845,212 plus or minus 10, 20, 30, 40, 50, 60, 80, 100, 150 nucleotides and chromosome 17 at nucleotide 17,080,829 plus or minus 10, 20, 30, 40, 50, 60, 80, 100, 150 nucleotides.

In one embodiment, the nucleic acid fragment hybridizes to a nucleotide sequence within a chromosomal rearrangement that creates an in-frame fusion of intron 21 of MPRIP with intron 11 or intron 13 of NTRK1. In one embodiment, the nucleic acid fragment hybridizes to a nucleotide sequence in the region In other embodiments, the nucleic acid molecules includes a nucleotide sequence in the region of nucleotides 156,845,212 of chromosome 1 coupled to (e.g., juxtaposed to) nucleotides in the region of nucleotides 17,080,829 of chromosome 17. In one embodiment, the nucleic acid fragment hybridizes to a nucleotide sequence that includes a breakpoint, e.g., the nucleotide sequence of: chromosome 1 at nucleotide 156,845,212 plus or minus 10, 20, 30, 40, 50, 60, 80, 100, 150 or more nucleotides and chromosome 17 at nucleotide 17,080,829 plus or minus 10, 20, 30, 40, 50, 60, 80, 100, 150 or more nucleotides. For example, the nucleic acid fragment can hybridize to a nucleotide sequence that includes the fusion junction between the MPRIP gene and the NTRK1 gene, e.g., a nucleotide sequence that includes a portion of a nucleotide sequence within introns 21 of a MPRIP gene and 11 or 13 of a NTRK1 gene.

In another embodiment, the nucleic acid fragment hybridizes to a nucleotide sequence that comprises at least 6, 12, 15, 20, 25, 50, 75, 100, 150 or more nucleotides from exon 21 of MPRIP (e.g., from the nucleotide sequence of MPRIP preceding the fusion junction with NTRK1, e.g., of the MPRIP sequence shown in FIG. 4 (SEQ ID NO:3)), and at least 6, 12, 15, 20, 25, 50, 75, 100, 150 or more nucleotides from exon 12 or exon 14 of NTRK1 (e.g., from the nucleotide sequence of NTRK1 following the fusion junction with MPRIP, e.g., of the NTRK1 sequence shown in FIG. 2 (SEQ ID NO:1)).

The probes or primers described herein can be used, for example, for FISH detection or PCR amplification. In one exemplary embodiment where detection is based on PCR, amplification of the MPRIP-NTRK1 fusion junction fusion junction can be performed using a primer or a primer pair, e.g., for amplifying a sequence flanking the fusion junctions described herein, e.g., the mutations or the junction of a chromosomal rearrangement described herein, e.g., MPRIP-NTRK1.

In one embodiment, a pair of isolated oligonucleotide primers can amplify a region containing or adjacent to a position in the MPRIP-NTRK1 fusion. For example, forward primers can be designed to hybridize to a nucleotide sequence within MPRIP genomic or mRNA sequence (e.g., a nucleotide sequence within exon 21 of MPRIP of SEQ ID NO:3), and the reverse primers can be designed to hybridize to a nucleotide sequence of NTRK1 (e.g., a nucleotide sequence within exon 12 or exon 14 of NTRK1, of SEQ ID NO: 1).

In another embodiment, the nucleic acid fragments can be used to identify, e.g., by hybridization, an MPRIP-NTRK1 fusion molecule. In one embodiment, the nucleic acid fragment hybridizes to a nucleotide sequence that includes a fusion junction between the MPRIP transcript and the NTRK1 transcript.

In certain embodiments, the nucleic acid fragments are used in a FISH assay. In one embodiment, the FISH assay is a break-apart FISH assay. In one embodiment, at least two nucleic acid fragments (e.g., probes) hybridize to (e.g., are complimentary to) at least two preselected nucleotide sequences of the MPRIP-NTRK1 fusion molecule, or an NTRK1 or MPRIP, such that a change in (e.g., the presence or absence of) a signal associated with the nucleic acid fragments, e.g., a fluorescent signal, is indicative of the presence or absence of the MPRIP-NTRK1 fusion molecule or an intact MPRIP or NTRK1. Typically, the nucleic acid fragments are associated with a label or signal, e.g., a covalently or non-covalently associated signal or label chosen from, e.g., a radiolabel, a fluorescent label, a bioluminescent label, a chemiluminescent label, an enzyme label, a binding pair label, or an affinity tag.

In some exemplary embodiments, at least one first nucleic acid fragment (e.g., probe) hybridizes to a nucleotide sequence in a 5'-region of the MPRIP genomic sequence (e.g., a nucleotide sequence within exons 1-21 of MPRIP of SEQ ID NO:3), and at least one second nucleic acid fragment (e.g., probe) hybridizes to a nucleotide sequence in a 3'-region of NTRK1 (e.g., a nucleotide sequence within exons 12-17 of NTRK1, of SEQ ID NO:1). The first and second fragments can be associated with a detectable label or signal, e.g., a fluorescent signal, such that a different signal is detected when the first and second nucleic acid fragments come to close proximity when the MPRIP-NTRK1 nucleotide sequences are present, compared to an intact, full length MPRIP or NTRK1 nucleotide sequence. The FISH assay provides an example of the aforesaid assays.

In other exemplary embodiments, at least one first nucleic acid fragment (e.g., probe) hybridizes to a nucleotide sequence in a 5'-region of the MPRIP or NTRK1 genomic sequence, and at least one second nucleic acid fragment (e.g., probe) hybridizes to a nucleotide sequence in a 3'-region of the MPRIP or NTRK1 genomic sequence, respectively. The first and second fragments can be associated with a detectable label or signal, e.g., a fluorescent signal, such that a different signal is detected when the first and second nucleic acid fragments come to close proximity when the MPRIP or NTRK1 nucleotide sequences are present, compared to an MPRIP-NTRK1 fusion nucleotide sequence. The separation of the 5'- and 3'-probes to MPRIP or NTRK1 in the MPRIP-NTRK1 fusion leads to a distinct signal compared to the signal generated when both 5'- and 3'-probes are bound to different regions of the intact, full length MPRIP or NTRK1 nucleotide sequence. The breakapart FISH assay provides an example of the aforesaid assays.

In other embodiments, the nucleic acid fragment includes a bait that comprises a nucleotide sequence that hybridizes to a MPRIP-NTRK1 fusion nucleic acid molecule described herein, and thereby allows the capture or isolation said nucleic acid molecule. In one embodiment, a bait is suitable for solution phase hybridization. In other embodiments, a bait includes a binding entity, e.g., an affinity tag, that allows capture and separation, e.g., by binding to a binding entity, of a hybrid formed by a bait and a nucleic acid hybridized to the bait.

In other embodiments, the nucleic acid fragment includes a library member comprising a MPRIP-NTRK1 nucleic acid molecule described herein. In one embodiment, the library member includes a rearrangement that results in a MPRIP-NTRK1 fusion described herein.

The nucleic acid fragment can be detectably labeled with, e.g., a radiolabel, a fluorescent label, a bioluminescent label, a chemiluminescent label, an enzyme label, a binding pair label, or can include an affinity tag; a tag, or identifier (e.g., an adaptor, barcode or other sequence identifier).

MPRIP-NTRK1 Fusion Polypeptides

In another embodiment, the MPRIP-NTRK1 fusion comprises an amino acid sequence (e.g., a fragment of the amino acid sequence) shown in FIG. 5 (SEQ ID NO:4) and an amino acid sequence (e.g., a fragment of the amino acid sequence) shown in FIG. 3 (SEQ ID NO:2), or a fragment of the fusion. In one embodiment, the MPRIP-NTRK1 fusion comprises an amino acid sequence substantially identical to the amino acid sequence (e.g., a fragment of the amino acid sequence) shown in FIG. 5 (SEQ ID NO:4) and the amino acid sequence (e.g., a fragment of the amino acid sequence) shown in FIG. 3 (SEQ ID NO:2), or a fragment thereof. In one embodiment, the MPRIP-NTRK1 fusion comprises an amino acid sequence at least 70%, at least 75%, at least 80%, at least 85%, at least 90%, at least 95%, at least 99%, at least 99.5 or greater, identical to the amino acid sequence (e.g., a fragment of the amino acid sequence) shown in FIG. 5 (SEQ ID NO:4) and the amino acid sequence (e.g., a fragment of the amino acid sequence) shown in FIG. 3 (SEQ ID NO:2). In one embodiment, the MPRIP-NTRK1 fusion comprises a sequence containing at least 10, 20, 50, 100, 500, 600, 700, 800, 900, 1000, or more amino acids of the amino acid sequence shown in FIG. 5 (SEQ ID NO:4) and FIG. 3 (SEQ ID NO:2). In one embodiment, the MPRIP-NTRK1 fusion comprises an amino acid sequence containing at least 5, 10, 20, 50, 100, 500, 600, 700, 800, 900, 1000, or more contiguous amino acids of the amino acid sequence shown in FIG. 5 (SEQ ID NO:4) and at least 5, 10, 20, 50, 100, 500, 600, 700, 800, 900, 1000, or more contiguous amino acids of the amino acid sequence shown in FIG. 3 (SEQ ID NO:2). In one embodiment, the 5' MPRIP-3' NTRK1 fusion polypeptide includes a NTRK1 receptor tyrosine kinase domain or a functional fragment thereof. In an embodiment, the 5'MPRIP-3'NTRK1 fusion polypeptide comprises sufficient NTRK1 and sufficient MPRIP sequence such that it has kinase activity, e.g., has elevated activity, e.g., NTRK1 kinase activity, as compared with wild type NTRK1, e.g., in a cell of a cancer described herein (e.g., a lung cancer, such as a lung adenocarcinoma).

In yet other embodiments, the MPRIP-NTRK1 fusion comprises the amino acid sequence of SEQ ID NO:7 (FIG. 11C), or an amino acid sequence substantially identical thereto (e.g., at least 70%, at least 75%, at least 80%, at least 85%, at least 90%, at least 95%, at least 99%, at least 99.5 or greater, identical to the amino acid sequence, or a fragment of the amino acid sequence).

In another aspect, the invention features a MPRIP-NTRK1 fusion polypeptide (e.g., a purified MPRIP-NTRK1 fusion polypeptide), a biologically active or antigenic fragment thereof, as well as reagents (e.g., antibody molecules that bind to a MPRIP-NTRK1 fusion polypeptide), methods for modulating a MPRIP-NTRK1 polypeptide activity and detection of a MPRIP-NTRK1 polypeptide.

In one embodiment, the MPRIP-NTRK1 fusion polypeptide has at least one biological activity, e.g., an NTRK1 kinase activity. In one embodiment, at least one biological activity of the MPRIP-NTRK1 fusion polypeptide is reduced or inhibited by an anti-cancer drug, e.g., a kinase inhibitor (e.g., a multikinase inhibitor or an NTRK1-specific inhibitor). Exemplary multikinase inhibitors include, but are not limited to, KRC-108 and K252a. In one embodiment, at least one biological activity of the MPRIP-NTRK1 fusion polypeptide is reduced or inhibited by an NTRK1 kinase inhibitor chosen from one or more of: lestaurtinib (CEP-701); AZ-23; indenopyrrolocarboazole 12a; GW 441756; oxindole 3; isothiazole 5n; thiazole 20h; pyridocarbazole; GNF 5837; AG 879 (Tyrphostin AG 879); Ro 08-2750; AZ623; AR523; a Pyrazolo[1;5a]pyrimidine; a Pyrrolidinyl urea; a pyrrolidinyl thiourea; a Pyrazole derivatives; a macrocyclic compound; a substituted pyrazolo[1;5a]pyrimidine; a pyridotriazole; a benzotriazole; a quinazolinyl; a pyridoquinazolinyl; a pyrrolo[2;3-d]pyrimidine; danusertib (PHA-739358); PHA-848125 (dual Ntrk/cyclin-dependent kinase inhibitor); CEP-2563; an anti-Trkl antibody; or ARRY-470, ARRY-523 or ARRY-772.

In yet other embodiments, the MPRIP-NTRK1 fusion polypeptide is encoded by a nucleic acid molecule described herein. In one embodiment, the MPRIP-NTRK1 fusion polypeptide is encoded by an in-frame fusion of intron 21 of MPRIP with intron 11 or intron 13 of NTRK1 (e.g., a sequence on chromosome 1). In another embodiment, the MPRIP-NTRK1 fusion polypeptide includes an amino acid sequence encoded by a nucleotide sequence comprising a fusion junction between the MPRIP transcript and the NTRK1 transcript.

In certain embodiments, the MPRIP-NTRK1 fusion polypeptide comprises one or more of encoded exons 1-21 from MPRIP and one or more of encoded exons 12-17 of SEQ ID NO:3 or 4, or exons 14-19 of NTRK1. In certain embodiments, the MPRIP-NTRK1 fusion polypeptide comprises at least 1, 2, 3, 4, 5, 6, 7, 8, 9, 10, 11, 12, 13, 14, 15, 16, 17, 18, 19, 20, 21 or more encoded exons from MPRIP and at least 1, 2, 3, 4, 5, 6 or more, encoded exons from NTRK1. In certain embodiments, the MPRIP-NTRK1 fusion polypeptide comprises a fusion of encoded exon 21 from MPRIP and encoded exon 12 from NTRK1 (or a fragment thereof). In other embodiments, the fusion comprises least 1, 2, 3, 4, 5, 6, 7, 8, 9, 10, 11, 12, 13, 14, 15, 16, 17, 18, 19, 20, 21 encoded exons from MPRIP; and at least 1, 2, 3, 4, 5, or 6 encoded exons from NTRK1. In certain embodiments, the MPRIP-NTRK1 fusion polypeptide comprises encoded exons 1-21 from MPRIP and exons 12-17 or exons 14-19 of NTRK1. In certain embodiments, the 5' MPRIP-3' NTRK1 fusion polypeptide comprises a fusion junction of the sequence of exon 21 from MPRIP and the sequence of exon 12 or exon 14 from NTRK1.

In certain embodiments, the MPRIP-NTRK1 fusion comprises the amino acid sequence corresponding to exon 21 or a fragment thereof from MPRIP, and the amino acid sequence corresponding to exon 12 or exon 14 or a fragment thereof from NTRK1 (e.g., as shown in FIG. 5 (SEQ ID NO:4) and FIG. 3 (SEQ ID NO:2)). In one embodiment, the MPRIP-NTRK1 fusion comprises at least 5, 10, 15, 20 or more amino acids from exon 21 of MPRIP (e.g., from the amino acid sequence of MPRIP preceding the fusion junction with NTRK1, e.g., of the MPRIP sequence shown in FIG. 5 (SEQ ID NO:4)), and at least 5, 10, 15, 20 or more amino acids from exon 12 or exon 14 of NTRK1 (e.g., from the amino acid sequence of NTRK1 following the fusion junction with MPRIP, e.g., of the NTRK1 sequence shown in FIG. 3 (SEQ ID NO:2)).

In one embodiment, the MPRIP-NTRK1 fusion polypeptide includes a NTRK1 tyrosine kinase domain or a functional fragment thereof. In a related aspect, the invention features MPRIP-NTRK1 fusion polypeptide or fragments operatively linked to heterologous polypeptides to form fusion proteins.

In another embodiment, the MPRIP-NTRK1 fusion polypeptide or fragment is a peptide, e.g., an immunogenic peptide or protein, that contains a fusion junction described herein. Such immunogenic peptides or proteins can be used to raise antibodies specific to the fusion protein. In other embodiments, such immunogenic peptides or proteins can be used for vaccine preparation. The vaccine preparation can include other components, e.g., an adjuvant.

In another aspect, the invention features antibody molecules that bind to a MPRIP-NTRK1 fusion polypeptide or fragment described herein. In embodiments, the antibody can distinguish wild type NTRK1 (or MPRIP) from MPRIP-NTRK1.

Detection Reagents and Detection of Mutations

In another aspect, the invention features a detection reagent, e.g., a purified or an isolated preparation thereof. Detection reagents can distinguish a nucleic acid, or protein sequence, having a breakpoint, e.g., a MPRIP-NTRK1 breakpoint; from a reference sequence. In one embodiment, the detection reagent detects (e.g., specifically detects) a MPRIP-NTRK1 fusion nucleic acid or a polypeptide (e.g., distinguishes a wild type NTRK1 or another NTRK1 fusion (or MPRIP) from a MPRIP-NTRK1 nucleic acid (e.g., as described herein in FIG. 4 (SEQ ID NO:3) and FIG. 3 (SEQ ID NO:2); or a MPRIP-NTRK1 polypeptide (e.g., as described herein in FIG. 5 (SEQ ID NO:4) and FIG. 3 (SEQ ID NO:2).

Detection reagents, e.g., nucleic acid-based detection reagents, can be used to identify mutations in a target nucleic acid, e.g., DNA, e.g., genomic DNA or cDNA, or RNA, e.g., in a sample, e.g., a sample of nucleic acid derived from a neoplasm or a cancer, or tumor, e.g., a lung cancer (e.g., a lung adenocarcinoma). Detection reagents, e.g., antibody-based detection reagents, can be used to identify mutations in a target protein, e.g., in a sample, e.g., a sample of protein derived from, or produced by, a neoplasm or a cancer, or tumor, e.g., a lung cancer (e.g., a lung adenocarcinoma).

Nucleic Acid Molecules

In one aspect, the invention features, an isolated nucleic acid molecule, or an isolated preparation of nucleic acid molecules, that includes a genetic alteration or mutation, e.g., a rearrangement, disclosed herein, e.g., in this section entitled Nucleic Acid Molecules, or in FIG. 1A or 1B. Such nucleic acid molecules or preparations thereof can be used to detect, e.g., sequence, a genetic alteration or mutation disclosed herein and to characterize a sample in which they are contained. The isolated nucleic acid can be a genomic or a transcribed sequence, e.g., cDNA sequence.

In another aspect, the invention features, a nucleic acid molecule (e.g., an isolated or purified) nucleic acid molecule that includes a fragment of a first gene, and a fragment of a second gene, typically a gene that encodes a kinase. In embodiments, the first gene is a gene from FIG. 1A or 1B and the second gene is a gene, e.g., a kinase from FIG. 1A or 1B. In an embodiment the fusion protein has the fusion partners of a fusion protein described in FIG. 1A or 1B.

The isolated nucleic acid molecule can comprise the entire sequence of the first fragment and the entire sequence of the second fragment, e.g., as shown in FIG. 1A or 1B.

In embodiments the isolated nucleic acid is a genomic nucleic acid molecule comprises sequence encoding the entire sequence, e.g., from the control region or beginning of the open reading frame, through the breakpoint, which may be in an intron or an exon, of the first gene, fused to the a sequence for the second gene which begins at its breakpoint and extends to the end of the gene, e.g., through the end of the open reading frame of that gene. In other embodiments the isolated nucleic acid will include the fusion junction but only a portion of the fragment of the first or second gene present in the rearrangement.

In embodiments the isolated nucleic acid is a transcribed nucleic acid, e.g., a cDNA or mRNA, and comprises sequence encoding the entire sequence, e.g., from the beginning of the mRNA through the breakpoint of the first gene fused to the a sequence for the second gene which begins at its breakpoint and extends to the end of the mRNA of the second gene. In other embodiments the isolated nucleic acid will include the fusion junction but only a portion of the fragment of the first or second gene present in the rearrangement. In embodiments a transcribed nucleic acid will have one or more exon from the first gene fused, in frame, to one or more exons of the second gene. In embodiments a transcribed nucleic acid will have comprise the fusion of the C terminus of C terminal exon of the first gene fragment with the N terminus of the N terminal exon of the second gene.

In embodiments the fusion puts the kinase activity of the second gene under the control of the first gene.

In embodiments the isolated nucleic acid, e.g., a genomic or transcribed nucleic acid, e.g., a cDNA or RNA, comprises the fusion junction, e.g., a fusion junction from FIG. 1A or 1B, and is at least 10, 20, 30, 40, 50, 60, 70, 80, 100, 125, 150, 200, 250, 300, 350, or 400 nucleotides in length, but optionally less than 1,000, 1,500, or 2,000 nucleotides in length. In embodiments, the isolated nucleic acid, e.g., a genomic or transcribed nucleic acid, e.g., a cDNA or RNA, comprises the fusion junction, e.g., a fusion junction from FIG. 1A or 1B, and is between 10 and 2,000, 10 and 1,500, 10 and 1,000, 10 and 500, 10 and 400, 10 and 300, 10 and 200, 10 and 100, 20 and 2,000, 20 and 1,500, 20 and 1,000, 20 and 500, 20 and 400, 20 and 300, 20 and 200, 20 and 100, 30 and 2,000, 30 and 1,500, 30 and 1,000, 30 and 500, 30 and 400, 30 and 300, 30 and 200, 30 and 100 nucleotides in length.

In one embodiment, the isolated nucleic acid, e.g., a transcribed nucleic acid, e.g., a cDNA or RNA, comprises a fusion, e.g., an in-frame fusion, from FIG. 1B or a fusion transcribed from a genomic fusion from FIG. 1A.

In an embodiment, the isolated nucleic acid, e.g., a transcribed nucleic acid, e.g., a cDNA or RNA, comprises a fusion, e.g., an in-frame fusion, of the 3' terminus of an exon of a fragment of the first gene of FIG. 1B to the 5' terminus of an exon of a fragment of the second gene of FIG. 1B. In an embodiment the fusion is between the exons listed in FIG. 1B. In embodiments, fusion is not be between the specific exons found in FIG. 1B but is between other exons of the first gene to other exons of the second gene of a fusion from FIG. 1B.

In an embodiment, the isolated nucleic acid, e.g., a transcribed nucleic acid, e.g., a cDNA or RNA, comprises a fusion, e.g., an in-frame fusion, of the C terminal exon of a fragment of first gene of FIG. 1B to the N terminus of an exon a fragment of the second gene other than the second gene exon shown in FIG. 1B. By way of example, an exon, e.g., exon 21 of MPRIP is fused to an exon of NTRK1 other than the exon listed in FIG. 1B, e.g., it is fused to an exon other than exon 14.

In an embodiment, the isolated nucleic acid, e.g., a transcribed nucleic acid, e.g., a cDNA or RNA, comprises a fusion, e.g., an in-frame fusion, of the N terminal exon of a fragment of the second gene of FIG. 1B to the C terminus of an exon of a fragment of the first gene other than the first-gene exon shown in FIG. 1B.

In an embodiment of the isolated nucleic acid, e.g., a genomic or transcribed nucleic acid, e.g., a cDNA or RNA, the second gene is a kinase and sufficient exonic sequence is present to confer kinase activity. In an embodiment of the isolated nucleic acid, e.g., a genomic or transcribed nucleic acid, e.g., a cDNA or mRNA, sufficient sequence of the first gene is present to allow expression of kinase activity of the fusion partner.

In an embodiment of the isolated nucleic acid, e.g., a transcribed nucleic acid, e.g., a cDNA or RNA, comprises a fusion junction between: MPRIP and NTRK1;

wherein sufficient exonic sequence from the kinase is present to confer kinase activity and sufficient sequence of the other gene is present to allow expression of kinase activity of the fusion partner.

Also included are genomic fusion that can be transcribed to provide a transcribed nucleic acid, e.g., a cDNA or RNA, described herein.

In one embodiment, the isolated nucleic acid, e.g., a genomic nucleic acid, comprises a fusion of a first and second gene from FIG. 1A.

In embodiments, the fusion is between genes that are fusion partners in a fusion described in FIG. 1A or 1B. In an embodiment sufficient sequence from the second gene is present to confer kinase activity on an encoded protein and sufficient sequence is present from the first gene to provide for expression of the kinase activity of the fusion partner in an encoded protein.

In an embodiment, the isolated nucleic acid, e.g., a genomic sequence, comprises a fusion of the 3' terminus of a fragment of a first gene to the 5' terminus of a fragment of a second gene, shown in FIG. 1A. In an embodiment, the 3' terminus of the fragment of the first gene is within 10, 20, 30, 40, 50, 60, 70, 80, 90, or 100 nucleotides (in either direction) of the 3-terminus provided in FIG. 1A for the first gene. In an embodiment, the 5' terminus of the fragment of the second gene is within 10, 20, 30, 40, 50, 60, 70, 80, 90, or 100 nucleotides (in either direction) of the 5' terminus provided in FIG. 1 for the second gene. By way of example, for MPRIP and NTRK1 fusion, the 3' terminus can be chr5:17,080,829+/−N nucleotides and the 5' terminus is chr1:156,845,212+/−N nucleotides, wherein N, independently is 10, 20, 30, 40, 50, 60, 70, 80, 90, or 100 nucleotides. In embodiments, N is 50 nucleotides.

The fusion need not be between the specific exons found in FIG. 1A or 1B but can be fusions of other exons of the first gene to other exons of the second gene, provided that sufficient sequence from the second gene is present to confer kinase activity on an encoded protein and sufficient sequence is present from the first gene to provide for expression of the kinase activity of the fusion partner in an encoded protein.

In another aspect, methods of producing the nucleic acid molecules and polypeptides described herein are also described.

Detection Reagents and Detection of Mutations

In another aspect, the invention features a detection reagent, e.g., a purified or an isolated preparation thereof. Detection reagents can distinguish a nucleic acid, e.g., a genomic or transcribed nucleic acid, e.g., a cDNA or RNA, or protein sequence, having a breakpoint or fusion junction described herein, e.g., in FIG. 1A or 1B, or in the section herein entitled Nucleic Acid Molecules, from a reference sequence, e.g., a sequence not having the breakpoint or fusion junction.

In one embodiment, the detection reagent detects (e.g., specifically detects) a fusion nucleic acid or a polypeptide (e.g., distinguishes a wild type or another fusion from a fusion described herein, e.g., in FIG. 1A or 1B or in the section herein entitled Nucleic Acid Molecules.

Detection reagents, e.g., nucleic acid-based detection reagents, can be used to identify mutations, e.g., rearrangements or fusion junctions described herein, e.g., in FIG. 1A or 1B or in the section herein entitled Nucleic Acid Molecules, in a target nucleic acid, e.g., DNA, e.g., genomic DNA or a transcribed nucleic acid, cDNA, or RNA, e.g., in a sample, e.g., a sample of nucleic acid derived from a neoplastic or tumor cell, e.g., a primary or metastatic cell. In an embodiment a rearrangement or fusion junction described in FIG. 1A or 1B or in the section herein entitled Nucleic Acid Molecules, is detected in a sample of the corresponding cancer listed in FIG. 1A. Detection reagents, e.g., antibody-based detection reagents, can be used to identify, mutations described herein, e.g., in FIG. 1A or 1B or in the section herein entitled Nucleic Acid Molecules, in a target protein, e.g., in a sample, e.g., a sample of protein derived from, or produced by, a primary or metastatic cell.

Nucleic Acid-based Detection Reagents

In an embodiment, the detection reagent comprises a nucleic acid molecule, e.g., a DNA, RNA or mixed DNA/RNA molecule, comprising sequence which is complementary with a nucleic acid sequence on a target nucleic acid, e.g., a nucleic acid that includes the rearrangement or fusion junction, (the sequence on the target nucleic acid that is bound by the detection reagent is referred to herein as the "detection reagent binding site" and the portion of the detection reagent that corresponds to the detection reagent binding site is referred to as the "target binding site"). In an embodiment, the detection reagent binding site is disposed in relationship to the interrogation position, e.g., one or both nucleotides flanking the fusion junction, such that binding (or in embodiments, lack of binding) of the detection reagent to the detection reagent binding site, or the proximity of binding to probes of a detection reagent to their detection binding sites, allows differentiation of mutant and reference sequences for a mutant described herein (e.g., a rearrangement having a breakpoint described herein, e.g., in FIG. 1A or 1B or in the section herein entitled Nucleic Acid Molecules, from a reference sequence. The detection reagent can be modified, e.g., with a label or other moiety, e.g., a moiety that allows capture.

In embodiments, a mutation described herein, e.g., in FIG. 1A or 1B or in the section herein entitled Nucleic Acid Molecules, is distinguished from reference by binding or lack of binding of a detection reagent.

In embodiments, e.g., with proximity based probes, e.g., FISH probes, a mutation described herein, e.g., in FIG. 1A or 1B or in the section herein entitled Nucleic Acid Molecules, and a reference are distinguished by the proximity of the binding of two probes of the detection reagent. E.g., a genomic rearrangement that alters the distance between two binding sites can be detected with proximity based probes, e.g., FISH probes.

In an embodiment, the detection reagent comprises a nucleic acid molecule, e.g., a DNA, RNA or mixed DNA/RNA molecule, which, e.g., in its target binding site, includes the interrogation position, e.g., one or more of the nucleotides that flank a fusion junction, and which can distinguish (e.g., by affinity of binding of the detection reagent to a target nucleic acid, e.g., a genomic or transcribed nucleic acid, e.g., a cDNA or RNA, or the ability for a reaction, e.g., a ligation or extension reaction with the detection reagent) between a mutation, e.g., a translocation described herein, and a reference sequence. In embodiments, the interrogation position, e.g., one or both nucleotides flanking the fusion junction can correspond to a terminal, e.g., to a 3' or 5' terminal nucleotide, a nucleotide immediately adjacent to a 3' or 5' terminal nucleotide, or to another internal nucleotide, of the detection reagent or target binding site.

In embodiments, the difference in the affinity of the detection reagent for a target nucleic acid, e.g., a genomic or transcribed nucleic acid, e.g., a cDNA or RNA, comprising the mutant, e.g., a rearrangement or fusion junction, described in FIG. 1A or 1B or in the section herein entitled Nucleic Acid Molecules, and that for a target nucleic acid comprising the reference sequence allows determination of the presence or absence of the mutation (or reference) sequence. Typically, such detection reagents, under assay conditions, will exhibit substantially higher levels of binding only to the mutant or only to the reference sequence, e.g., will exhibit substantial levels of binding only to the mutant or only to the reference sequence.

In embodiments, binding allows (or inhibits) a subsequent reaction, e.g., a subsequent reaction involving the detection reagent or the target nucleic acid. E.g., binding can allow ligation, or the addition of one or more nucleotides to a nucleic acid, e.g., the detection reagent, e.g., by DNA polymerase, which can be detected and used to distinguish mutant from reference. In embodiments, the interrogation position, e.g., one or both nucleotides flanking the fusion junction is located at the terminus, or sufficiently close to the terminus, of the detection reagent or its target binding site, such that hybridization, or a chemical reaction, e.g., the addition of one or more nucleotides to the detection reagent, e.g., by DNA polymerase, only occurs, or occurs at a substantially higher rate, when there is a perfect match between the detection reagent and the target nucleic acid at the interrogation position, e.g., one or both nucleotides flanking the fusion junction or at a nucleotide position within 1, 2, or 3 nucleotides of the interrogation position, e.g., one or both nucleotides flanking the fusion junction.

In an embodiment, the detection reagent comprises a nucleic acid, e.g., a DNA, RNA or mixed DNA/RNA molecule wherein the molecule, or its target binding site, is adjacent (or flanks), e.g., directly adjacent, to the interrogation position, e.g., one or more of the nucleotides that flank a fusion junction, and which can distinguish between a mutation, e.g., a mutant, e.g., a rearrangement or fusion junction, described in FIG. 1A or 1B or in the section herein entitled Nucleic Acid Molecules, and a reference sequence, in a target nucleic acid, e.g., a genomic or transcribed nucleic acid, e.g., a cDNA or RNA.

In embodiments, the detection reagent binding site is adjacent to the interrogation position, e.g., one or both nucleotides flanking the fusion junction, e.g., the 5' or 3'terminal nucleotide of the detection reagent, or its target binding site, is adjacent, e.g., between 0 (directly adjacent) and 1,000, 500, 400, 200, 100, 50, 10, 5, 4, 3, 2, or 1 nucleotides from the interrogation position, e.g., one or both nucleotides flanking the fusion junction. In embodiments, the outcome of a reaction will vary with the identity of the nucleotide at the interrogation position, e.g., one or both nucleotides flanking the fusion junction, allowing one to distinguish between mutant and reference sequences. E.g., in the presence of a first nucleotide at the interrogation position, e.g., one or both nucleotides flanking the fusion junction, a first reaction will be favored over a second reaction. E.g., in a ligation or primer extension reaction, the product will differ, e.g., in charge, sequence, size, or susceptibility to a further reaction (e.g., restriction cleavage) depending on the identity of the nucleotide at the interrogation position, e.g., one or both nucleotides flanking the fusion junction. In embodiments the detection reagent comprises paired molecules (e.g., forward and reverse primers), allowing for amplification, e.g., by PCR amplification, of a duplex containing the interrogation position, e.g., one or both nucleotides flanking the fusion junction. In such embodiments, the presence of the mutation can be determined by a difference in the property of the amplification product, e.g., size, sequence, charge, or susceptibility to a reaction, resulting from a sequence comprising the interrogation position, e.g., one or both nucleotides flanking the fusion junction, and a corresponding sequence having a reference nucleotide at the interrogation position, e.g., one or both nucleotides flanking the fusion junctions. In embodiments, the presence or absence of a characteristic amplification product is indicative of the identity of the nucleotide at the interrogation site and thus allows detection of the mutation.

In embodiments, the detection reagent, or its target binding site, is directly adjacent to the interrogation position, e.g., one or both nucleotides flanking the fusion junction, e.g., the 5' or 3'terminal nucleotide of the detection reagent is directly adjacent to the interrogation position, e.g., one or both nucleotides flanking the fusion junction. In embodiments, the identity of the nucleotide at the interrogation position, e.g., one or both nucleotides flanking the fusion junction, will determine the nature of a reaction, e.g., a reaction involving the detection reagent, e.g., the modification of one end of the detection reagent. E.g., in the presence of a first nucleotide at the interrogation position, e.g., one or both nucleotides flanking the fusion junction, a first reaction will be favored over a second reaction. By way of example, the presence of a first nucleotide at the interrogation position, e.g., one or both nucleotides flanking the fusion junction, e.g., a nucleotide associated with a mutation, can promote a first reaction, e.g., the addition of a complementary nucleotide to the detection reagent. By way of example, the presence of an A at the interrogation position, e.g., one or both nucleotides flanking the fusion junction, will cause the incorporation of a T, having, e.g., a first colorimetric label, while the presence of a G and the interrogation position, e.g., one or both nucleotides flanking the fusion junction, will cause the incorporation for a C, having, e.g., a second colorimetric label. In an embodiment, the presence of a first nucleotide at the nucleotide will result in ligation of the detection reagent to a second nucleic acid. E.g., a third nucleic acid can be hybridized to the target nucleic acid sufficiently close to the interrogation site that if the third nucleic acid has an exact match at the interrogation site it will be ligated to the detection reagent. Detection of the ligation product, or its absence, is indicative of the identity of the nucleotide at the interrogation site and thus allows detection of the mutation.

A variety of readouts can be employed. E.g., binding of the detection reagent to the mutant or reference sequence can be followed by a moiety, e.g., a label, associated with the detection reagent, e.g., a radioactive or enzymatic label. In embodiments the label comprises a quenching agent and a signaling agent and hybridization results in altering the distance between those two elements, e.g., increasing the distance and un-quenching the signaling agent. In embodiments, the detection reagent can include a moiety that allows separation from other components of a reaction mixture. In embodiments, binding allows cleavage of the bound detection reagent, e.g., by an enzyme, e.g., by the nuclease activity of the DNA polymerase or by a restriction enzyme. The cleavage can be detected by the appearance or disappearance of a nucleic acid or by the separation of a quenching agent and a signaling agent associated with the detection reagent. In embodiments, binding protects, or renders the target susceptible, to further chemical reaction, e.g., labeling or degradation, e.g., by restriction enzymes. In embodiments binding with the detection reagent allows capture separation or physical manipulation of the target nucleic acid to thereby allow for identification. In embodiments binding can result in a detect localization of the detection reagent or target, e.g., binding could capture the target nucleic acid or displace a third nucleic acid. Binding can allow for determination of the presence of mutant or reference sequences with FISH, particularly in the case of rearrangements. Binding can allow for the extension or other size change in a component, e.g., the detection reagent, allowing distinction between mutant and reference sequences. Binding can allow for the production, e.g., by PCR, of an amplicon that distinguishes mutant from reference sequence.

In an embodiment the detection reagent, or the target binding site, is between 5 and 2000, 5 and 1000, 5 and 500, 5 and 300, 5 and 250, 5 and 200, 5 and 150, 5 and 100, 5 and 50, 5 and 25, 5 and 20, 5 and 15, or 5 and 10 nucleotides in length. In an embodiment the detection reagent, or the target binding site, is between 10 and 2000, 10 and 1000, 10 and 500, 10 and 300, 10 and 250, 10 and 200, 10 and 150, 10 and 100, 10 and 50, 10 and 25, 10 and 20, or 10 and 15, nucleotides in length. In an embodiment the detection reagent, or the target binding site, is between 10 and 2000, 10 and 1000, 20 and 500, 20 and 300, 20 and 250, 20 and 200, 20 and 150, 20 and 100, 20 and 50, or 20 and 25 nucleotides in length. In an embodiment the detection reagent, or the target binding site, is sufficiently long to distinguish between mutant and reference sequences and is less than 100, 200, 300, 400, 500, 1,000, 1,500, and 2,000 nucleotides in length.

In embodiments, the detection reagent comprises two probes which will bind with a first proximity to one another if a mutation described herein, e.g, a rearrangement or fusion junction, described in FIG. 1A or 1B or in the section herein entitled Nucleic Acid Molecules, is present and with a second proximity if the mutation is not present. Typically, one of the proximities will result in production of a signal and the other will not. E.g., one probe can comprise a signal generator and the other can comprise a signal quencher. If the proximity is close there will be no signal and if the proximity is less close then signal will be produced.

Preparations of Mutant Nucleic Acid and Uses Thereof

In another aspect, the invention features purified or isolated preparations of a neoplastic or tumor cell nucleic acid, e.g., DNA, e.g., genomic DNA or cDNA, or RNA, containing an interrogation position described herein, useful for determining if a mutation disclosed herein is present. The nucleic acid includes the interrogation position, and typically additional fusion sequence on one or both sides of the interrogation position. In addition the nucleic acid can contain heterologous sequences, e.g., adaptor or priming sequences, typically attached to one or both terminus of the nucleic acid. The nucleic acid also includes a label or other moiety, e.g., a moiety that allows separation or localization.

In embodiments, the nucleic acid is between 20 and 1,000, 30 and 900, 40 and 800, 50 and 700, 60 and 600, 70 and 500, 80 and 400, 90 and 300, or 100 and 200 nucleotides in length (with or without heterologous sequences). In one embodiment, the nucleic acid is between 40 and 1,000, 50 and 900, 60 and 800, 70 and 700, 80 and 600, 90 and 500, 100 and 400, 110 and 300, or 120 and 200 nucleotides in length (with or without heterologous sequences). In another embodiment, the nucleic acid is between 50 and 1,000, 50 and 900, 50 and 800, 50 and 700, 50 and 600, 50 and 500, 50 and 400, 50 and 300, or 50 and 200 nucleotides in length (with or without heterologous sequences). In embodiments, the nucleic acid is of sufficient length to allow sequencing (e.g., by chemical sequencing or by determining a difference in $T_m$ between mutant and reference preparations) but is optionally less than 100, 200, 300, 400, or 500 nucleotides in length (with or without heterologous sequences).

Such preparations can be used to sequence nucleic acid from a sample, e.g., a neoplastic or tumor sample. In an embodiment the purified preparation is provided by in situ amplification of a nucleic acid provided on a substrate. In embodiments the purified preparation is spatially distinct from other nucleic acids, e.g., other amplified nucleic acids, on a substrate.

In an embodiment, the purified or isolated preparation of nucleic acid is derived from a neoplasm or tumor of a type described herein, e.g., neoplasm and/or cancer, e.g., a lung cancer.

In one embodiment, the fusion nucleic acid is derived from a lung adenocarcinoma.

Such preparations can be used to determine if a sample comprises mutant sequence, e.g., a translocation as described herein. In one embodiment, the translocation includes a breakpoint.

Nucleic acids that include the aforesaid breakpoint, e.g., a breakpoint described herein, are collectively referred to herein as fusion nucleic acids.

In another aspect, the invention features, a method of determining the sequence of an interrogation position for a mutation described herein, comprising:

providing a purified or isolated preparations of nucleic acid or fusion nucleic acid, e.g., DNA, e.g., genomic DNA or cDNA, or RNA, containing an interrogation position described herein, sequencing, by a method that breaks or forms a chemical bond, e.g., a covalent or non-covalent chemical bond, e.g., in a detection reagent or a target sequence, the nucleic acid so as to determine the identity of the nucleotide at an interrogation position. The method allows determining if a mutation described herein is present.

In an embodiment, sequencing comprises contacting the fusion nucleic acid with a detection reagent described herein.

In an embodiment, sequencing comprises determining a physical property, e.g., stability of a duplex form of the fusion nucleic acid, e.g., $T_m$, that can distinguish mutant from reference sequence.

In an embodiment, the fusion nucleic acid is derived from a neoplasm or a tumor of a type described herein, e.g., a neoplasm and/or a cancer, e.g., a lung cancer. In one embodiment, the fusion nucleic acid is derived from a lung adenocarcinoma.

Reaction Mixtures and Devices

In another aspect, the invention features, a reaction mixture comprising:

a) a sample, or nucleic acid, e.g., DNA, e.g., genomic DNA or cDNA, or RNA, e.g., from a cancer, containing:

an interrogation position for a mutation, e.g., a rearrangement or fusion junction, described in FIG. 1A, 1B or 1C or in the section herein entitled Nucleic Acid Molecules; or a mutation, e.g., a rearrangement or fusion junction, described in FIG. 1A or 1B or in the section herein entitled Nucleic Acid Molecules; and b) a detection reagent described herein, e.g., a detection reagent described in the section herein entitled, Detection Reagents and Detection of Mutations, e.g., in the section herein entitled, Nucleic Acid-based Detection Reagents.

In an embodiment, the sample comprises nucleic acid from a cancer, e.g., a lung cancer (e.g., a lung adenocarcinoma).

In an embodiment the sample, or nucleic acid in the sample, is from a cancer, e.g., a lung cancer (e.g., a lung adenocarcinoma), and the detection reagent detects a mutant, e.g., a rearrangement or fusion junction disclosed in FIG. 1A, 1B or 1C; or in the section herein entitled Nucleic Acid Molecules.

In an embodiment, the sample, or nucleic acid in the sample, is from a cancer listed in FIG. 1A, and the detection reagent detects a mutant, e.g., a rearrangement or fusion junction disclosed in FIG. 1A, 1B or 1C; or in the section herein entitled Nucleic Acid Molecules, in a fusion of the two genes in the fusion associated with that cancer in FIG. 1A, e.g., a lung cancer (e.g., a lung adenocarcinoma).

In an embodiment:

the sample, or nucleic acid in the sample, is from a lung adenocarcinoma, and the detection reagent is one that detects a fusion of the MPRIP and NTRK1 genes, e.g., a detection reagent that detects a mutant, e.g., a rearrangement or fusion junction described in FIG. 1A, 1B or 1C or in the section herein entitled Nucleic Acid Molecules, for a fusion of MPRIP and NTRK1.

In another aspect, the invention features, purified or isolated preparations of a fusion nucleic acid, e.g., DNA, e.g., genomic DNA or cDNA, or RNA, containing an interrogation position, e.g., one or both nucleotides flanking the fusion junction, described herein or a mutation, e.g., a rearrangement or fusion junction, described in FIG. 1A, 1B or 1C or in the section herein entitled Nucleic Acid Molecules. In embodiments the preparation is useful for determining if a mutation disclosed herein is present. In embodiments the preparation is disposed in a device, e.g., a sequencing device, or a sample holder for use in such a device. In an embodiment, the fusion nucleic acid is derived from a neoplasm or a tumor of a type described herein, e.g., a lung cancer (e.g., a lung adenocarcinoma). In an embodiment the nucleic acid is from a lung cancer (e.g., a lung adenocarcinoma). In an embodiment the nucleic acid is from a lung cancer (e.g., a lung adenocarcinoma) and the device also includes a detection reagent is one that detects a fusion of the genes associate with that cancer, e.g., a detection reagent that detects a mutant, e.g., a rearrangement or fusion junction described in FIG. FIG. 1A, 1B or 1C or in the section herein entitled Nucleic Acid Molecules, for a fusion of the genes that are the fusion partners with the fusion associated with a lung cancer (e.g., a lung adenocarcinoma).

In another aspect, the invention features, purified or isolated preparations of a fusion nucleic acid, e.g., DNA, e.g., genomic DNA or cDNA, or RNA, containing an interrogation position, e.g., one or both nucleotides flanking the fusion junction, described herein or a mutation, e.g., a rearrangement or fusion junction, described in FIG. 1A or 1B or in the section herein entitled Nucleic Acid Molecules, useful for determining if a mutation disclosed herein is present, disposed in a device for determining a physical or chemical property, e.g., stability of a duplex, e.g., $T_m$ or a sample holder for use in such a device. In an embodiment, the device is a calorimeter. In an embodiment the fusion nucleic acid is derived from a neoplasm or a tumor of a type described herein, e.g., a lung cancer (e.g., a lung adenocarcinoma).

The detection reagents described herein can be used to determine if a mutation described herein is present in a sample. In embodiments, the sample comprises a nucleic acid that is derived from a neoplastic or a tumor cell, e.g. a cancer described herein, e.g., a lung cancer (e.g., a lung adenocarcinoma). The cell can be from a neoplastic or a tumor sample, e.g., a biopsy taken from the neoplasm or the tumor; from circulating tumor cells, e.g., from peripheral blood; or from a blood or plasma sample.

In another aspect, the invention features, a method of making a reaction mixture by combining:

a) a sample, or nucleic acid, e.g., DNA, e.g., genomic DNA or cDNA, or RNA, e.g., from a cancer, containing:

an interrogation position for a mutation, e.g., a rearrangement or fusion junction, described in FIG. 1A, 1B or 1C or in the section herein entitled Nucleic Acid Molecules; or a mutation, e.g., a rearrangement or fusion junction, described in FIG. 1A, 1B or 1C or in the section herein entitled Nucleic Acid Molecules; and b) a detection reagent described herein, e.g., a detection reagent described in the section herein entitled, Detection Reagents and Detection of Mutations, e.g., in the section herein entitled, Nucleic Acid-based Detection Reagents.

A mutation described herein, can be distinguished from a reference, e.g., a non-mutant or wildtype sequence, by reaction with an enzyme that reacts differentially with the mutation and the reference. E.g., they can be distinguished by cleavage with a restriction enzyme that has differing activity for the mutant and reference sequences. E.g., the invention includes a method of contacting a nucleic acid comprising a mutation described herein with such an enzyme and determining if a product of that cleavage which can distinguish mutant form reference sequence is present.

In one aspect the inventions provides, a purified preparation of a restriction enzyme cleavage product which can distinguish between mutant and reference sequence, wherein one end of the cleavage product is defined by an enzyme that cleaves differentially between mutant and reference sequence. In an embodiment, the cleavage product includes the interrogation position, e.g., one or both nucleotides flanking the fusion junction.

Protein-Based Detection Reagents, Methods, Reaction Mixtures and Devices

A mutant protein described herein can be distinguished from a reference, e.g., a non-mutant or wild-type protein, by reaction with a reagent, e.g., a substrate, e.g, a substrate for catalytic activity, e.g., phosphorylation or other fusion protein activity, or an antibody that reacts differentially with the mutant and reference protein. In one aspect, the invention includes a method of contacting a sample comprising a mutant protein described herein with such reagent and determining if the mutant protein is present in the sample.

Accordingly, in another aspect, the invention features, a reaction mixture comprising:

a) a sample, e.g., a cancer sample, comprising a fusion protein having fusion partners described in FIG. 1A, 1B or 1C, e.g., a fusion protein encoded by a mutation described in FIG. 1A, 1B or 1C or in the section herein entitled Nucleic Acid Molecules; and b) a detection reagent, e.g., a substrate, e.g, a substrate for catalytic activity, e.g., phosphorylation or other fusion protein activity, or an antibody, that reacts differentially with the mutant and reference protein.

In another aspect, the invention features, a method of making a reaction mixture comprising combining:

a) a sample, e.g., a cancer sample, comprising a fusion protein having fusion partners described in FIG. 1A, 1B or 1C, e.g., a fusion protein encoded by a mutation described in FIG. 1A, 1B or 1C or in the section herein entitled Nucleic Acid Molecules; and b) a detection reagent, e.g., a substrate, e.g, a substrate for catalytic activity, e.g., phosphorylation or other fusion protein activity, or an antibody, that reacts differentially with the mutant and reference protein.

Kits

In another aspect, the invention features a kit comprising a detection reagent as described herein.

Methods of Treating and/or Reducing NTRK1-Fusion Molecule Activity

In another aspect, the invention features a method of reducing an activity of a fusion molecule described herein. The method includes contacting the fusion molecule, or a fusion molecule-expressing cell, with an agent that inhibits an activity or expression of the fusion molecule (e.g., an inhibitor, e.g., a kinase inhibitor). In one embodiment, the contacting step can be effected in vitro, e.g., in a cell lysate or in a reconstituted system. Alternatively, the method can be performed on cells in culture, e.g., in vitro or ex vivo. In other embodiments, the method can be performed on fusion molecule-expressing cells present in a subject, e.g., as part of an in vivo (e.g., therapeutic or prophylactic) protocol. In an embodiment the method is practiced on an animal subject (e.g., an in vivo animal model). In certain embodiments, the fusion molecule is a nucleic acid molecule or a polypeptide as described herein.

In a related aspect, a method of inhibiting, reducing, or treating a hyperproliferative disorder, e.g., a neoplasm (including benign, pre-malignant or malignant (e.g., a cancer), in a subject is provided. The method includes administering to the subject a preselected therapeutic agent, e.g., an anti-cancer agent (e.g., an inhibitor, e.g., a kinase inhibitor as described herein), as a single agent, or in combination, in an amount sufficient to reduce, inhibit or treat the activity or expression of MPRIP-NTRK1 (e.g., a MPRIP-NTRK1 fusion described herein), thereby inhibiting, reducing, or treating the hyperproliferative disorder in the subject. "Treatment" as used herein includes, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

In one embodiment, the subject is a mammal, e.g., a human. In one embodiment, the subject has, or at risk of having a cancer at any stage of disease. In other embodiments, the subject is a patient, e.g., a cancer patient. In one embodiment, the subject treated has a MPRIP-NTRK1 fusion; e.g., the subject has a tumor or cancer harboring a MPRIP-NTRK1 fusion. In other embodiments, the subject has been previously identified as having a MPRIP-NTRK1 fusion. In yet other embodiments, the subject has been previously identified as being likely or unlikely to respond to treatment with a protein kinase inhibitor, e.g., a subject that has previously participated in a clinical trial. In other embodiments, the subject has been previously identified as being likely or unlikely to respond to treatment with a protein kinase inhibitor, based on the presence of the MPRIP-NTRK1 fusion.

In one embodiment, the inhibitor, e.g., the kinase inhibitor, is administered based on a determination that a fusion molecule described herein (e.g., an MPRIP-NTRK1 fusion) is present in a subject, e.g., based on its present in a subject's sample. Thus, treatment can be combined with fusion molecule detection or evaluation method, e.g., as described herein, or administered in response to a determination made by a fusion molecule detection or evaluation method, e.g., as described herein. In certain embodiments, the kinase inhibitor is administered responsive to acquiring knowledge or information of the presence of the fusion molecule in a subject. In one embodiment, the kinase inhibitor is administered responsive to acquiring knowledge or information on the subject's genotype, e.g., acquiring knowledge or information that the patient's genotype has a fusion molecule. In other embodiments, the kinase inhibitor is administered responsive to receiving a communication (e.g., a report) of the presence of the fusion molecule in a subject (e.g., a subject's sample). In yet other embodiments, the kinase inhibitor is administered responsive to information obtained from a collaboration with another party that identifies the presence of the fusion molecule in a subject (e.g., a subject's sample). In other embodiments, the kinase inhibitor is administered responsive to a determination that the fusion molecule is present in a subject. In one embodiment, the determination of the presence of the fusion molecule is carried out using one or more of the methods, e.g., the sequencing methods, described herein. In other embodiments, the determination of the presence of the fusion molecule includes receiving information on the subject's fusion molecule genotype, e.g., from another party or source.

The methods can, optionally, further include the step(s) of identifying (e.g., evaluating, diagnosing, screening, and/or selecting) a subject at risk of having, or having, a fusion molecule described herein. In one embodiment, the method further includes one or more of: acquiring knowledge or information of the presence of the fusion molecule in a subject (e.g., a subject's sample); acquiring knowledge or information on the subject's genotype, e.g., acquiring a knowledge or information that the patient's genotype has a fusion molecule; receiving a communication (e.g., a report) of the presence of the fusion molecule in a subject (e.g., a subject's sample); or collaborating with another party that identifies the presence of the fusion molecule in a subject.

In one embodiment, the subject treated has a fusion molecule described herein; e.g., the subject has a tumor or cancer harboring a fusion molecule described herein. In other embodiments, the subject has been previously identified as having a fusion molecule described herein. In yet other embodiments, the subject has been previously identified as being likely or unlikely to respond to treatment with a protein kinase inhibitor, e.g., a subject that has previously participated in a clinical trial. In other embodiments, the subject has been previously identified as being likely or unlikely to respond to treatment with a protein kinase inhibitor, based on the presence of the fusion molecule described herein. In one embodiment, the subject is a mammal, e.g., a human. In one embodiment, the subject has, or at risk of having a cancer at any stage of disease. In other embodiments, the subject is a patient, e.g., a cancer patient.

In other embodiments, the subject treated is a cancer patient who has participated in a clinical trial. For example, the subject participated in a clinical trial that evaluated a kinase inhibitor (e.g., a multikinase inhibitor, a specific kinase inhibitor). In other embodiment, the subject participated in a clinical trial that evaluates upstream or downstream targets of the specific kinase. In one embodiment, said cancer patient responded to the kinase inhibitor evaluated.

In certain embodiments, the neoplasm or neoplastic cell is a benign, pre-malignant, malignant (cancer) or metastasis. In certain embodiments, the cancer is a solid tumor, a soft tissue tumor, or a metastatic lesion. In one embodiment, the cancer is chosen from lung adenocarcinoma, cervical adenocarcinoma, uterus endometrial adenocarcinoma, glioblastoma, melanoma, spindle cell sarcoma, ameloblastic fibroscarcoma, adenocarcinoma, cholangiocarcinoma, urothelial (transitional cell) carcinoma, ovarian epithelial carcinoma, colorectal adenocarcinoma, breast carcinoma, prostate carcinoma, or pancreas ductal adenocarcinoma. In one embodiment, the cancer is chosen from a lung cancer, a pancreatic cancer, melanoma, a colorectal cancer, an esophageal-gastric cancer, a thyroid cancer, or an adenocarcinoma.

In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, a lung carcinoid tumor, large cell carcinoma, a lung neuroendocrine tumor, or a combination thereof. In one embodiment, the lung cancer is NSCLC or SCC. In another embodiment, the cancer is a lung cancer (e.g., lung adenocarcinoma) that has an alteration in NTRK, e.g., has an MPRIP-NTRK molecule described herein. In another embodiment, the cancer is a lung cancer (e.g., lung adenocarcinoma) that has no detectable altered level or activity in one or more of EGFR, KRAS, ALK, ROS1 or RET.

In one embodiment, the anti-cancer agent or inhibitor is a kinase inhibitor. For example, the kinase inhibitor is a multi-kinase inhibitor (e.g., KRC-108 or K252a) or a NTRK1-specific inhibitor. In one embodiment, the kinase inhibitor is a NTRK1-inhibitor including, but not limited to, lestaurtinib (CEP-701); AZ-23; indenopyrrolocarboazole 12a; GW 441756; oxindole 3; isothiazole 5n; thiazole 20h; pyridocarbazole; GNF 5837; AG 879 (Tyrphostin AG 879); Ro 08-2750; AZ623; AR523; a Pyrazolo[1;5a]pyrimidine; a Pyrrolidinyl urea; a pyrrolidinyl thiourea; a Pyrazole derivatives; a macrocyclic compound; a substituted pyrazolo[1; 5a]pyrimidine; a pyridotriazole; a benzotriazole; a quinazolinyl; a pyridoquinazolinyl; a pyrrolo[2;3-d]pyrimidine; danusertib (PHA-739358); PHA-848125 (dual Ntrk/cyclin-dependent kinase inhibitor); CEP-2563; an anti-Trkl antibody; and ARRY-470, ARRY-523 or ARRY-772.

In other embodiments, the anti-cancer agent or inhibitor is an HSP90 inhibitor. Previous studies have shown that the HSP90 inhibitor 17-DMAG disrupted Ntrk1/Hsp90 binding, which results in degradation and depletion of Ntrk1, and reduced the growth of myeloid leukemia cells (Rao R, Nalluri S, Fiskus W, et al. (2010) *Mol Cancer Ther* 9(8): 2232-42). In one embodiment, the HSP90 inhibitor is a geldanamycin derivative, e.g., a benzoquinone or hygroquinone ansamycin HSP90 inhibitor. For example, the HSP90 inhibitor can be chosen from one or more of 17-AAG (also known as tanespimycin or CNF-1010), 17-DMAG, BIIB-021 (CNF-2024), BIIB-028, AUY-922 (also known as VER-49009), SNX-5422, STA-9090, AT-13387, XL-888, MPC-3100, CU-0305, CNF-1010, Macbecin I, Macbecin II, CCT-018159, CCT-129397, IPI-493, IPI-504, PU-H71, or PF-04928473 (SNX-2112).

In other embodiments, the anti-cancer agent or inhibitor is an antagonist of a fusion molecule described herein which inhibits the expression of nucleic acid encoding the fusion molecule. Examples of such fusion molecule antagonists include nucleic acid molecules, for example, antisense molecules, ribozymes, RNAi, triple helix molecules that hybridize to a nucleic acid encoding a fusion molecule described herein, or a transcription regulatory region, and blocks or reduces mRNA expression of the fusion molecule.

In other embodiments, the anti-cancer agent or inhibitor, e.g., kinase inhibitor, is administered in combination with a second therapeutic agent or a different therapeutic modality, e.g., anti-cancer agents, and/or in combination with surgical and/or radiation procedures. For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

In one embodiment, the kinase inhibitor (e.g., the multi-kinase inhibitor or the NTRK1-specific inhibitor as described herein) is administered in combination with an HSP90 inhibitor, e.g., an HSP90 inhibitor as described herein.

Screening Methods

In another aspect, the invention features a method, or assay, for screening for agents that modulate, e.g., inhibit, the expression or activity of a fusion molecule described herein. The method includes contacting a fusion molecule described herein, or a cell expressing a fusion molecule described herein, with a candidate agent; and detecting a change in a parameter associated with a fusion molecule described herein, e.g., a change in the expression or an activity of the fusion molecule. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the fusion molecule is detected, the candidate agent is identified as an inhibitor. In another embodiment, if an increase in expression or activity of the fusion molecule is detected, the candidate agent is identified as an activator. In certain embodiments, the fusion molecule is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a fusion molecule described herein (e.g., a mammalian cell, a tumor cell or cell line, a recombinant cell). In yet other embodiments, the contacting step is effected in a cell in vivo (a fusion molecule-expressing cell present in a subject, e.g., an animal subject (e.g., an in vivo animal model).

Exemplary parameters evaluated include one or more of:

(i) a change in binding activity, e.g., direct binding of the candidate agent to a fusion polypeptide described herein; a binding competition between a known ligand and the candidate agent to a fusion polypeptide described herein;

(ii) a change in kinase activity, e.g., phosphorylation levels of a fusion polypeptide described herein (e.g., an increased or decreased autophosphorylation); or a change in phosphorylation of a target of an kinase. In certain embodiments, a change in kinase activity, e.g., phosphorylation, is detected by any of Western blot (e.g., using an antibody specific for either of the genes associated with a fusion molecule described herein; a phosphor-specific antibody, detecting a shift in the molecular weight of a fusion polypeptide described herein), mass spectrometry, immunoprecipitation, immunohistochemistry, immunomagnetic beads, among others;

(iii) a change in an activity of a cell containing a fusion molecule described herein (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a fusion polypeptide or nucleic acid molecule described herein.

In one embodiment, a change in a cell free assay in the presence of a candidate agent is evaluated. For example, an activity of a fusion molecule described herein, or interaction of a fusion molecule described herein with a downstream ligand can be detected. In one embodiment, a fusion polypeptide described herein is contacted with a ligand, e.g., in solution, and a candidate agent is monitored for an ability to modulate, e.g., inhibit, an interaction, e.g., binding, between the fusion polypeptide and the ligand.

In other embodiments, a change in an activity of a cell is detected in a cell in culture, e.g., a cell expressing a fusion molecule described herein (e.g., a mammalian cell, a tumor cell or cell line, a recombinant cell). In one embodiment, the cell is a recombinant cell that is modified to express a fusion nucleic acid described herein, e.g., is a recombinant cell transfected with a fusion nucleic acid described herein. The transfected cell can show a change in response to the expressed fusion molecule, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a fusion molecule described herein. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a fusion molecule described herein (e.g., tumorigenic cells expressing a fusion molecule described herein). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In other embodiments, a change in expression of a fusion molecule described herein can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is a small molecule compound, e.g., a kinase inhibitor, a nucleic acid (e.g., antisense, siRNA, aptamer, ribozymes, microRNA), an antibody molecule (e.g., a full antibody or antigen binding fragment thereof that binds to a gene of a fusion molecule described herein). The candidate agent can be obtained from a library (e.g., a commercial library of kinase inhibitors) or rationally designed (e.g., based on the kinase domain of a fusion described herein).

Methods for Detecting Fusions

In another aspect, the invention features a method of determining the presence of a fusion as described herein. In one embodiment, the fusion is detected in a nucleic acid molecule or a polypeptide. The method includes detecting whether a fusion nucleic acid molecule or polypeptide is present in a cell (e.g., a circulating cell), a tissue (e.g., a tumor), or a sample, e.g., a tumor sample, from a subject. In one embodiment, the sample is a nucleic acid sample. In one embodiment, the nucleic acid sample comprises DNA, e.g., genomic DNA or cDNA, or RNA, e.g., mRNA. In other embodiments, the sample is a protein sample.

In one embodiment, the sample is, or has been, classified as non-malignant using other diagnostic techniques, e.g., immunohistochemistry.

In one embodiment, the sample is acquired from a subject (e.g., a subject having or at risk of having a cancer, e.g., a patient), or alternatively, the method further includes acquiring a sample from the subject. The sample can be chosen from one or more of: tissue, e.g., cancerous tissue (e.g., a tissue biopsy), whole blood, serum, plasma, buccal scrape, sputum, saliva, cerebrospinal fluid, urine, stool, circulating tumor cells, circulating nucleic acids, or bone marrow. In certain embodiments, the sample is a tissue (e.g., a tumor biopsy), a circulating tumor cell or nucleic acid.

In one embodiment, the cancer is chosen from lung adenocarcinoma, cervical adenocarcinoma, uterus endometrial adenocarcinoma, glioblastoma, melanoma, spindle cell sarcoma, ameloblastic fibroscarcoma, adenocarcinoma, cholangiocarcinoma, urothelial (transitional cell) carcinoma, ovarian epithelial carcinoma, colorectal adenocarcinoma, breast carcinoma, prostate carcinoma, or pancreas ductal adenocarcinoma. In embodiments, the tumor is from a cancer described herein, e.g., is chosen from a lung cancer, a colorectal cancer, an esophageal-gastric cancer, a thyroid cancer, an adenocarcinoma or a melanoma.

In one embodiment, the cancer is a lung cancer, e.g., a lung adenocarcinoma. In other embodiment, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, a lung carcinoid tumor, large cell carcinoma, a lung neuroendocrine tumor, or a combination thereof. In one embodiment, the lung cancer is NSCLC or SCC. In another embodiment, the cancer is a lung cancer (e.g., lung adenocarcinoma) that has an alteration in NTRK, e.g., has an MPRIP-NTRK molecule described herein. In another embodiment, the cancer is a lung cancer (e.g., lung adenocarcinoma) that has no detectable altered level or activity in one or more of EGFR, KRAS, ALK, ROS1 or RET.

In one embodiment, the subject is at risk of having, or has a cancer (e.g., a patient with a cancer described herein).

In other embodiments, the fusion molecule is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

In one embodiment, the method includes: contacting a nucleic acid sample, e.g., a genomic DNA sample (e.g., a chromosomal sample or a fractionated, enriched or otherwise pre-treated sample) or a gene product (mRNA, cDNA), obtained from the subject, with a nucleic acid fragment (e.g., a probe or primer as described herein (e.g., an exon-specific probe or primer) under conditions suitable for hybridization, and determining the presence or absence of the fusion nucleic acid molecule. The method can, optionally, include enriching a sample for the gene or gene product.

In a related aspect, a method for determining the presence of a fusion nucleic acid molecule described herein is provided. The method includes: acquiring a sequence for a position in a nucleic acid molecule, e.g., by sequencing at least one nucleotide of the nucleic acid molecule (e.g., sequencing at least one nucleotide in the nucleic acid molecule that comprises the fusion), thereby determining that the fusion molecule is present in the nucleic acid molecule. Optionally, the sequence acquired is compared to a reference sequence, or a wild type reference sequence. In one embodiment, the nucleic acid molecule is from a cell (e.g., a circulating cell), a tissue (e.g., a tumor), or any sample from a subject (e.g., blood or plasma sample). In other embodiments, the nucleic acid molecule from a tumor sample (e.g., a tumor or cancer sample) is sequenced. In one embodiment, the sequence is determined by a next generation sequencing method. The method further can further include acquiring, e.g., directly or indirectly acquiring, a sample, e.g., a tumor or cancer sample, from a subject (e.g., a patient). In certain embodiments, the cancer is chosen from a lung cancer, colorectal cancer, esophageal-gastric cancer or melanoma.

In another aspect, the invention features a method of analyzing a tumor or a circulating tumor cell. The method includes acquiring a nucleic acid sample from the tumor or the circulating cell; and sequencing, e.g., by a next generation sequencing method, a nucleic acid molecule, e.g., a nucleic acid molecule that includes a fusion molecule as described herein.

In yet other embodiment, a fusion polypeptide is detected. The method includes: contacting a protein sample with a reagent which specifically binds to a fusion polypeptide described herein; and detecting the formation of a complex of the fusion polypeptide and the reagent. In one embodiment, the reagent is labeled with a detectable group to facilitate detection of the bound and unbound reagent. In one embodiment, the reagent is an antibody molecule, e.g., is selected from the group consisting of an antibody, and antibody derivative, and an antibody fragment.

In yet another embodiment, the level (e.g., expression level) or activity the fusion molecule is evaluated. For example, the level (e.g., expression level) or activity of the fusion molecule (e.g., mRNA or polypeptide) is detected and (optionally) compared to a pre-determined value, e.g., a reference value (e.g., a control sample).

In yet another embodiment, the fusion molecule is detected prior to initiating, during, or after, a treatment, e.g., treatment with a kinase inhibitor, in a subject having a fusion described herein.

In one embodiment, the fusion molecule is detected at the time of diagnosis with a cancer. In other embodiment, the fusion molecule is detected at a pre-determined interval, e.g., a first point in time and at least at a subsequent point in time.

In certain embodiments, responsive to a determination of the presence of the fusion molecule, the method further includes one or more of:

(1) stratifying a patient population (e.g., assigning a subject, e.g., a patient, to a group or class);

(2) identifying or selecting the subject as likely or unlikely to respond to a treatment, e.g., a kinase inhibitor treatment as described herein;

(3) selecting a treatment option, e.g., administering or not administering a preselected therapeutic agent, e.g., a kinase inhibitor as described herein; or (4) prognosticating the time course of the disease in the subject (e.g., evaluating the likelihood of increased or decreased patient survival).

In certain embodiments, the kinase inhibitor is a multi-kinase inhibitor or a specific inhibitor.

In certain embodiments, responsive to the determination of the presence of a fusion molecule described herein, the subject is classified as a candidate to receive treatment with a kinase inhibitor, e.g., a kinase inhibitor as described herein. In one embodiment, responsive to the determination of the presence of a fusion molecule described herein, the subject, e.g., a patient, can further be assigned to a particular class if a fusion is identified in a sample of the patient. For example, a patient identified as having a fusion molecule described herein can be classified as a candidate to receive treatment with a kinase inhibitor, e.g., a specific kinase inhibitor as described herein. In one embodiment, the subject, e.g., a patient, is assigned to a second class if the mutation is not present. For example, a patient who has a lung tumor that does not contain a fusion molecule described herein, may be determined as not being a candidate to receive a kinase inhibitor, e.g., a specific kinase inhibitor as described herein.

In another embodiment, responsive to the determination of the presence of the fusion molecule, the subject is identified as likely to respond to a treatment that comprises a kinase inhibitor e.g., a kinase inhibitor as described herein.

In yet another embodiment, responsive to the determination of the presence of the fusion molecule, the method includes administering a kinase inhibitor, e.g., a kinase inhibitor as described herein, to the subject.

Method of Evaluating a Tumor or a Subject

In another aspect, the invention features a method of evaluating a subject (e.g., a patient), e.g., for risk of having or developing a cancer, e.g., a lung cancer, colorectal cancer or skin cancer. The method includes: acquiring information or knowledge of the presence of a fusion as described herein in a subject (e.g., acquiring genotype information of the subject that identifies a fusion as being present in the subject); acquiring a sequence for a nucleic acid molecule identified herein (e.g., a nucleic acid molecule that includes a fusion molecule sequence described herein); or detecting the presence of a fusion nucleic acid or polypeptide in the subject), wherein the presence of the fusion is positively correlated with increased risk for, or having, a cancer associated with such a fusion.

The method can further include acquiring, e.g., directly or indirectly, a sample from a patient and evaluating the sample for the present of a fusion molecule described herein.

The method can further include the step(s) of identifying (e.g., evaluating, diagnosing, screening, and/or selecting) the subject as being positively correlated with increased risk for, or having, a cancer associated with the fusion molecule.

In another embodiment, a subject identified has having a fusion molecule described herein is identified or selected as likely or unlikely to respond to a treatment, e.g., a kinase inhibitor treatment as described herein. The method can further include treating the subject with a kinase inhibitor, e.g., a kinase inhibitor as described herein.

In certain embodiments, the subject is a patient or patient population that has participated in a clinical trial. In one embodiment, the subject has participated in a clinical trial for evaluating a kinase inhibitor (e.g., a multi-kinase inhibitor or a specific kinase inhibitor). In one embodiment, the clinical trial is discontinued or terminated. In one embodiment, the subject responded favorably to the clinical trial, e.g., experience an improvement in at least one symptom of a cancer (e.g., decreased in tumor size, rate of tumor growth, increased survival). In other embodiments, the subject did not respond in a detectable way to the clinical trial.

In a related aspect, a method of evaluating a patient or a patient population is provided. The method includes: identifying, selecting, or obtaining information or knowledge that the patient or patient population has participated in a clinical trial; acquiring information or knowledge of the presence of a fusion molecule described herein in the patient or patient population (e.g., acquiring genotype information of the subject that identifies a fusion molecule described herein as being present in the subject); acquiring a sequence for a nucleic acid molecule identified herein (e.g., a nucleic acid molecule that includes a fusion sequence); or detecting the presence of a fusion nucleic acid or polypeptide described herein, in the subject), wherein the presence of the fusion identifies the patient or patient population as having an increased risk for, or having, a cancer associated with the fusion molecule.

In some embodiments, the method further includes treating the subject with a kinase inhibitor, e.g., a kinase inhibitor as described herein.

Reporting

Methods described herein can include providing a report, such as, in electronic, web-based, or paper form, to the patient or to another person or entity, e.g., a caregiver, e.g., a physician, e.g., an oncologist, a hospital, clinic, third-party payor, insurance company or government office. The report can include output from the method, e.g., the identification of nucleotide values, the indication of presence or absence of a fusion molecule described herein, or wildtype sequence. In one embodiment, a report is generated, such as in paper or electronic form, which identifies the presence or absence of an alteration described herein, and optionally includes an identifier for the patient from which the sequence was obtained.

The report can also include information on the role of a fusion molecule described herein, or wildtype sequence, in disease. Such information can include information on prognosis, resistance, or potential or suggested therapeutic options. The report can include information on the likely effectiveness of a therapeutic option, the acceptability of a therapeutic option, or the advisability of applying the therapeutic option to a patient, e.g., a patient having a sequence, alteration or mutation identified in the test, and in embodiments, identified in the report. For example, the report can include information, or a recommendation on, the administration of a drug, e.g., the administration at a preselected dosage or in a preselected treatment regimen, e.g., in combination with other drugs, to the patient. In an embodiment, not all mutations identified in the method are identified in the report. For example, the report can be limited to mutations in genes having a preselected level of correlation with the occurrence, prognosis, stage, or susceptibility of the cancer to treatment, e.g., with a preselected therapeutic option. The report can be delivered, e.g., to an entity described herein, within 7, 14, or 21 days from receipt of the sample by the entity practicing the method.

In another aspect, the invention features a method for generating a report, e.g., a personalized cancer treatment report, by obtaining a sample, e.g., a tumor sample, from a subject, detecting a fusion molecule described herein in the sample, and selecting a treatment based on the mutation identified. In one embodiment, a report is generated that annotates the selected treatment, or that lists, e.g., in order of preference, two or more treatment options based on the mutation identified. In another embodiment, the subject, e.g., a patient, is further administered the selected method of treatment.

Unless otherwise defined, all technical and scientific terms used herein have the same meaning as commonly understood by one of ordinary skill in the art to which this invention belongs. Although methods and materials similar or equivalent to those described herein can be used in the practice or testing the invention, suitable methods and materials are described below. All publications, patent applications, patents, and other references mentioned herein are incorporated by reference in their entirety. In case of conflict, the present specification, including definitions, will control. In addition, the materials, methods, and the example are illustrative only and not intended to be limiting.

The details of one or more embodiments featured in the invention are set forth in the accompanying drawings and the description below. Other features, objects, and advantages featured in the invention will be apparent from the description and drawings, and from the claims.

BRIEF DESCRIPTION OF DRAWINGS

FIGS. 1A-1C are tables summarizing the fusion molecules and the rearrangement events described herein.

FIG. 1A summarizes the following: the name of the fusion (referred to as "fusion"); the tissue source (referred to as "disease"); the approximate locations of the first and second breakpoints that give rise to the rearrangement events (±50 nucleotides) (referred to as "Breakpoint 1" and "Breakpoint 2," respectively); and the type of rearrangement (referred to as "rearrangement").

FIG. 1B summarizes the following: the name of the fusion (referred to as "fusion"); the accession number of the full length sequences that contain the 5'- and the 3'-exon sequences (referred to as "5' Transcript ID" and "3' Transcript ID," respectively); and the identity of the last exon of the 5' transcript and the first exon of the 3' transcript. The sequences corresponding to the accession numbers provided in FIG. 1B are set forth in the figures appended herein. Alternatively, the sequences can be found by searching the RefSeq Gene as databased at UCSC Genome Browser (genome.ucsc.edu). For example, the following link can be used: genome.ucsc.edu/cgi-bin/hgc?hgsid=309144129&c=chr4&o=1795038&t=1810599&g=refGene&i=NM_000142 to search for Accession Number=NM_002529.

FIG. 1C summarizes the following: the name of the fusion; the SEQ ID NOs. of the nucleotide (Nt) and amino acid (Aa) sequences of the fusion (if shown), the 5' partner, and the 3' partner; and the figure in which the sequence is shown. For example, Nt and Aa sequences of MPRIP have SEQ ID NOs: 3 and 4, respectively, which are shown in FIGS. 4 and 5, respectively. The Nt and Aa sequences of NTRK1 have SEQ ID NOs: 1 and 2, which are shown in FIGS. 2 and 3 respectively.

FIG. 2 depicts the nucleotide sequence of NTRK1 cDNA (NM_002529, SEQ ID NO: 1). The exon boundaries are shown in bold and underlined. The start of the first exon is shown by a single underline. Further exons (second, third, fourth) are indicated consecutively from 5' to 3' orientation by the underline of two consecutive nucleotides. The start codon is shown in bold and italics. The stop codon is shown in italics and underlined.

FIG. 3 depicts the amino acid sequence of NTRK1 (SEQ ID NO: 2).

FIG. 4 depicts the nucleotide sequence of MPRIP cDNA (NM_015134, SEQ ID NO: 3). The exon boundaries are shown in bold and underlined. The start of the first exon is shown by a single underline. Further exons (second, third, fourth) are indicated consecutively from 5' to 3' orientation by the underline of two consecutive nucleotides. The start codon is shown in bold and italics. The stop codon is shown in italics and underlined.

FIG. 5 depicts the amino acid sequence of MPRIP (SEQ ID NO: 4).

Figure 10A:
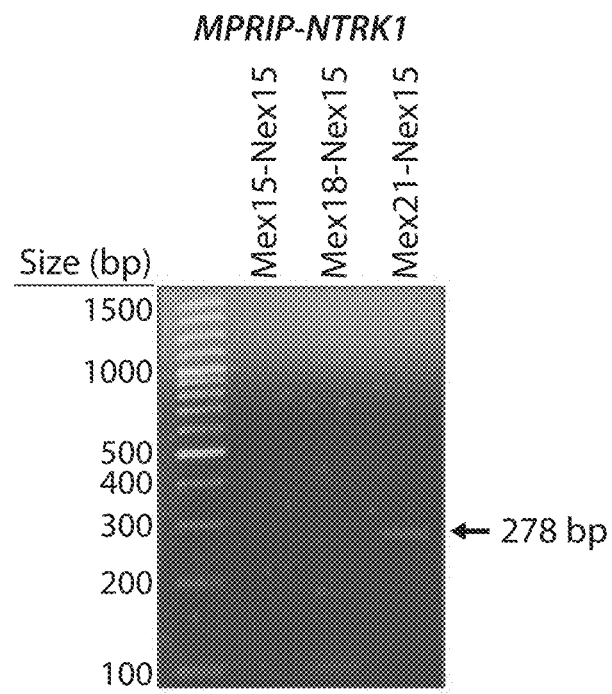
Figure 10B:
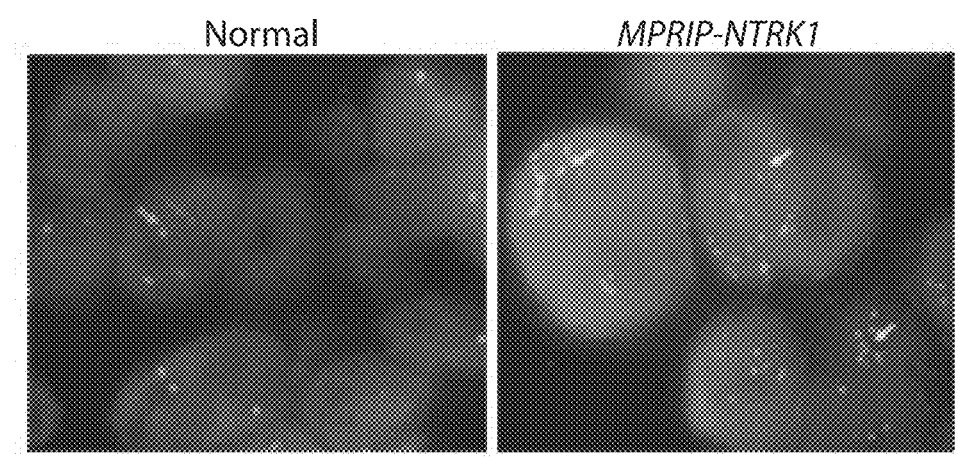

FIGS. 10A-10B show RT-PCR analysis of MPRIP-NTRK1 samples and fusion FISH analysis of MPRIP-NTRK1 translocation. RT-PCR demonstrates mRNA expression of the novel fusion transcripts. RNA extracted from frozen tumor sample harboring the (a) MPRIP-NTRK1 was subject to RT-PCR followed by agarose gel electrophoresis and DNA sequencing (FIG. 6b). (b) Fusion FISH analysis of negative control tumor sample (left) or tumor cells from index patient harboring MPRIP-NTRK1 fusion (right) hybridized with fusion probe set specific for MPRIP (chromosome 17) and NTRK1 (chromosome 1) showing clear separation of the signals in the negative control cells, but close proximity of the signals in tumor cells from the index patient indicating a chromosomal translocation.

FIG. 11A shows the DNA sequence of NTRK1 fusion cDNA (SEQ ID NO:5). The complete cDNA sequence of MPRIP-NTRK1 (M21;N14) with sequence derived from MPRIP and that of NTRK1. Capital letters represent nucleotides contained within the open reading frame. The start of the NTRK1 sequence is indicated by the underlined nucleotides.

FIG. 11B depicts the nucleotide sequence of an MPRIP-NTRK1 fusion (exons 1-21 of MPRIP fused to exons 12-17 of NTRK1, SEQ ID NO: 6). In this fusion, exon 21 of MPRIP is fused to exon 12 of NTRK1. The nucleotide sequence of NTRK1 is indicated by the shaded nucleic acids.

FIG. 11C depicts the corresponding amino acid sequence of an MPRIP-NTRK1 fusion (SEQ ID NO: 7). In this fusion, the amino acid sequence encoded by exons 1-21 of MPRIP is fused to the amino acid sequence encoded by exons 12-17 of NTRK1. The amino acid sequence of NTRK1 is indicated by the shaded amino acids. The G amino acid indicated in bold and dark shading is a Glycine residue encoded by the nucleotides "GCC" in which the G nucleotide is derived from MPRIP and CC nucleotides are derived from NTRK1.

Figure 12A:
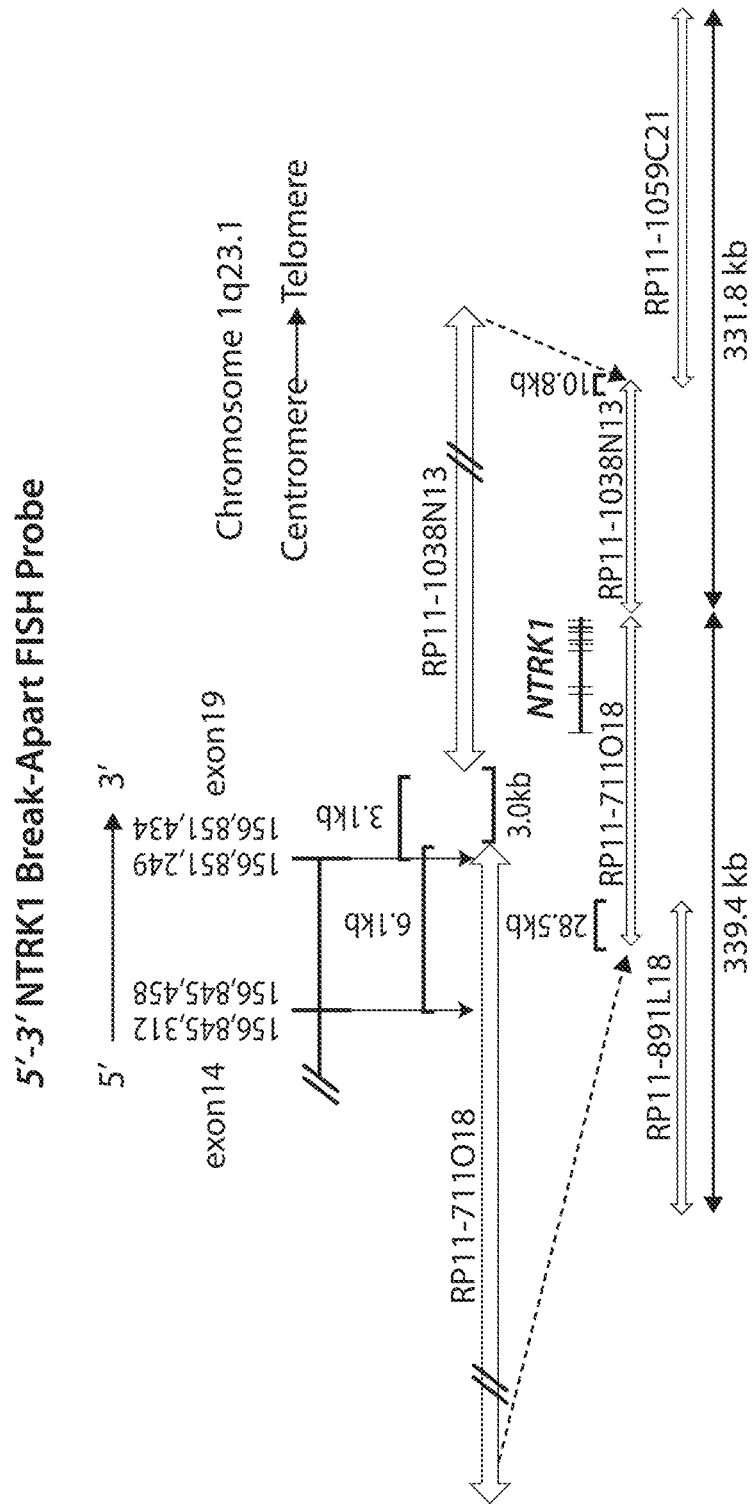
Figure 12B:
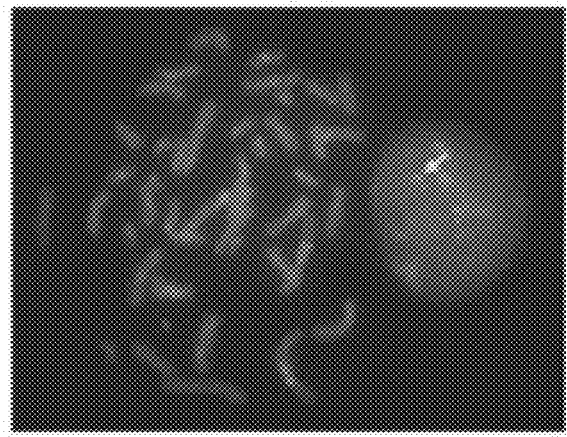
Figure 12C:
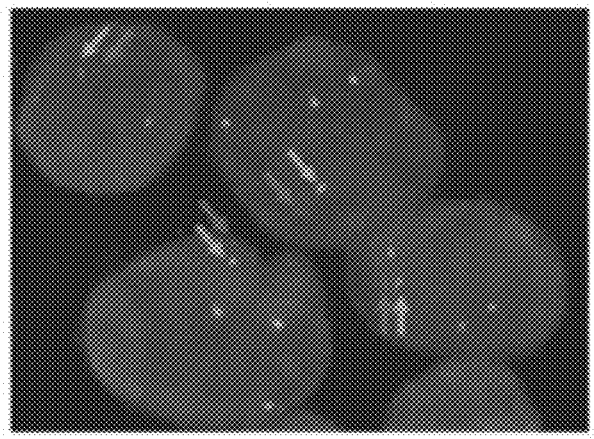

FIGS. 12A-12C depict the design and testing of NTRK1 break-apart FISH probe. (a) Design of NTRK1 break-apart probe set aligned against the NTRK1 encoding region of chromosome 1q23.1. (b) Cell line GM09948 with a normal karyotype showing metaphase spread and interphase nuclei demonstrating close proximity of the 5' (green) and 3' (red) signals indicating an intact NTRK1 gene. (c) KM12 cells which harbor a TPM3-NTRK1 gene fusion showing clear separation of the 5' (green) and 3' (red) signals indicating a rearrangement of the NTRK1 gene.

Figure 13:
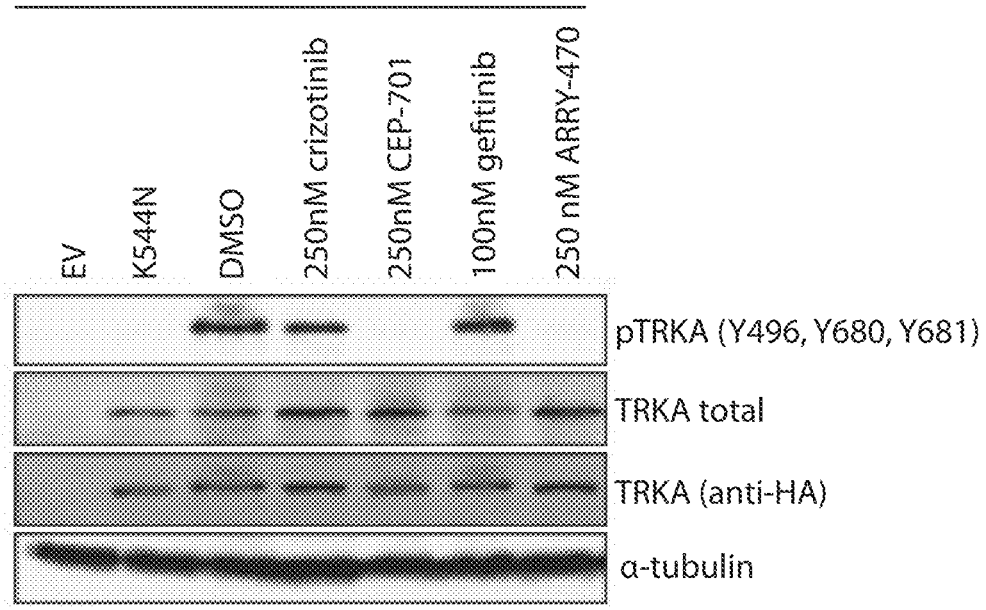

FIG. 13 shows the expression and drug inhibition of NTRK1 fusions in NIH3T3 cells. NIH3T3 cells expressing (a) RIP-TRKA were treated with the indicated doses of drugs for 5 h prior to cell lysis and immunoblot analysis of pTRKA, TRKA, pAKT, AKT, pERK1/2, ERK1/2, pSTAT3, and STAT3 as indicated.

Figure 14:
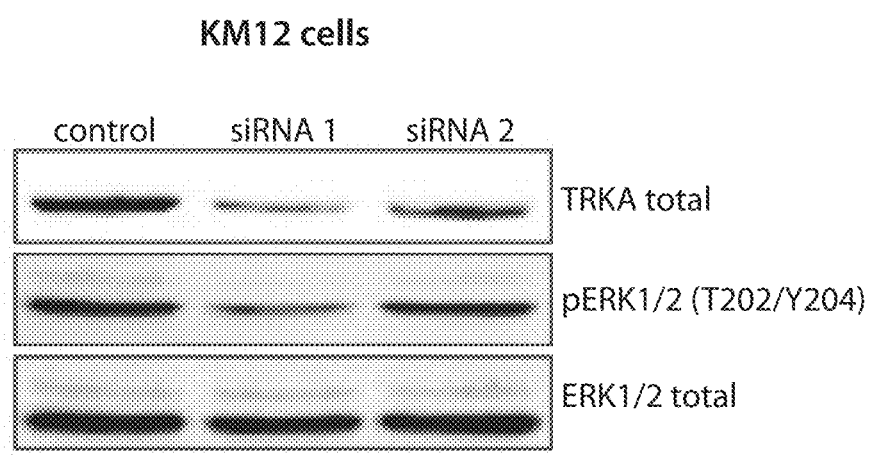

FIG. 14 shows siRNA-mediated knock-down of TRKA inhibits proliferative signaling and cellular proliferation in KM12 cells. KM12 cells were transfected with siRNAs targeting NTRK1 and then harvested 48 hr later. Cell lysates were analyzed by immunoblot to detect TRKA, pERK1/2 and ERK1/2.

Figure 15:
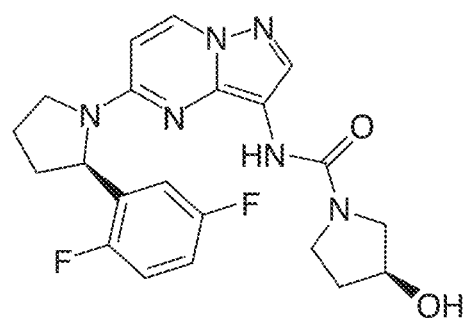

FIG. 15 depicts the chemical structure of ARRY-470.

Figure 16:
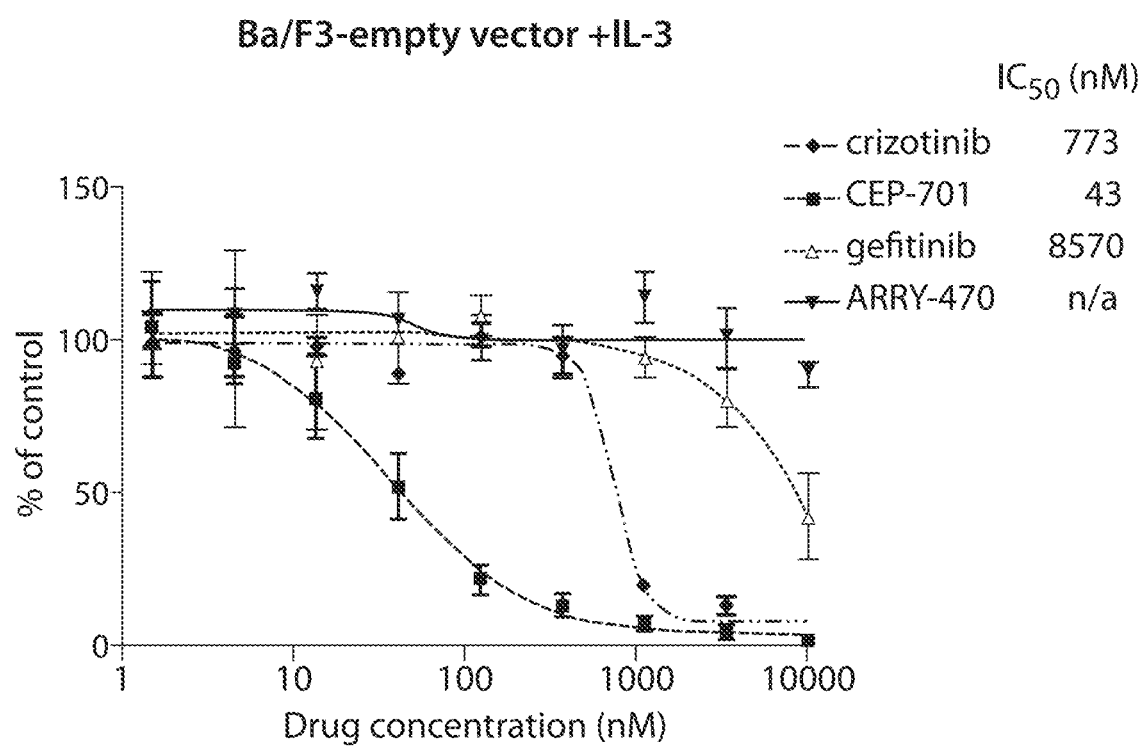

FIG. 16 shows treatment of Ba/F3 cells in the presence of IL-3. Ba/F3 cells expressing empty vector were grown in the presence of IL-3 and treated with a range of doses of ARRY-470, CEP-701, crizotinib, or gefitinib. $IC_{50}$ values are listed (n=3). Values represent the mean±SEM.

Figure 17A:
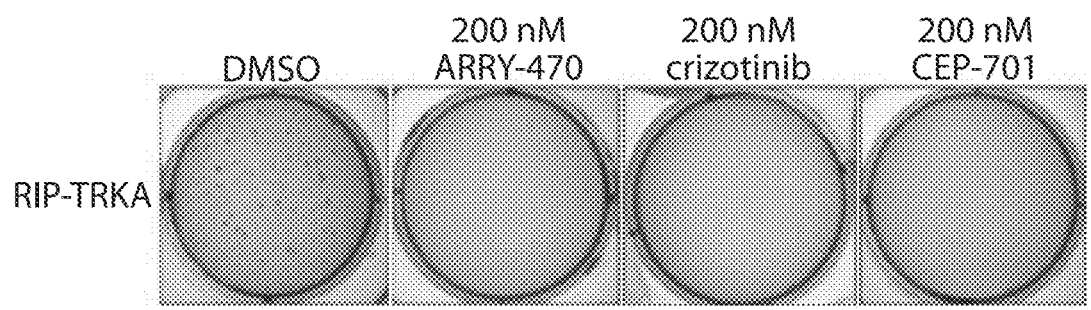
Figure 17B:
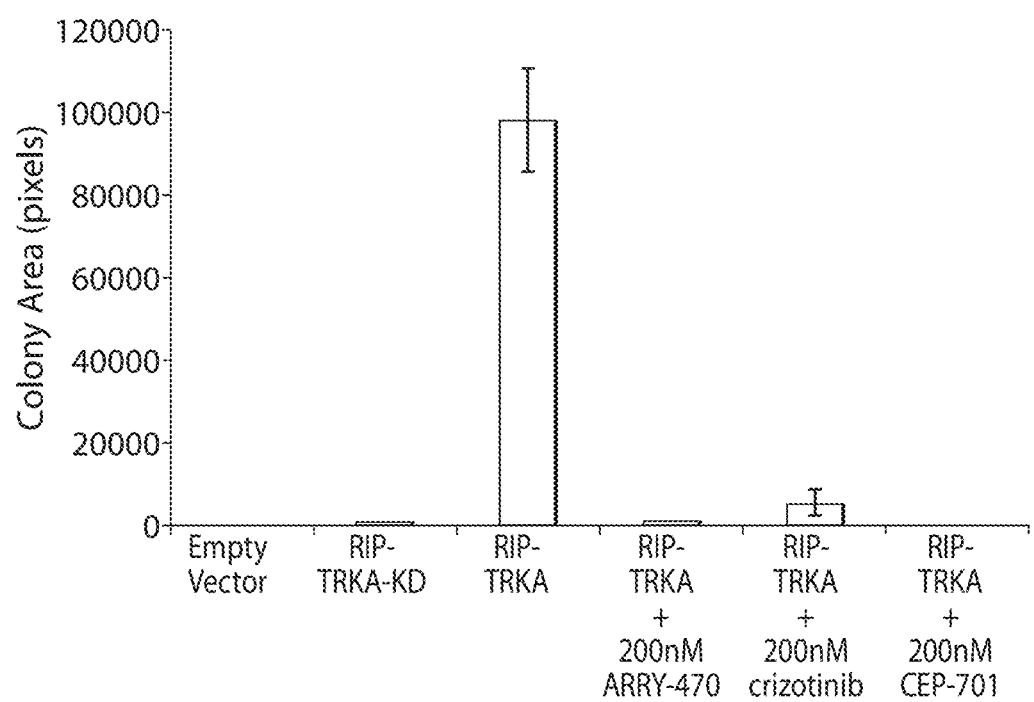

FIGS. 17A-17B show the inhibition of anchorage-independent growth by drugs with TRKA activity. (a) NIH3T3 cells expressing empty RIP-TRKA were seeded in triplicate in soft agar and treated with DMSO (control) or 200 nM of ARRY-470, crizotinib, or CEP-701 for 2 weeks (n=4). Values represent the mean±SEM. (b) Total colony area for each plate was quantified using MetaMorph software and plotted for each condition.

Figure 18:
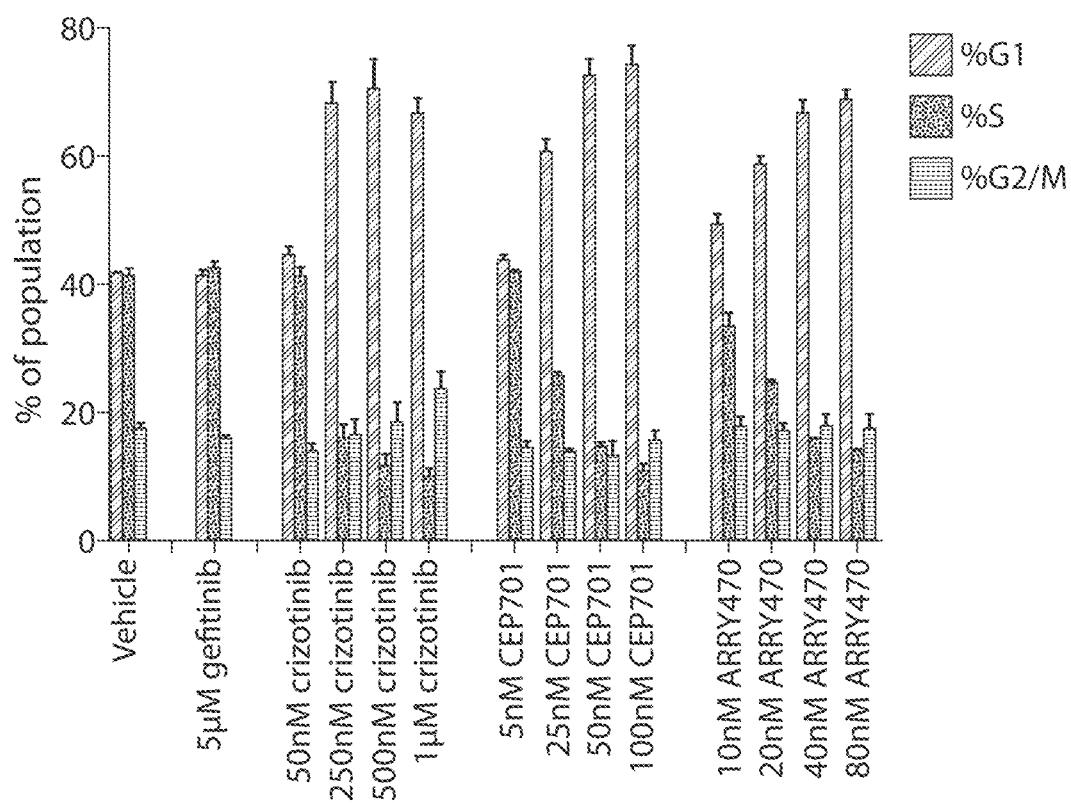

FIG. 18 shows TRKA inhibition results in the accumulation of KM12 cells in G1 phase. KM12 cells were treated with the indicated doses of drugs for 24 hr. Cells were then stained with propidium iodide and analyzed by flow cytometry. ModFit analysis was used to quantify cell cycle profiles (n=3). The bar graph shows the percentage of cells in G1, S, and G2/M (from left to right in the order of G1, S, G2/M) for each treatment group. Values represent the mean±SEM.

Figure 19A:
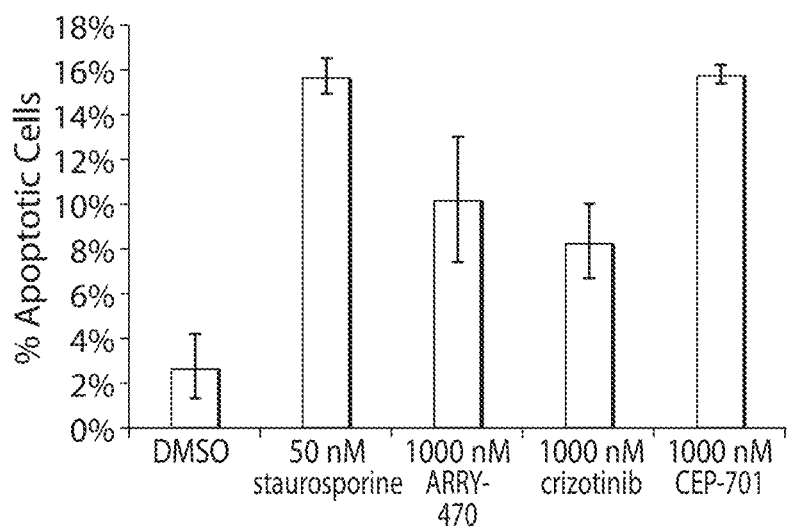
Figure 19B:
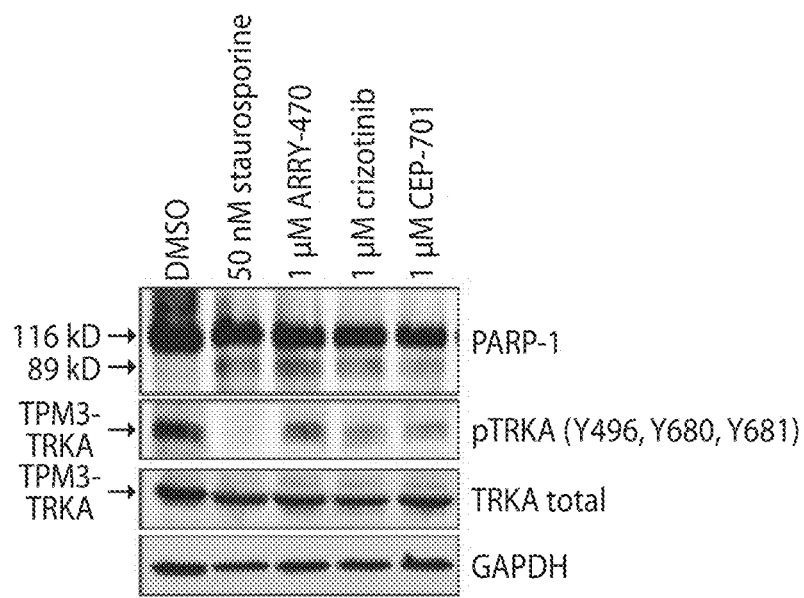
Figure 20A:
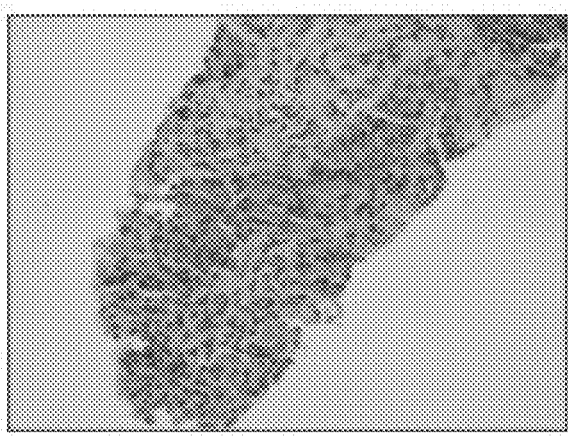
Figure 20B:
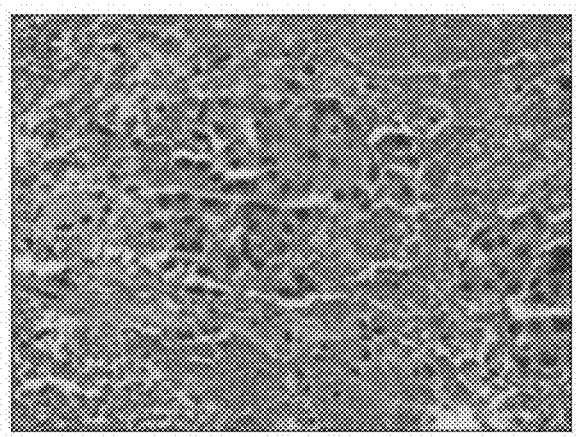
Figure 20C:
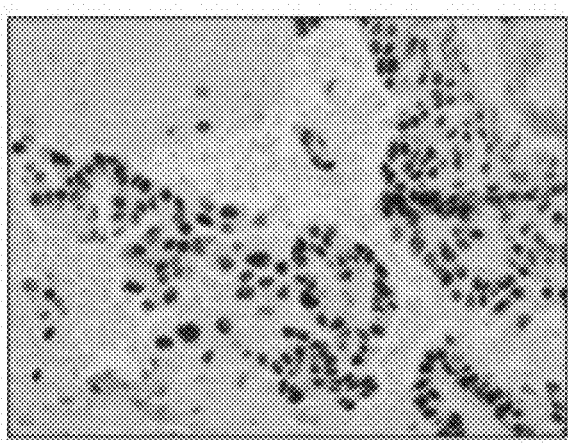
Figure 20D:
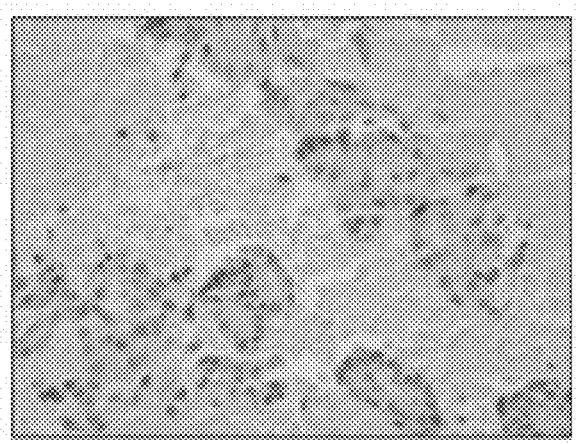

FIGS. 19A-19B shows treatment with TRKA inhibitors induces apoptosis in KM12 cells. (a) KM12 cells were treated for 24 h with the indicated drugs and doses, trypsinized, stained with YO-PRO® and propidium iodide (PI), and analyzed by flow-cytometry. The percent of cells undergoing apoptosis (YO-PRO® positive and PI negative) are plotted (n=4). Values represent the mean±SEM. (b) TRKA inhibitors induce cleavage of PARP-1. KM12 cells were treated for 24 h with the indicated drugs and doses. Cells were lysed, separated by SDS-PAGE and subject to immunoblot analysis with the indicated antibodies.

FIGS. 20A-20D shows histopathology from index patient harboring MPRIP-NTRK1 demonstrating lung adenocarcinoma. (a) Needle core biopsy of primary lung left lower lung mass showing adenocarcinoma. (b) Cell block of fine needle aspirate from the same procedure showing tumor cells. (c) TTF-1 immunohistochemistry (IHC) demonstrating strong nuclear staining in tumor cells. (d) Thyrogloblin IHC demonstrating negative staining in tumor cells.

FIG. 21 is a table showing the characteristics os the patients used to identify additional potential oncogenes in lung cancer.

FIG. 22 is a table showing the 56 additional lung adenocarcinoma samples without detectable EGFR, KRAS, ALK, ROS1, or RET oncogenic mutations screened for NTRK1 rearrangements.

FIG. 23 is a table showing the kinase selectivity of ARRY-470.

FIG. 24 is a table showing the full-length cDNA of each fusion gene was confirmed by sequencing. Primer sequences (SEQ ID NOS 9-17, respectively, in order of appearance) used for cloning.

FIG. 25 is a table depicting three TRKA inhibitors, including ARRY-470, ARRY-523, and CEP-701.

Figure 26:
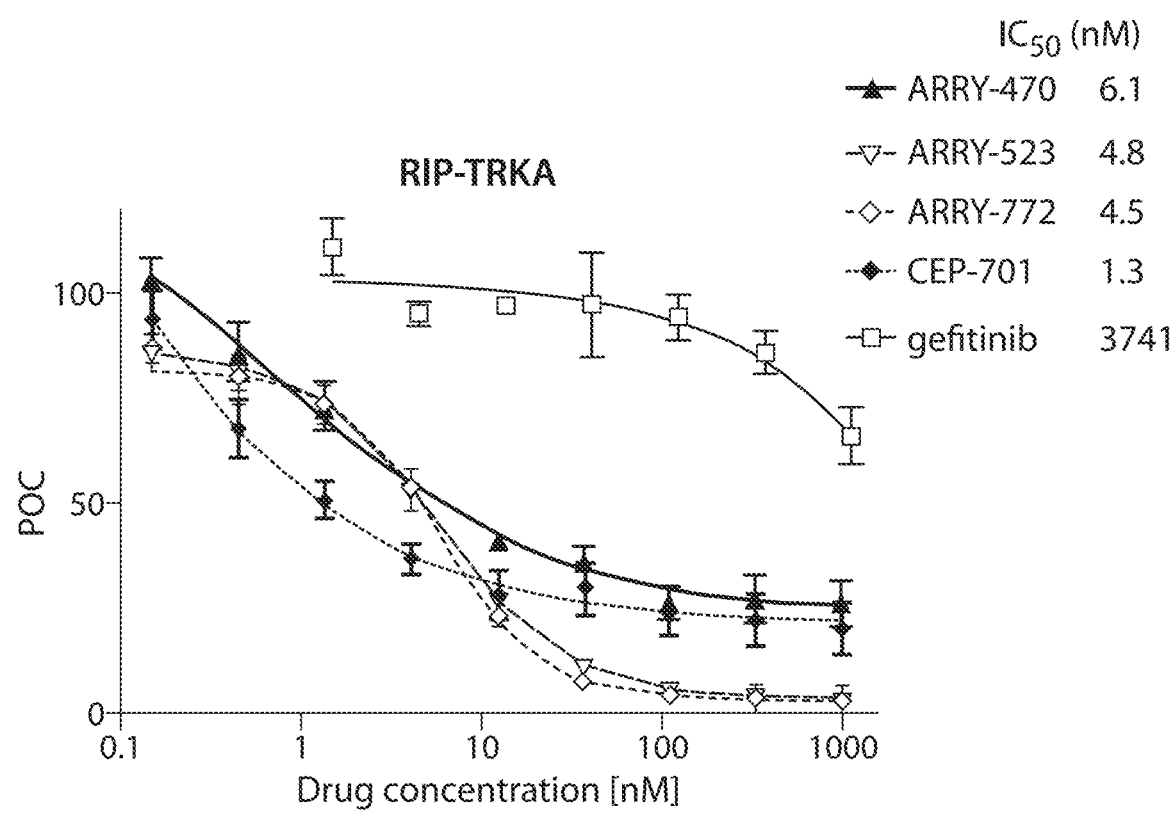

FIG. 26 depicts the proliferation of BAF3 cells expressing the RIP-TRKA construct by MTS. Proliferation is shown in the presence of ARRY-470, ARRY-523, ARRY-772, CEP-701, and gefitnib.

FIG. 27A depicts NTRK1 FISH analysis of CUTO-3 cells grown in short term culture derived from the index patient (derived from pleural effusion) demonstrating expression of the MPRIP-NTKR1 fusion.

FIG. 27B depicts immunoblot analysis of the CUTO-3 cells demonstrating inhibition of pTRKA and pERK by the pan-TRK inhibitor ARRY-470.

DETAILED DESCRIPTION

Novel NTRK1 rearrangement events that give rise to fusion molecules that include all or part of MPRIP (Myosin phosphatase Rho-interacting protein) and all or part of NTRK1 (Neurotrophic tyrosine kinase receptor type 1), referred to herein as "MPRIP-NTRK1 fusion molecules" are disclosed.

NTRK1 encodes the "High affinity nerve growth factor receptor", also called "Neurotrophic tyrosine kinase receptor type 1". This is a receptor tyrosine kinase that plays a role in the development of the nervous system by regulating cell proliferation, differentiation and survival of neurons. NTRK1 is activated upon binding of its ligand NGF (Klein R, Jing S Q, Nanduri V, et al. (1991) Cell 65(1):189-97), to promote several downstream signaling pathways including GRB2-Ras-MAPK, NF-Kappa-B, and Ras-PI3 kinase-AKT1 (Wooten M W, Seibenhener M L, Mamidipudi V, et al. (2001) J Biol Chem 276(11):7709-12; Stephens R M, Loeb D M, Copeland T D, et al. (1994) Neuron 12(3):691-705; Tacconelli A, Farina A R, Cappabianca L, et al. (2004) Cancer Cell 6(4):347-60).

NTRK1 mutations have been reported in approximately 2% of 1440 cancers analyzed in COSMIC (Catalog Of Somatic Mutations In Cancer, May 2012). Chromosomal rearrangements have been shown to produce NTRK1 oncogenes, which contain the tyrosine-kinase domain of NTRK1 fused to an activating sequence of another gene, and generate fusion proteins with constitutive kinase activity (Greco A, Mariani C, Miranda C, et al. (1993) Genomics 18(2): 397-400). Such NTRK1 fusions are frequently found in thyroid papillary carcinoma, including translocations between NTRK1 and TGF, TPM3, or TPR (Greco A, Mariani C, Miranda C, et al. (1995) Mol Cell Biol 15(11):6118-27; Greco A, Pierotti M A, Bongarzone I, et al. (1992) Oncogene 7(2):237-42; Martin-Zanca D, Hughes S H, Barbacid M (1986) Nature 319(6056):743-8). Oncogenic splice variant TrkAIII has been reported in neuroblastoma (Tacconelli A, Farina A R, Cappabianca L, et al. (2004) Cancer Cell 6(4):347-60). NTRK1 mutations are also associated with the genetic disorder "hereditary sensory and autonomic neuropathy type IV" (HSAN IV), also called "congenital insensitivity to pain with anidrosis" (CIPA) (Miura Y, Mardy S, Awaya Y, et al. (2000) Mutation and polymorphism analysis of the TRKA (NTRK1) gene encoding a high-affinity receptor for nerve growth factor in congenital insensitivity to pain with anhidrosis (CIPA) families. Hum Genet 106(1):116-24; Huehne K, Zweier C, Raab K, et al. (2008) Neuromuscul Disord 18(2):159-66).

In certain embodiments, the MPRIP-NTRK1 fusion molecules include all or part of MPRIP fused in-frame to the C-terminal portion of NTRK1, e.g., the C-terminal portion of NTRK1 which include the full NTRK1 tyrosine kinase domain. For example, a fragment of the MPRIP gene and a fragment of a NTRK1 gene, e.g., a fusion that includes a 5'-exon and a 3'-exon summarized in FIGS. 1A-1C (e.g., corresponding to exons 1-21 from MPRIP and exons 12-17 of NTRK). The NTRK1 tyrosine kinase domain is encoded by exons 13-17 (Indo Y, Mardy S, Tsuruta M, et al. (1997) Jpn J Hum Genet 42(2):343-51). The fusion protein reported here contains the entire NTK1 tyrosine kinase domain fused in-frame to another protein suggesting that it may have constitutive kinase activity and behave as an oncogene, by comparison to other NTRK1 fusions reported in thyroid papillary carcinoma (Greco A, Mariani C, Miranda C, et al. (1995) Mol Cell Biol 15(11):6118-27; Greco A, Pierotti M A, Bongarzone I, et al. (1992) Oncogene 7(2):237-42; Martin-Zanca D, Hughes S H, Barbacid M (1986) Nature 319 (6056):743-8).

Applicants further disclose that an MPRIP-NTRK1 fusion molecule disclosed herein has constitutive TRKA kinase activity, and is oncogenic (e.g., capable of transforming cell lines in vitro (e.g., Ba/F3 and NIH3T3 cells), which cells are tumorigenic when injected in vivo). Further disclosed herein are experiments demonstrating that tyrosine kinase inhibitors, including TRK- or TRKA-specific inhibitors reduce and/or inhibit the activity of the MPRIP-NTRK1 fusion molecule by e.g., reducing and/or inhibiting downstream signaling and/or cellular proliferation. Further embodiments disclosed herein show that a human subject with lung cancer (e.g., lung adenocarcinoma) treated with crizotinib, a weak TRKA-inhibitor, showed tumor shrinkage consistent with the level of in vitro inhibition and predicted patient drug levels. Other embodiments disclosed herein identified the MPRIP-NTRK1 fusion molecules in approximately 3.3% of enriched lung adenocarcinomas that did not harbor other oncogenic alterations tested, e.g., no alteration in EGFR, KRAS, ALK, ROS1 or RET was detected.

Certain terms are first defined. Additional terms are defined throughout the specification.

As used herein, the articles "a" and "an" refer to one or to more than one (e.g., to at least one) of the grammatical object of the article.

The term "or" is used herein to mean, and is used interchangeably with, the term "and/or", unless context clearly indicates otherwise.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" as the term is used herein, refers to obtaining possession of a nucleotide sequence or amino acid sequence, by "directly acquiring" or "indirectly acquiring" the sequence. "Directly acquiring a sequence" means performing a process (e.g., performing a synthetic or analytical method) to obtain the sequence, such as performing a sequencing method (e.g., a Next Generation Sequencing (NGS) method). "Indirectly acquiring a sequence" refers to receiving information or knowledge of, or receiving, the sequence from another party or source (e.g., a third party laboratory that directly acquired the sequence). The sequence acquired need not be a full sequence, e.g., sequencing of at least one nucleotide, or obtaining information or knowledge, that identifies a fusion molecule disclosed herein as being present in a subject constitutes acquiring a sequence.

Directly acquiring a sequence includes performing a process that includes a physical change in a physical substance, e.g., a starting material, such as a tissue sample, e.g., a biopsy, or an isolated nucleic acid (e.g., DNA or RNA) sample. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above.

"Acquiring a sample" as the term is used herein, refers to obtaining possession of a sample, e.g., a tissue sample or nucleic acid sample, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Binding entity" means any molecule to which molecular tags can be directly or indirectly attached that is capable of specifically binding to an analyte. The binding entity can be an affinity tag on a nucleic acid sequence. In certain embodiments, the binding entity allows for separation of the nucleic acid from a mixture, such as an avidin molecule, or an antibody that binds to the hapten or an antigen-binding fragment thereof. Exemplary binding entities include, but are not limited to, a biotin molecule, a hapten, an antibody, an antibody binding fragment, a peptide, and a protein.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The term "cancer" or "tumor" is used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers. In certain embodiments, the cancer is a solid tumor, a soft tissue tumor, or a metastatic lesion.

The term "neoplasm" or "neoplastic" cell refers to an abnormal proliferative stage, e.g., a hyperproliferative stage, in a cell or tissue that can include a benign, pre-malignant, malignant (cancer) or metastatic stage.

Cancer is "inhibited" if at least one symptom of the cancer is alleviated, terminated, slowed, or prevented. As used herein, cancer is also "inhibited" if recurrence or metastasis of the cancer is reduced, slowed, delayed, or prevented.

"Chemotherapeutic agent" means a chemical substance, such as a cytotoxic or cytostatic agent, that is used to treat a condition, particularly cancer.

As used herein, "cancer therapy" and "cancer treatment" are synonymous terms.

As used herein, "chemotherapy" and "chemotherapeutic" and "chemotherapeutic agent" are synonymous terms.

The terms "homology" or "identity," as used interchangeably herein, refer to sequence similarity between two polynucleotide sequences or between two polypeptide sequences, with identity being a more strict comparison. The phrases "percent identity or homology" and "% identity or homology" refer to the percentage of sequence similarity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value there between. Identity or similarity can be determined by comparing a position in each sequence that can be aligned for purposes of comparison. When a position in the compared sequence is occupied by the same nucleotide base or amino acid, then the molecules are identical at that position. A degree of similarity or identity between polynucleotide sequences is a function of the number of identical or matching nucleotides at positions shared by the polynucleotide sequences. A degree of identity of polypeptide sequences is a function of the number of identical amino acids at positions shared by the polypeptide sequences. A degree of homology or similarity of polypeptide sequences is a function of the number of amino acids at positions shared by the polypeptide sequences. The term "substantially identical," as used herein, refers to an identity or homology of at least 75%, at least 80%, at least 85%, at least 90%, 91%, 92%, 93%, 94%, 95%, 96%, 97%, 98%, 99%, or more.

"Likely to" or "increased likelihood," as used herein, refers to an increased probability that an item, object, thing or person will occur. Thus, in one example, a subject that is likely to respond to treatment with a kinase inhibitor, alone or in combination, has an increased probability of responding to treatment with the inhibitor alone or in combination, relative to a reference subject or group of subjects.

"Unlikely to" refers to a decreased probability that an event, item, object, thing or person will occur with respect to a reference. Thus, a subject that is unlikely to respond to treatment with a kinase inhibitor, alone or in combination, has a decreased probability of responding to treatment with a kinase inhibitor, alone or in combination, relative to a reference subject or group of subjects.

"Sequencing" a nucleic acid molecule requires determining the identity of at least 1 nucleotide in the molecule. In embodiments, the identity of less than all of the nucleotides in a molecule are determined. In other embodiments, the identity of a majority or all of the nucleotides in the molecule is determined.

"Next-generation sequencing or NGS or NG sequencing" as used herein, refers to any sequencing method that determines the nucleotide sequence of either individual nucleic acid molecules (e.g., in single molecule sequencing) or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference. Next generation sequencing can detect a variant present in less than 5% of the nucleic acids in a sample.

"Sample," "tissue sample," "patient sample," "patient cell or tissue sample" or "specimen" each refers to a collection of similar cells obtained from a tissue of a subject or patient. The source of the tissue sample can be solid tissue as from a fresh, frozen and/or preserved organ, tissue sample, biopsy, or aspirate; blood or any blood constituents; bodily fluids such as cerebral spinal fluid, amniotic fluid, peritoneal fluid or interstitial fluid; or cells from any time in gestation or development of the subject. The tissue sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample.

A "tumor nucleic acid sample" as used herein, refers to nucleic acid molecules from a tumor or cancer sample. Typically, it is DNA, e.g., genomic DNA, or cDNA derived from RNA, from a tumor or cancer sample. In certain embodiments, the tumor nucleic acid sample is purified or isolated (e.g., it is removed from its natural state).

A "control" or "reference" "nucleic acid sample" as used herein, refers to nucleic acid molecules from a control or reference sample. Typically, it is DNA, e.g., genomic DNA, or cDNA derived from RNA, not containing the alteration or variation in the gene or gene product, e.g., not containing a fusion molecule described herein. In certain embodiments, the reference or control nucleic acid sample is a wild type or a non-mutated sequence. In certain embodiments, the reference nucleic acid sample is purified or isolated (e.g., it is removed from its natural state). In other embodiments, the reference nucleic acid sample is from a non-tumor sample, e.g., a blood control, a normal adjacent tumor (NAT), or any other non-cancerous sample from the same or a different subject.

"Adjacent to the interrogation position," as used herein, means that a site sufficiently close such that a detection reagent complementary with the site can be used to distinguish between a mutation, e.g., a mutation described herein, and a reference sequence, e.g., a non-mutant or wild-type sequence, in a target nucleic acid. Directly adjacent, as used herein, is where 2 nucleotides have no intervening nucleotides between them.

"Associated mutation," as used herein, refers to a mutation within a preselected distance, in terms of nucleotide or primary amino acid sequence, from a definitional mutation, e.g., a mutant as described herein, e.g., a translocation, breakpoint or fusion molecule described herein. In embodiments, the associated mutation is within n, wherein n is 2, 5, 10, 20, 30, 50, 100, or 200 nucleotides from the definitional mutation (n does not include the nucleotides defining the associated and definitional mutations). In embodiments, the associated mutation is a translocation mutation.

"Interrogation position," as used herein, comprises at least one nucleotide (or, in the case of polypeptides, an amino acid residue) which corresponds to a nucleotide (or amino acid residue) that is mutated in a mutation, including, e.g., in the case of a rearrangement, one or both of the nucleotides (or amino acid residues) flanking the breakpoint, or other residue which can be used to distinguish the mutation, of interest, e.g., a mutation being identified, or in a nucleic acid (or protein) being analyzed, e.g., sequenced, or recovered. By way of example, the interrogation position in the breakpoint shown in FIG. 1A, 1B or 1C, includes one, two, or more nucleotide positions at the junction site.

A "reference sequence," as used herein, e.g., as a comparator for a mutant sequence, is a sequence which has a different nucleotide or amino acid at an interrogation position than does the mutant(s) being analyzed. In an embodiment, the reference sequence is wild-type for at least the interrogation position.

Headings, e.g., (a), (b), (i) etc, are presented merely for ease of reading the specification and claims. The use of headings in the specification or claims does not require the steps or elements be performed in alphabetical or numerical order or the order in which they are presented.

Various aspects featured in the invention are described in further detail below. Additional definitions are set out throughout the specification.

Isolated Nucleic Acid Molecules

One aspect featured in the invention pertains to isolated nucleic acid molecules that include a fusion molecule described herein, including nucleic acids which encode fusion polypeptide or a portion of such a polypeptide. The nucleic acid molecules include those nucleic acid molecules which reside in genomic regions identified herein. As used herein, the term "nucleic acid molecule" includes DNA molecules (e.g., cDNA or genomic DNA) and RNA molecules (e.g., mRNA) and analogs of the DNA or RNA generated using nucleotide analogs. The nucleic acid molecule can be single-stranded or double-stranded; in certain embodiments the nucleic acid molecule is double-stranded DNA.

Isolated nucleic acid molecules also include nucleic acid molecules sufficient for use as hybridization probes or primers to identify nucleic acid molecules that correspond to a fusion molecule described herein, e.g., those suitable for use as PCR primers for the amplification or mutation of nucleic acid molecules.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material or culture medium when produced by recombinant techniques, or substantially free of chemical precursors or other chemicals when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

A fusion nucleic acid molecule can be isolated using standard molecular biology techniques and the sequence information in the database records described herein. Using all or a portion of such nucleic acid sequences, fusion nucleic acid molecules as described herein can be isolated using standard hybridization and cloning techniques (e.g., as described in Sambrook et al., ed., *Molecular Cloning: A Laboratory Manual*, 2nd ed., Cold Spring Harbor Laboratory Press, Cold Spring Harbor, N.Y., 1989).

A fusion nucleic acid molecule (e.g., fusion molecule described herein) can be amplified using cDNA, mRNA, or genomic DNA as a template and appropriate oligonucleotide primers according to standard PCR amplification techniques. The nucleic acid molecules so amplified can be cloned into an appropriate vector and characterized by DNA sequence analysis. Furthermore, oligonucleotides corresponding to all or a portion of a nucleic acid molecule featured in the invention can be prepared by standard synthetic techniques, e.g., using an automated DNA synthesizer.

In another embodiment, a fusion nucleic acid molecule (e.g., fusion molecule described herein) comprises a nucleic acid molecule which has a nucleotide sequence complementary to the nucleotide sequence of the fusion nucleic acid molecule or to the nucleotide sequence of a nucleic acid encoding a fusion protein. A nucleic acid molecule which is complementary to a given nucleotide sequence is one which is sufficiently complementary to the given nucleotide sequence that it can hybridize to the given nucleotide sequence thereby forming a stable duplex.

Moreover, a fusion nucleic acid molecule can comprise only a portion of a nucleic acid sequence, wherein the full length nucleic acid sequence or which encodes a fusion polypeptide. Such nucleic acid molecules can be used, for example, as a probe or primer. The probe/primer typically is used as one or more substantially purified oligonucleotides. The oligonucleotide typically comprises a region of nucleotide sequence that hybridizes under stringent conditions to at least about 7, at least about 15, at least about 25, at least about 50, at least about 75, at least about 100, at least about 125, at least about 150, at least about 175, at least about 200, at least about 250, at least about 300, at least about 350, at least about 400, at least about 500, at least about 600, at least about 700, at least about 800, at least about 900, at least about 1 kb, at least about 2 kb, at least about 3 kb, at least about 4 kb, at least about 5 kb, at least about 6 kb, at least about 7 kb, at least about 8 kb, at least about 9 kb, at least about 10 kb, at least about 15 kb, at least about 20 kb, at least about 25 kb, at least about 30 kb, at least about 35 kb, at least about 40 kb, at least about 45 kb, at least about 50 kb, at least about 60 kb, at least about 70 kb, at least about 80 kb, at least about 90 kb, at least about 100 kb, at least about 200 kb, at least about 300 kb, at least about 400 kb, at least about 500 kb, at least about 600 kb, at least about 700 kb, at least about 800 kb, at least about 900 kb, at least about 1 mb, at least about 2 mb, at least about 3 mb, at least about 4 mb, at least about 5 mb, at least about 6 mb, at least about 7 mb, at least about 8 mb, at least about 9 mb, at least about 10 mb or more consecutive nucleotides of a fusion nucleic acid described herein.

The invention further encompasses nucleic acid molecules that are substantially identical to the gene mutations and/or gene products described herein, such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater. The invention further encompasses nucleic acid molecules that are substantially identical to the gene mutations and/or gene products described herein, such that they are at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or greater.

In other embodiments, the invention further encompasses nucleic acid molecules that are substantially homologous to fusion gene mutations and/or gene products described herein, such that they differ by only or at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 30, at least 40, at least 50, at least 60, at least 70, at least 80, at least 90, at least 100, at least 200, at least 300, at least 400, at least 500, at least 600 nucleotides or any range in between.

In another embodiment, an isolated fusion nucleic acid molecule described herein is at least 7, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 125, at least 150, at least 175, at least 200, at least 250, at least 300, at least 350, at least 400, at least 450, at least 550, at least 650, at least 700, at least 800, at least 900, at least 1000, at least 1200, at least 1400, at least 1600, at least 1800, at least 2000, at least 2200, at least 2400, at least 2600, at least 2800, at least 3000, or more nucleotides in length and hybridizes under stringent conditions to a fusion nucleic acid molecule or to a nucleic acid molecule encoding a protein corresponding to a marker featured in the invention.

As used herein, the term "hybridizes under stringent conditions" is intended to describe conditions for hybridization and washing under which nucleotide sequences at least 60%, at least 65%, at least 70%, at least 75%, at least 80%, or at least 85% identical to each other typically remain hybridized to each other. Such stringent conditions are known to those skilled in the art and can be found in sections 6.3.1-6.3.6 of *Current Protocols in Molecular Biology*, John Wiley & Sons, N.Y. (1989). Another, non-limiting example of stringent hybridization conditions are hybridization in 6× sodium chloride/sodium citrate (SSC) at about 45° C., followed by one or more washes in 0.2×SSC, 0.1% SDS at 50-65° C.

The invention also includes molecular beacon nucleic acid molecules having at least one region which is complementary to a fusion nucleic acid molecule described herein, such that the molecular beacon is useful for quantitating the presence of the nucleic acid molecule featured in the invention in a sample. A "molecular beacon" nucleic acid is a nucleic acid molecule comprising a pair of complementary regions and having a fluorophore and a fluorescent quencher associated therewith. The fluorophore and quencher are associated with different portions of the nucleic acid in such an orientation that when the complementary regions are annealed with one another, fluorescence of the fluorophore is quenched by the quencher. When the complementary regions of the nucleic acid molecules are not annealed with one another, fluorescence of the fluorophore is quenched to a lesser degree. Molecular beacon nucleic acid molecules are described, for example, in U.S. Pat. No. 5,876,930.

Probes

The invention also provides isolated nucleic acid molecules useful as probes. Such nucleic acid probes can be designed based on the sequence of a fusion molecule described herein.

Probes based on the sequence of a fusion nucleic acid molecule as described herein can be used to detect transcripts or genomic sequences corresponding to one or more markers featured in the invention. The probe comprises a label group attached thereto, e.g., a radioisotope, a fluorescent compound, an enzyme, or an enzyme co-factor. Such probes can be used as part of a test kit for identifying cells or tissues which express the fusion protein (e.g., a fusion described herein), such as by measuring levels of a nucleic acid molecule encoding the protein in a sample of cells from a subject, e.g., detecting mRNA levels or determining whether a gene encoding the protein has been mutated or deleted.

Probes featured in the invention include those that will specifically hybridize to a gene sequence described in the Examples, e.g., fusion molecule described herein. Typically these probes are 12 to 20, e.g., 17 to 20 nucleotides in length (longer for large insertions) and have the nucleotide sequence corresponding to the region of the mutations at their respective nucleotide locations on the gene sequence. Such molecules can be labeled according to any technique known in the art, such as with radiolabels, fluorescent labels, enzymatic labels, sequence tags, biotin, other ligands, etc. As used herein, a probe that "specifically hybridizes" to a fusion gene sequence will hybridize under high stringency conditions.

A probe will typically contain one or more of the specific mutations described herein. Typically, a nucleic acid probe will encompass only one mutation. Such molecules may be labeled and can be used as allele-specific probes to detect the mutation of interest.

In one aspect, the invention features a probe or probe set that specifically hybridizes to a nucleic acid comprising an inversion resulting in a fusion molecule described herein. In another aspect, the invention features a probe or probe set that specifically hybridizes to a nucleic acid comprising a deletions resulting in a fusion molecule described herein.

Isolated pairs of allele specific oligonucleotide probes are also provided, where the first probe of the pair specifically hybridizes to the mutant allele, and the second probe of the pair specifically hybridizes to the wildtype allele. For example, in one exemplary probe pair, one probe will recognize the fusion junction in the MPRIP-NTRK1 fusion, and the other probe will recognize a sequence downstream or upstream of MPRIP or NTRK1, neither of which includes the fusion junction. These allele-specific probes are useful in detecting a NTRK1 somatic mutation in a tumor sample, e.g., lung adenocarcinoma sample. In a similar manner, probe pairs can be designed and produced for any of the fusion molecule described herein, and are useful in detecting a somatic mutation in a tumor sample.

Primers

The invention also provides isolated nucleic acid molecules useful as primers.

The term "primer" as used herein refers to a sequence comprising two or more deoxyribonucleotides or ribonucleotides, e.g., more than three, and more than eight, or at least 20 nucleotides of a gene described in the Example, where the sequence corresponds to a sequence flanking one of the mutations or a wild type sequence of a gene identified in the Example, e.g., any gene described herein involved in a fusion described herein. Primers may be used to initiate DNA synthesis via the PCR (polymerase chain reaction) or a sequencing method. Primers featured in the invention include the sequences recited and complementary sequences which would anneal to the opposite DNA strand of the sample target. Since both strands of DNA are complementary and mirror images of each other, the same segment of DNA will be amplified.

Primers can be used to sequence a nucleic acid, e.g., an isolated nucleic acid described herein, such as by an NGS method, or to amplify a gene described in the Example, such as by PCR. The primers can specifically hybridize, for example, to the ends of the exons or to the introns flanking the exons. The amplified segment can then be further analyzed for the presence of the mutation such as by a sequencing method. The primers are useful in directing amplification of a target polynucleotide prior to sequencing. In another aspect, the invention features a pair of oligonucleotide primers that amplify a region that contains or is adjacent to a fusion junction identified in the Example. Such primers are useful in directing amplification of a target region that includes a fusion junction identified in the Example, e.g., prior to sequencing. The primer typically contains 12 to 20, or 17 to 20, or more nucleotides, although a primer may contain fewer nucleotides.

A primer is typically single stranded, e.g., for use in sequencing or amplification methods, but may be double stranded. If double stranded, the primer may first be treated to separate its strands before being used to prepare extension products. A primer must be sufficiently long to prime the synthesis of extension products in the presence of the inducing agent for polymerization. The exact length of primer will depend on many factors, including applications (e.g., amplification method), temperature, buffer, and nucleotide composition. A primer typically contains 12-20 or more nucleotides, although a primer may contain fewer nucleotides.

Primers are typically designed to be "substantially" complementary to each strand of a genomic locus to be amplified. Thus, the primers must be sufficiently complementary to specifically hybridize with their respective strands under conditions which allow the agent for polymerization to perform. In other words, the primers should have sufficient complementarity with the 5' and 3' sequences flanking the mutation to hybridize therewith and permit amplification of the genomic locus.

The term "substantially complementary to" or "substantially the sequence" refers to sequences that hybridize to the sequences provided under stringent conditions and/or sequences having sufficient homology with a sequence comprising a fusion junction identified in the Example, or the wildtype counterpart sequence, such that the allele specific oligonucleotides hybridize to the sequence. In one embodiment, a sequence is substantially complementary to a fusion junction in an inversion event, e.g., to a fusion junction in any fusion molecule described herein. "Substantially the same" as it refers to oligonucleotide sequences also refers to the functional ability to hybridize or anneal with sufficient specificity to distinguish between the presence or absence of the mutation. This is measurable by the temperature of melting being sufficiently different to permit easy identification of whether the oligonucleotide is binding to the normal or mutant gene sequence identified in the Example.

In one aspect, the invention features a primer or primer set for amplifying a nucleic acid comprising an inversion resulting in a fusion described herein. In another aspect, the invention features a primer or primer set for amplifying a nucleic acid comprising a deletion resulting in fusion described herein.

Isolated pairs of allele specific oligonucleotide primer are also provided, where the first primer of the pair specifically hybridizes to the mutant allele, and the second primer of the pair specifically hybridizes to a sequence upstream or downstream of a mutation, or a fusion junction resulting from, e.g., an inversion, duplication, deletion, insertion or translocation. In one exemplary primer pair, one probe will recognize a MPRIP-NTRK1 fusion, such as by hybridizing to a sequence at the fusion junction between the MPRIP and NTRK1 transcripts, and the other primer will recognize a sequence upstream or downstream of the fusion junction. These allele-specific primers are useful for amplifying a MPRIP-NTRK1 fusion sequence from a tumor sample, e.g., a biopsy, e.g., a biopsy from a suspected lung cancer, e.g., lung adenocarcinoma.

In another exemplary primer pair, one primer can recognize an MPRIP-NTRK1 translocation (e.g., the reciprocal of the MPRIP-NTRK1 translocation), such as by hybridizing to a sequence at the fusion junction between the MPRIP and NTRK1 transcripts, and the other primer will recognize a sequence upstream or downstream of the fusion junction. These allele-specific primers are useful for amplifying a MPRIP-NTRK1 fusion sequence from a tumor sample, e.g., a lung cancer sample or biopsy or lung biopsy sample.

Primers can be prepared using any suitable method, such as conventional phosphotriester and phosphodiester methods or automated embodiments thereof. In one such automated embodiment, diethylphosphoramidites are used as starting materials and may be synthesized as described by Beaucage, et al., Tetrahedron Letters, 22:1859-1862, (1981). One method for synthesizing oligonucleotides on a modified solid support is described in U.S. Pat. No. 4,458,066.

An oligonucleotide probe or primer that hybridizes to a mutant or wildtype allele is said to be the complement of the allele. As used herein, a probe exhibits "complete complementarity" when every nucleotide of the probe is complementary to the corresponding nucleotide of the allele. Two polynucleotides are said to be "minimally complementary" if they can hybridize to one another with sufficient stability to permit them to remain annealed to one another under at least conventional "low-stringency" conditions. Similarly, the polynucleotides are said to be "complementary" if they can hybridize to one another with sufficient stability to permit them to remain annealed to one another under conventional "high-stringency" conditions. Conventional stringency conditions are known to those skilled in the art and can be found, for example in *Molecular Cloning: A Laboratory Manual,* 3rd edition Volumes 1, 2, and 3. J. F. Sambrook, D. W. Russell, and N. Irwin, Cold Spring Harbor Laboratory Press, 2000.

Departures from complete complementarity are therefore permissible, as long as such departures do not completely preclude the capacity of a probe to hybridize to an allele. Thus, in order for a polynucleotide to serve as a primer or probe it need only be sufficiently complementary in sequence to be able to form a stable double-stranded structure under the particular solvent and salt concentrations employed. Appropriate stringency conditions which promote DNA hybridization are, for example, 6.0× sodium chloride/sodium citrate (SSC) at about 45° C., followed by a wash of 2.0×SSC at 50° C. Such conditions are known to those skilled in the art and can be found, for example in *Current Protocols in Molecular Biology,* John Wiley & Sons, N.Y. (1989). Salt concentration and temperature in the wash step can be adjusted to alter hybridization stringency. For example, conditions may vary from low stringency of about 2.0×SSC at 40° C. to moderately stringent conditions of about 2.0×SSC at 50° C. to high stringency conditions of about 0.2×SSC at 50° C.

Fusion Proteins and Antibodies

One aspect featured in the invention pertains to purified fusion polypeptides, and biologically active portions thereof. The fusion polypeptide can be any fusion molecule described herein. In one embodiment, the native fusion polypeptide can be isolated from cells or tissue sources by an appropriate purification scheme using standard protein purification techniques. In another embodiment, a fusion polypeptide is produced by recombinant DNA techniques. Alternative to recombinant expression, a fusion polypeptide described herein can be synthesized chemically using standard peptide synthesis techniques.

An "isolated" or "purified" protein or biologically active portion thereof is substantially free of cellular material or other contaminating proteins from the cell or tissue source from which the protein is derived, or substantially free of chemical precursors or other chemicals when chemically synthesized. The language "substantially free of cellular material" includes preparations of protein in which the protein is separated from cellular components of the cells from which it is isolated or recombinantly produced. Thus, protein that is substantially free of cellular material includes preparations of protein having less than about 30%, less than about 20%, less than about 10%, or less than about 5% (by dry weight) of heterologous protein (also referred to herein as a "contaminating protein"). When the protein or biologically active portion thereof is recombinantly produced, it can be substantially free of culture medium, i.e., culture medium represents less than about 20%, less than about 10%, or less than about 5% of the volume of the protein preparation. When the protein is produced by chemical synthesis, it can substantially be free of chemical precursors or other chemicals, i.e., it is separated from chemical precursors or other chemicals which are involved in the synthesis of the protein. Accordingly such preparations of the protein have less than about 30%, less than about 20%, less than about 10%, less than about 5% (by dry weight) of chemical precursors or compounds other than the polypeptide of interest.

Biologically active portions of a fusion polypeptide include polypeptides comprising amino acid sequences sufficiently identical to or derived from the amino acid sequence of the fusion protein, which include fewer amino acids than the full length protein, and exhibit at least one activity of the corresponding full-length protein, e.g., a kinase activity e.g., an NTRK1 kinase activity. A biologically active portion of a protein featured in the invention can be a polypeptide which is, for example, 10, 25, 50, 100 or more amino acids in length. Moreover, other biologically active portions, in which other regions of the protein are deleted, can be prepared by recombinant techniques and evaluated for one or more of the functional activities of the native form of a polypeptide.

In certain embodiments, the fusion polypeptide described herein has an amino acid sequence of a protein encoded by a nucleic acid molecule disclosed herein. Other useful proteins are substantially identical (e.g., at least 60, at least 65, at least 70, at least 75, at least 80, at least 85, at least 86, at least 87, at least 88, at least 89, at least 90, at least 91, at least 92, at least 93, at least 94, at least 95, at least 96, at least 97, at least 98, at least 99, at least 99.5% or greater) to one of these sequences and retain the functional activity of the protein of the corresponding full-length protein yet differ in amino acid sequence.

To determine the percent identity of two amino acid sequences or of two nucleic acids, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In one embodiment the two sequences are the same length.

The determination of percent identity between two sequences can be accomplished using a mathematical algorithm. Another, non-limiting example of a mathematical algorithm utilized for the comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul, et al. (1990) *J. Mol. Biol.* 215:403-410. BLAST nucleotide searches can be performed with the NBLAST program, score=100, wordlength=12 to obtain nucleotide sequences homologous to a nucleic acid molecules featured in the invention. BLAST protein searches can be performed with the XBLAST program, score=50, word length=3 to obtain amino acid sequences homologous to protein molecules featured in the invention. To obtain gapped alignments for comparison purposes, Gapped BLAST can be utilized as described in Altschul et al. (1997) *Nucleic Acids Res.* 25:3389-3402. Alternatively, PSI-Blast can be used to perform an iterated search which detects distant relationships between molecules. When utilizing BLAST, Gapped BLAST, and PSI-Blast programs, the default parameters of the respective programs (e.g., XBLAST and NBLAST) can be used. See www.ncbi.nlm.nih.gov. Another non-limiting example of a mathematical algorithm utilized for the comparison of sequences is the algorithm of Myers and Miller, (1988) *Comput Appl Biosci,* 4:11-7. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An isolated fusion polypeptide (e.g., a fusion described herein), or a fragment thereof, can be used as an immunogen to generate antibodies using standard techniques for polyclonal and monoclonal antibody preparation. The full-length fusion polypeptide can be used or, alternatively, the invention provides antigenic peptide fragments for use as immunogens. The antigenic peptide of a protein featured in the invention comprises at least 8 (or at least 10, at least 15, at least 20, or at least 30 or more) amino acid residues of the amino acid sequence of one of the polypeptides featured in the invention, and encompasses an epitope of the protein such that an antibody raised against the peptide forms a specific immune complex with a marker featured in the invention to which the protein corresponds. Exemplary epitopes encompassed by the antigenic peptide are regions that are located on the surface of the protein, e.g., hydrophilic regions. Hydrophobicity sequence analysis, hydrophilicity sequence analysis, or similar analyses can be used to identify hydrophilic regions.

An immunogen typically is used to prepare antibodies by immunizing a suitable (i.e., immunocompetent) subject such as a rabbit, goat, mouse, or other mammal or vertebrate. An appropriate immunogenic preparation can contain, for example, recombinantly-expressed or chemically-synthesized polypeptide. The preparation can further include an adjuvant, such as Freund's complete or incomplete adjuvant, or a similar immunostimulatory agent.

Accordingly, another aspect featured in the invention pertains to antibodies directed against a fusion polypeptide described herein. In one embodiment, the antibody molecule specifically binds to fusion molecule described herein, e.g., specifically binds to an epitope formed by the fusion. In embodiments the antibody can distinguish wild type genes that make up the fusion, from the fusion of the genes, e.g., the antibody can distinguish wild type genes, e.g., MPRIP (or NTRK1) from MPRIP-NTRK1.

The terms "antibody" and "antibody molecule" as used interchangeably herein refer to immunoglobulin molecules and immunologically active portions of immunoglobulin molecules, i.e., molecules that contain an antigen binding site which specifically binds an antigen, such as a polypeptide featured in the invention. A molecule which specifically binds to a given polypeptide featured in the invention is a molecule which binds the polypeptide, but does not substantially bind other molecules in a sample, e.g., a biological sample, which naturally contains the polypeptide. Examples of immunologically active portions of immunoglobulin molecules include F(ab) and F(ab')$_2$ fragments which can be generated by treating the antibody with an enzyme such as pepsin. The invention provides polyclonal and monoclonal antibodies. The term "monoclonal antibody" or "monoclonal antibody composition," as used herein, refers to a population of antibody molecules that contain only one species of an antigen binding site capable of immunoreacting with a particular epitope.

Polyclonal antibodies can be prepared as described above by immunizing a suitable subject with a fusion polypeptide as an immunogen. Antibody-producing cells can be obtained from the subject and used to prepare monoclonal antibodies by standard techniques, such as the hybridoma technique originally described by Kohler and Milstein (1975) *Nature* 256:495-497, the human B cell hybridoma technique (see Kozbor et al., 1983, *Immunol. Today* 4:72), the EBV-hybridoma technique (see Cole et al., pp. 77-96 In *Monoclonal Antibodies and Cancer Therapy*, Alan R. Liss, Inc., 1985) or trioma techniques. The technology for producing hybridomas is well known (see generally *Current Protocols in Immunology*, Coligan et al. ed., John Wiley & Sons, New York, 1994). Hybridoma cells producing a monoclonal antibody are detected by screening the hybridoma culture supernatants for antibodies that bind the polypeptide of interest, e.g., using a standard ELISA assay.

Alternative to preparing monoclonal antibody-secreting hybridomas, a monoclonal antibody can be identified and isolated by screening a recombinant combinatorial immunoglobulin library (e.g., an antibody phage display library) with the polypeptide of interest. Kits for generating and screening phage display libraries are commercially available (e.g., the Pharmacia Recombinant Phage Antibody System, Catalog No. 27-9400-01; and the Stratagene SurfZAP Phage Display Kit, Catalog No. 240612). Additionally, examples of methods and reagents particularly amenable for use in generating and screening antibody display library can be found in, for example, U.S. Pat. No. 5,223,409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; PCT Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246:1275-1281; Griffiths et al. (1993) *EMBO J.* 12:725-734.

Additionally, recombinant antibodies, such as chimeric and humanized monoclonal antibodies, comprising both human and non-human portions can be made using standard recombinant DNA techniques. Such chimeric and humanized monoclonal antibodies can be produced by recombinant DNA techniques known in the art, for example using methods described in PCT Publication No. WO 87/02671; European Patent Application 184,187; European Patent Application 171,496; European Patent Application 173,494; PCT Publication No. WO 86/01533; U.S. Pat. No. 4,816,567; European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura et al. (1987) *Cancer Res.* 47:999-1005; Wood et al. (1985) *Nature* 314:446-449; and Shaw et al. (1988) *J. Natl. Cancer Inst.* 80:1553-1559; Morrison (1985) *Science* 229:1202-1207; Oi et al. (1986) *Bio/Techniques* 4:214; U.S. Pat. No. 5,225,539; Jones et al. (1986) *Nature* 321:552-525; Verhoeyan et al. (1988) *Science* 239: 1534; and Beidler et al. (1988) *J. Immunol.* 141:4053-4060.

Completely human antibodies can be produced using transgenic mice which are incapable of expressing endogenous immunoglobulin heavy and light chains genes, but which can express human heavy and light chain genes. For an overview of this technology for producing human antibodies, see Lonberg and Huszar (1995) *Int. Rev. Immunol.* 13:65-93). For a detailed discussion of this technology for producing human antibodies and human monoclonal antibodies and protocols for producing such antibodies, see, e.g., U.S. Pat. Nos. 5,625,126; 5,633,425; 5,569,825; 5,661, 016; and 5,545,806. In addition, companies such as Abgenix, Inc. (Freemont, Calif.), can be engaged to provide human antibodies directed against a selected antigen using technology similar to that described above.

An antibody directed against a fusion polypeptide described herein (e.g., a monoclonal antibody) can be used to isolate the polypeptide by standard techniques, such as affinity chromatography or immunoprecipitation. Moreover, such an antibody can be used to detect the marker (e.g., in a cellular lysate or cell supernatant) in order to evaluate the level and pattern of expression of the marker. Detection can be facilitated by coupling the antibody to a detectable substance. Examples of detectable substances include, but are not limited to, various enzymes, prosthetic groups, fluorescent materials, luminescent materials, bioluminescent materials, and radioactive materials. Examples of suitable enzymes include, but are not limited to, horseradish peroxidase, alkaline phosphatase, 3-galactosidase, or acetylcholinesterase; examples of suitable prosthetic group complexes include, but are not limited to, streptavidin/biotin and avidin/biotin; examples of suitable fluorescent materials include, but are not limited to, umbelliferone, fluorescein, fluorescein isothiocyanate, rhodamine, dichlorotriazinylamine fluorescein, dansyl chloride or phycoerythrin; an example of a luminescent material includes, but is not limited to, luminol; examples of bioluminescent materials include, but are not limited to, luciferase, luciferin, and aequorin, and examples of suitable radioactive materials include, but are not limited to, $^{125}$I, $^{131}$I, $^{35}$S or $^{3}$H.

An antibody directed against a fusion polypeptide described herein, can also be used diagnostically to monitor protein levels in tissues or body fluids (e.g., in a tumor cell-containing body fluid) as part of a clinical testing procedure, e.g., to, for example, determine the efficacy of a given treatment regimen.

Antigens and Vaccines

Embodiments featured in the invention include preparations, e.g., antigenic preparations, of the entire fusion or a fragment thereof, e.g., a fragment capable of raising antibodies specific to the fusion protein, e.g., a fusion junction containing fragment (collectively referred to herein as a "fusion-specific polypeptides" or FSP). The preparation can include an adjuvant or other component.

An FSP can be used as an antigen or vaccine. For example, an FSP can be used as an antigen to immunize an animal, e.g., a rodent, e.g., a mouse or rat, rabbit, horse, goat, dog, or non-human primate, to obtain antibodies, e.g., fusion protein specific antibodies. In an embodiment a fusion specific antibody molecule is an antibody molecule described herein, e.g., a polyclonal. In other embodiments a fusion specific antibody molecule is monospecific, e.g., monoclonal, human, humanized, chimeric or other monospecific antibody molecule. An anti-fusion protein specific antibody molecule can be used to treat a subject having a cancer, e.g., a cancer described herein.

Embodiments featured include vaccine preparations that comprise an FSP capable of stimulating an immune response in a subject, e.g., by raising, in the subject, antibodies specific to the fusion protein. The vaccine preparation can include other components, e.g., an adjuvant. The vaccine preparations can be used to treat a subject having cancer, e.g., a cancer described herein.

Rearrangement Based Cancer Vaccines

Embodiments featured in the invention include preparations of a fusion polypeptide described herein. The fusion polypeptide can be derived from, but is not limited to, any fusion molecule described herein.

A fusion junction polypeptide can be used as an antigen or vaccine, for the treatment of a disease, e.g., a cancer, e.g., a cancer described herein. For example, antigen presenting cells (APCs) derived from a patient with a disease, e.g., cancer, e.g., a cancer described herein; can be incubated with a fusion junction polypeptide, wherein the disease from which the patient's APCs are derived is known, has been determined, or is suspected of expressing the fusion molecule from which the fusion junction polypeptide is derived. In certain embodiments, the APCs are also incubated with one or more cytokines. In certain embodiments, the cytokine induces maturation of the APCs. In certain embodiments, the cytokine is one or more of GMCSF, TNF-alpha, IL-4, IL-2, IL-6, IL-7, IL-13, IL-15, HGF. In certain embodiments, the cytokine is GMCSF. The APCs are incubated with the fusion polypeptide under conditions which allow the APCs to uptake or endocytose the fusion polypeptide, and process the polypeptide for presentation on a cell surface molecule, e.g., major histocompatibility class MHC class I molecules. The cell culture conditions are known to one of skill in the art. The APCs can then be infused back into the same patient from whom the cells were derived.

In certain embodiments the APCs are purified prior to incubation with a fusion polypeptide. In certain embodiments, the APCs are dendritic cells. In certain embodiments, the APCs include one or more of dendritic cells, macrophages, and B cells. In certain embodiments, the APCs are incubated with one, two, three, four, or more fusion polypeptides.

In certain embodiments, the disclosure includes preparations of or a vaccine preparation of mature APCs which have been incubated with a fusion polypeptide described herein.

In certain embodiments, the method includes determining or acquiring a determination of whether a patient expresses a fusion molecule described herein. In certain embodiments, the method includes selecting a fusion polypeptide based on the determination of whether a patient expresses a fusion molecule described herein. In some embodiments, the method further comprises the incubation of APCs derived from the patient with the selected fusion polypeptide. In some embodiments, the method further comprises the infusion of the APCs back into the patient from which they were derived.

Expression Vectors, Host Cells and Recombinant Cells

In another aspect, the invention includes vectors (e.g., expression vectors), containing a nucleic acid encoding a fusion polypeptide described herein. As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

A vector can include a fusion nucleic acid in a form suitable for expression of the nucleic acid in a host cell. Preferably the recombinant expression vector includes one or more regulatory sequences operatively linked to the nucleic acid sequence to be expressed. The term "regulatory sequence" includes promoters, enhancers and other expression control elements (e.g., polyadenylation signals). Regulatory sequences include those which direct constitutive expression of a nucleotide sequence, as well as tissue-specific regulatory and/or inducible sequences. The design of the expression vector can depend on such factors as the choice of the host cell to be transformed, the level of expression of protein desired, and the like. The expression vectors can be introduced into host cells to thereby produce a fusion polypeptide, including fusion proteins or polypeptides encoded by nucleic acids as described herein, mutant forms thereof, and the like).

The term "recombinant host cell" (or simply "host cell" or "recombinant cell"), as used herein, is intended to refer to a cell into which a recombinant expression vector has been introduced. It should be understood that such terms are intended to refer not only to the particular subject cell, but to the progeny of such a cell. Because certain modifications may occur in succeeding generations due to either mutation or environmental influences, such progeny may not, in fact, be identical to the parent cell, but are still included within the scope of the term "host cell" as used herein.

The recombinant expression vectors can be designed for expression of a fusion polypeptide (e.g., a fusion described herein) in prokaryotic or eukaryotic cells. For example, polypeptides featured in the invention can be expressed in *E. coli*, insect cells (e.g., using baculovirus expression vectors), yeast cells or mammalian cells. Suitable host cells are discussed further in Goeddel, (1990) *Gene Expression Technology: Methods in Enzymology* 185, Academic Press, San Diego, Calif. Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion polypeptides described herein can be used in activity assays (e.g., direct assays or competitive assays described in detail below), or to generate antibodies specific for fusion polypeptides described herein.

To maximize recombinant protein expression in *E. coli* is to express the protein in a host bacteria with an impaired capacity to proteolytically cleave the recombinant protein (Gottesman, S., (1990) *Gene Expression Technology: Methods in Enzymology* 185, Academic Press, San Diego, Calif. 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences can be carried out by standard DNA synthesis techniques.

The fusion polypeptide expression vector can be a yeast expression vector, a vector for expression in insect cells, e.g., a baculovirus expression vector or a vector suitable for expression in mammalian cells.

When used in mammalian cells, the expression vector's control functions can be provided by viral regulatory elements. For example, commonly used promoters are derived from polyoma, Adenovirus 2, cytomegalovirus and Simian Virus 40.

In another embodiment, the promoter is an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard (1992) *Proc. Natl. Acad. Sci. USA* 89:5547, and Paillard (1989) *Human Gene Therapy* 9:983).

In another embodiment, the recombinant mammalian expression vector is capable of directing expression of the nucleic acid preferentially in a particular cell type (e.g., tissue-specific regulatory elements are used to express the nucleic acid). Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873, 316 and European Application Publication No. 264,166). Developmentally-regulated promoters are also encompassed, for example, the murine hox promoters (Kessel and Gruss (1990) *Science* 249:374-379) and the fetoprotein promoter (Campes and Tilghman (1989) *Genes Dev.* 3:537-546).

The invention further provides a recombinant expression vector comprising a DNA molecule featured in the invention cloned into the expression vector in an antisense orientation. Regulatory sequences (e.g., viral promoters and/or enhancers) operatively linked to a nucleic acid cloned in the antisense orientation can be chosen which direct the constitutive, tissue specific or cell type specific expression of antisense RNA in a variety of cell types. The antisense expression vector can be in the form of a recombinant plasmid, phagemid or attenuated virus.

Another aspect the invention provides a host cell which includes a nucleic acid molecule described herein, e.g., a fusion nucleic acid molecule described herein within a recombinant expression vector or a fusion nucleic acid molecule described herein containing sequences which allow it to homologous recombination into a specific site of the host cell's genome.

A host cell can be any prokaryotic or eukaryotic cell. For example, a fusion polypeptide can be expressed in bacterial cells (such as *E. coli*), insect cells, yeast or mammalian cells (such as Chinese hamster ovary cells (CHO) or COS cells, e.g., COS-7 cells, CV-1 origin SV40 cells; Gluzman (1981) *Cell* 23:175-182). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation.

A host cell can be used to produce (e.g., express) a fusion polypeptide (e.g., a fusion molecule described herein). Accordingly, the invention further provides methods for producing a fusion polypeptide using the host cells. In one embodiment, the method includes culturing the host cell (into which a recombinant expression vector encoding a polypeptide has been introduced) in a suitable medium such that the fusion polypeptide is produced. In another embodiment, the method further includes isolating a fusion polypeptide from the medium or the host cell.

In another aspect, the invention features, a cell or purified preparation of cells which include a fusion molecule described herein transgene, or which otherwise misexpress the fusion. For example, a cell or purified preparation of cells which include a MPRIP-NTRK1 fusion transgene, or which otherwise misexpress MPRIP-NTRK1 fusion.

The cell preparation can consist of human or non-human cells, e.g., rodent cells, e.g., mouse or rat cells, rabbit cells, or pig cells. In embodiments, the cell or cells include a fusion transgene, e.g., a heterologous form of a fusion described herein, e.g., a gene derived from humans (in the case of a non-human cell) or a fusion transgene, e.g., a heterologous form of a fusion described herein. The fusion transgene can be misexpressed, e.g., overexpressed or underexpressed. In other preferred embodiments, the cell or cells include a gene that mis-expresses an endogenous fusion, e.g., a gene the expression of which is disrupted, e.g., a knockout. Such cells can serve as a model for studying disorders that are related to mutated or mis-expressed fusion alleles (e.g., cancers) or for use in drug screening, as described herein.

Therapeutic Methods

The MPRIP-NTRK1 fusion molecules disclosed herein have been shown to have constitutive TRKA kinase activity and to be oncogenic (see the Examples herein). Further experiments disclosed herein demonstrate that tyrosine kinase inhibitors, including TRK- or TRKA-specific inhibitors reduce and/or inhibit the activity of the MPRIP-NTRK1 fusion molecule. Further embodiments disclosed herein show that a human subject with lung cancer (e.g., lung adenocarcinoma) treated with crizotinib showed tumor shrinkage consistent with the level of in vitro inhibition and predicted patient drug levels. Other embodiments disclosed herein identified the MPRIP-NTRK1 fusion molecules in approximately 3.3% of enriched lung adenocarcinomas that did not harbor other oncogenic alterations tested, such as.

Accordingly, methods of treating a neoplasm, a cancer or a tumor harboring a NTRK1 fusion molecule described herein are disclosed. The methods include administering an anti-cancer agent, e.g., a kinase inhibitor as described herein, alone or in combination, e.g., in combination with other agents, e.g., chemotherapeutic agents, or procedures, in an amount sufficient to reduce or inhibit the tumor cell growth, and/or treat or prevent the cancer(s), in the subject.

"Treat," "treatment," and other forms of this word refer to the administration of a kinase inhibitor, alone or in combination with a second agent to impede growth of a cancer, to cause a cancer to shrink by weight or volume, to extend the expected survival time of the subject and or time to progression of the tumor or the like. In those subjects, treatment can include, but is not limited to, inhibiting tumor growth, reducing tumor mass, reducing size or number of metastatic lesions, inhibiting the development of new metastatic lesions, prolonged survival, prolonged progression-free survival, prolonged time to progression, and/or enhanced quality of life.

As used herein, unless otherwise specified, the terms "prevent," "preventing" and "prevention" contemplate an action that occurs before a subject begins to suffer from the re-growth of the cancer and/or which inhibits or reduces the severity of the cancer.

As used herein, and unless otherwise specified, a "therapeutically effective amount" of a compound is an amount sufficient to provide a therapeutic benefit in the treatment or management of the cancer, or to delay or minimize one or more symptoms associated with the cancer. A therapeutically effective amount of a compound means an amount of therapeutic agent, alone or in combination with other therapeutic agents, which provides a therapeutic benefit in the treatment or management of the cancer. The term "therapeutically effective amount" can encompass an amount that improves overall therapy, reduces or avoids symptoms or causes of the cancer, or enhances the therapeutic efficacy of another therapeutic agent.

As used herein, and unless otherwise specified, a "prophylactically effective amount" of a compound is an amount sufficient to prevent re-growth of the cancer, or one or more symptoms associated with the cancer, or prevent its recurrence. A prophylactically effective amount of a compound means an amount of the compound, alone or in combination with other therapeutic agents, which provides a prophylactic benefit in the prevention of the cancer. The term "prophylactically effective amount" can encompass an amount that improves overall prophylaxis or enhances the prophylactic efficacy of another prophylactic agent.

As used herein, the term "patient" or "subject" refers to an animal, typically a human (i.e., a male or female of any age group, e.g., a pediatric patient (e.g, infant, child, adolescent) or adult patient (e.g., young adult, middle-aged adult or senior adult) or other mammal, such as a primate (e.g., cynomolgus monkey, rhesus monkey). When the term is used in conjunction with administration of a compound or drug, then the patient has been the object of treatment, observation, and/or administration of the compound or drug.

In certain embodiments, the neoplasm or neoplastic cell is a benign, pre-malignant, malignant (cancer) or metastasis.

In certain embodiments, the cancer includes, but is not limited to, a solid tumor, a soft tissue tumor, and a metastatic lesion (e.g., a cancer as described herein). In one embodiment, the cancer is chosen from a lung cancer, a pancreatic cancer, melanoma, a colorectal cancer, an esophageal-gastric cancer, a thyroid cancer, or an adenocarcinoma. Exemplary cancers that can be treated include, but are not limited to, lung adenocarcinoma, cervical adenocarcinoma, uterus endometrial adenocarcinoma, glioblastoma, melanoma, spindle cell sarcoma, ameloblastic fibroscarcoma, adenocarcinoma, cholangiocarcinoma, urothelial (transitional cell) carcinoma, ovarian epithelial carcinoma, colorectal adenocarcinoma, breast carcinoma, prostate carcinoma, and pancreas ductal adenocarcinoma.

In other embodiments, the cancer is chosen from lung cancer, thyroid cancer, colorectal cancer, adenocarcinoma, melanoma, B cell cancer, breast cancer, bronchus cancer, cancer of the oral cavity or pharynx, cancer of hematological tissues, cervical cancer, colon cancer, esophageal cancer, esophageal-gastric cancer, gastric cancer, kidney cancer, liver cancer, multiple myeloma, ovarian cancer, pancreatic cancer, prostate cancer, salivary gland cancer, small bowel or appendix cancer, stomach cancer, testicular cancer, urinary bladder cancer, uterine or endometrial cancer, inflammatory myofibroblastic tumors, gastrointestinal stromal tumor (GIST), and the like.

In yet other embodiments, the lung cancer is chosen from one or more of the following: non-small cell lung cancer (NSCLC), small cell lung cancer (SCLC), squamous cell carcinoma (SCC), adenocarcinoma of the lung, bronchogenic carcinoma, a lung carcinoid tumor, large cell carcinoma, a lung neuroendocrine tumor, or a combination thereof. In one embodiment, the lung cancer is NSCLC or SCC. In another embodiment, the cancer is a lung cancer (e.g., lung adenocarcinoma) that has an alteration in NTRK, e.g., has an MPRIP-NTRK molecule described herein. In another embodiment, the cancer is a lung cancer (e.g., lung adenocarcinoma) that has no detectable altered level or activity in one or more of EGFR, KRAS, ALK, ROS1 or RET.

Kinase Inhibitors

In one embodiment, the anti-cancer agent is a kinase inhibitor. For example, the kinase inhibitor is a multi-kinase inhibitor or a TrK- or NTRK-specific inhibitor. Exemplary multikinase inhibitors include, but are not limited to, KRC-108 and K252a.

Several TRK family inhibitors, and kinase inhibitors that also inhibit NTRK1, are under clinical and preclinical investigation in solid tumors. The aurora kinase inhibitor danusertib (PHA-739358), in clinical trials in solid tumors, was shown to inhibit Ntrk1 as well as several other kinases (reviewed in Meulenbeld H J, Mathijssen R H, Verweij J, et al. (2012) *Expert Opin Investig Drugs* 21(3):383-93). A Phase 1 clinical trial of danusertib in 56 solid tumor patients reported an objective response in one non-small cell lung cancer patient and tumor regression in an ovarian cancer patient (Cohen R B, Jones S F, Aggarwal C, et al. (2009) *Clin Cancer Res* 15(21):6694-701). The selective Trk inhibitor lestaurtinib, which is currently in clinical trials in neuroblastoma, was shown to inhibit tumor growth in preclinical xenograft models of neuroblastoma (Iyer R, Evans A E, Qi X, et al. (2010) *Clin Cancer Res* 16(5):1478-85). The selective Trk inhibitor AZ-23 was also shown to inhibit tumor growth in preclinical xenograft models of neuroblastoma (Thress K, Macintyre T, Wang H, et al. (2009) *Mol Cancer Ther* 8(7):1818-27). The dual Ntrk/cyclin-dependent kinase inhibitor PHA-848125 was shown to have anti-tumor effect in a variety of preclinical tumor xenograft models (Albanese C, Alzani R, Amboldi N, et al. (2010) *Mol Cancer Ther* 9(8):2243-54), and to inhibit tumor growth in a mouse model of lung adenocarcinoma with KRAS mutation (Degrassi A, Russo M, Nanni C, et al. (2010) *Mol Cancer Ther* 9(3):673-81). A Phase 1 clinical trial of PHA-848125 in solid tumors reported partial response in 2/14 patients and stable disease in 9/28 (Weiss G J, Hidalgo M, Borad M J, et al. (2011) Phase I study of the safety, tolerability and pharmacokinetics of PHA-848125AC, a dual tropomyosin receptor kinase A and cyclin-dependent kinase inhibitor, in patients with advanced solid malignancies. ePub December 2011). The Trk inhibitor CEP-2563 was shown to have anti-tumor activity in a variety of preclinical models, and a Phase 1 clinical trial of CEP-2563 demonstrated feasibility (Undevia S D, Vogelzang N J, Mauer A M, et al. (2004) *Invest New Drugs* 22(4):449-58). The Trk inhibitor K252a was shown in a lung adenocarcinoma cell line to block Akt activation, promote cell death, and reduce tumor cell growth (Perez-Pinera P, Hernandez T, Garcia-Suirez O, et al. (2007) *Mol Cell Biochem* 295(1-2):19-26). The multi-kinase inhibitor KRC-108 was shown to inhibit NTRK1 and to have antiproliferative activity in preclinical tumor models including a xenograft model of lung cancer (Han S Y, Lee C O, Ahn S H, et al. (2012) *Invest New Drugs* 30(2):518-23).

In one embodiment, the anti-cancer agent is a kinase inhibitor. Exemplary multikinase inhibitors include, but are not limited to, KRC-108 and K252a. In another embodiment, the NTRK1 kinase inhibitor is chosen from one or more of: lestaurtinib (CEP-701); AZ-23; indenopyrrolocarboazole 12a; GW 441756; oxindole 3; isothiazole 5n; thiazole 20h; pyridocarbazole; GNF 5837; AG 879 (Tyrphostin AG 879); Ro 08-2750; AZ623; AR523; a Pyrazolo[1;5a]pyrimidine; a Pyrrolidinyl urea; a pyrrolidinyl thiourea; a Pyrazole derivatives; a macrocyclic compound; a substituted pyrazolo[1;5a]pyrimidine; a pyridotriazole; a benzotriazole; a quinazolinyl; a pyridoquinazolinyl; a pyrrolo[2;3-d]pyrimidine; danusertib (PHA-739358); PHA-848125 (dual Ntrk/cyclin-dependent kinase inhibitor); CEP-2563; an anti-Trk1 antibody; or ARRY-470, ARRY-523 or ARRY-772.

In one embodiment, the kinase inhibitor is lestaurtinib (also known as CEP-701, rINN, KT 5555, SP 924). Lesraurtinib is an orally bioavailable indolocarbazole derivative with antineoplastic properties. Lestaurtinib is a tyrosine kinase inhibitor, with inhibitory activity against TrkA, TrkB, TrkC, FLT3, and JAK2. Lestaurtinib has the chemical name: (5S,6S,8R)-6-hydroxy-6-(hydroxymethyl)-5-methyl-7,8,14, 15-tetrahydro-5H-16-oxa-4b,8a,14-triaza-5,8-methanodibenzo[b,h]cycloocta[jkl]cyclopenta[e]-as-indacen-13(6H)-one; and has the following structure:

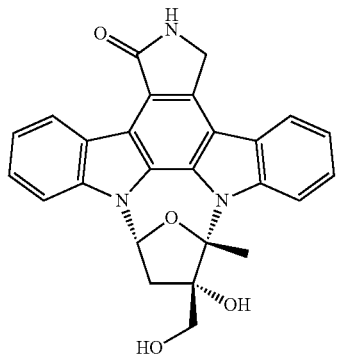 [SMILES: C[C@]12O[C@H](C[C@]1(O)CO)n1c3ccccc3c3c4c(c5c6ccccc6n2c5c31)CNC4=O]

Lestaurtinib Chemical Structure

Molecular Weight: 439.4626.

In another embodiment, the inhibitor is AZ-23. AZ-23 is selective tyrosine kinase Trk inhibitor with IC50 of 2 and 8 nM for TrkA and TrkB, respectively. AZ-23 has the chemical name: 5-chloro-N-[(1S)-1-(5-fluoropyridin-2-yl)ethyl]-N'-(5-propan-2-yloxy-1H-pyrazol-3-yl)pyrimidine-2,4-diamine; and the chemical structure:

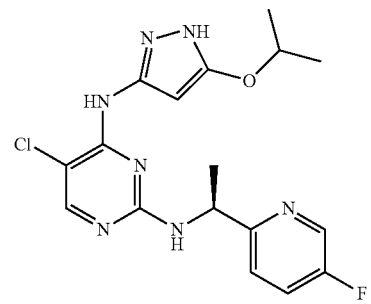 [SMILES: CC(C)Oc1cc(Nc2nc(N[C@@H](C)c3ccc(F)cn3)ncc2Cl)n[nH]1]

AZ-23 Chemical Structure

Molecular Weight: 391.83.

In another embodiment, the inhibitor is GW 441756. GW 441756 is a potent and orally active TrkA kinase inhibitor (IC50=2 nM); more than 100 fold selective over a range of other kinases. GW 441756 has the chemical name: 3-[1-(1-Methyl-1H-indol-3-yl)-meth-(Z)-ylidene]-1,3-dihydro-pyrrolo[3,2-b]pyridin-2-one; and the chemical structure:

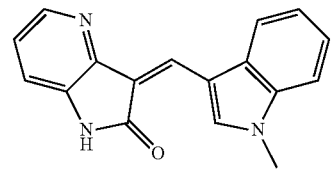 [SMILES: Cn1cc(/C=C2\C(=O)Nc3cccnc32)c2ccccc21]

GW 441756 Chemical Structure

Molecular Weight: 275.31.

In another embodiment, the inhibitor is isothiazole 5n. Isothiazole 5n is a TrkA kinase inhibitor with an IC50 of less than 1 nM. Isothiazole 5n has the chemical structure:

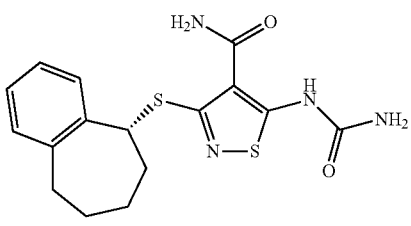 [SMILES: NC(=O)Nc1snc(S[C@@H]2CCCCc3ccccc32)c1C(N)=O]

Isothiazole 5n Chemical Structure

In another embodiment, the kinase inhibitor is indenopyrrolocarboazole 12a. Indenopyrrolocarboazole 12a is a TrkA kinase inhibitor with an IC50 of 8 nM. Indenopyrrolocarboazole 12a has the following structure:

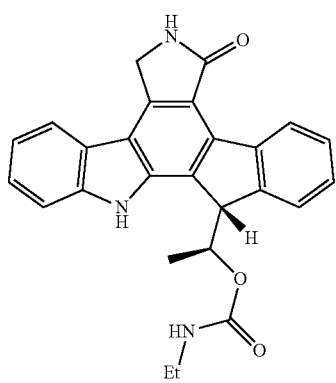 [SMILES: CCNC(=O)O[C@@H](C)[C@H]1c2ccccc2-c2c3c(c4c([nH]c5ccccc54)c21)CNC3=O]

Indenopyrrolocarboazole 12a Chemical Structure

In another embodiment, the kinase inhibitor is thiazole 20h. Thiazole 20h is a TrkA kinase inhibitor with an IC50 of 0.6 nM. Thiazole 20h has the following structure:

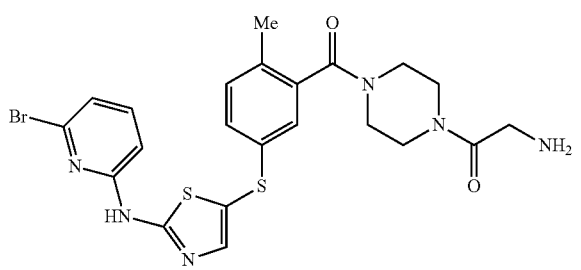 [SMILES: Cc1ccc(Sc2cnc(Nc3cccc(Br)n3)s2)cc1C(=O)N1CCN(C(=O)CN)CC1]

Thiazole 20h Chemical Structure

In another embodiment, the kinase inhibitor is oxindole 3. Oxindole 3 is a TrkA kinase inhibitor with an IC50 of 2 nM. Oxindole 3 has the following structure:

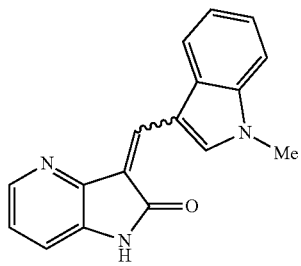 [SMILES: Cn1cc(C=C2C(=O)Nc3cccnc32)c2ccccc21]

Oxindole 3 Chemical Structure

In another embodiment, the kinase inhibitor is pyridocarbazole. Pyridocarbazole is a TrkA kinase inhibitor with an IC50 of 6 nM. Pyridocarbazole has the following structure:

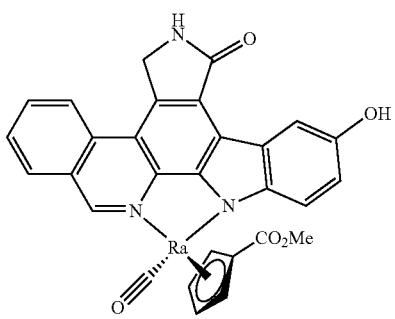

Pyridocarbazole Chemical Structure

In another embodiment, the kinase inhibitor is AR523. AR523 is a pan-Trk inhibitor which demonstrates similar activity against TrkA, TrkB and TrkC receptors.

In another embodiment, the kinase inhibitor is K252a. K252a is a Trk inhibitor, which inhibits tyrosine phosphorylation of Trk A. K252a has the chemical name: (9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one; and has the following structure:

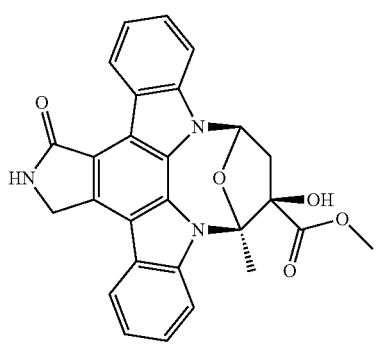 [SMILES: COC(=O)[C@@]1(O)C[C@H]2O[C@]1(C)n1c3ccccc3c3c4c(c5c6ccccc6n2c5c31)C(=O)NC4]

K252a Chemical Structure

Molecular Weight: 467.47274.

In another embodiment, the kinase inhibitor is GNF-5837. GNF-5837 is a potent pan-Trk inhibitor. GNF-5837 has the chemical name: N-[3-[[2,3-Dihydro-2-oxo-3-(1H-pyrrol-2-ylmethylene)-1H-indol-6-yl]amino]-4-methylphenyl]-N-[2-fluoro-5-(trifluoromethyl)phenyl]urea; and has the following structure:

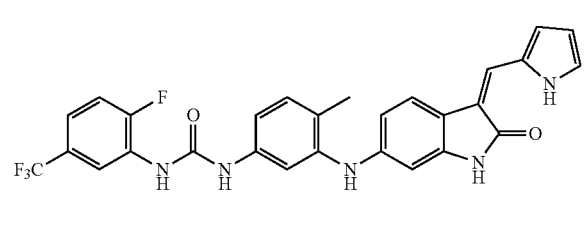 [SMILES: Cc1ccc(NC(=O)Nc2cc(C(F)(F)F)ccc2F)cc1Nc1ccc2c(c1)NC(=O)/C2=C\c1ccc[nH]1]

GNF-5837 Chemical Structure

Molecular Weight: 535.49.

In another embodiment, the kinase inhibitor is AG 879 (Tyrphostin AG 879). AG 879 is an inhibitor of the tyrosine kinase activity of nerve growth factor (NGF) TrkA. AG 879 has the chemical name (2E)-3-[3,5-Bis(1,1-dimethylethyl)-4-hydroxyphenyl]-2-cyano-2-propenethioamide; and has the following structure:

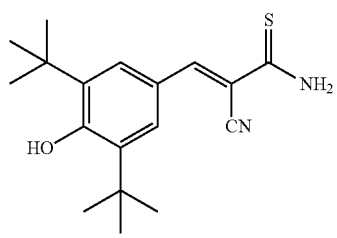 [SMILES: CC(C)(C)c1cc(/C=C(\C#N)C(N)=S)cc(C(C)(C)C)c1O]

AG 879 Chemical Structure

Molecular Weight: 316.46.

In another embodiment, the kinase inhibitor is Ro 08-2750. Ro 08-2750 is a non-peptide inhibitor of NGF that binds the NGF dimer ($K_D$~1 μM) possibly causing a conformational change. Ro 08-2750 has the following structure:

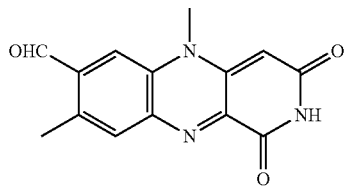 [SMILES: Cc1cc2nc3c(=O)[nH]c(=O)cc-3n(C)c2cc1C=O]

Ro 08-2750 Chemical Structure

Molecular Weight: 270.24.

In another embodiment, the kinase inhibitor is AZ623. AZ623 is a novel potent and selective inhibitor of the Trk family of tyrosine kinases.

In another embodiment, the kinase inhibitor is ARRY-470. ARRY-470 is a pan-Trk inhibitor which demonstrates with an IC50 of 9.5, 24, and 24 against TrkA, TrkB and TrkC, respectively.

ARRY-470 has the following chemical name and chemical structure:

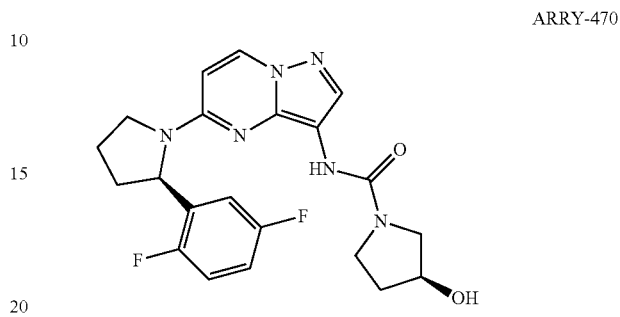

ARRY-470

(S)—N-(5-((R)-2-(2,5-difluorophenyl)pyrolidin-1-yl)pyrazolol[1,5-a]pyrimidin-3-hydroxypyrrolidine-1-carboxamide In another embodiment, the kinase inhibitor is ARRY-523. ARRY-772 is a pan-Trk inhibitor which demonstrates with an IC50 of 10, 8.1, and 10 against TrkA, TrkB and TrkC, respectively.

In another embodiment, the kinase inhibitor is ARRY-772. ARRY-772 is a pan-Trk inhibitor which demonstrates with an IC50 of 2, 2.1, and 2.3 against TrkA, TrkB and TrkC, respectively.

In other embodiments, the anti-cancer agent is a fusion antagonist inhibits the expression of nucleic acid encoding a fusion described herein. Examples of such fusion antagonists include nucleic acid molecules, for example, antisense molecules, ribozymes, RNAi, triple helix molecules that hybridize to a nucleic acid encoding a fusion described herein, or a transcription regulatory region, and blocks or reduces mRNA expression of a fusion described herein.

Other approaches to Ntrk1 inhibition are also under investigation. Research has shown that HSP90 inhibitor 17-DMAG disrupted Ntrk1/Hsp90 binding, which results in degradation and depletion of Ntrk1, and reduced the growth of myeloid leukemia cells (Rao et al., 2010, supra). In one embodiment, the HSP90 inhibitor is a geldanamycin derivative, e.g., a benzoquinone or hygroquinone ansamycin HSP90 inhibitor. For example, the HSP90 inhibitor can be chosen from one or more of 17-AAG (also known as tanespimycin or CNF-1010), 17-DMAG, BIIB-021 (CNF-2024), BIIB-028, AUY-922 (also known as VER-49009), SNX-5422, STA-9090, AT-13387, XL-888, MPC-3100, CU-0305, CNF-1010, Macbecin I, Macbecin II, CCT-018159, CCT-129397, IPI-493, IPI-504, PU-H71, or PF-04928473 (SNX-2112).

In one embodiment, the kinase inhibitor (e.g., the multi-kinase inhibitor or the NTRK1-specific inhibitor as described herein) is administered in combination with an HSP90 inhibitor, e.g., an HSP90 inhibitor as described herein.

In other embodiments, the kinase inhibitor is administered in combination with a second therapeutic agent or a different therapeutic modality, e.g., anti-cancer agents, and/or in combination with surgical and/or radiation procedures.

By "in combination with," it is not intended to imply that the therapy or the therapeutic agents must be administered at the same time and/or formulated for delivery together, although these methods of delivery are within the scope of the invention. The pharmaceutical compositions can be administered concurrently with, prior to, or subsequent to, one or more other additional therapies or therapeutic agents. In general, each agent will be administered at a dose and/or on a time schedule determined for that agent. In will further be appreciated that the additional therapeutic agent utilized in this combination can be administered together in a single composition or administered separately in different compositions. The particular combination to employ in a regimen will take into account compatibility of the inventive pharmaceutical composition with the additional therapeutically active agent and/or the desired therapeutic effect to be achieved.

For example, the second therapeutic agent can be a cytotoxic or a cytostatic agent. Exemplary cytotoxic agents include antimicrotubule agents, topoisomerase inhibitors, or taxanes, antimetabolites, mitotic inhibitors, alkylating agents, intercalating agents, agents capable of interfering with a signal transduction pathway, agents that promote apoptosis and radiation. In yet other embodiments, the methods can be used in combination with immunodulatory agents, e.g., IL-1, 2, 4, 6, or 12, or interferon alpha or gamma, or immune cell growth factors such as GM-CSF.

Anti-cancer agents, e.g., kinase inhibitors, used in therapeutic methods can be evaluated using the screening assays described herein. In one embodiment, the anti-cancer agents are evaluated in a cell-free system, e.g., a cell lysate or in a reconstituted system. In other embodiments, the anti-cancer agents are evaluated in a cell in culture, e.g., a cell expressing fusion molecule described herein (e.g., a mammalian cell, a tumor cell or cell line, a recombinant cell). In yet other embodiments, the anti-cancer agents are evaluated cell in vivo (a fusion molecule-expressing cell present in a subject, e.g., an animal subject (e.g., an in vivo animal model).

Exemplary parameters evaluated include one or more of:
(i) a change in binding activity, e.g., direct binding of the candidate agent to a fusion polypeptide described herein; a binding competition between a known ligand and the candidate agent to a fusion polypeptide described herein;
(ii) a change in kinase activity, e.g., phosphorylation levels of a fusion polypeptide described herein (e.g., an increased or decreased autophosphorylation); or a change in phosphorylation of a target of an kinase;
(iii) a change in an activity of a cell containing a fusion described herein (e.g., a tumor cell or a recombinant cell), e.g., a change in proliferation, morphology or tumorigenicity of the cell;
(iv) a change in tumor present in an animal subject, e.g., size, appearance, proliferation, of the tumor; or
(v) a change in the level, e.g., expression level, of a fusion polypeptide described herein or nucleic acid molecule described herein.

In one embodiment, a change in a cell free assay in the presence of a candidate agent is evaluated. For example, an activity of a fusion molecule described herein, or interaction of a fusion molecule described herein with a downstream ligand can be detected.

In other embodiments, a change in an activity of a cell is detected in a cell in culture, e.g., a cell expressing a fusion molecule described herein (e.g., a mammalian cell, a tumor cell or cell line, a recombinant cell). In one embodiment, the cell is a recombinant cell that is modified to express a fusion nucleic acid described herein, e.g., is a recombinant cell transfected with a fusion nucleic acid described herein. The transfected cell can show a change in response to the expressed fusion molecule described herein, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a fusion molecule described herein. In other embodiments, a change in binding activity or phosphorylation as described herein is detected.

In yet other embodiment, a change in a tumor present in an animal subject (e.g., an in vivo animal model) is detected. In one embodiment, the animal model is a tumor containing animal or a xenograft comprising cells expressing a fusion molecule described herein (e.g., tumorigenic cells expressing a fusion molecule described herein). The anti-cancer agents can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

The screening methods and assays are described in more detail herein below.

Screening Methods

In another aspect, the invention features a method, or assay, for screening for agents that modulate, e.g., inhibit, the expression or activity of a fusion molecule described herein. The method includes contacting a fusion molecule described herein, or a cell expressing a fusion molecule described herein, with a candidate agent; and detecting a change in a parameter associated with a fusion molecule described herein, e.g., a change in the expression or an activity of the fusion molecule described herein. The method can, optionally, include comparing the treated parameter to a reference value, e.g., a control sample (e.g., comparing a parameter obtained from a sample with the candidate agent to a parameter obtained from a sample without the candidate agent). In one embodiment, if a decrease in expression or activity of the fusion molecule described herein is detected, the candidate agent is identified as an inhibitor. In another embodiment, if an increase in expression or activity of the fusion molecule described herein is detected, the candidate agent is identified as an activator. In certain embodiments, the fusion molecule described herein is a nucleic acid molecule or a polypeptide as described herein.

In one embodiment, the contacting step is effected in a cell-free system, e.g., a cell lysate or in a reconstituted system. In other embodiments, the contacting step is effected in a cell in culture, e.g., a cell expressing a fusion molecule described herein (e.g., a mammalian cell, a tumor cell or cell line, a recombinant cell). In yet other embodiments, the contacting step is effected in a cell in vivo (a fusion molecule described herein-expressing cell present in a subject, e.g., an animal subject (e.g., an in vivo animal model).

Exemplary parameters evaluated include one or more of:
(i) a change in binding activity, e.g., direct binding of the candidate agent to a fusion polypeptide described herein; a binding competition between a known ligand and the candidate agent to a fusion polypeptide described herein;
(ii) a change in kinase activity, e.g., phosphorylation levels of a fusion polypeptide described herein (e.g., an increased or decreased autophosphorylation); or a change in phosphorylation of a target of an kinase. In certain embodiments, a change in kinase activity, e.g., phosphorylation, is detected by any of Western blot (e.g., using an anti-MPRIP-NTRK1 fusion antibody; a phosphor-specific antibody, detecting a shift in the molecular weight of a MPRIP-NTRK1 fusion polypeptide), mass spectrometry, immunoprecipitation, immunohistochemistry, immunomagnetic beads, among others;

(iii) a change in an activity of a cell containing a fusion molecule described herein (e.g., a tumor cell or a recombinant cell), e.g., a change in proliferation, morphology or tumorigenicity of the cell;

(iv) a change in tumor present in an animal subject, e.g., size, appearance, proliferation, of the tumor; or (v) a change in the level, e.g., expression level, of a fusion polypeptide described herein or nucleic acid molecule described herein.

In one embodiment, a change in a cell free assay in the presence of a candidate agent is evaluated. For example, an activity of a fusion molecule described herein, or interaction of a fusion molecule described herein with a downstream ligand can be detected. In one embodiment, a fusion polypeptide described herein is contacted with a ligand, e.g., in solution, and a candidate agent is monitored for an ability to modulate, e.g., inhibit, an interaction, e.g., binding, between the fusion polypeptide described herein and the ligand. In one exemplary assay, purified fusion protein described herein is contacted with a ligand, e.g., in solution, and a candidate agent is monitored for an ability to inhibit interaction of the fusion protein with the ligand, or to inhibit phosphorylation of the ligand by the fusion protein. An effect on an interaction between the fusion protein and a ligand can be monitored by methods known in the art, such as by absorbance, and an effect on phosphorylation of the ligand can be assayed, e.g., by Western blot, immunoprecipitation, or immunomagnetic beads.

In other embodiments, a change in an activity of a cell is detected in a cell in culture, e.g., a cell expressing a fusion molecule described herein (e.g., a mammalian cell, a tumor cell or cell line, a recombinant cell). In one embodiment, the cell is a recombinant cell that is modified to express a fusion nucleic acid described herein, e.g., is a recombinant cell transfected with a fusion nucleic acid described herein. The transfected cell can show a change in response to the expressed fusion molecule, e.g., increased proliferation, changes in morphology, increased tumorigenicity, and/or acquired a transformed phenotype. A change in any of the activities of the cell, e.g., the recombinant cell, in the presence of the candidate agent can be detected. For example, a decrease in one or more of: proliferation, tumorigenicity, transformed morphology, in the presence of the candidate agent can be indicative of an inhibitor of a fusion molecule described herein. In other embodiments, a change in binding activity or phosphorylation as described herein is detected.

In an exemplary cell-based assay, a nucleic acid comprising a fusion molecule described herein can be expressed in a cell, such as a cell (e.g., a mammalian cell) in culture. The cell containing a nucleic acid expressing the fusion molecule can be contacted with a candidate agent, and the cell is monitored for an effect of the candidate agent. A candidate agent that causes decreased cell proliferation or cell death can be determined to be a candidate for treating a tumor (e.g., a cancer) that carries a fusion described herein.

In one embodiment, a cell containing a nucleic acid expressing a fusion molecule described herein can be monitored for expression of the fusion protein. Protein expression can be monitored by methods known in the art, such as by, e.g., mass spectrometry (e.g., tandem mass spectrometry), a reporter assay (e.g., a fluorescence-based assay), Western blot, and immunohistochemistry. By one method, decreased fusion expression is detected. A candidate agent that causes decreased expression of the fusion protein as compared to a cell that does not contain the nucleic acid fusion can be determined to be a candidate for treating a tumor (e.g., a cancer) that carries a fusion described herein.

A cell containing a nucleic acid expressing a fusion molecule described herein can be monitored for altered kinase activity. Kinase activity can be assayed by measuring the effect of a candidate agent on a known kinase target protein.

In yet other embodiment, a change in a tumor present in an animal subject (e.g., an in vivo animal model) is detected. In one embodiment, the animal model is a tumor containing animal or a xenograft comprising cells expressing a fusion molecule described herein (e.g., tumorigenic cells expressing a fusion molecule described herein). The candidate agent can be administered to the animal subject and a change in the tumor is detected. In one embodiment, the change in the tumor includes one or more of a tumor growth, tumor size, tumor burden, survival, is evaluated. A decrease in one or more of tumor growth, tumor size, tumor burden, or an increased survival is indicative that the candidate agent is an inhibitor.

In one exemplary animal model, a xenograft is created by injecting cells into mouse. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. The health of the animal is also monitored, such as to determine if an animal treated with a candidate agent survives longer. A candidate agent that causes growth of the tumor to slow or stop, or causes the tumor to shrink in size, or causes decreased tumor burden, or increases survival time, can be considered to be a candidate for treating a tumor (e.g., a cancer) that carries a fusion described herein.

In another exemplary animal assay, cells expressing a fusion described herein are injected into the tail vein, e.g., of a mouse, to induce metastasis. A candidate agent is administered to the mouse, e.g., by injection (such as subcutaneous, intraperitoneal, or tail vein injection, or by injection directly into the tumor) or oral delivery, and the tumor is observed to determine an effect of the candidate anti-cancer agent. A candidate agent that inhibits or prevents or reduces metastasis, or increases survival time, can be considered to be a candidate for treating a tumor (e.g., a cancer) that carries a fusion described herein.

Cell proliferation can be measured by methods known in the art, such as PCNA (Proliferating cell nuclear antigen) assay, 5-bromodeoxyuridine (BrdUrd) incorporation, Ki-67 assay, mitochondrial respiration, or propidium iodide staining. Cells can also be measured for apoptosis, such as by use of a TUNEL (Terminal Deoxynucleotide Transferase dUTP Nick End Labeling) assay. Cells can also be assayed for presence of angiogenesis using methods known in the art, such as by measuring endothelial tube formation or by measuring the growth of blood vessels from subcutaneous tissue, such as into a solid gel of basement membrane.

In other embodiments, a change in expression of a fusion molecule described herein can be monitored by detecting the nucleic acid or protein levels, e.g., using the methods described herein.

In certain embodiments, the screening methods described herein can be repeated and/or combined. In one embodiment, a candidate agent that is evaluated in a cell-free or cell-based described herein can be further tested in an animal subject.

In one embodiment, the candidate agent is identified and re-tested in the same or a different assay. For example, a test compound is identified in an in vitro or cell-free system, and re-tested in an animal model or a cell-based assay. Any order or combination of assays can be used. For example, a high throughput assay can be used in combination with an animal model or tissue culture.

Candidate agents suitable for use in the screening assays described herein include, e.g., small molecule compounds, nucleic acids (e.g., siRNA, aptamers, short hairpin RNAs, antisense oligonucleotides, ribozymes, antagomirs, microRNA mimics or DNA, e.g., for gene therapy) or polypeptides, e.g., antibodies (e.g., full length antibodies or antigen-binding fragments thereof, Fab fragments, or scFv fragments). The candidate anti-cancer agents can be obtained from a library (e.g., a commercial library), or can be rationally designed, such as to target an active site in a functional domain (e.g., a kinase domain).

In other embodiments, the method, or assay, includes providing a step based on proximity-dependent signal generation, e.g., a two-hybrid assay that includes a first fusion protein (e.g., a fusion protein described herein), and a second fusion protein (e.g., a ligand), contacting the two-hybrid assay with a test compound, under conditions wherein said two hybrid assay detects a change in the formation and/or stability of the complex, e.g., the formation of the complex initiates transcription activation of a reporter gene.

In one non-limiting example, the three-dimensional structure of the active site of fusion molecule described herein is determined by crystallizing the complex formed by the fusion molecule and a known inhibitor. Rational drug design is then used to identify new test agents by making alterations in the structure of a known inhibitor or by designing small molecule compounds that bind to the active site of the fusion.

The candidate agents can be obtained using any of the numerous approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner, U.S. Pat. No. 5,223,409), spores (Ladner U.S. Pat. No. 5,223,409), plasmids (Cull et al. (1992) *Proc Natl Acad Sci USA* 89:1865-1869) or on phage (Scott and Smith (1990) *Science* 249:386-390; Devlin (1990) *Science* 249:404-406; Cwirla et al. (1990) *Proc. Natl. Acad. Sci.* 87:6378-6382; Felici (1991) *J. Mol. Biol.* 222:301-310; Ladner supra.).

The interaction between two molecules can also be detected, e.g., using fluorescence energy transfer (FET) (see, for example, Lakowicz et al., U.S. Pat. No. 5,631,169; Stavrianopoulos, et al., U.S. Pat. No. 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means known in the art (e.g., using a fluorimeter).

In another embodiment, determining the ability of the fusion protein to bind to a target molecule can be accomplished using real-time Biomolecular Interaction Analysis (BIA) (see, e.g., Sjolander, S. and Urbaniczky, C. (1991) *Anal. Chem.* 63:2338-2345 and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Nucleic Acid Inhibitors

In another embodiment, a fusion inhibitor inhibits the expression of a nucleic acid encoding a fusion described herein. Examples of such fusion inhibitors include nucleic acid molecules, for example, antisense molecules, dsRNA, siRNA, ribozymes, or triple helix molecules, which hybridize to a nucleic acid encoding a fusion described herein, or a transcription regulatory region, and blocks or reduces mRNA expression of the fusion. Accordingly, isolated nucleic acid molecules that are nucleic acid inhibitors, e.g., antisense, siRNA, RNAi, to a fusion-encoding nucleic acid molecule are provided.

Antisense

In some embodiments, the nucleic acid fusion inhibitor is an antisense nucleic acid molecule. An "antisense" nucleic acid can include a nucleotide sequence which is complementary to a "sense" nucleic acid encoding a protein, e.g., complementary to the coding strand of a double-stranded cDNA molecule or complementary to an mRNA sequence. The antisense nucleic acid can be complementary to an entire fusion coding strand, or to only a portion thereof. In another embodiment, the antisense nucleic acid molecule is antisense to a "noncoding region" of the coding strand of a nucleotide sequence encoding fusion (e.g., the 5' and 3' untranslated regions). Anti-sense agents can include, for example, from about 8 to about 80 nucleobases (i.e., from about 8 to about 80 nucleotides), e.g., about 8 to about 50 nucleobases, or about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. Antisense compounds can include a stretch of at least eight consecutive nucleobases that are complementary to a sequence in the target gene. An oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment or, in the case of in vitro assays, under conditions in which the assays are conducted.

Hybridization of antisense oligonucleotides with mRNA can interfere with one or more of the normal functions of mRNA. The functions of mRNA to be interfered with include all key functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

Exemplary antisense compounds include DNA or RNA sequences that specifically hybridize to the target nucleic acid, e.g., the mRNA encoding a fusion described herein. The complementary region can extend for between about 8 to about 80 nucleobases. The compounds can include one or more modified nucleobases. Modified nucleobases may include, e.g., 5-substituted pyrimidines such as 5-iodouracil, 5-iodocytosine, and C5-propynyl pyrimidines such as C5-propynylcytosine and C5-propynyluracil. Other suitable modified nucleobases include $N^4$—$(C_1$-$C_{12})$ alkylaminocytosines and $N^4,N^4$—$(C_1$-$C_{12})$ dialkylaminocytosines. Modified nucleobases may also include 7-substituted-8-aza-7-deazapurines and 7-substituted-7-deazapurines such as, for example, 7-iodo-7-deazapurines, 7-cyano-7-deazapurines, 7-aminocarbonyl-7-deazapurines. Examples of these include 6-amino-7-iodo-7-deazapurines, 6-amino-7-cyano-7-deazapurines, 6-amino-7-aminocarbonyl-7-deazapurines, 2-amino-6-hydroxy-7-iodo-7-deazapurines, 2-amino-6-hydroxy-7-cyano-7-deazapurines, and 2-amino-6-hydroxy-7-aminocarbonyl-7-deazapurines. Furthermore, $N^6$—$(C_1$-$C_{12})$ alkylaminopurines and $N^6,N^6$—$(C_1$-$C_{12})$ dialkylaminopurines, including $N^6$-methylaminoadenine and $N^6,N^6$-dimethylaminoadenine, are also suitable modified nucleobases. Similarly, other 6-substituted purines including, for example, 6-thioguanine may constitute appropriate modified nucleobases. Other suitable nucleobases include 2-thiouracil, 8-bromoadenine, 8-bromoguanine, 2-fluoroadenine, and 2-fluoroguanine. Derivatives of any of the aforementioned modified nucleobases are also appropriate. Substituents of any of the preceding compounds may include $C_1$-$C_{30}$ alkyl, C2-C30 alkenyl, C2-C30 alkynyl, aryl, aralkyl, heteroaryl, halo, amino, amido, nitro, thio, sulfonyl, carboxyl, alkoxy, alkylcarbonyl, alkoxycarbonyl, and the like. Descriptions of other types of nucleic acid agents are also available. See, e.g., U.S. Pat. Nos. 4,987,071; 5,116,742; and 5,093,246; Woolf et al. (1992) *Proc Natl Acad Sci USA; Antisense RNA and DNA*, D. A. Melton, Ed., Cold Spring Harbor Laboratory, Cold Spring Harbor, N.Y. (1988); 89:7305-9; Haselhoff and Gerlach (1988) *Nature* 334:585-59; Helene, C. (1991) *Anticancer Drug Des.* 6:569-84; Helene (1992) *Ann. N.Y. Acad. Sci.* 660:27-36; and Maher (1992) *Bioassays* 14:807-15.

In yet another embodiment, the antisense nucleic acid molecule is an α-anomeric nucleic acid molecule. An α-anomeric nucleic acid molecule forms specific double-stranded hybrids with complementary RNA in which, contrary to the usual 3-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

The antisense nucleic acid molecules are typically administered to a subject (e.g., by direct injection at a tissue site), or generated in situ such that they hybridize with or bind to cellular mRNA and/or genomic DNA encoding a fusion described herein to thereby inhibit expression of the protein, e.g., by inhibiting transcription and/or translation. Alternatively, antisense nucleic acid molecules can be modified to target selected cells and then be administered systemically. For systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

Ribozyme

In another embodiment, an antisense nucleic acid featured in the invention is a ribozyme. A ribozyme having specificity for a fusion-encoding nucleic acid can include one or more sequences complementary to the nucleotide sequence of a fusion cDNA disclosed herein, and a sequence having known catalytic sequence responsible for mRNA cleavage (see U.S. Pat. No. 5,093,246 or Haselhoff and Gerlach (1988) *Nature* 334:585-591). For example, a derivative of a Tetrahymena L-19 IVS RNA can be constructed in which the nucleotide sequence of the active site is complementary to the nucleotide sequence to be cleaved in a fusion-encoding mRNA. See, e.g., Cech et al. U.S. Pat. No. 4,987,071; and Cech et al. U.S. Pat. No. 5,116,742. Alternatively, fusion mRNA can be used to select a catalytic RNA having a specific ribonuclease activity from a pool of RNA molecules. See, e.g., Bartel, D. and Szostak, J. W. (1993) *Science* 261:1411-1418.

Triple Helix Molecules

Inhibition of a fusion gene described herein can be accomplished by targeting nucleotide sequences complementary to the regulatory region of the fusion to form triple helical structures that prevent transcription of the fusion gene in target cells. See generally, Helene, C. (1991) *Anticancer Drug Des.* 6:569-84; Helene, C. i (1992) *Ann. N.Y. Acad. Sci.* 660:27-36; and Maher, L. J. (1992) *Bioassays* 14:807-15. The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

dsRNAs

In some embodiments, the nucleic acid fusion inhibitor is a dsRNA molecule. dsRNAs having a duplex structure of between about 20 and 23 base pairs, e.g., 21, base pairs are effective at inducing RNA interference (RNAi) (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226).

In one embodiment, the dsRNA, is un-modified, and does not comprise, e.g., chemical modifications and/or conjugations known in the art or described herein. In another embodiment, the dsRNA, is chemically modified to enhance stability or other beneficial characteristics. The dsRNA can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. While a target sequence of a dsRNA can be generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with a dsRNA molecule, mediate the best inhibition of target gene expression. Thus, while the sequences identified herein represent effective target sequences, it is contemplated that further optimization of inhibition efficiency can be achieved by progressively "walking the window" one nucleotide upstream or downstream of the given sequences to identify sequences with equal or better inhibition characteristics.

In some embodiments, the nucleic acid fusion inhibitor is a siRNA molecule. siRNAs are small double stranded RNAs (dsRNAs) that optionally include overhangs. For example, the duplex region of an siRNA is about 18 to 25 nucleotides in length, e.g., about 19, 20, 21, 22, 23, or 24 nucleotides in length. Typically, the siRNA sequences are exactly complementary to the target mRNA. dsRNAs and siRNAs in particular can be used to silence gene expression in mammalian cells (e.g., human cells). siRNAs also include short hairpin RNAs (shRNAs) with 29-base-pair stems and 2-nucleotide 3' overhangs. See, e.g., Clemens et al. (2000) *Proc. Natl. Acad. Sci. USA* 97:6499-6503; Billy et al. (2001) *Proc. Natl. Sci. USA* 98:14428-14433; Elbashir et al. (2001) *Nature*. 411:494-8; Yang et al. (2002) *Proc. Natl. Acad. Sci. USA* 99:9942-9947; Siolas et al. (2005), *Nat. Biotechnol.* 23(2):227-31; 20040086884; U.S. 20030166282; 20030143204; 20040038278; and 20030224432.

Modifications of Nucleic Acid Fusion Inhibitor Molecules

A nucleic acid fusion inhibitor can be modified to enhance or obtain beneficial characteristics. For example, a nucleic acid fusion inhibitor can be modified at the base moiety, sugar moiety or phosphate backbone to improve, e.g., the stability, hybridization, or solubility of the molecule. For non-limiting examples of synthetic oligonucleotides with modifications see Toulmè (2001) *Nature Biotech*. 19:17 and Faria et al. (2001) *Nature Biotech*. 19:40-44. Such phosphoramidite oligonucleotides can be effective antisense agents.

A nucleic acid fusion inhibitor molecule can be modified to include one or more bridged nucleic acids (BNAs). A bridged nucleic acid is a nucleotide bearing a conformationally restricted sugar moiety. Oligonucleotides containing BNAs show high binding affinity with RNA complementary strands, and are more tolerant to endinucleolytic and exonucleolytic degradation (Roongjang, S. et al., (2007) *Nucleic Acids Symp Ser* (Oxf) 51:113-114). Exemplary BNAs include, but are not limited to 2'4'-BNA (also known as LNA (see below); 3'-amino2',4'-BNA, 3',4'-BNA; $BNA^{COC}$; $BNA^{NC}$, and $BNA^{(ME)}$. The structure of the BNA will influence the binding affinity of the nucleic acid molecule with complementary single stranded DNA and double stranded DNA, as well as its enzymatic stability against nuclease degradation. The synthesis and purification of BNA molecules can be performed using standard protocols, (e.g., see Imanishi T, et al., (2002) *Chem. Commun.* 16: 1653-1659).

In some embodiments, the nucleic acid can be modified to generate peptide nucleic acids (see Hyrup B. et al. (1996) *Bioorganic & Medicinal Chemistry* 4: 5-23). As used herein, the terms "peptide nucleic acid" or "PNA" refers to a nucleic acid mimic, e.g., a DNA or RNA mimic, in which the deoxyribose or ribose phosphate backbone is replaced by a pseudopeptide backbone and only the four natural nucleobases are retained. The neutral backbone of a PNA can allow for specific hybridization to DNA and RNA under conditions of low ionic strength.

PNAs of nucleic acid fusion inhibitor molecules can be used in therapeutic and diagnostic applications. For example, PNAs can be used as antisense, antigene, siRNA, or RNAi agents for sequence-specific modulation of gene expression by, for example, inducing transcription or translation arrest or inhibiting replication. PNAs of nucleic acid fusion inhibitor molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. et al. (1996) supra)); or as probes or primers for DNA sequencing or hybridization (Hyrup B. et al. (1996) supra; Perry-O'Keefe supra).

The synthesis of PNA oligomers can be performed using standard solid phase peptide synthesis protocols as described in Hyrup B. et al. (1996) supra and Perry-O'Keefe et al. *Proc. Natl. Acad. Sci.* 93: 14670-675. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in RNA molecules are described in, for example, in Nielsen et al., *Science*, 1991, 254, 1497-1500.

The nucleic acid fusion inhibitor molecules can also be modified to include one or more locked nucleic acids (LNA). A locked nucleic acid is a nucleotide having a modified sugar moiety in which the sugar moiety comprises an extra bridge connecting the 2' and 4' carbons. This structure effectively "locks" the ribose in the 3'-endo structural conformation. LNA containing nucleic acid molecules possess high affinity to complementary DNA and RNA and improved mismatch discrimination relative to unmodified nucleic acid molecules (Jepson, J., et al., (2004) *Oligonucleotides* 14:130-146). The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Representative U.S. patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

A nucleic acid fusion inhibitor molecule can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

Potentially stabilizing modifications to the ends of nucleic acid fusion inhibitor molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT (idT) and others. Disclosure of this modification can be found in PCT Publication No. WO 2011/005861.

In other embodiments, the nucleic acid fusion inhibitor molecule may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; WO88/09810) or the blood-brain barrier (see, e.g., WO 89/10134). In addition, oligonucleotides can be modified with hybridization-triggered cleavage agents (see, e.g., Krol et al. (1988) *Bio-Techniques* 6:958-976) or intercalating agents (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

In some embodiment, modifications to the fusion nucleic acid molecules can include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples include, but are not limited to fusion nucleic acid molecules containing modified backbones or no natural internucleoside linkages. fusion nucleic acid molecules having modified backbones include, among others, those that do not have a phosphorus atom in the backbone.

Modified nucleic acid backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476, 301; 5,023,243; 5,177,195; 5,188,897; 5,264,423; 5,276, 019; 5,278,302; 5,286,717; 5,321,131; 5,399,676; 5,405, 939; 5,453,496; 5,455,233; 5,466,677; 5,476,925; 5,519, 126; 5,536,821; 5,541,316; 5,550,111; 5,563,253; 5,571, 799; 5,587,361; 5,625,050; 6,028,188; 6,124,445; 6,160, 109; 6,169,170; 6,172,209; 6,239,265; 6,277,603; 6,326, 199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified nucleic acid backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

Some embodiments include nucleic acid fusion inhibitor molecules with phosphorothioate backbones and oligonucleosides with heteroatom backbones, and in particular —$CH_2$—NH—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$— [wherein the native phosphodiester backbone is represented as —O—P—O—$CH_2$—] of the above-referenced U.S. Pat. No. 5,489,677, and the amide backbones of the above-referenced U.S. Pat. No. 5,602,240.

Modified nucleic acid fusion inhibitor molecules can also contain one or more substituted sugar moieties. The nucleic acid, e.g., RNA, molecules can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$).$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an RNA molecule, or a group for improving the pharmacodynamic properties of an RNA molecule, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$.

Other modifications can include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an RNA molecule, particularly the 3' position of the sugar on the 3' terminal nucleotide or in 2'-5' linked dsRNAs and the 5' position of 5' terminal nucleotide. RNA molecules can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

Evaluation of Subjects

Subjects, e.g., patients, can be evaluated for the presence of a fusion molecule described herein. A patient can be evaluated, for example, by determining the genomic sequence of the patient, e.g., by an NGS method. Alternatively, or in addition, evaluation of a patient can include directly assaying for the presence of a fusion described herein, in the patient, such as by an assay to detect a fusion nucleic acid (e.g., DNA or RNA), such as by, Southern blot, Northern blot, or RT-PCR, e.g., qRT-PCR. Alternatively, or in addition, a patient can be evaluated for the presence of a protein fusion, such as by immunohistochemistry, Western blot, immunoprecipitation, or immunomagnetic bead assay.

Evaluation of a patient can also include a cytogenetic assay, such as by fluorescence in situ hybridization (FISH), to identify the chromosomal rearrangement resulting in the fusion. FISH is commonly used to evaluate patient tumor samples for the presence of chromosomal aberrations that result in gene fusions (Davies, K. D., et al. *Clin Cancer Res* 18, 4570-4579 (2012); Kwak, E. L., et al. *N Engl J Med* 363, 1693-1703 (2010)). For example, to perform FISH, at least a first probe tagged with a first detectable label can be designed to target MPRIP, such as in one or more exons of MPRIP and at least a second probe tagged with a second detectable label can be designed to target NTRK1, such as in one or more exons of NTRK1 (e.g., the exons containing the part of the protein that includes the tyrosine kinase domain). The at least one first probe and the at least one second probe will be closer together in patients who carry the MPRIP-NTRK1 fusion than in patients who do not carry the fusion.

Other embodiments include a break-apart FISH assay to detect chromosomal rearrangements within the NTRK1 gene, regardless of the identity of the 5' fusion partner. In such assays, at least a first probe tagged with a first detectable label can be designed to target NTRK1 (or MPRIP), such as in one or more exons of NTRK1 (or MPRIP) and at least a second probe tagged with a second detectable label can be designed to target NTRK1 (or MPRIP). Hybridization of these probes can show a separation of the 5' and 3' probes in the samples containing the MPRIP-NTRK1 gene fusions, but not in a control sample having intact full length NTRK1 (or MPRIP).

These methods can be utilized in a similar manner for any fusion described herein.

Additional methods for fusion detection are provided below.

In one aspect, the results of a clinical trial, e.g., a successful or unsuccessful clinical trial, can be repurposed to identify agents that target a fusion described herein. By one exemplary method, a candidate agent used in a clinical trial can be reevaluated to determine if the agent in the trial targets a fusion, or is effective to treat a tumor containing a particular fusion. For example, subjects who participated in a clinical trial for an agent, such as a kinase inhibitor, can be identified. Patients who experienced an improvement in symptoms, e.g., cancer (e.g., lung cancer) symptoms, such as decreased tumor size, or decreased rate of tumor growth, can be evaluated for the presence of a fusion described herein. Patients who did not experience an improvement in cancer symptoms can also be evaluated for the presence of a fusion described herein. Where patients carrying a fusion described herein are found to have been more likely to respond to the test agent than patients who did not carry such a fusion, then the agent is determined to be an appropriate treatment option for a patient carrying the fusion.

"Reevaluation" of patients can include, for example, determining the genomic sequence of the patients, or a subset of the clinical trial patients, e.g., by an NGS method. Alternatively, or in addition, reevaluation of the patients can include directly assaying for the presence of a fusion described herein, in the patient, such as by an assay to detect a fusion nucleic acid (e.g., RNA), such as by RT-PCR, e.g., qRT-PCR. Alternatively, or in addition, a patient can be evaluated for the presence of a protein fusion, such as by immunohistochemistry, Western blot, immunoprecipitation, or immunomagnetic bead assay.

Clinical trials suitable for repurposing as described above include trials that tested tyrosine kinase inhibitors, and multikinase inhibitors.

Methods for Detection of Fusion Nucleic Acids and Polypeptides

Methods for evaluating a fusion gene, mutations and/or gene products are known to those of skill in the art. In one embodiment, the fusion is detected in a nucleic acid molecule by a method chosen from one or more of: nucleic acid hybridization assay, amplification-based assays (e.g., polymerase chain reaction (PCR)), PCR-RFLP assay, real-time PCR, sequencing, screening analysis (including metaphase cytogenetic analysis by standard karyotype methods, FISH (e.g., break away FISH), spectral karyotyping or MFISH, comparative genomic hybridization), in situ hybridization, SSP, HPLC or mass-spectrometric genotyping.

Additional exemplary methods include, traditional "direct probe" methods such as Southern blots or in situ hybridization (e.g., fluorescence in situ hybridization (FISH) and FISH plus SKY), and "comparative probe" methods such as comparative genomic hybridization (CGH), e.g., cDNA-based or oligonucleotide-based CGH, can be used. The methods can be used in a wide variety of formats including, but not limited to, substrate (e.g., membrane or glass) bound methods or array-based approaches.

In certain embodiments, the evaluation methods include the probes/primers described herein. In one embodiment, probes/primers can be designed to detect a fusion molecule described herein or a reciprocal thereof. Probes/primers are suitable, e.g., for FISH or PCR amplification. For PCR, e.g., to amply a region including a fusion junction described herein, forward primers can be designed to hybridize to a gene sequence from nucleotides corresponding to one of the genes of a fusion described herein, and reverse primers can be designed to hybridize to a sequence from nucleotides corresponding to the second gene involved in the fusion. For example, probes/primers can be designed to detect a MPRIP-NTRK1 fusion or a reciprocal thereof. The MPRIP-NTRK1 probes/primers can hybridize to the nucleotides encoding one or more exons of the MPRIP protein. The MPRIP-NTRK1 probes/primers can hybridize to the nucleotides encoding one or more exons of the NTRK1 protein). These probes/primers are suitable, e.g., for FISH or PCR amplification.

The probes/primers described above use MPRIP-NTRK1 as an example, and such methods can be readily applied to any of the fusions described herein by one of skill in the art.

In one embodiment, FISH analysis is used to identify the chromosomal rearrangement resulting in the fusions as described above. For example, to perform FISH, at least a first probe tagged with a first detectable label can be designed to target a first gene of a fusion described herein, such as in one or more exons of the gene and at least a second probe tagged with a second detectable label can be designed to target a second gene of the fusion, such as in one or more exons of genes (e.g., the exons containing the part of the protein that includes the tyrosine kinase domain). The at least one first probe and the at least one second probe will be closer together in a subject who carries the fusion compared to a subject who does not carry the fusion.

In one approach, a variation of a FISH assay, e.g., "break-away FISH", is used to evaluate a patient. By this method, at least one probe targeting the fusion junction and at least one probe targeting an individual gene of the fusion, e.g., at one or more exons and or introns of the gene, are utilized. In normal cells, both probes will be observed (or a secondary color will be observed due to the close proximity of the two genes of the gene fusion), and only the single gene probe will be observed when the translocation occurs. Other variations of the FISH method known in the art are suitable for evaluating a patient.

For example, by this method, at least one probe targeting the NTRK1 intron 13/MPRIP intron 21 and at least one probe targeting MPRIP (or NTRK1) e.g., at one or more exons and or introns of MPRIP or NTRK1, are utilized. In normal cells, both probes will be observed (or a secondary color will be observed due to the close proximity of the MPRIP or NTRK1 genes), and only the MPRIP probe will be observed when the translocation occurs. Other variations of the FISH method known in the art are suitable for evaluating a patient.

The FISH methods described herein above use MPRIP-NTRK1 as an example, and such methods can be readily applied to any of the fusions described herein by one of skill in the art.

Probes are used that contain DNA segments that are essentially complementary to DNA base sequences existing in different portions of chromosomes. Examples of probes useful according to the invention, and labeling and hybridization of probes to samples are described in two U.S. patents to Vysis, Inc. U.S. Pat. Nos. 5,491,224 and 6,277,569 to Bittner, et al.

Additional protocols for FISH detection are described below.

Chromosomal probes are typically about 50 to about $10^5$ nucleotides in length. Longer probes typically comprise smaller fragments of about 100 to about 500 nucleotides in length.

Probes that hybridize with centromeric DNA and locus-specific DNA are available commercially, for example, from Vysis, Inc. (Downers Grove, Ill.), Molecular Probes, Inc. (Eugene, Oreg.) or from Cytocell (Oxfordshire, UK). Alternatively, probes can be made non-commercially from chromosomal or genomic DNA through standard techniques. For example, sources of DNA that can be used include genomic DNA, cloned DNA sequences, somatic cell hybrids that contain one, or a part of one, chromosome (e.g., human chromosome) along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, Biotechnic Histochem., 1998, 73(1):6-22, Wheeless et al., Cytometry 1994, 17:319-326, and U.S. Pat. No. 5,491,224.

The probes to be used hybridize to a specific region of a chromosome to determine whether a cytogenetic abnormality is present in this region. One type of cytogenetic abnormality is a deletion. Although deletions can be of one or more entire chromosomes, deletions normally involve loss of part of one or more chromosomes. If the entire region of a chromosome that is contained in a probe is deleted from a cell, hybridization of that probe to the DNA from the cell will normally not occur and no signal will be present on that chromosome. If the region of a chromosome that is partially contained within a probe is deleted from a cell, hybridization of that probe to the DNA from the cell can still occur, but less of a signal can be present. For example, the loss of a signal is compared to probe hybridization to DNA from control cells that do not contain the genetic abnormalities which the probes are intended to detect. In some embodiments, at least 1, 5, 10, 20, 30, 40, 50, 60, 70, 80, 90, 100, 110, 120, 130, 140, 150, 160, 170, 180, 190, 200, or more cells are enumerated for presence of the cytogenetic abnormality.

Cytogenetic abnormalities to be detected can include, but are not limited to, non-reciprocal translocations, balanced translocations, intra-chromosomal inversions, point mutations, deletions, gene copy number changes, gene expression level changes, and germ line mutations. In particular, one type of cytogenetic abnormality is a duplication. Duplications can be of entire chromosomes, or of regions smaller than an entire chromosome. If the region of a chromosome that is contained in a probe is duplicated in a cell, hybridization of that probe to the DNA from the cell will normally produce at least one additional signal as compared to the number of signals present in control cells with no abnormality of the chromosomal region contained in the probe.

Chromosomal probes are labeled so that the chromosomal region to which they hybridize can be detected. Probes typically are directly labeled with a fluorophore, an organic molecule that fluoresces after absorbing light of lower wavelength/higher energy. The fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, U.S. Pat. No. 5,491,224.

U.S. Pat. No. 5,491,224 describes probe labeling as a number of the cytosine residues having a fluorescent label covalently bonded thereto. The number of fluorescently labeled cytosine bases is sufficient to generate a detectable fluorescent signal while the individual so labeled DNA segments essentially retain their specific complementary binding (hybridizing) properties with respect to the chromosome or chromosome region to be detected. Such probes are made by taking the unlabeled DNA probe segment, transaminating with a linking group a number of deoxycytidine nucleotides in the segment, covalently bonding a fluorescent label to at least a portion of the transaminated deoxycytidine bases.

Probes can also be labeled by nick translation, random primer labeling or PCR labeling. Labeling is done using either fluorescent (direct)- or haptene (indirect)-labeled nucleotides. Representative, non-limiting examples of labels include: AMCA-6-dUTP, CascadeBlue-4-dUTP, Fluorescein-12-dUTP, Rhodamine-6-dUTP, TexasRed-6-dUTP, Cy3-6-dUTP, Cy5-dUTP, Biotin (BIO)-11-dUTP, Digoxygenin (DIG)-11-dUTP or Dinitrophenyl (DNP)-11-dUTP.

Probes also can be indirectly labeled with biotin or digoxygenin, or labeled with radioactive isotopes such as $^{32}P$ and $^{3}H$, although secondary detection molecules or further processing then is required to visualize the probes. For example, a probe labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

Probes can also be prepared such that a fluorescent or other label is not part of the DNA before or during the hybridization, and is added after hybridization to detect the probe hybridized to a chromosome. For example, probes can be used that have antigenic molecules incorporated into the DNA. After hybridization, these antigenic molecules are detected using specific antibodies reactive with the antigenic molecules. Such antibodies can themselves incorporate a fluorochrome, or can be detected using a second antibody with a bound fluorochrome.

However treated or modified, the probe DNA is commonly purified in order to remove unreacted, residual products (e.g., fluorochrome molecules not incorporated into the DNA) before use in hybridization.

Prior to hybridization, chromosomal probes are denatured according to methods well known in the art. Probes can be hybridized or annealed to the chromosomal DNA under hybridizing conditions. "Hybridizing conditions" are conditions that facilitate annealing between a probe and target chromosomal DNA. Since annealing of different probes will vary depending on probe length, base concentration and the like, annealing is facilitated by varying probe concentration, hybridization temperature, salt concentration and other factors well known in the art.

Hybridization conditions are facilitated by varying the concentrations, base compositions, complexities, and lengths of the probes, as well as salt concentrations, temperatures, and length of incubation. For example, in situ hybridizations are typically performed in hybridization buffer containing 1-2×SSC, 50-65% formamide and blocking DNA to suppress non-specific hybridization. In general, hybridization conditions, as described above, include temperatures of about 25° C. to about 55° C., and incubation lengths of about 0.5 hours to about 96 hours.

Non-specific binding of chromosomal probes to DNA outside of the target region can be removed by a series of washes. Temperature and concentration of salt in each wash are varied to control stringency of the washes. For example, for high stringency conditions, washes can be carried out at about 65° C. to about 80° C., using 0.2× to about 2×SSC, and about 0.1% to about 1% of a non-ionic detergent such as Nonidet P-40 (NP40). Stringency can be lowered by decreasing the temperature of the washes or by increasing the concentration of salt in the washes. In some applications it is necessary to block the hybridization capacity of repetitive sequences. Thus, in some embodiments, tRNA, human genomic DNA, or Cot-I DNA is used to block non-specific hybridization. After washing, the slide is allowed to drain and air dry, then mounting medium, a counterstain such as DAPI, and a coverslip are applied to the slide. Slides can be viewed immediately or stored at −20° C. before examination.

For fluorescent probes used in fluorescence in situ hybridization (FISH) techniques, fluorescence can be viewed with a fluorescence microscope equipped with an appropriate filter for each fluorophore, or by using dual or triple bandpass filter sets to observe multiple fluorophores. See, for example, U.S. Pat. No. 5,776,688. Alternatively, techniques such as flow cytometry can be used to examine the hybridization pattern of the chromosomal probes.

In CGH methods, a first collection of nucleic acids (e.g., from a sample, e.g., a possible tumor) is labeled with a first label, while a second collection of nucleic acids (e.g., a control, e.g., from a healthy cell/tissue) is labeled with a second label. The ratio of hybridization of the nucleic acids is determined by the ratio of the two (first and second) labels binding to each fiber in the array. Where there are chromosomal deletions or multiplications, differences in the ratio of the signals from the two labels will be detected and the ratio will provide a measure of the copy number. Array-based CGH can also be performed with single-color labeling (as opposed to labeling the control and the possible tumor sample with two different dyes and mixing them prior to hybridization, which will yield a ratio due to competitive hybridization of probes on the arrays). In single color CGH, the control is labeled and hybridized to one array and absolute signals are read, and the possible tumor sample is labeled and hybridized to a second array (with identical content) and absolute signals are read. Copy number difference is calculated based on absolute signals from the two arrays. Hybridization protocols suitable for use with the methods featured in the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology*, Vol. 33: In situ Hybridization Protocols, Choo, ed., Humana Press, Totowa, N.J. (1994), etc. In one embodiment, the hybridization protocol of Pinkel, et al. (1998) *Nature Genetics* 20: 207-211, or of Kallioniemi (1992) *Proc. Natl Acad Sci USA* 89:5321-5325 (1992) is used. Array-based CGH is described in U.S. Pat. No. 6,455,258, the contents of each of which are incorporated herein by reference.

In still another embodiment, amplification-based assays can be used to measure presence/absence and copy number. In such amplification-based assays, the nucleic acid sequences act as a template in an amplification reaction (e.g., Polymerase Chain Reaction (PCR). In a quantitative amplification, the amount of amplification product will be proportional to the amount of template in the original sample. Comparison to appropriate controls, e.g., healthy tissue, provides a measure of the copy number.

Methods of "quantitative" amplification are well known to those of skill in the art. For example, quantitative PCR involves simultaneously co-amplifying a known quantity of a control sequence using the same primers. This provides an internal standard that can be used to calibrate the PCR reaction. Detailed protocols for quantitative PCR are provided in Innis, et al. (1990) PCR Protocols, *A Guide to Methods and Applications*, Academic Press, Inc. N.Y.). Measurement of DNA copy number at microsatellite loci using quantitative PCR analysis is described in Ginzonger, et al. (2000) *Cancer Research* 60:5405-5409. The known nucleic acid sequence for the genes is sufficient to enable one of skill in the art to routinely select primers to amplify any portion of the gene. Fluorogenic quantitative PCR can also be used. In fluorogenic quantitative PCR, quantitation is based on amount of fluorescence signals, e.g., TaqMan and sybr green.

Other suitable amplification methods include, but are not limited to, ligase chain reaction (LCR) (see Wu and Wallace (1989) *Genomics* 4: 560, Landegren, et al. (1988) *Science* 241:1077, and Barringer et al. (1990) *Gene* 89: 117), transcription amplification (Kwoh, et al. (1989) *Proc. Natl. Acad. Sci. USA* 86: 1173), self-sustained sequence replication (Guatelli, et al. (1990) *Proc. Nat. Acad. Sci. USA* 87: 1874), dot PCR, and linker adapter PCR, etc.

Nucleic Acid Samples

A variety of tissue samples can be the source of the nucleic acid samples used in the present methods. Genomic or subgenomic DNA fragments can be isolated from a subject's sample (e.g., a tumor sample, a normal adjacent tissue (NAT), a blood sample or any normal control)). In certain embodiments, the tissue sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. The isolating step can include flow-sorting of individual chromosomes; and/or micro-dissecting a subject's sample (e.g., a tumor sample, a NAT, a blood sample).

Protocols for DNA isolation from a tissue sample are known in the art. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No. AM1975, September 2008), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. QIAamp® DNA FFPE Tissue Kit uses QIAamp® DNA Micro technology for purification of genomic and mitochondrial DNA.

The isolated nucleic acid samples (e.g., genomic DNA samples) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, i.e., where the complexity of the genome is reduced by design. In some embodiments, any selected portion of the genome can be used with the methods described herein. In certain embodiments, the entire exome or a subset thereof is isolated.

Methods can further include isolating a nucleic acid sample to provide a library (e.g., a nucleic acid library). In certain embodiments, the nucleic acid sample includes whole genomic, subgenomic fragments, or both. The isolated nucleic acid samples can be used to prepare nucleic acid libraries. Thus, in one embodiment, the methods featured in the invention further include isolating a nucleic acid sample to provide a library (e.g., a nucleic acid library as described herein). Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a tumor sample, a normal adjacent tissue (NAT), a blood sample or any normal control)). In one embodiment, the sample (e.g., the tumor or NAT sample) is a preserved. For example, the sample is embedded in a matrix, e.g., an FFPE block or a frozen sample. In certain embodiments, the isolating step includes flow-sorting of individual chromosomes; and/or microdissecting a subject's sample (e.g., a tumor sample, a NAT, a blood sample). In certain embodiments, the nucleic acid sample used to generate the nucleic acid library is less than 5, less than 1 microgram, less than 500 ng, less than 200 ng, less than 100 ng, less than 50 ng or less than 20 ng (e.g., 10 ng or less).

In still other embodiments, the nucleic acid sample used to generate the library includes RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

The method can further include amplifying the nucleic acid sample (e.g., DNA or RNA sample) by specific or non-specific nucleic acid amplification methods that are well known to those skilled in the art. In some embodiments, certain embodiments, the nucleic acid sample is amplified, e.g., by whole-genome amplification methods such as random-primed strand-displacement amplification.

In other embodiments, the nucleic acid sample is fragmented or sheared by physical or enzymatic methods and ligated to synthetic adapters, size-selected (e.g., by preparative gel electrophoresis) and amplified (e.g., by PCR). In other embodiments, the fragmented and adapter-ligated group of nucleic acids is used without explicit size selection or amplification prior to hybrid selection.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA. Protocols for isolating and preparing libraries from whole genomic or subgenomic fragments are known in the art (e.g., Illumina's genomic DNA sample preparation kit). Alternative DNA shearing methods can be more automatable and/or more efficient (e.g., with degraded FFPE samples). Alternatives to DNA shearing methods can also be used to avoid a ligation step during library preparation.

The methods described herein can be performed using a small amount of nucleic acids, e.g., when the amount of source DNA is limiting (e.g., even after whole-genome amplification). In one embodiment, the nucleic acid comprises less than about 5 µg, 4 µg, 3 µg, 2 µg, 1 µg, 0.8 µg, 0.7 µg, 0.6 µg, 0.5 µg, or 400 ng, 300 ng, 200 ng, 100 ng, 50 ng, or 20 ng or less of nucleic acid sample. For example, to prepare 500 ng of hybridization-ready nucleic acids, one typically begins with 3 µg of genomic DNA. One can start with less, however, if one amplifies the genomic DNA (e.g., using PCR) before the step of solution hybridization. Thus it is possible, but not essential, to amplify the genomic DNA before solution hybridization.

In some embodiments, a library is generated using DNA (e.g., genomic DNA) from a sample tissue, and a corresponding library is generated with RNA (or cDNA) isolated from the same sample tissue.

Design of Baits

A bait can be a nucleic acid molecule, e.g., a DNA or RNA molecule, which can hybridize to (e.g., be complementary to), and thereby allow capture of a target nucleic acid. In one embodiment, a bait is an RNA molecule. In other embodiments, a bait includes a binding entity, e.g., an affinity tag, that allows capture and separation, e.g., by binding to a binding entity, of a hybrid formed by a bait and a nucleic acid hybridized to the bait. In one embodiment, a bait is suitable for solution phase hybridization.

Baits can be produced and used by methods and hybridization conditions as described in US 2010/0029498 and Gnirke, A. et al. (2009) *Nat Biotechnol.* 27(2):182-189, and U.S. Ser. No. 61/428,568, filed Dec. 30, 2010, incorporated herein by reference. For example, biotinylated RNA baits can be produced by obtaining a pool of synthetic long oligonucleotides, originally synthesized on a microarray, and amplifying the oligonucleotides to produce the bait sequences. In some embodiments, the baits are produced by adding an RNA polymerase promoter sequence at one end of the bait sequences, and synthesizing RNA sequences using RNA polymerase. In one embodiment, libraries of synthetic oligodeoxynucleotides can be obtained from commercial suppliers, such as Agilent Technologies, Inc., and amplified using known nucleic acid amplification methods.

Each bait sequence can include a target-specific (e.g., a member-specific) bait sequence and universal tails on each end. As used herein, the term "bait sequence" can refer to the target-specific bait sequence or the entire oligonucleotide including the target-specific "bait sequence" and other nucleotides of the oligonucleotide. In one embodiment, a target-specific bait hybridizes to a nucleic acid sequence comprising a nucleic acid sequence in an intron of one gene of a fusion described herein, in an intron of the other gene of a fusion described herein, or a fusion junction joining the introns. In one embodiment, the bait is an oligonucleotide about 200 nucleotides in length, of which 170 nucleotides are target-specific "bait sequence". The other 30 nucleotides (e.g., 15 nucleotides on each end) are universal arbitrary tails used for PCR amplification. The tails can be any sequence selected by the user.

The bait sequences described herein can be used for selection of exons and short target sequences. In one embodiment, the bait is between about 100 nucleotides and 300 nucleotides in length. In another embodiment, the bait is between about 130 nucleotides and 230 nucleotides in length. In yet another embodiment, the bait is between about 150 nucleotides and 200 nucleotides in length. The target-specific sequences in the baits, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

Sequencing

The invention also includes methods of sequencing nucleic acids. In one embodiment, any of a variety of sequencing reactions known in the art can be used to directly sequence at least a portion of a fusion molecule described herein. In one embodiment, the fusion sequence is compared to a corresponding reference (control) sequence.

In one embodiment, the sequence of the fusion nucleic acid molecule is determined by a method that includes one or more of: hybridizing an oligonucleotide, e.g., an allele specific oligonucleotide for one alteration described herein to said nucleic acid; hybridizing a primer, or a primer set (e.g., a primer pair), that amplifies a region comprising the mutation or a fusion junction of the allele; amplifying, e.g., specifically amplifying, a region comprising the mutation or a fusion junction of the allele; attaching an adapter oligonucleotide to one end of a nucleic acid that comprises the mutation or a fusion junction of the allele; generating an optical, e.g., a colorimetric signal, specific to the presence of the one of the mutation or fusion junction; hybridizing a nucleic acid comprising the mutation or fusion junction to a second nucleic acid, e.g., a second nucleic acid attached to a substrate; generating a signal, e.g., an electrical or fluorescent signal, specific to the presence of the mutation or fusion junction; and incorporating a nucleotide into an oligonucleotide that is hybridized to a nucleic acid that contains the mutation or fusion junction.

In another embodiment, the sequence is determined by a method that comprises one or more of: determining the nucleotide sequence from an individual nucleic acid molecule, e.g., where a signal corresponding to the sequence is derived from a single molecule as opposed, e.g., from a sum of signals from a plurality of clonally expanded molecules; determining the nucleotide sequence of clonally expanded proxies for individual nucleic acid molecules; massively parallel short-read sequencing; template-based sequencing; pyrosequencing; real-time sequencing comprising imaging the continuous incorporation of dye-labeling nucleotides during DNA synthesis; nanopore sequencing; sequencing by hybridization; nano-transistor array based sequencing; polony sequencing; scanning tunneling microscopy (STM) based sequencing; or nanowire-molecule sensor based sequencing.

Any method of sequencing known in the art can be used. Exemplary sequencing reactions include those based on techniques developed by Maxam and Gilbert (*Proc. Natl Acad Sci USA* (1977) 74:560) or Sanger (Sanger et al. (1977) *Proc. Nat. Acad. Sci* 74:5463). Any of a variety of automated sequencing procedures can be utilized when performing the assays (*Biotechniques* (1995) 19:448), including sequencing by mass spectrometry (see, for example, U.S. Pat. No. 5,547,835 and international patent application Publication Number WO 94/16101, entitled DNA Sequencing by Mass Spectrometry by H. Köster; U.S. Pat. No. 5,547,835 and international patent application Publication Number WO 94/21822 entitled DNA Sequencing by Mass Spectrometry Via Exonuclease Degradation by H. Köster), and U.S. Pat. No. 5,605,798 and International Patent Application No. PCT/US96/03651 entitled DNA Diagnostics Based on Mass Spectrometry by H. Köster; Cohen et al. (1996) *Adv Chromatogr* 36:127-162; and Griffin et al. (1993) *Appl Biochem Biotechnol* 38:147-159).

Sequencing of nucleic acid molecules can also be carried out using next-generation sequencing (NGS). Next-generation sequencing includes any sequencing method that determines the nucleotide sequence of either individual nucleic acid molecules or clonally expanded proxies for individual nucleic acid molecules in a highly parallel fashion (e.g., greater than $10^5$ molecules are sequenced simultaneously). In one embodiment, the relative abundance of the nucleic acid species in the library can be estimated by counting the relative number of occurrences of their cognate sequences in the data generated by the sequencing experiment. Next generation sequencing methods are known in the art, and are described, e.g., in Metzker, M. (2010) *Nature Biotechnology Reviews* 11:31-46, incorporated herein by reference.

In one embodiment, the next-generation sequencing allows for the determination of the nucleotide sequence of an individual nucleic acid molecule (e.g., Helicos BioSciences' HeliScope Gene Sequencing system, and Pacific Biosciences' PacBio RS system). In other embodiments, the sequencing method determines the nucleotide sequence of clonally expanded proxies for individual nucleic acid molecules (e.g., the Solexa sequencer, Illumina Inc., San Diego, Calif.; 454 Life Sciences (Branford, Conn.), and Ion Torrent). e.g., massively parallel short-read sequencing (e.g., the Solexa sequencer, Illumina Inc., San Diego, Calif.), which generates more bases of sequence per sequencing unit than other sequencing methods that generate fewer but longer reads. Other methods or machines for next-generation sequencing include, but are not limited to, the sequencers provided by 454 Life Sciences (Branford, Conn.), Applied Biosystems (Foster City, Calif.; SOLiD sequencer), and Helicos BioSciences Corporation (Cambridge, Mass.).

Platforms for next-generation sequencing include, but are not limited to, Roche/454's Genome Sequencer (GS) FLX System, Illumina/Solexa's Genome Analyzer (GA), Life/APG's Support Oligonucleotide Ligation Detection (SOLiD) system, Polonator's G.007 system, Helicos BioSciences' HeliScope Gene Sequencing system, and Pacific Biosciences' PacBio RS system.

NGS technologies can include one or more of steps, e.g., template preparation, sequencing and imaging, and data analysis.

Template Preparation

Methods for template preparation can include steps such as randomly breaking nucleic acids (e.g., genomic DNA or cDNA) into smaller sizes and generating sequencing templates (e.g., fragment templates or mate-pair templates). The spatially separated templates can be attached or immobilized to a solid surface or support, allowing massive amounts of sequencing reactions to be performed simultaneously. Types of templates that can be used for NGS reactions include, e.g., clonally amplified templates originating from single DNA molecules, and single DNA molecule templates.

Methods for preparing clonally amplified templates include, e.g., emulsion PCR (emPCR) and solid-phase amplification.

EmPCR can be used to prepare templates for NGS. Typically, a library of nucleic acid fragments is generated, and adapters containing universal priming sites are ligated to the ends of the fragment. The fragments are then denatured into single strands and captured by beads. Each bead captures a single nucleic acid molecule. After amplification and enrichment of emPCR beads, a large amount of templates can be attached or immobilized in a polyacrylamide gel on a standard microscope slide (e.g., Polonator), chemically crosslinked to an amino-coated glass surface (e.g., Life/APG; Polonator), or deposited into individual PicoTiterPlate (PTP) wells (e.g., Roche/454), in which the NGS reaction can be performed.

Solid-phase amplification can also be used to produce templates for NGS. Typically, forward and reverse primers are covalently attached to a solid support. The surface density of the amplified fragments is defined by the ratio of the primers to the templates on the support. Solid-phase amplification can produce hundreds of millions spatially separated template clusters (e.g., Illumina/Solexa). The ends of the template clusters can be hybridized to universal sequencing primers for NGS reactions.

Other methods for preparing clonally amplified templates also include, e.g., Multiple Displacement Amplification (MDA) (Lasken R. S. *Curr Opin Microbiol.* 2007; 10(5): 510-6). MDA is a non-PCR based DNA amplification technique. The reaction involves annealing random hexamer primers to the template and DNA synthesis by high fidelity enzyme, typically D29 at a constant temperature. MDA can generate large sized products with lower error frequency.

Template amplification methods such as PCR can be coupled with NGS platforms to target or enrich specific regions of the genome (e.g., exons). Exemplary template enrichment methods include, e.g., microdroplet PCR technology (Tewhey R. et al., *Nature Biotech.* 2009, 27:1025-1031), custom-designed oligonucleotide microarrays (e.g., Roche/NimbleGen oligonucleotide microarrays), and solution-based hybridization methods (e.g., molecular inversion probes (MIPs) (Porreca G. J. et al., *Nature Methods,* 2007, 4:931-936; Krishnakumar S. et al., *Proc. Natl. Acad. Sci. USA,* 2008, 105:9296-9310; Turner E. H. et al., *Nature Methods,* 2009, 6:315-316), and biotinylated RNA capture sequences (Gnirke A. et al., *Nat. Biotechnol.* 2009; 27(2): 182-9)

Single-molecule templates are another type of templates that can be used for NGS reaction. Spatially separated single molecule templates can be immobilized on solid supports by various methods. In one approach, individual primer molecules are covalently attached to the solid support. Adapters are added to the templates and templates are then hybridized to the immobilized primers. In another approach, single-molecule templates are covalently attached to the solid support by priming and extending single-stranded, single-molecule templates from immobilized primers. Universal primers are then hybridized to the templates. In yet another approach, single polymerase molecules are attached to the solid support, to which primed templates are bound.

Sequencing and Imaging

Exemplary sequencing and imaging methods for NGS include, but are not limited to, cyclic reversible termination (CRT), sequencing by ligation (SBL), single-molecule addition (pyrosequencing), and real-time sequencing.

CRT uses reversible terminators in a cyclic method that minimally includes the steps of nucleotide incorporation, fluorescence imaging, and cleavage. Typically, a DNA polymerase incorporates a single fluorescently modified nucleotide corresponding to the complementary nucleotide of the template base to the primer. DNA synthesis is terminated after the addition of a single nucleotide and the unincorporated nucleotides are washed away. Imaging is performed to determine the identity of the incorporated labeled nucleotide. Then in the cleavage step, the terminating/inhibiting group and the fluorescent dye are removed. Exemplary NGS platforms using the CRT method include, but are not limited to, Illumina/Solexa Genome Analyzer (GA), which uses the clonally amplified template method coupled with the four-color CRT method detected by total internal reflection fluorescence (TIRF); and Helicos BioSciences/HeliScope, which uses the single-molecule template method coupled with the one-color CRT method detected by TIRF.

SBL uses DNA ligase and either one-base-encoded probes or two-base-encoded probes for sequencing. Typically, a fluorescently labeled probe is hybridized to its complementary sequence adjacent to the primed template. DNA ligase is used to ligate the dye-labeled probe to the primer. Fluorescence imaging is performed to determine the identity of the ligated probe after non-ligated probes are washed away. The fluorescent dye can be removed by using cleavable probes to regenerate a $5'-PO_4$ group for subsequent ligation cycles. Alternatively, a new primer can be hybridized to the template after the old primer is removed. Exemplary SBL platforms include, but are not limited to, Life/APG/SOLiD (support oligonucleotide ligation detection), which uses two-base-encoded probes.

Pyrosequencing method is based on detecting the activity of DNA polymerase with another chemiluminescent enzyme. Typically, the method allows sequencing of a single strand of DNA by synthesizing the complementary strand along it, one base pair at a time, and detecting which base was actually added at each step. The template DNA is immobile, and solutions of A, C, G, and T nucleotides are sequentially added and removed from the reaction. Light is produced only when the nucleotide solution complements the first unpaired base of the template. The sequence of solutions which produce chemiluminescent signals allows the determination of the sequence of the template. Exemplary pyrosequencing platforms include, but are not limited to, Roche/454, which uses DNA templates prepared by emPCR with 1-2 million beads deposited into PTP wells.

Real-time sequencing involves imaging the continuous incorporation of dye-labeled nucleotides during DNA synthesis. Exemplary real-time sequencing platforms include, but are not limited to, Pacific Biosciences platform, which uses DNA polymerase molecules attached to the surface of individual zero-mode waveguide (ZMW) detectors to obtain sequence information when phospholinked nucleotides are being incorporated into the growing primer strand; Life/VisiGen platform, which uses an engineered DNA polymerase with an attached fluorescent dye to generate an enhanced signal after nucleotide incorporation by fluorescence resonance energy transfer (FRET); and LI-COR Biosciences platform, which uses dye-quencher nucleotides in the sequencing reaction.

Other sequencing methods for NGS include, but are not limited to, nanopore sequencing, sequencing by hybridization, nano-transistor array based sequencing, polony sequencing, scanning tunneling microscopy (STM) based sequencing, and nanowire-molecule sensor based sequencing.

Nanopore sequencing involves electrophoresis of nucleic acid molecules in solution through a nano-scale pore which provides a highly confined space within which single-nucleic acid polymers can be analyzed. Exemplary methods of nanopore sequencing are described, e.g., in Branton D. et al., *Nat Biotechnol.* 2008; 26(10): 1146-53.

Sequencing by hybridization is a non-enzymatic method that uses a DNA microarray. Typically, a single pool of DNA is fluorescently labeled and hybridized to an array containing known sequences. Hybridization signals from a given spot on the array can identify the DNA sequence. The binding of one strand of DNA to its complementary strand in the DNA double-helix is sensitive to even single-base mismatches when the hybrid region is short or is specialized mismatch detection proteins are present. Exemplary methods of sequencing by hybridization are described, e.g., in Hanna G. J. et al., *J. Clin. Microbiol.* 2000; 38 (7): 2715-21; and Edwards J. R. et al., *Mut. Res.* 2005; 573 (1-2): 3-12.

Polony sequencing is based on polony amplification and sequencing-by-synthesis via multiple single-base-extensions (FISSEQ). Polony amplification is a method to amplify DNA in situ on a polyacrylamide film. Exemplary polony sequencing methods are described, e.g., in US Patent Application Publication No. 2007/0087362.

Nano-transistor array based devices, such as Carbon NanoTube Field Effect Transistor (CNTFET), can also be used for NGS. For example, DNA molecules are stretched and driven over nanotubes by micro-fabricated electrodes. DNA molecules sequentially come into contact with the carbon nanotube surface, and the difference in current flow from each base is produced due to charge transfer between the DNA molecule and the nanotubes. DNA is sequenced by recording these differences. Exemplary Nano-transistor array based sequencing methods are described, e.g., in U.S. Patent Application Publication No. 2006/0246497.

Scanning tunneling microscopy (STM) can also be used for NGS. STM uses a piezo-electric-controlled probe that performs a raster scan of a specimen to form images of its surface. STM can be used to image the physical properties of single DNA molecules, e.g., generating coherent electron tunneling imaging and spectroscopy by integrating scanning tunneling microscope with an actuator-driven flexible gap. Exemplary sequencing methods using STM are described, e.g., in U.S. Patent Application Publication No. 2007/0194225.

A molecular-analysis device which is comprised of a nanowire-molecule sensor can also be used for NGS. Such device can detect the interactions of the nitrogenous material disposed on the nanowires and nucleic acid molecules such as DNA. A molecule guide is configured for guiding a molecule near the molecule sensor, allowing an interaction and subsequent detection. Exemplary sequencing methods using nanowire-molecule sensor are described, e.g., in U.S. Patent Application Publication No. 2006/0275779.

Double ended sequencing methods can be used for NGS. Double ended sequencing uses blocked and unblocked primers to sequence both the sense and antisense strands of DNA. Typically, these methods include the steps of annealing an unblocked primer to a first strand of nucleic acid; annealing a second blocked primer to a second strand of nucleic acid; elongating the nucleic acid along the first strand with a polymerase; terminating the first sequencing primer; deblocking the second primer; and elongating the nucleic acid along the second strand. Exemplary double ended sequencing methods are described, e.g., in U.S. Pat. No. 7,244,567.

Data Analysis

After NGS reads have been generated, they can be aligned to a known reference sequence or assembled de novo.

For example, identifying genetic variations such as single-nucleotide polymorphism and structural variants in a sample (e.g., a tumor sample) can be accomplished by aligning NGS reads to a reference sequence (e.g., a wild-type sequence). Methods of sequence alignment for NGS are described e.g., in Trapnell C. and Salzberg S. L. *Nature Biotech.*, 2009, 27:455-457.

Examples of de novo assemblies are described, e.g., in Warren R. et al., *Bioinformatics,* 2007, 23:500-501; Butler J. et al., *Genome Res.,* 2008, 18:810-820; and Zerbino D. R. and Birney E., *Genome Res.,* 2008, 18:821-829.

Sequence alignment or assembly can be performed using read data from one or more NGS platforms, e.g., mixing Roche/454 and Illumina/Solexa read data.

Algorithms and methods for data analysis are described in U.S. Ser. No. 61/428,568, filed Dec. 30, 2010, incorporated herein by reference.

Fusion Expression Level

In certain embodiments, expression level of a fusion described herein can also be assayed. Fusion expression can be assessed by any of a wide variety of methods for detecting expression of a transcribed molecule or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In certain embodiments, activity of a particular gene is characterized by a measure of gene transcript (e.g., mRNA), by a measure of the quantity of translated protein, or by a measure of gene product activity. Fusion expression can be monitored in a variety of ways, including by detecting mRNA levels, protein levels, or protein activity, any of which can be measured using standard techniques. Detection can involve quantification of the level of gene expression (e.g., genomic DNA, cDNA, mRNA, protein, or enzyme activity), or, alternatively, can be a qualitative assessment of the level of gene expression, in particular in comparison with a control level. The type of level being detected will be clear from the context.

Methods of detecting and/or quantifying the fusion gene transcript (mRNA or cDNA made therefrom) using nucleic acid hybridization techniques are known to those of skill in the art (see Sambrook et al. supra). For example, one method for evaluating the presence, absence, or quantity of cDNA involves a Southern transfer as described above. Briefly, the mRNA is isolated (e.g., using an acid guanidinium-phenol-chloroform extraction method, Sambrook et al. supra.) and reverse transcribed to produce cDNA. The cDNA is then optionally digested and run on a gel in buffer and transferred to membranes. Hybridization is then carried out using the nucleic acid probes specific for the cDNA of a fusion described herein, e.g., using the probes and primers described herein.

In other embodiments, expression of a fusion molecule described herein is assessed by preparing genomic DNA or mRNA/cDNA (i.e., a transcribed polynucleotide) from cells in a subject sample, and by hybridizing the genomic DNA or mRNA/cDNA with a reference polynucleotide which is a complement of a polynucleotide comprising the fusion, and fragments thereof. cDNA can, optionally, be amplified using any of a variety of polymerase chain reaction methods prior to hybridization with the reference polynucleotide. Expression of a fusion as described herein can likewise be detected using quantitative PCR (QPCR) to assess the level of expression.

Detection of Fusion Polypeptide

The activity or level of a fusion polypeptide described herein can also be detected and/or quantified by detecting or quantifying the expressed polypeptide. The fusion polypeptide can be detected and quantified by any of a number of means known to those of skill in the art. These can include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunoelectrophoresis, radioimmunoassay (RIA), enzyme-linked immunosorbent assays (ELISAs), immunofluorescent assays, Western blotting, immunohistochemistry (IHC) and the like. A skilled artisan can adapt known protein/antibody detection methods.

Another agent for detecting a fusion polypeptide is an antibody molecule capable of binding to a polypeptide corresponding to a marker, e.g., an antibody with a detectable label. Techniques for generating antibodies are described herein. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

In another embodiment, the antibody is labeled, e.g., a radio-labeled, chromophore-labeled, fluorophore-labeled, or enzyme-labeled antibody. In another embodiment, an antibody derivative (e.g., an antibody conjugated with a substrate or with the protein or ligand of a protein-ligand pair {e.g., biotin-streptavidin}), or an antibody fragment (e.g., a single-chain antibody, an isolated antibody hypervariable domain, etc.) which binds specifically with a fusion protein described herein, is used.

Fusion polypeptides from cells can be isolated using techniques that are known to those of skill in the art. The protein isolation methods employed can, for example, be such as those described in Harlow and Lane (Harlow and Lane, 1988, *Antibodies: A Laboratory Manual*, Cold Spring Harbor Laboratory Press, Cold Spring Harbor, N.Y.).

Means of detecting proteins using electrophoretic techniques are well known to those of skill in the art (see generally, R. Scopes (1982) *Protein Purification*, Springer-Verlag, N.Y.; Deutscher, (1990) *Methods in Enzymology* Vol. 182: *Guide to Protein Purification*, Academic Press, Inc., N.Y.).

In another embodiment, Western blot (immunoblot) analysis is used to detect and quantify the presence of a polypeptide in the sample.

In another embodiment, the polypeptide is detected using an immunoassay. As used herein, an immunoassay is an assay that utilizes an antibody to specifically bind to the analyte. The immunoassay is thus characterized by detection of specific binding of a polypeptide to an anti-antibody as opposed to the use of other physical or chemical properties to isolate, target, and quantify the analyte.

The fusion polypeptide is detected and/or quantified using any of a number of immunological binding assays (see, e.g., U.S. Pat. Nos. 4,366,241; 4,376,110; 4,517,288; and 4,837,168). For a review of the general immunoassays, see also Asai (1993) *Methods in Cell Biology* Volume 37: *Antibodies in Cell Biology*, Academic Press, Inc. New York; Stites & Terr (1991) *Basic and Clinical Immunology* 7th Edition.

Kits

In one aspect, the invention features, a kit, e.g., containing an oligonucleotide having a mutation described herein, e.g., a fusion molecule described herein. Optionally, the kit can also contain an oligonucleotide that is the wildtype counterpart of the mutant oligonucleotide.

A kit featured in the invention can include a carrier, e.g., a means being compartmentalized to receive in close confinement one or more container means. In one embodiment the container contains an oligonucleotide, e.g., a primer or probe as described above. The components of the kit are useful, for example, to diagnose or identify a mutation in a tumor sample in a patient. The probe or primer of the kit can be used in any sequencing or nucleotide detection assay known in the art, e.g., a sequencing assay, e.g., an NGS method, RT-PCR, or in situ hybridization.

In some embodiments, the components of the kit are useful, for example, to diagnose or identify a fusion described herein in a tumor sample in a patient, and to accordingly identify an appropriate therapeutic agent to treat the cancer.

A kit featured in the invention can include, e.g., assay positive and negative controls, nucleotides, enzymes (e.g., RNA or DNA polymerase or ligase), solvents or buffers, a stabilizer, a preservative, a secondary antibody, e.g., an anti-HRP antibody (IgG) and a detection reagent.

An oligonucleotide can be provided in any form, e.g., liquid, dried, semi-dried, or lyophilized, or in a form for storage in a frozen condition.

Typically, an oligonucleotide, and other components in a kit are provided in a form that is sterile. An oligonucleotide, e.g., an oligonucleotide that contains a mutation, e.g., a fusion described herein, or an oligonucleotide complementary to a fusion described herein, is provided in a liquid solution, the liquid solution generally is an aqueous solution, e.g., a sterile aqueous solution. When the oligonucleotide is provided as a dried form, reconstitution generally is accomplished by the addition of a suitable solvent. The solvent, e.g., sterile buffer, can optionally be provided in the kit.

The kit can include one or more containers for the composition containing an oligonucleotide in a concentration suitable for use in the assay or with instructions for dilution for use in the assay. In some embodiments, the kit contains separate containers, dividers or compartments for the oligonucleotide and assay components, and the informational material. For example, the oligonucleotides can be contained in a bottle or vial, and the informational material can be contained in a plastic sleeve or packet. In other embodiments, the separate elements of the kit are contained within a single, undivided container. For example, an oligonucleotide composition is contained in a bottle or vial that has attached thereto the informational material in the form of a label. In some embodiments, the kit includes a plurality (e.g., a pack) of individual containers, each containing one or more unit forms (e.g., for use with one assay) of an oligonucleotide. For example, the kit includes a plurality of ampoules, foil packets, or blister packs, each containing a single unit of oligonucleotide for use in sequencing or detecting a mutation in a tumor sample. The containers of the kits can be air tight and/or waterproof. The container can be labeled for use.

For antibody-based kits, the kit can include: (1) a first antibody (e.g., attached to a solid support) which binds to a fusion polypeptide; and, optionally, (2) a second, different antibody which binds to either the polypeptide or the first antibody and is conjugated to a detectable agent.

In one embodiment, the kit can include informational material for performing and interpreting the sequencing or diagnostic. In another embodiment, the kit can provide guidance as to where to report the results of the assay, e.g., to a treatment center or healthcare provider. The kit can include forms for reporting the results of a sequencing or diagnostic assay described herein, and address and contact information regarding where to send such forms or other related information; or a URL (Uniform Resource Locator) address for reporting the results in an online database or an online application (e.g., an app). In another embodiment, the informational material can include guidance regarding whether a patient should receive treatment with a particular chemotherapeutic drug, depending on the results of the assay.

The informational material of the kits is not limited in its form. In many cases, the informational material, e.g., instructions, is provided in printed matter, e.g., a printed text, drawings, and/or photographs, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit can obtain substantive information about the sequencing or diagnostic assay and/or its use in the methods described herein. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a blood or tissue sample, e.g., a biopsy sample, and evaluates the sample using an assay described herein, e.g., a sequencing assay or in situ hybridization assay, and determines that the sample contains a fusion described herein. The assay provider, e.g., a service provider or healthcare provider, can then conclude that the subject is, or is not, a candidate for a particular drug or a particular cancer treatment regimen.

The assay provider can provide the results of the evaluation, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

Incorporated by reference herein in their entirety are any polynucleotide and polypeptide sequences which reference an accession number correlating to an entry in a public database, such as those maintained by the COSMIC database, available on the worldwide web at sanger.ac.uk/genetics/CGP/cosmic/; and the Institute for Genomic Research (TIGR) on the world wide web at tigr.org and/or the National Center for Biotechnology Information (NCBI) on the world wide web at ncbi.nlm.nih.gov.

EXAMPLES

Example 1. Oncogenic and Drug Sensitive NTRK1 Rearrangements in Lung Cancer

Orally active kinase inhibitors crizotinib and erlotinib or gefitinib are superior to standard chemotherapy with respect to both tumor response and progression free survival in lung cancer patients with ALK fusions or EGFR mutations, respectively (Shaw, A. T., et al. *ESMO Congress* 2012, LBA1_PR (2012); Mok, T. S., et al. *N Engl J Med* 361, 947-957 (2009)). Additional oncogenes such as ROS1 and RET fusions have recently been identified in lung cancer and demonstrate great potential for therapeutic intervention (Davies, K. D., et al. *Clin Cancer Res* 18, 4570-4579 (2012); Takeuchi, K., et al. *Nat Med* 18, 378-381 (2012)). Many of these oncogenes also occur in several other common malignancies including, but not limited to, colorectal cancer, thyroid cancer, cholangiocarcinoma, and ovarian cancer potentially expanding the relevance of this therapeutic approach to other tumor types (Lipson, D., et al. *Nat Med* 18, 382-384 (2012); Alberti, L., Carniti, C., Miranda, C., Roccato, E. & Pierotti, M. A. *J Cell Physiol* 195, 168-186 (2003); Gu, T. L., et al. *PLoS One* 6, e15640 (2011); Birch, A. H., et al. *PLoS One* 6, e28250 (2011)).

In order to identify additional potential oncogenes in lung cancer a targeted next generation sequencing (NGS) assay for ~200 cancer-related genes was performed on tumor samples from 36 patients with lung adenocarcinoma (Lipson, D., et al. *Nat Med* 18, 382-384 (2012)). These patient tumors tested negative for activating genetic alterations in EGFR, KRAS, ALK, and ROS1 using standard clinical assays to detect activating mutations or chromosomal breaks with FISH. Patient characteristics are FIG. 21.

Figure 6A:
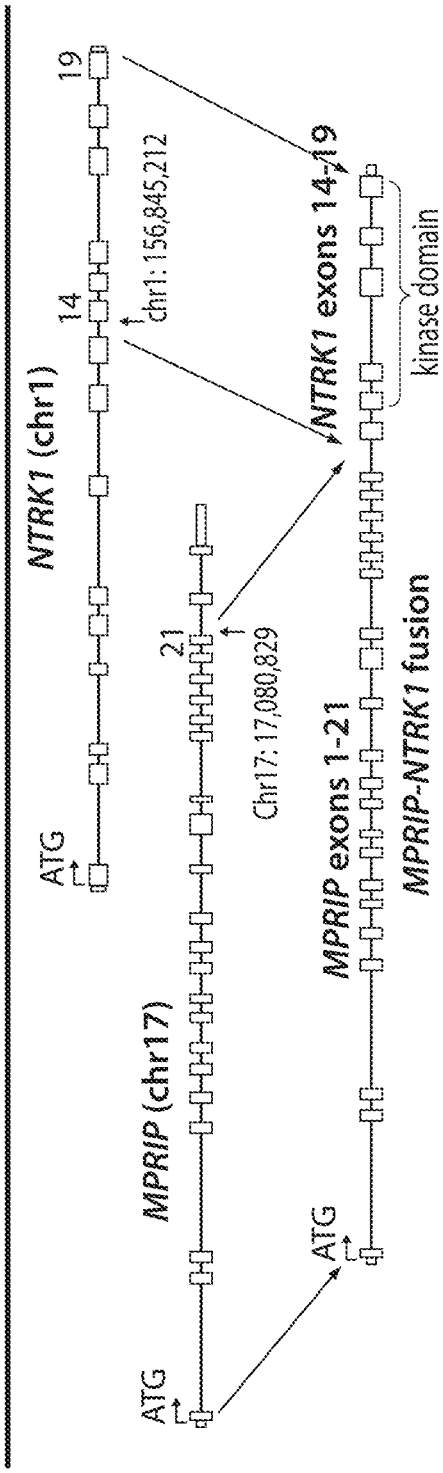
FIGS. 6A-6E show the discovery and confirmation of NTRK1 gene fusions in lung cancer samples. (a) Schematic of genomic rearrangement from tumor samples harboring MPRIP-NTRK1 using the FoundationOne Next Generation Sequencing Assay. The relative locations of Breakpoint 1 (chr1:156,845,212) of NTRK1 and Breakpoint 2 (chr17:17,080,829) of MPRIP are shown in schematic form. It is noted that the exons for NTRK1 are depicted as exons 14-19, which correspond to exons 12-17 of NTRK1 (as shown in FIGS. 4-5, corresponding to SEQ ID NOs: 3-4 for the nucleotide and amino acid sequence, respectively). (b) Sanger sequencing chromatograms of RT-PCR products of RNA isolated from tumor samples with MPRIP-NTRK1 (SEQ ID NO: 8). (c) Break-apart FISH analysis of MPRIP-NTRK1 tumor samples showing clear separation of green (5') and red (3') signals corresponding to the NTRK1 gene. (d) Immunoblot analysis of 293T cells transiently transfected with empty vector (EV), full length NTRK1 cDNA, MPRIP-NTRK1 cDNA compared to tumor cells from a frozen pleural fluid sample or early passage cells in culture (CUTO-3) from the index patient with the MPRIP-NTRK1 fusion gene. (e) Schematic demonstrating fusion break-point and domains of predicted fusion protein product (TM=transmembrane, CCD=coiled coil domain, oligomerization domain and kinase domain).
Figure 6B:
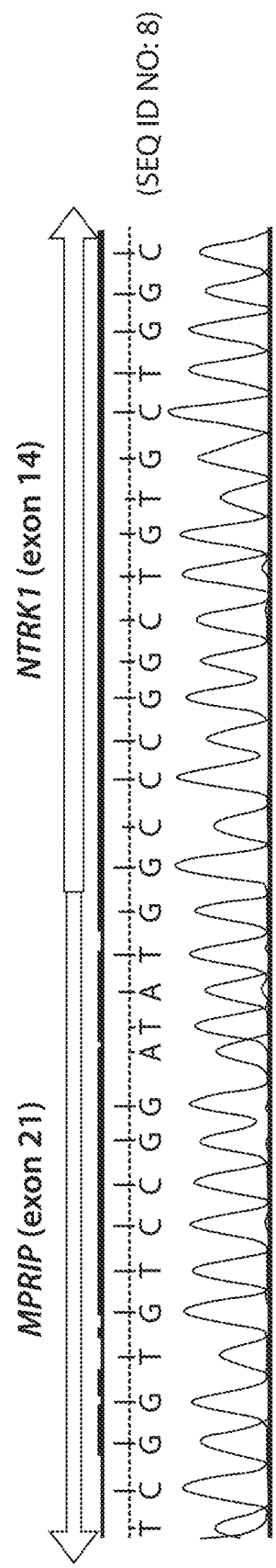

In tumors from two patients, this NGS assay detected evidence of an in-frame gene fusion event involving the kinase domain of the NTRK1 gene, which encodes the high affinity nerve growth factor receptor, also known as the TRKA receptor tyrosine kinase (FIG. 6A). In the index case, the 5' end of the myosin phosphatase Rho interacting protein (MPRIP) gene is joined with the 3' end of NTRK1. MPRIP is involved in regulation of the actin cytoskeleton and has recently been implicated as a gene fusion partner with TP53 in small cell lung cancer, putatively causing early termination of TP53 (Peifer, M., et al. *Nat Genet* 44, 1104-1110 (2012)). MPRIP harbors three coiled-coil domains, a common feature of 5' fusion gene partners whose function is likely to mediate dimerization and consequently activation of the TRKA kinase domain (Surks, H. K., Richards, C. T. & Mendelsohn, M. E. Myosin phosphatase-Rho interacting protein. A new member of the myosin phosphatase complex that directly binds RhoA. *J Biol Chem* 278, 51484-51493 (2003); Soda, M., et al. *Nature* 448, 561-566 (2007)). The full-length cDNA of each fusion was cloned by RT-PCR from tumor tissue (data not shown). The chromosomal translocation was confirmed by a fusion FISH assay demonstrating the proximity of the 5' probe (MPRIP; chrom. 17) and the 3' probe (NTRK1; chrom. 1) (FIG. 12).

FISH is commonly used to evaluate patient tumor samples for the presence of chromosomal aberrations that result in gene fusions (Davies, K. D., et al. *Clin Cancer Res* 18, 4570-4579 (2012); Kwak, E. L., et al. *N Engl J Med* 363, 1693-1703 (2010)). We therefore developed a break-apart FISH assay to detect chromosomal rearrangements within the NTRK1 gene, regardless of the identity of the 5' fusion partner (FIG. 12). Hybridization of these probes showed clear separation of the 5' and 3' probes in the tumor samples containing the MPRIP-NTRK1 gene fusions, but not in a control sample (FIG. 6 and FIG. 12B). Chromosomal rearrangements in which the 5' region of TPM3, TFG, or TPR is fused to the 3' end of the NTRK1 gene have previously been identified in colorectal and thyroid cancers (Alberti, L., Carniti, C., Miranda, C., Roccato, E. & Pierotti, M. A. *J Cell Physiol* 195, 168-186 (2003); Martin-Zanca, D., Hughes, S.

Figure 6C:
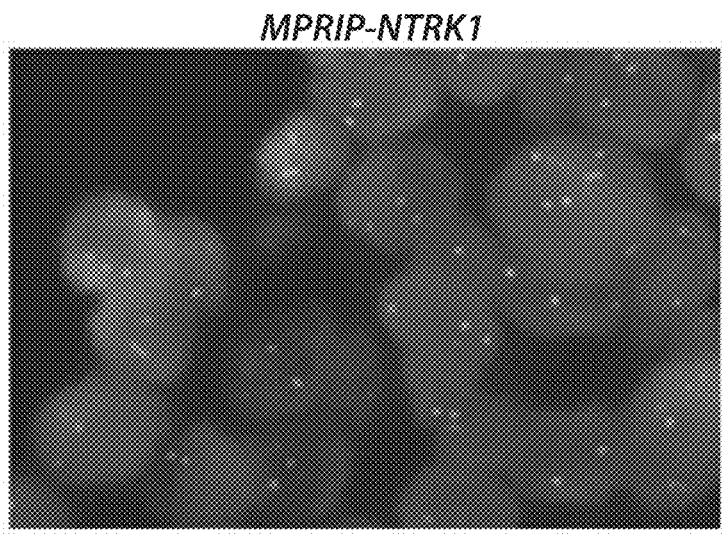

H. & Barbacid, M. *Nature* 319, 743-748 (1986)). Although the TPM3 (1q22-23) and TPR (1q25) genes lie in close proximity to NTRK1 (1q21-22) on chromosome 1q, FISH could also detect a separation in signals in the KM12 colorectal cell line that harbors a TPM3-NTRK1 fusion (FIG. 12C) Bouhana, K. S., et al. In: *Proceedings of the 103rd Annual Meeting of the American Association for Cancer Research;* 2012 Mar. 31-Apr. 4; Chicago, Ill. Philadelphia (Pa): AACR; Cancer Res 2012; 72(8 Suppl):Abstract nr 1798)). Using this FISH assay, 56 additional lung adenocarcinoma samples without detectable EGFR, KRAS, ALK, ROS1, or RET oncogenic mutations were screened for NTRK1 rearrangements (FIG. 22). One case was identified with a clear separation of the signals (FIG. 6C).

Figure 6D:
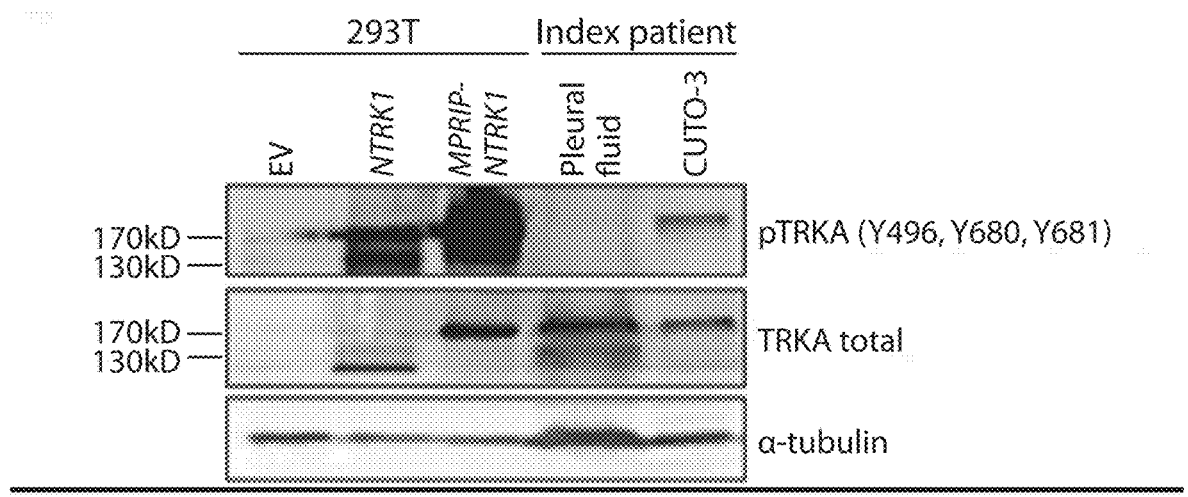
Figure 6E:
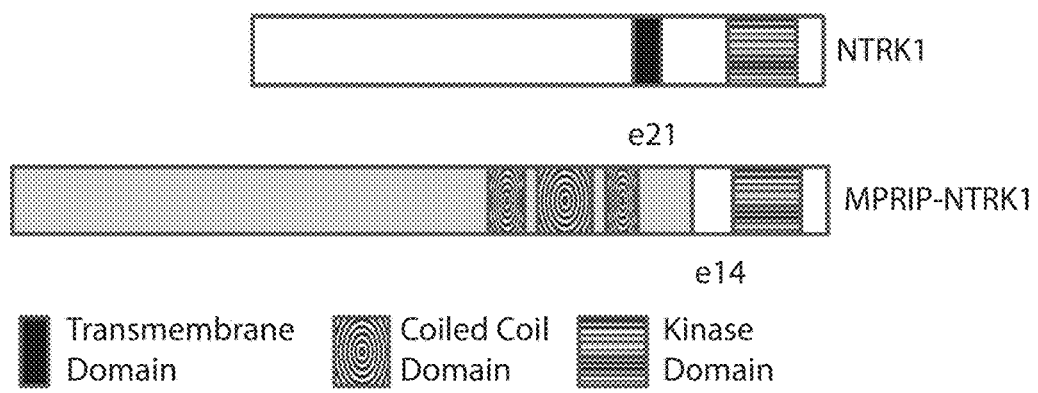

To demonstrate expression of the fusion protein derived from MPRIP-NTRK1, we performed immunoblot analysis on cells from a frozen pleural fluid sample or early passage cells growing in culture (CUTO-3) from the index patient (FIG. 6D). Cells from both samples show expression of the fusion protein, RIP-TRKA (encoded by MPRIP-NTRK1). The actively growing cells also demonstrated autophosphorylation of this novel protein at critical tyrosine residues Stephens, R. M., et al. *Neuron* 12, 691-705 (1994)).

Figure 7A:
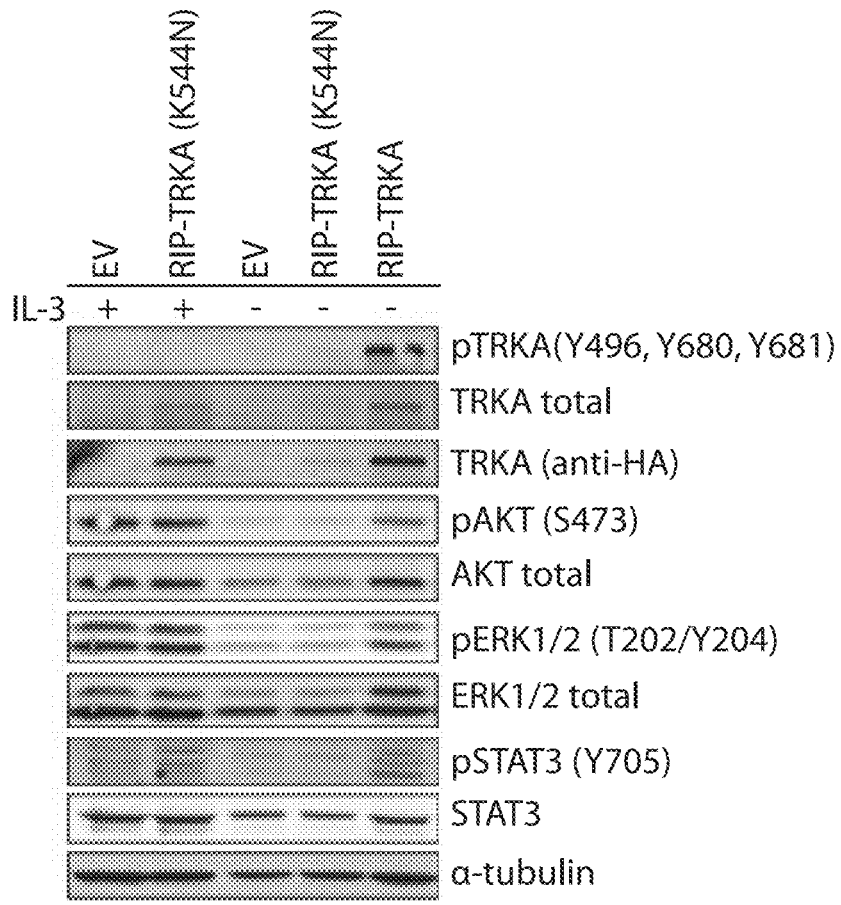
FIGS. 7A-7D show that the NTRK1 gene fusion are oncogenic. (a) TRKA (NTRK1) fusions are autophosphorylated and activate key downstream signaling pathways. Representative immunoblot analyses (n=3) of cell lysates from Ba/F3 cells expressing RIP-TRKA, the protein product of MPRIP-NTRK1 but not its kinase dead (KD) variant display phosphorylation of critical tyrosine residues and activation of pAKT, pERK and pSTAT3 in the absence of IL-3. The term "RIP" is used throughout as an abbreviation of "MPRIP," both terms are used interchangeably herein and in the Figures. (b) NTRK1 fusions support cellular proliferation. MTS assay of Ba/F3 demonstrates that cells expressing RIP-TRKA, EML4-ALK, or full length TRKA supplemented with NGF proliferate in the absence of IL-3, whereas Ba/F3 cells expressing EV or the kinase dead variant of RIP-TRKA do not proliferate (n=3). Values represent the mean±SEM. (c) NTRK1 fusions support anchorage independent growth. Representative images (n=4) from anchorage independent growth assays of NIH3T3 cells expressing EV, RIP-TRKA-KD, or RIP-TRKA in soft agar. (d) RNAi knockdown of NTRK1 inhibits cell proliferation in a cell line harboring TPM3-NTRK1. KM12 cells were analyzed by MTS proliferation assay 96 hr after siRNA transfection (n=3). ANOVA analysis followed by Bonferroni's multiple comparison test indicated a significant inhibition of proliferation induced by siRNA 1 ($p<0.05$). Values represent the mean±SEM.

To formally prove that these novel fusion proteins possess oncogenic activity, MPRIP-NTRK1 cDNA constructs were expressed in both murine NIH3T3 fibroblasts and Ba/F3 cells. Similar to the CUTO-3 cells, introduction of these genes led to expression of the appropriate-sized chimeric protein and autophosphorylation (FIG. 7A and FIG. 13). Introduction of the kinase-dead mutant variants, MPRIP-NTRK1 (K544N) yielded protein expression but not autophosphorylation Stephens, R. M., et al. *Neuron* 12, 691-705 (1994)).

Figure 7B:
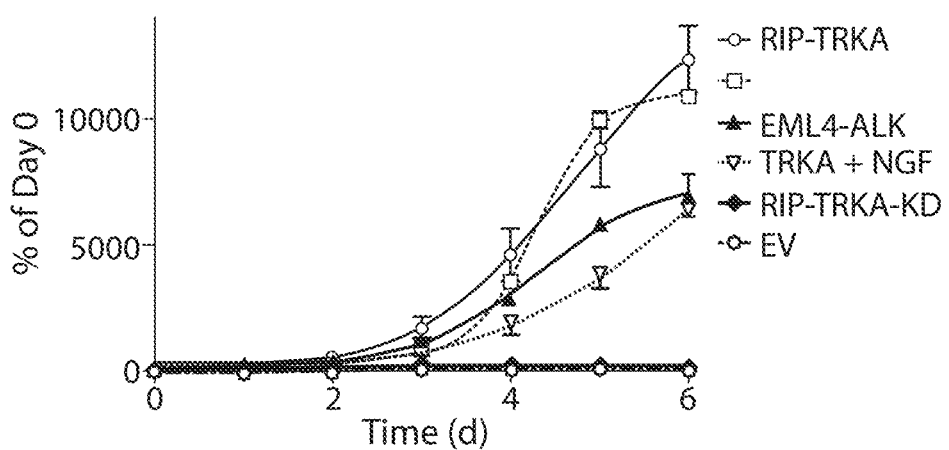
Figure 7C:
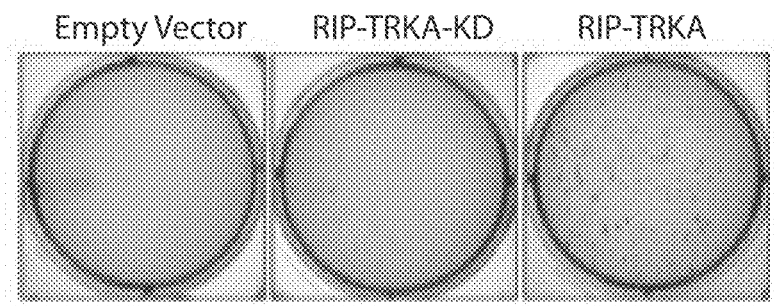
Figure 7D:
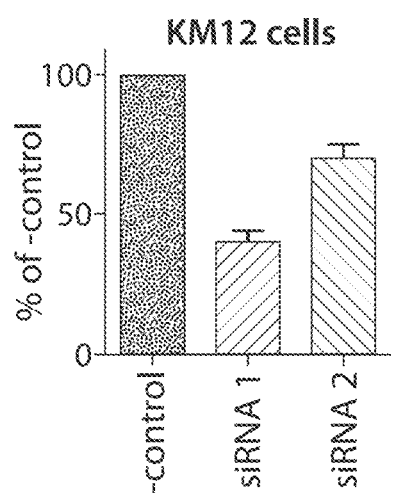

Introduction of the gene fusions, but not the kinase dead variants, increased activation of ERK and AKT. Similar results were obtained in NIH3T3 cells expressing these constructs (FIG. 13). To measure the ability of these genes to sustain cellular proliferation, IL-3 was removed from the medium of Ba/F3 cells and proliferation was assayed (FIG. 7B). MPRIP-NTRK1, but not their kinase-dead counterparts, induced IL-3 independent proliferation of Ba/F3 cells. Similarly, MPRIP-NTRK1, but not the kinase-dead variant, supported anchorage-independent growth of NIH3T3 cells (FIG. 7C). MPRIP-NTRK1 fusion was also shown to be tumorgenic in NIH3T3 cells injected in nude mice (data not shown). Knockdown of NTRK1 by siRNA in KM12 cells resulted in decreased protein expression of TPM3-TRKA and reduced proliferation, further supporting the role of NTRK1 fusions as oncogenes (FIG. 14 and FIG. 7D).

Given the prior success of treating ALK and ROS1 fusion positive patients with targeted kinase inhibitors, whether NTRK1 fusions might provide a similar oncogene target in patients with lung cancer or other malignancies was determined by testing several candidate inhibitors with reported activity against TRKA. ARRY-470 is a selective kinase inhibitor with nanomolar activity against TRKA, TRKB, and TRKC but no other significant kinase inhibition below 1000 nM (FIG. 15 and FIG. 23). CEP-701 and crizotinib also have activity against TRKA as well as other kinases (George, D. J., et al. *Cancer Res* 59, 2395-2401 (1999)); Cui, J. J., et al. *J Med Chem* 54, 6342-6363 (2011)).

Figure 8A:
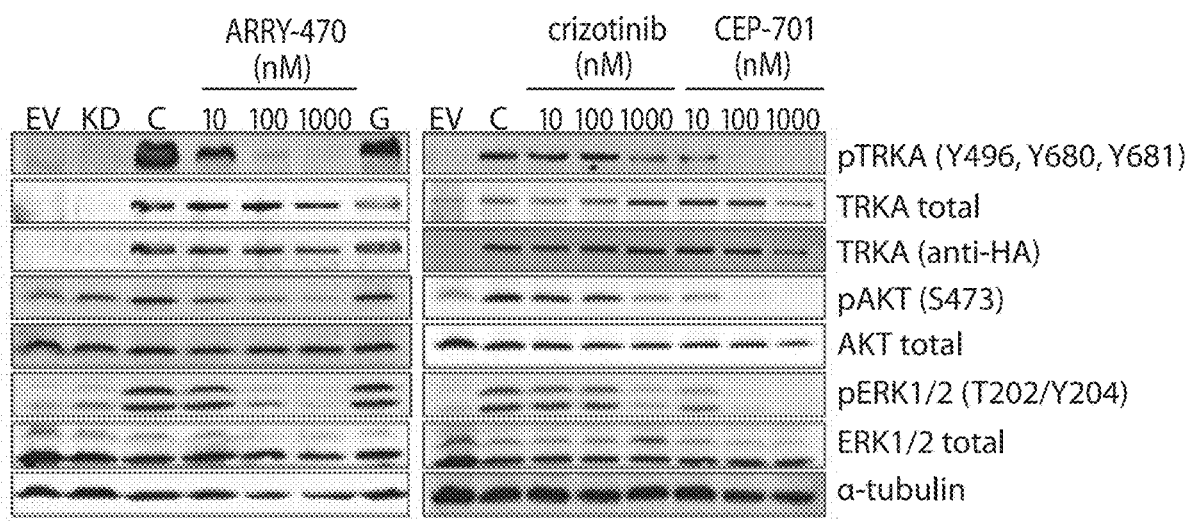
FIGS. 8A-8B show the effects of treatment with an NTRK1 inhibitor inhibits activation of TRKA and downstream signaling. Ba/F3 cells expressing (a) MPRIP-NTRK1 (RIP-TRKA) or empty vector (EV) were lysed after 5 h of treatment with the indicated doses of drugs (G=gefitinib 1000 nM) or DMSO control (C). (b) KM12 cells harboring the TPM3-NTRK1 fusion were similarly lysed following 5 h treatment with the indicated doses of inhibitors and subject to immunoblot analysis (n=3).
Figure 8B:
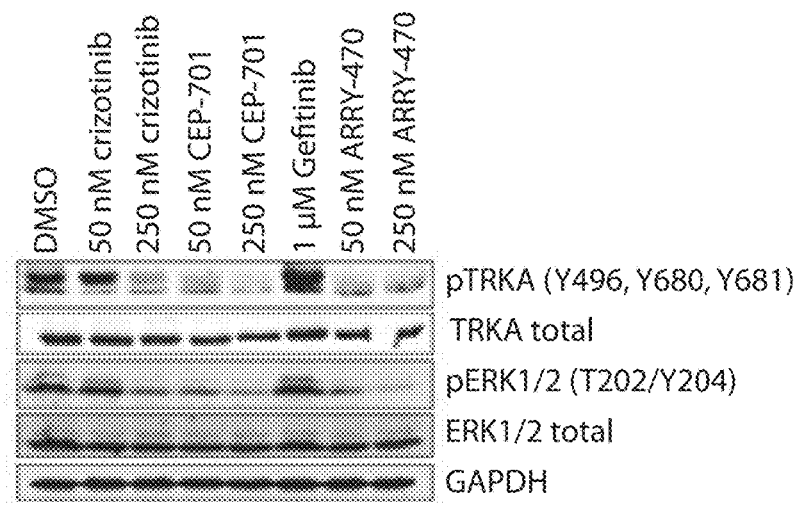
Figure 9A:
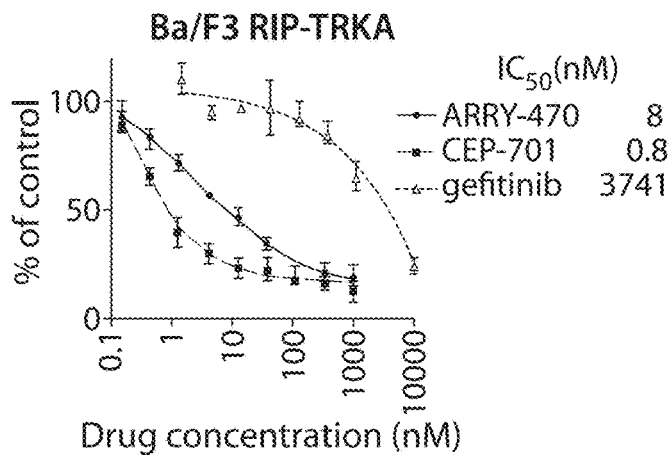
FIGS. 9A-9E show the effects of treatment with an NTRK1 inhibitor that reduces NTRK1 fusion-mediated Ba/F3 cell proliferation and treatment of index patient with crizotinib. Treatment of Ba/F3 cells expressing NTRK1 fusions with TRKA inhibitors inhibits cell proliferation as measured by MTS assay (a-c, n=5). Values represent the mean±SEM. Ba/F3 cells expressing MPRIP-NTRK1 (a) demonstrate inhibition of proliferation by the pan-TRK inhibitor, ARRY-470, and the multi-kinase inhibitor, CEP-701, but not the EGFR inhibitor, gefitinib. (b) Crizotinib leads to inhibition of Ba/F3 expressing NTRK1 fusions, similar to Ba/F3 cells expressing ALK or ROS1 fusion constructs. The half maximal inhibitory concentration ($IC_{50}$) values are listed (nM). (c) Proliferation of KM12 cells is inhibited by ARRY-470, CEP-701, and crizotinib, but not gefitinib. Panels (d)-(e) depict the radiographic response of a lung cancer patient before and after treatment with crizotinib.
Figure 9B:
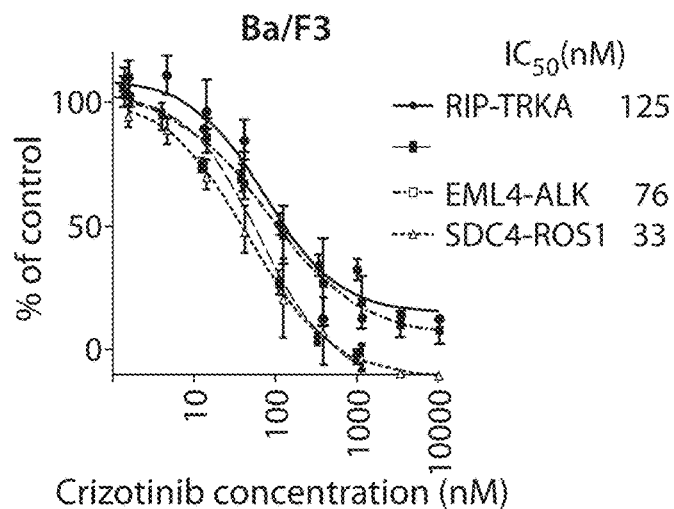

Treatment of Ba/F3 cells with ARRY-470, CEP-701 and, to a lesser extent, crizotinib inhibited phosphorylation of RIP-TRKA (FIG. 8A). Activation of the MAPK and AKT pathways was also inhibited in Ba/F3 cells expressing TRKA fusion proteins (FIG. 8). Similar results were obtained in NIH3T3 cells expressing TRKA fusion proteins (FIG. 13). Phosphorylation of TPM3-TRKA in KM12 cells is similarly inhibited by all three drugs (FIG. 8B). In order to test whether these inhibitors would be a potentially effective treatment for patients harboring NTRK1 gene fusions, Ba/F3 cells expressing NTRK1 gene fusions were treated with ARRY-470, CEP-701 or crizotinib (FIG. 9A-B). Inhibition of proliferation was greatest with CEP-701 and ARRY-470. Crizotinib was a less potent inhibitor of Ba/F3 cells harboring both fusion genes, although in a similar range seen for inhibition of EML4-ALK or SDC4-ROS1 (Davies, K. D., et al. *Clin Cancer Res* 18, 4570-4579 (2012)).

Figure 9C:
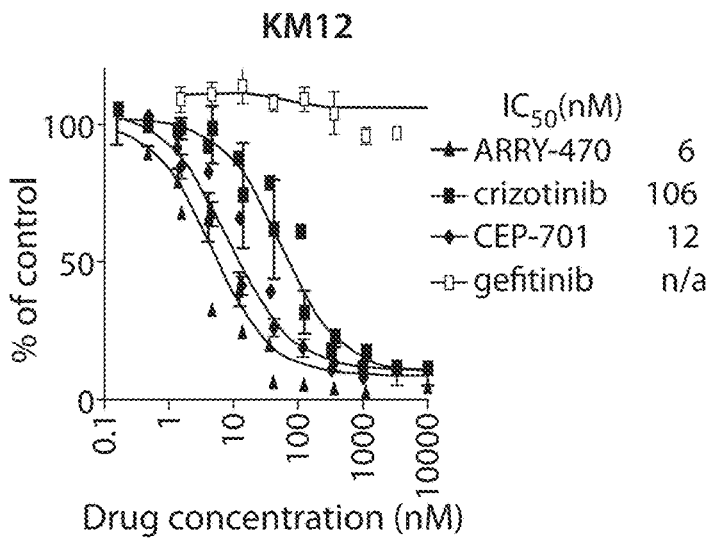

The less potent effects of crizotinib on cell proliferation are consistent with decreased inhibition of pTRKA and downstream pERK (FIG. 8). Ba/F3 cells expressing empty vector supplemented with IL-3 demonstrated intrinsic sensitivity to CEP-701 and crizotinib, but not ARRY-470 (FIG. 16). All three drugs also inhibited colony formation of NIH3T3 cells expressing NTRK1 fusions in soft agar (FIG. 17). KM12 cells were similarly sensitive to ARRY-470 and CEP-701, but less so to crizotinib (FIG. 9C). All three inhibitors induced cell-cycle arrest in G1 in KM12 cells (FIG. 18). Importantly, gefitinib, an epidermal growth factor receptor (EGFR) inhibitor, had no effect on the NTRK1 rearranged Ba/F3 or KM12 cells. Finally, ARRY-470, CEP-701, and crizotinib induce apoptosis in KM12 cells (FIG. 19). The lack of TRKA inhibition by crizotinib at doses that inhibit cell growth of Ba/F3 and NIH3T3 cells suggest off-target effects by this drug. Additionally, proliferation of BA/F3 cells expressing the RIP-TRKA construct shown, in the presence of ARRY-470, ARRY-523, ARRY-772, CEP-701, and gefitnib was analyzed by MTS (FIG. 26). ARRY-470, ARRY-523, ARRY-772 and CEP-701 showed dose dependent inhibition of expression, while gefitinib did not (FIG. 26).

Figure 9D:
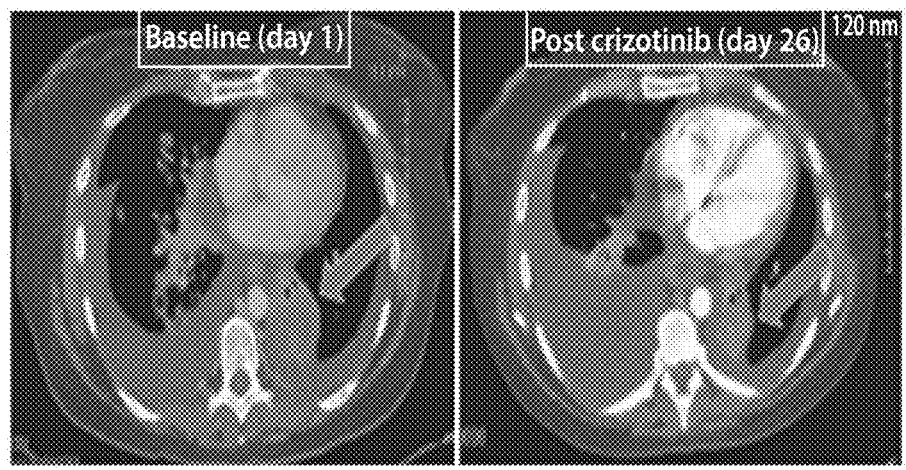
Figure 9E:
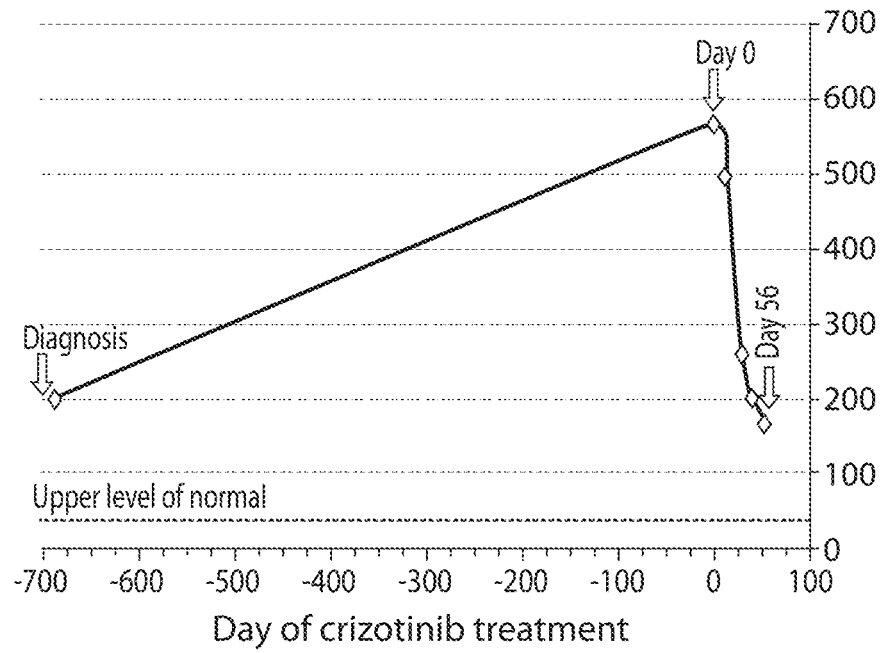

The index patient (MPRIP-NTRK1) had previously been treated with a number of standard lung cancer therapies including carboplatin/paclitaxel/bevacizumab, pemetrexed, erlotinib, and gemcitabine prior to identification of the NTRK1 rearrangement. The patient was treated with crizotinib (250 mg twice daily). The patient experienced a minor radiographic response at first evaluation with a decrease in serum levels of CA125 (FIGS. 9D and 4e). However, the patient had persistent ascites and malignant pleural effusion and developed clinical progression after ~3 months on treatment. The clinical activity of crizotinib is consistent with the in vitro results. In order to rule out the possibility that this patient had a thyroid carcinoma, which like lung adenocarcinoma expresses TTF-1, additional immunohistochemical analysis with thyroglobulin was performed confirming the lung adenocarcinoma histology (FIG. 20).

NTRK1 FISH analysis of CUTO-3 cells grown in short term culture derived from the index patient (derived from pleural effusion) demonstrated expression of the MPRIP-NTKR1 fusion (FIG. 27A). In addition immunoblot analysis of the CUTO-3 cells demonstrated inhibition of pTRKA and pERK by the pan-TRK inhibitor ARRY-470 (FIG. 27B). We have identified novel, recurrent oncogenic NTRK1 fusions in a subset of patients (3/91; 3.3%) with lung adenocarcinoma that were negative for other common oncogenic alterations. Based on the findings and the patient example described above, further studies of selective TRKA inhibitors in NTRK1 rearranged NSCLC are warranted.

Materials and Methods

Patients

Local IRB approval was obtained for all patients in this study. FoundationOne testing and FISH analysis were performed in CLIA certified laboratories. The index patient who underwent treatment with crizotinib consented to this treatment outside of a clinical trial.

Next Generation DNA Sequencing

DNA was extracted from 40 am of FFPE or frozen tissue using the Maxwell 16 FFPE Plus LEV DNA Purification kit (Promega) and quantified using a standardized PicoGreen fluorescence assay (Invitrogen). Library Construction was performed as previously described using 50-200 ng of DNA sheared by sonication to ~100-400 bp prior to end-repair, dA addition and ligation of indexed, Illumina sequencing adaptors (Gnirke, A., et al. Nat Biotechnol 27, 182-189 (2009)). Enrichment of target sequences (3,320 exons of 182 cancer-related genes and 37 introns from 14 genes recurrently rearranged in cancer representing approximately 1.1 Mb of the human genome) was achieved by solution-based hybrid capture with a custom Agilent SureSelect biotinylated RNA baitset (Gnirke, A., et al. Nat Biotechnol 27, 182-189 (2009)). The selected libraries were sequenced on an Illumina HiSeq 2000 platform using 49×49 paired-end reads. Sequence data from genomic DNA was mapped to the reference human genome (hg19) using the Burrows-Wheeler Aligner and were processed using the publicly available SAMtools, Picard, and Genome Analysis Toolkit (Li, H., et al. Bioinformatics 25, 2078-2079 (2009); McKenna, A., et al. Genome Res 20, 1297-1303 (2010)). Genomic rearrangements were detected by clustering chimeric reads mapped to targeted introns.

RNA Extraction from FFPE and Frozen Tissues

RNA was isolated from FFPE or frozen tumor samples as described previously (Davies, K. D., et al. Clin Cancer Res 18, 4570-4579 (2012)). Briefly, FFPE samples were processed using the RecoverAll™ Total Nucleic Acid Isolation Kit (Ambion) following deparaffinization in xylene and washed with 100% ethanol prior to the Protease K digest. Extraction of RNA from frozen tissue samples was accomplished using TriReagent (Ambion). Alternatively, tumors from NSCLC patients obtained at surgery were snap frozen in liquid nitrogen, embedded in OCT and sectioned. RNA was prepared using Trizol (Invitrogen) and purified using RNeasy mini-eluate cleanup kit (Qiagen).

RT-PCR and Sequencing of MPRIP-NTRK1

To identify the fusion breakpoint of MPRIP to NTRK1 from the RNA sample, RT-PCR was carried out using the SuperScript® III First-Strand Synthesis System (SSIII RT) from Invitrogen with a NTRK1 primer located in exon 15 ('NTRK1 Y490R1') for reverse transcription by PCR using the same reverse primer, 'NTRK1 Y490R1', and a primer to MPRIP located in its $3^{rd}$ coil-coiled domain ('MPRIP CC3F1'). PCR products were resolved on a 1.5% agarose gel and the fragments were excised and treated with ExoSapIT (Affymetrix) prior to sequencing by the University of Colorado Cancer Center DNA Sequencing and Analysis Core using the BigDye Terminator Cycle Sequencing Ready Reaction kit version 1.1 (Applied Biosystems) using the same forward and reverse primer in the RT-PCR reaction. Primer sequences used for RT-PCR and sequencing are available in FIG. 24. The reference sequences used for exon alignment are NCBI Reference Sequences: NM_002529.3 (NTRK1) and NM_015134.3 (MPRIP).

Cloning Full Length MPRIP-NTRK1 cDNA was generated from the patient using the SSIII RT kit describe above along with a primer located at the end of NTRK1 (Ntrk1stopR2). This cDNA was then used to amplify two separated fragments of the fusion transcript: 1) a 2.2 kb portion of the 5' end MPRIP-NTRK1 with the primer pair MPRIPStart and MPRIP XhoR1 and 2) 1.9 kb fragment of the 3' end of the fusion gene using MPRIPcc1F1 and Ntrk1stopR1. Full length MPRIP-NTRK1 was generated by overlap extension PCR using the two fragment alone for 10 cycles and then adding the MPRIPStart and Ntrk1StopR1 primers for an additional 30 cycles of PCR amplification. The resulting 4 kb PCR product was gel isolated and confirmed by Sanger Sequencing. A 3' HA tag was added to MPRIP-NTRK1 by using the primer pair of 'EcoRI MPRIP Kozak ATG' and 'NTRK1 HAstop Not1' to amplify the 4 kb PCR template. The amplified product was subsequently digested with EcoRI and NotI and directionally cloned into the pCDH-CMV-MSC1-EF1-Puro lentiviral expression plasmid (System Biosciences). cDNA was transcribed with Quantiscript Reverse Transcriptase (Qiagen). The full-length cDNA of each fusion gene was confirmed by sequencing. Primer sequences used for cloning are available in FIG. 24.

Quantitative PCR of NTRK1

Relative Quantification Polymerase Chain Reaction (RQ-PCR) assay of the NTRK1 tyrosine-kinase domain (Hs01021011_m1; Applied Biosystems) was used to evaluate its level of mRNA expression. The relative quantification method (AACT) in the StepOnePlus Real-time PCR system (Applied Biosystems) was used with GUSB (Applied Biosystems) as an endogenous control. All samples were evaluated in triplicate.

Cell Lines and Reagents

NIH3T3 and HEK-293T cells were purchased from ATCC, and Ba/F3 cells were a kind gift from Dan Theoderescu. KM12 cells were a kind gift from Gail Eckhardt. The lymphoblastoid cell line, GM09948 (Coriell Cell Repository), was used for genomic mapping in FISH studies.

KM12 cells and CUTO-3 cells were maintained in RPMI media with 10% calf serum. NIH3T3 and Ba/F3 cells transduced with full length NTRK1 were supplemented with 100 ng/ml and 200 ng/ml 3-NGF (R&D Systems), respectively. Crizotinib and gefitinib were purchased from Selleck Chemicals, CEP-701 from Sigma Aldrich or Santa Cruz Biotechnology, K252a from Tocris, and ARRY-470 was supplied by Array BioPharma. Total AKT, AKT pSer473, total ERK, ERK pThr202/Tyr204, total Stat3, STAT3 pY705, PARP, and TRKA pY490 and pY674/675 (corresponding to Y496, Y680, and Y681 in TRKA, respectively) antibodies were purchased from Cell-Signaling Technologies. Total TrkA (C-14), GAPDH, and α-tubulin were purchased from Santa Cruz Biotechnologies Inc.

Lentivirus or Retrovirus Production and Cell Transduction

MPRIP-NTRK1 or the kinase dead variant was introduced into cells via lentivirus, which was produced by transfection of HEK-293T cells followed by incubation of lentivirus-containing supernatant with the target cells as previously described in Doebele, R. C., et al. Clin Cancer Res 18, 1472-1482 (2012)). NIH3T3 cells transduced with lentivirus were cultured in DMEM medium with 5% calf serum and 0.75 ug/ml puromycin. Ba/F3 cells transduced with lentivirus were cultured in RPMI medium supplemented with 10% calf serum, 2 ug/ml puromycin, and with or without 1 ng/ml IL-3 (R&D Systems). Cell proliferation and growth were performed as previously described (Zhou, W., et al. Nature 462, 1070-1074 (2009); Sasaki, T., et al. Cancer Res 71, 6051-6060 (2011)).

Immunoblotting

Immunoblotting was performed as previously described.[24] Briefly, cells were lysed in RIPA buffer with Halt protease and phosphatase inhibitor cocktail (Thermo- Scientific) and diluted in loading buffer (LI-COR Biosciences). Membranes were scanned and analyzed using the Odyssey Imaging System and software (LI-COR). Alternatively, immunoblotting was performed according to the antibody manufacturer's recommendations using chemiluminescent detection (Perkin Elmer).

Proliferation Assays

All assays were performed as previously described by seeding 1000 cells/well, drug treatments were performed 24 hours after seeding, and Cell Titer 96 MTS (Promega) was added 72 hours later. ( ); Doebele, R. C., et al. *Clin Cancer Res* 18, 1472-1482 (2012)). IL3 was removed from Ba/F3 cells 48 hours prior to seeding.

Soft Agar

Anchorage-independent growth was measured by seeding 100,000 cells per well of soft agar in 6 well plates as previously described (Doebele, R. C., et al. *Clin Cancer Res* 18, 1472-1482 (2012)0. Media was changed every 4 days for 2 weeks. Quantification was performed with Metamorph Offline Version 7.5.0.0 (Molecular Devices).

Fluorescence In-Situ Hybridization

Formalin-fixed, paraffin-embedded (FFPE) tissue sections were submitted to a dual-color FISH assay using the laboratory developed NTRK1 break-apart probe (3' NTRK1 [SpectrumRed] and 5' NTRK1 [SpectrumGreen]) or the fusion MPRIP [SpectrumGreen]-NTRK1 [SpectrumRed] probe. The pre-hybridization treatment was performed using the reagents from the Vysis Paraffin Kit IV (Abbott Molecular). Hybridization and analysis was performed as previously described previously (Davies, K. D., et al. *Clin Cancer Res* 18, 4570-4579 (2012); Doebele, R. C., et al. *Clin Cancer Res* 18, 1472-1482 (2012)). Samples were deemed positive for NTRK1 rearrangement if ≥15% of tumor cells demonstrated an isolated 3' signal or a separation of 5' and 3' signals that was greater than one signal diameter.

siRNA Transfection

KM12 cells were transfected with 30 nM NTRK1 Silencer Select siRNAs (Life Technologies) using siPORT NeoFX transfection reagent (Life Technologies) at 4 μL/mL.

Flow Cytometry

Cell cycle analysis of KM12 cells was performed as previously described previously (Davies, K. D., et al. *Clin Cancer Res* 18, 4570-4579 (2012)). Apoptosis was measured in KM12 cells using the Vybrant apoptosis YO-PRO/PI kit (Invitrogen). Briefly, KM12 cells were seeded 24 hours prior to treatment at 500,000 cells/well prior to trypsinization and staining.

Immunohistochemistry

Immunohistochemical studies for TTF-1 and thyroglobulin were performed using standard procedures. Briefly, pre-baked slides were subjected to 30 min. HIER antigen retrieval. Antibody against TTF-1 (Cell Marque, Cat #CMC 573) was applied at 1:100 dilution and thyroglobulin (Signet, Cat #228-13) was applied at 1:25 dilution and incubated at 37° C. for 32 min. Detection for TTF-1 was performed using Ventana multiview (UltraView) and detection for thyroglobulin was performed using Ventana Avidin-Biotin (iView).

EQUIVALENTS

Those skilled in the art will recognize, or be able to ascertain using no more than routine experimentation, many equivalents to the specific embodiments described herein. Such equivalents are intended to be encompassed by the following claims.

We claim:

1. A method of treating a subject having a lung cancer, comprising:
    detecting a presence of an MPRIP-NTRK1 fusion in said subject, wherein said MPRIP-NTRK1 fusion is:
        (a) a nucleic acid molecule comprising (i) a fusion between intron 21 of MPRIP, or a fragment thereof, and intron 11 of NTRK1, or a fragment thereof, or (ii) an in-frame fusion between exon 21 of MPRIP, or a fragment thereof, and exon 12 of NTRK1, or a fragment thereof; or
        (b) a polypeptide comprising a fusion between encoded exon 21 of MPRIP, or a fragment thereof, and encoded exon 12 of NTRK1, or a fragment thereof; and
    administering to the subject an effective amount of an anti-cancer agent, thereby treating the lung cancer in the subject, wherein said anti-cancer agent is a kinase inhibitor.

2. The method of claim 1, wherein said lung cancer is a small cell lung cancer (SCLC), an adenocarcinoma of the lung, a bronchogenic carcinoma, or a combination thereof.

3. The method of claim 2, wherein the lung cancer is non-small cell lung cancer (NSCLC) or squamous cell carcinoma (SCC).

4. The method of claim 2, wherein the lung cancer is an adenocarcinoma of the lung.

5. The method of claim 2, wherein the lung cancer has no detectable altered level or activity in one or more of EGFR, KRAS, ALK, ROS1 or RET.

6. The method of claim 1, wherein the kinase inhibitor selectively inhibits the kinase activity of the MPRIP-NTRK1 fusion.

7. The method of claim 1, wherein the kinase inhibitor comprises lestaurtinib (CEP-701); AZ-23; indenopyrrolocarboazole 12a; GW 441756; oxindole 3; isothiazole 5n; thiazole 20h; pyridocarbazole; GNF 5837; AG 879 (Tyrphostin AG 879); Ro 08-2750; AZ623; AR523; a Pyrazolo [1;5a]pyrimidine; a Pyrrolidinyl urea; a pyrrolidinyl thiourea; a Pyrazole derivatives; a macrocyclic compound; a substituted pyrazolo[1;5a]pyrimidine; a pyridotriazole; a benzotriazole; a quinazolinyl; a pyridoquinazolinyl; a pyrrolo[2;3-d]pyrimidine; danusertib (PHA-739358); PHA-848125; CEP-2563; an anti-Trkl antibody; or ARRY-470.

8. The method of claim 1, wherein the kinase inhibitor is danusertib (PHA-739358), lestaurtinib (CEP-701), AZ-23, or ARRY-470.

9. The method of claim 1, wherein the kinase inhibitor comprises an antisense molecule, a ribozyme, an RNAi molecule, or a triple helix molecule that hybridizes to a nucleic acid encoding the MPRIP-NTRK1 fusion; or a transcription regulatory region that blocks or reduces mRNA expression of the MPRIP-NTRK1 fusion.

10. The method of claim 1, wherein the kinase inhibitor is administered in combination with a second therapeutic agent or a different therapeutic modality.

11. A method of treating a subject for a cancer, comprising:
  detecting a presence of a MPRIP-NTRK1 fusion in the subject, wherein said MPRIP-NTRK1 fusion is:
    (a) a nucleic acid molecule comprising (i) a fusion between intron 21 of MPRIP, or a fragment thereof, and intron 11 of NTRK1, or a fragment thereof, or (ii) an in-frame fusion between exon 21 of MPRIP, or a fragment thereof, and exon 12 of NTRK1, or a fragment thereof; or
    (b) a polypeptide comprising a fusion between encoded exon 21 of MPRIP, or a fragment thereof, and encoded exon 12 of NTRK1, or a fragment thereof; and
  administering an effective amount of a kinase inhibitor to the subject.

12. The method of claim 1, wherein the kinase inhibitor inhibits NTRK1 kinase activity.

13. The method of claim 1, wherein the MPRIP-NTRK1 fusion is a nucleic acid molecule comprising a fusion between intron 21 of MPRIP, or a fragment thereof, and intron 11 of NTRK1, or a fragment thereof.

14. The method of claim 1, wherein the MPRIP-NTRK1 fusion is a nucleic acid molecule comprising an in-frame fusion between exon 21 of MPRIP, or a fragment thereof, and exon 12 of NTRK1, or a fragment thereof.

15. The method of claim 1, wherein the MPRIP-NTRK1 fusion is a polypeptide comprising a fusion between encoded exon 21 of MPRIP, or a fragment thereof, and encoded exon 12 of NTRK1, or a fragment thereof.

16. The method of claim 1, wherein the MPRIP-NTRK1 fusion is a polypeptide comprising a sequence according to SEQ ID NO: 7.

17. The method of claim 1, wherein the MPRIP-NTRK1 fusion is a nucleic acid molecule comprising a sequence according to SEQ ID NO: 6.

18. The method of claim 11, wherein the kinase inhibitor inhibits NTRK1 kinase activity.

19. The method of claim 11, wherein the MPRIP-NTRK1 fusion is a nucleic acid molecule comprising a fusion between intron 21 of MPRIP, or a fragment thereof, and intron 11 of NTRK1, or a fragment thereof.

20. The method of claim 11, wherein the MPRIP-NTRK1 fusion is a nucleic acid molecule comprising an in-frame fusion between exon 21 of MPRIP, or a fragment thereof, and exon 12 of NTRK1, or a fragment thereof.

21. The method of claim 11, wherein the MPRIP-NTRK1 fusion is a polypeptide comprising a fusion between encoded exon 21 of MPRIP, or a fragment thereof, and encoded exon 12 of NTRK1, or a fragment thereof.

22. The method of claim 11, wherein the MPRIP-NTRK1 fusion is a polypeptide comprising a sequence according to SEQ ID NO: 7.

23. The method of claim 11, wherein the MPRIP-NTRK1 fusion is a nucleic acid molecule comprising a sequence according to SEQ ID NO: 6.

\* \* \* \* \*

SEQUENCE LISTING

```
<160> NUMBER OF SEQ ID NOS: 17

<210> SEQ ID NO 1
<211> LENGTH: 2663
<212> TYPE: DNA
<213> ORGANISM: Homo sapiens

<400> SEQUENCE: 1
tgcagctggg agcgcacaga cggctgcccc gcctgagcga ggcgggcgcc gccgcgatgc    60
tgcgaggcgc acggcgcggg cagcttggct ggcacagctg ggctgcgggg ccgggcagcc   120
tgctggcttg gctgatactg gcatctgcgg gcgccgcacc ctgccccgat gcctgctgcc   180
cccacggctc ctcgggactg cgatgcaccc gggatgggc  cctggatagc ctccaccacc   240
tgcccggcgc agagaacctg actgagctct acatcgagaa ccagcagcat ctgcagcatc   300
tggagctccg tgatctgagg ggcctggggg agctgagaaa cctcaccatc gtgaagagtg   360
gtctccgttt cgtggcgcca gatgccttcc atttcactcc tcggctcagt cgcctgaatc   420
tctccttcaa cgctctggag tctctctcct ggaaaactgt gcagggcctc tccttacagg   480
aactggtcct gtcggggaac cctctgcact gttcttgtgc cctgcgctgg ctacagcgct   540
gggaggagga gggactgggc ggagtgcctg aacagaagct gcagtgtcat gggcaagggc   600
ccctggccca catgccaat gccagctgtg gtgtgccac gctgaaggtc caggtgccca   660
atgcctcggt ggatgtgggg gacgacgtgc tgctgcggtg ccaggtggag gggcggggcc   720
tggagcaggc cggctggatc ctcacagagc tggagcagtc agccacggtg atgaaatctg   780
ggggtctgcc atccctgggg ctgaccctgg ccaatgtcac cagtgaccTc aacaggaaga   840
```

```
acgtgacgtg ctgggcagag aacgatgtgg gccgggcaga ggtctctgtt caggtcaacg    900
tctccttccc ggccagtgtg cagctgcaca cggcggtgga gatgcaccac tggtgcatcc    960
ccttctctgt ggatgggcag ccggcaccgt ctctgcgctg gctcttcaat ggctccgtgc   1020
tcaatgagac cagcttcatc ttcactgagt tcctggagcc ggcagccaat gagaccgtgc   1080
ggcacgggtg tctgcgcctc aaccagccca cccacgtcaa caacggcaac tacacgctgc   1140
tggctgccaa ccccttcggc caggcctccg cctccatcat ggctgccttc atggacaacc   1200
ctttcgagtt caaccccgag accccatcc ctgtctcctt ctcgccggtg gacactaaca   1260
gcacatctgg agacccggtg gagaagaagg acgaaacacc ttttgggggtc tcggtggctg   1320 tgggcctggc cgtctttgcc tgcctcttcc tttctacgct gctccttgtg ctcaacaaat   1380
gtggacggag aaacaagttt gggatcaacc gcccggctgt gctggctcca gaggatgggc   1440
tggccatgtc cctgcatttc atgacattgg gtggcagctc cctgtccccc accgagggca   1500
aaggctctgg gctccaaggc cacatcatcg agaacccaca atacttcagt gatgcctgtg   1560
ttcaccacat caagcgccgg gacatcgtgc tcaagtggga gctggggag ggcgcctttg   1620 ggaaggtctt cctgctgag tgccacaacc tcctgcctga gcaggacaag atgctggtgg   1680
ctgtcaaggc actgaaggag gcgtccgaga gtgctcggca ggacttccag cgtgaggctg   1740
agctgctcac catgctgcag caccagcaca tcgtgcgctt cttcggcgtc tgcaccgagg   1800 gccgcccct gctcatggtc tttgagtata tgcggcacgg ggacctcaac cgcttcctcc   1860
gatcccatgg acctgatgcc aagctgctgg ctggtgggga ggatgtggct ccaggccccc   1920
tgggtctggg gcagctgctg gccgtggcta gccaggtcgc tgcggggatg gtgtacctgg   1980
cgggtctgca ttttgtgcac cgggacctgg ccacacgcaa ctgtctagtg gccagggac   2040 tggtggtcaa gattggtgat tttggcatga gcagggatat ctacagcacc gactattacc   2100
gtgtgggagg ccgcaccatg ctgcccattc gctggatgcc gcccgagagc atcctgtacc   2160
gtaagttcac caccgagagc gacgtgtgga gcttcggcgt ggtgctctgg gagatcttca   2220
cctacggcaa gcagccctgg taccagctct ccaacacgga ggcaatcgac tgcatcacgc   2280
agggacgtga gttggagcgg ccacgtgcct gcccaccaga ggtctacgcc atcatgcggg   2340
gctgctggca gcgggagccc cagcaacgcc acagcatcaa ggatgtgcac gcccggctgc   2400
aagccctggc ccaggcacct cctgtctacc tggatgtcct gggctagggg gccggcccag   2460
gggctgggag tggttagccg aatactggg gcctgccctc agcatccccc atagctccca   2520
gcagccccag ggtgatctca aagtatctaa ttcacccctca gcatgtggga agggacaggt   2580
gggggctggg agtagaggat gttcctgctt ctctaggcaa ggtcccgtca tagcaattat   2640
atttattatc ccttgaaaaa aaa                                            2663

<210> SEQ ID NO 2
<211> LENGTH: 796
<212> TYPE: PRT
<213> ORGANISM: Homo sapiens

<400> SEQUENCE: 2

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45
```

```
Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
        115                 120                 125

Ser Leu Ser Trp Lys Thr Val Gln Gly Leu Ser Leu Gln Glu Leu Val
130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
            180                 185                 190

Val Pro Thr Leu Lys Val Gln Val Pro Asn Ala Ser Val Asp Val Gly
        195                 200                 205

Asp Asp Val Leu Leu Arg Cys Gln Val Glu Gly Arg Gly Leu Glu Gln
210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
            260                 265                 270

Arg Ala Glu Val Ser Val Gln Val Asn Val Ser Phe Pro Ala Ser Val
        275                 280                 285

Gln Leu His Thr Ala Val Glu Met His His Trp Cys Ile Pro Phe Ser
290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
            340                 345                 350

His Val Asn Asn Gly Asn Tyr Thr Leu Leu Ala Ala Asn Pro Phe Gly
        355                 360                 365

Gln Ala Ser Ala Ser Ile Met Ala Ala Phe Met Asp Asn Pro Phe Glu
370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
            420                 425                 430

Ser Thr Leu Leu Leu Val Leu Asn Lys Cys Gly Arg Arg Asn Lys Phe
        435                 440                 445

Gly Ile Asn Arg Pro Ala Val Leu Ala Pro Glu Asp Gly Leu Ala Met
450                 455                 460
```

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
            485                 490                 495

Phe Ser Asp Ala Cys Val His His Ile Lys Arg Arg Asp Ile Val Leu
                500                 505                 510

Lys Trp Glu Leu Gly Glu Gly Ala Phe Gly Lys Val Phe Leu Ala Glu
            515                 520                 525

Cys His Asn Leu Leu Pro Glu Gln Asp Lys Met Leu Val Ala Val Lys
            530                 535                 540

Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
                580                 585                 590

Arg His Gly Asp Leu Asn Arg Phe Leu Arg Ser His Gly Pro Asp Ala
            595                 600                 605

Lys Leu Leu Ala Gly Gly Glu Asp Val Ala Pro Gly Pro Leu Gly Leu
            610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
                660                 665                 670

Arg Asp Ile Tyr Ser Thr Asp Tyr Tyr Arg Val Gly Gly Arg Thr Met
            675                 680                 685

Leu Pro Ile Arg Trp Met Pro Pro Glu Ser Ile Leu Tyr Arg Lys Phe
            690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
                740                 745                 750

Pro Pro Glu Val Tyr Ala Ile Met Arg Gly Cys Trp Gln Arg Glu Pro
            755                 760                 765

Gln Gln Arg His Ser Ile Lys Asp Val His Ala Arg Leu Gln Ala Leu
            770                 775                 780

Ala Gln Ala Pro Pro Val Tyr Leu Asp Val Leu Gly
785                 790                 795

<210> SEQ ID NO 3
<211> LENGTH: 10960
<212> TYPE: DNA
<213> ORGANISM: Homo sapiens

<400> SEQUENCE: 3
gcggccgcgc tgagccccta gcccgccggg agcgccaggc cggccaggcc tgcgccgccg     60
ccgccgccgc cgtcgccgcc gcgccgacca tgtcggcagc caaggagaac ccgtgcagga    120
aattccaggc caacatcttc aacaagagca gtgtcagaa ctgcttcaag ccccgcgagt    180
cgcatctgct caacgacgag gacctgacgc aggcaaaacc catttatggc ggttggctgc    240

```
tcctggctcc agatgggacc gactttgaca acccagtgca ccggtctcgg aaatggcagc   300
gacggttctt catcctttac gagcacggcc tcttgcgcta cgccctggat gagatgccca   360
cgacccttcc tcagggcacc atcaacatga accagtgcac agatgtggtg gatggggagg   420
gccgcacggg ccagaagttc tccctgtgta ttctgacgcc tgagaaggag catttcatcc   480
gggcggagac caaggagatc gtcagtgggt ggctggagat gctcatggtc tatccccgga   540
ccaacaagca gaatcagaag aagaaacgga agtggagcc ccccacacca caggagcctg   600
ggcctgccaa ggtggctgtt accagcagca gcagcagcag cagcagcagc agcagcatcc   660
ccagtgctga aaagtcccc accaccaagt ccacactctg gcaggaagaa atgaggacca   720
aggaccagcc agatggcagc agcctgagtc cagctcagag tcccagccag agccagcctc   780
ctgctgccag ctccctgcgg gaacctgggc tagagagcaa agaagaggag agcgccatga   840
gtagcgaccg catggactgt ggccgcaaag tccgggtgga gagcggctac ttctctctgg   900
agaagaccaa acaggacttg aaggctgaag aacagcagct gccccgccg ctctcccctc   960
ccagccccag caccccaac acaggaggt cccaggtgat tgaaaagttt gaggccttgg   1020
acattgagaa ggcagagcac atggagacca atgcagtggg gccctcacca tccagcgaca   1080
cacgccaggg ccgcagcgag aagagggcgt tccctaggaa gcgggacttc accaatgaag   1140
cccccccagc tcctctccca gacgcctcgg cttccccct gtctccacac cgaagagcca   1200
agtcactgga caggaggtcc acggagccct ccgtgacgcc cgacctgctg aatttcaaga   1260
aaggctggct gactaagcag tatgaggacg gccagtggaa gaaacactgg tttgtcctcg   1320
ccgatcaaag cctgagatac tacagggatt cagtggctga ggaggcagcc gacttggatg   1380
gagaaattga cttgtccgca tgttacgatg tcacagagta tccagttcag agaaactatg   1440
gcttccagat acatcaaaag gagggcgagt ttacccctgtc ggccatgaca tctgggattc   1500
ggcggaactg gatccagacc atcatgaagc acgtgcaccc gaccactgcc ccggatgtga   1560
ccagctcgtt gccagaggaa aaaaacaaga gcagctgctt ttttgagacc tgcccgaggc   1620
ctactgagaa gcaagaggca gagctggggg agccggaccc tgagcagaag aggagccgcg   1680
cacgggagcg gaggcgagag ggccgctcca agacctttga ctgggctgag ttccgtccca   1740
tccagcaggc cctggctcag gagcgggtgg gcggcgtggg gcctgctgac acccacgagc   1800
ccctgcgccc tgaggcggag cctggggagc tggagcggga gcgtgcacgg aggcgggagg   1860
agcgccgcaa gcgcttcggg atgctcgacg ccacagacgg gccaggcact gaggatgcag   1920
ccctgcgcat ggaggtggac cggagcccag ggctgcctat gagcgacctc aaaacgcata   1980
acgtccacgt ggagattgag cagcggtggc atcaggtgga gaccacacct ctccgggaag   2040
agaagcaggt gccatcgcc cccgtccacc tgtcttctga agatgggggt gaccggctct   2100
ccacacacga gctgacctct ctgctcgaga aggagctgga gcagagccag aaggaggcct   2160
cagaccttct ggagcagaac cggctcctgc aggaccagct gagggtggcc ctgggccggg   2220
agcagagcgc ccgtgagggc tacgtgctgc aggccacgtg cgagcgaggg tttgcagcaa   2280
tggaagaaac gcaccagaag aagattgaag atctccagag gcagcaccag cgggagctag   2340
agaaacttcg agaagagaaa gaccgcctcc tagccgagga gacagcggcc accatctcag   2400
ccatcgaagc catgaagaac gcccaccggg aggaaatgga gcgggagctg gagaagagcc   2460
agcggtccca gatcagcagc gtcaactcgg atgttgaggc cctgcggcgc cagtacctgg   2520
aggagctgca gtcggtgcag cgggaactgg aggtcctctc ggagcagtac tcgcagaagt   2580
gcctggagaa tgcccatctg gcccaggcgc tggaggccga gcggcaggcc ctgcggcagt   2640
```

```
gccagcgtga gaaccaggag ctcaatgccc acaaccagga gctgaacaac cgcctggctg    2700
cagagatcac acggttgcgg acgctgctga ctggggacgg cggtggggag gccactgggt    2760 cacccttgc acagggcaag gatgcctatg aactagaggt cttattgcgg gtaaaggaat     2820
cggaaataca gtacctgaaa caggagatta gctccctcaa ggatgagctg cagacggcac    2880
tgcgggacaa gaagtacgca agtgacaagt acaagacat ctacacagag ctcagcatcg     2940
cgaaggctaa ggctgactgt gacatcagca ggttgaagga gcagctcaag gctgcaacgg    3000
aagcactggg ggagaagtcc cctgacagtg ccacggtgtc cggatatgat ataatgaaat    3060
ctaaaagcaa ccctgacttc ttgaagaaag acagatcctg tgtcacccgg caactcagaa    3120
acatcaggtc caagagtctg aaggaaggcc tgacggtgca agaacggttg aagctctttg    3180
aatccaggga cttgaagaaa gactaggtgt gtcccatcca agttgagcac gcgccttccc    3240
cagcttgcag cagcacaccc caagcgctgc ttttcacctg tacctttgtt ttattattat    3300
tattattatt gctgttgttg tcatcgttaa ctgtgggcat ggaatgcgtg aggctggctt    3360
ctgggttgtc cacaccactc tctgctgtgt tgacttcctg ttgtcttcat caaagctttt    3420
ttccgtggta ttctaaaatt aggccagcag tgggggctgg gagggcatct gtgttagtcc    3480
tttcctggct gtgacccgcc acactcactg tcagtattaa ggcccagcag cctgttgata    3540
agctaccctg tctcaccatg tgctggtgtg gaaacggggc ccagcagca cgcctcaagg      3600 tagatggaat ccccactggt cagagaaaaa gctatgcgga cactccagct tggcctgggt    3660
cacagcactg actcctcacc cgctagtctg gctgttaaga ggagaaagtg cactgccttc    3720
cagcccagga ggaggacagc attttgtatt tgttccactg atgcagctta gaaccacacc    3780
cctgagagtc gtggcaaacc tttcacaacc tggaaaatgt tgaaagcaac cattcctatt    3840
tttgtttgtt ttttattaaa tcttgcacaa aatccccggc ccctctcctt ccttccttcc    3900
ttccttcctc cgctcgttcc ttttcttggtc tccagtaacc ctggtctttt cataactgct    3960
cgagattgtt gacctgcagc ccaggtttca gactctgatt gcaaaaaaca aatgaattcc    4020
ccccaggaat cattcaaaat gggggaaggt ttgggggttt gggtttttttt tttacctttt    4080 ggaaaagaaa ccgtcacatt gctttggaaa aggttgagag gagaccctg ttaagtcaag      4140 aagaaagtac agaggatgtc agaatctgat gagaacagca cattagtgtt tattgagact    4200
ccgatcttaa ctctcatttta attaatctga gctctgaaaa cctatcttgc agcatttatc    4260
tttaaaagag cctggttaaa gtaaacctat actaacaatt ttgcttttc taacagtttg      4320 aggaagacct ttttaaccac cacaaaacat tctatggcaa ttcttgaaaa tctcttaaat    4380
tggagtctat tatggcccca tgaaaccat taatcccatt aagatagggga gtataaaccc    4440 ctggctggtg gaacaggttc tgctacttta ggagcaaggt ggggtgtgag tagatggttt    4500
tcatgccaag aacatgcttt cactttgtat tcatgcttgt gttggtgtga tggtctctgt    4560
gggtgggtgg atgctttggg cgttgaaatc tagaaatcct gttgctcagt ttctagatga    4620
agtcatgagc aaggccatca gtggagctct ggccccgccc caatgtgca gaagggccgg     4680 gagcaaggcc tggagttttc atgtgttttc agacccaggt ttaggtgctc tcttctcact    4740
gaaataacta agtgctctcc actggcatcg agccctttcc acaagttttt aaggctctta    4800
acccacactt tcactcctct gctactagtc ttcagtgttg ttaacagcaa gagaaaattg    4860
ggtttgttta aaaatctact tctctgaggt ggcacagttg cgtagctgta gtcccagcta    4920
ctcaggaggc tgaggtagta ggattgcttg agcccgggag gtcgaggctg caatcagtca    4980
```

```
tgatcgtgtc actgcactcc agcctgggtg acaaagcaag gccccatatc agatatagat    5040
atacttatca gaccccccct gaccatttag attggcagtg ctttgagaaa tgcactatga    5100
cctttctgtg tcaatgggaa tatacagaag gaacattcgg gaccccgctg tcccccacag    5160
cctcattgtt gtctccagga cactgctggg tcacacgaat gctccaggac agacagggac    5220
ctggagtgca tcaggatctg accagatagg agttttttgcc tcgtgtctgg gtgctacgat   5280
tttgtgccgt tctctgaggt ccaccacctg cccttcctgg catggtttcc ttcgtgacca    5340
tccctgctgc ccctgggggt ggacccccact ggcccttctg cagacagctc cctgccttct   5400
gccctccagg gggttctggc cagagtccat gcttggagac aggatcatct gccttcagcc    5460
ctcacagtgc tttaaattaa agcaagtttg cccataggac aaaagagcat ttgattccct    5520
ttttctgtc acatatccct tgaggctgga cttcaggaat cctggaaaat taatatgagt     5580
gcagcatgtg aggggtcaga gacaggccag cagggcgtct gcattcctcc ctgccacagg    5640
tctctcccca gaggctggtt tagtgtaggg tattgccagg aaacggactg aggctgcttt    5700
gctaagagct cctgaaaatg ccctgggcct gtcctggcgt ttctgaagag ccctcataca    5760
gggacagcca ccatctgggt caaggaagtc tgggttccct gctggtgggc tccatcctgc    5820
gatggagtga accaggcgag aaaggatgac gatgttcttc atgttgcacc tggacatgcc    5880
ccaggaacag agacttgccc aggtggcaaa ctggcacag atgttgacgg ctgcccaact    5940
ggtgccacac tgagcaggga gccttgtgct gcacagggct gggccctctc tccagtttcc    6000
ttcctgcagg catccaaata ccctggaagg gatttaaccc ctgaattcca gagggaagaa    6060
agaagaacag tgaagaagta gaactggttt ctgtatgggg agaggaaagt cttagggaca    6120
gctgcaggcg gggtctcagg ctgctccttg gcaccagcta cacagtagtg agctttccca    6180
gctttaccga tgaggaagaa gttcaaatag atagacttca gcattttaat tattttccta    6240
taaatgtatt tatgtgtagt atgctagcac cagccagtaa gctgtgccac acatatgaat    6300
gggaaagcga ggcagttgtg ctcgtgtgag tttctgcagg cttgtgggta attaccttgt    6360
gtgcacgcct gcacgtgcag aatagtcact ttctgctggt cagtttcttt atccacccat    6420
ggtgccccag ccccaggcag gtgtggagac cagcatttca gaggacgcgc tgtccacagc    6480
ctcccgggtc tgagtggatc attgggcagg ggtggagaca gtgcgctgcc ctctgagctg    6540
gaagcctgtg cttcagggag tcataatggg cctgtgctaa gtgggtgatg cagtggacat    6600
cccagggcga ctagaggtgg cagtatcgcg aatttgcagg tttattgaac aagaggtaac    6660
atcggagagg atcttgcctt cggattcagc aagtatgaag gcagaagagc atggagagca    6720
aggcccccaca gcctgcttag tgagttggaa ggcccagcaa gaacctgttt ctgcagcagc    6780
caccagctcc catcacccct tgaccctcca gctcatgctg gagaagaggg aattttggct   6840
gtttaaagaa cacagttgtg aatctcagaa tgtgcctgaa aggaatactg acagataagg    6900
ccggaaacaa aactgatggc ttgaaaaaca ttttatgga atgtatttac tatcattttg     6960
ttttactata gaggtagatg ggactcttaa cttttgggta catggaaaca tgctgaaaac    7020
tgaacacaat cctgatcatc actcctgcct ggctgtctcc tgggaggctg ccgggtgcca    7080
cggagctgga acacagcaga gcccgctagg tgttgcaggg ccctggaggc caaggccacc    7140
ctgtgtgggg tccctgttgg cagccaggtc cctacacaaa caagtaatcc tgtttggcct    7200
cctaggtttt gcatatgacc tgcagcctaa tttggggtgt aggggaagct ctgctggccc    7260
ctgctccttt gtatgttggg tgactttaat ggctggccac ataccccttt ctcccagcta    7320
ctcattcact gacttgggta agttctaaga cagttcgcac ttagaaaaga atgtgacaca    7380
```

```
tcaacattaa cttttcctga aaagaagagt ttgcctaaca tggtcctaaa gaagcttgga    7440
atttataaga ctttccttta taagatatag tgggggtttt tttgggtgga gggggggttgt   7500 tttttgtttt ttgttttcaa gacagagtct cgctctgttg tccaggctgg agtgtagtgg    7560
catgatctcg gctcactgca acctctgcct cccaggttca tgccattctc ctgcctcagc    7620
ctcccgagta gctgggacta caggtgtctg ccgccacgcc tggctaattt ttttgtattt    7680
ttagtagaga cggggtttca ccatgttggt caggatggtc tcgatttcct gacctcgtga    7740
tccgcctgtc tcggcctccc aaagtgctgg gattacaggc gtgagccacc gcgcctggcc    7800
tataagatac ggtaaaaaaa aaaaactgtg acccctttgt cactaaggga gaaagaaatt    7860
aagtattgtc aaagttctat aaagaatgga aatgtatgat attatacttc aaaggaattt    7920
gatgttgaaa ttttaaagaa aatttgtcat gttgatgaga agcttcactt tcctgggaac    7980
ttcattcgtt ttagggcatg agataaaagt cctggctagg ggagccatag gtctgttgta    8040
caaggaattt gctttctaaa caagttgtaa cttgccctaa ggtccctgtt ggagcactaa    8100
gaggtgacac aggccagaga caacgtttcg tttccccttc cctgcaagct gggatcagcc    8160
ctgtgttttc tccttttcagc tgaagtgagc gaaggttctc agtgctggca aaagagccca    8220 cttttctaaaa ggacttggga agaaagctgc tgggaacttg cttattaaaa agttccttag    8280
aattaaggta tctacccact gttttcgcac ctttcacctt cctgggcttt cctgccctcc    8340
agcattcttc tctagagagg ttcctagccc gctcagcgcg agcgtctcca gtaggtaata    8400
gcagctgaac gtgggttttc cacggacttc aggcttggag gtgccatata caagcacact    8460
tcttccttcc cctggcttct ccatgccacc acccacttta aagatgtaaa ctcagtagat    8520
ttttcatcca gtgaacggtc atcttcacat cgaaaggtga aggccaccac tgttctcaat    8580
gccaagcaac agaacgttct gagatggccg ttcttccttg cacagcagct acggcaggtt    8640
gttctgcagc cacccttag aggggggctct tcgttttacc tttgtacagt tcttgtgttt    8700
acacatttgg gccaaacagc tttcagcaag ggcatgtgtc cacagctgat gggcagttaa    8760
gaaccagcct gagctgaagg ctagtaatac cgtgctgtag gctctttaaa aggaaagcct    8820
ggcataaacc cagcatggaa aggaacatta tcagttatct caaattttgt ctgccaggga    8880
caagaccctg ttcattcttt tgccctttc agaactgtga gcttcaagta ttcttgcttc    8940
tctgtaaagg aagacatct cccttctctg aaatccttca acaaaagaaa aggctcttgg    9000
cagggtaggg gagtcagtag ctcaacacta gatcatccct agagatgggg caagtttctg    9060
tctgaacacg tcttgggtcc gagtccttag gtgttcggat gcagtacttt gtgaatactt    9120
aagctactgc atgcttggtg tagcttgcaa tttctctgta tttaaaagca gctgtgttta    9180
ttttcttcaa ataacctgt atattattta gagcaagcaa tgtaaatatt actgagaagt     9240
tactgcaggg attttttgtga cagagtttgt atgggttttt aaaaaaatct tagacacccc    9300
tttttaagat ggggagaaca gggttgactg caccgttgaa gcccgcccag cattataagg    9360
aaatgttttt aatgactgct gcatctttgt aaaacgtttg gtcatctaac agatggtttt    9420
aaagtgtaca atatccaaaa taacgatagc cctgtatcca tacattgttt cattgaaaga    9480
attctctatt gcctcttctt ggtagagcca gagtccttaa ggaaaatcag gaaaattaag    9540
aaaatgatgg tgccatcttg accagacttc tgcacagtaa tttaacgcta tcctagggag    9600
acttggttga aggcacagtt ctgggatcag ggtctaaatg tgcagtttct gagaaccttc    9660
aagaccactc actgggcagg gctctgtgga gcactggagc tgtttggatt ccccagccct    9720
```

-continued

```
ttggtcatat cctggaattc cgtggaggct gcagaactta gatgcagctg ttttttacag    9780
cacctatttt tgtcagattg gtaaggaaac actgagtcac agaatactta agaattggag    9840
actccagtaa tgtaggatgg cctgagagga cgtccaagtc ccaaggggtg gacacggcat    9900
gttcctcggg cacagcctca gtgggggcct tccccaggcg cagctcggcc acctgaggaa    9960
agggtgtttc ggaggcgcag ccacacacac agcgctggca gcctcacggt cacgcccatc   10020
actccctgcc ccccactgcc cttgagaagt tagtggtgtc acatccttag ttttatagac   10080
agctaggaat agattgtgaa gaacactcag ttcactactg tgttacattt atatcacaag   10140
cttcaattaa aatggatttt aaaggatttt aggatttacc tttagtatta acaacgtatc   10200
tactgacata ctgttaggat tcaaaaccag ttaagtataa gaattacttc atgtggtttt   10260
cctagggtac aatttataaa aggtagaaag catccaagtg gctcctcaac aattacaatt   10320
cttaatgatt tttctcacag ctgtgccctt ctgtcagggt cagtgtcaaa attcgttatc   10380
aaaggcaaaa cctactgtgc caagctgggg cgctatatgt gaacggagtg gaaatgcttc   10440
agtcacctct gccgcagctt gtgattccag cagttctcac aaacgttctg tcacatgatg   10500
aaaagaagca gcttgtataa ttccaactgg tgtttcattt ctgttctaat gctaagtggt   10560
aacgcttaac aaacagacta aaagctgtgt gcagaagaaa gggctgaatg agtaccgcct   10620
ccctaggttc cagcacagcg ctcgggtcta agaagtagag ccccggggta gggtgggcca   10680
tccactgtca ggccagtgtc tcaagaaagc ctgaccagct gagctgctgc ttttttttg    10740
ggggggggggg gggagggggc gtcttgaggc tttttttttt tttacaaagt tagtttgtga   10800
tcaacgattc actacaattg aagtgttact ttgtcagaat atttattcct ttgtgtgaca   10860
tgctagattc cctggatgta gctgatcatt tttattttgt aaatattacc taactttaca   10920
taaactatat cataataaac tattttttgca tcacccttg                         10960
```

<210> SEQ ID NO 4
<211> LENGTH: 1038
<212> TYPE: PRT
<213> ORGANISM: Homo sapiens

<400> SEQUENCE: 4

```
Met Ser Ala Ala Lys Glu Asn Pro Cys Arg Lys Phe Gln Ala Asn Ile
 1               5                  10                  15

Phe Asn Lys Ser Lys Cys Gln Asn Cys Phe Lys Pro Arg Glu Ser His
            20                  25                  30

Leu Leu Asn Asp Glu Asp Leu Thr Gln Ala Lys Pro Ile Tyr Gly Gly
        35                  40                  45

Trp Leu Leu Leu Ala Pro Asp Gly Thr Asp Phe Asp Asn Pro Val His
    50                  55                  60

Arg Ser Arg Lys Trp Gln Arg Phe Phe Ile Leu Tyr Glu His Gly
65                  70                  75                  80

Leu Leu Arg Tyr Ala Leu Asp Glu Met Pro Thr Thr Leu Pro Gln Gly
                85                  90                  95

Thr Ile Asn Met Asn Gln Cys Thr Asp Val Val Asp Gly Glu Gly Arg
            100                 105                 110

Thr Gly Gln Lys Phe Ser Leu Cys Ile Leu Thr Pro Glu Lys Glu His
        115                 120                 125

Phe Ile Arg Ala Glu Thr Lys Glu Ile Val Ser Gly Trp Leu Glu Met
    130                 135                 140

Leu Met Val Tyr Pro Arg Thr Asn Lys Gln Asn Gln Lys Lys Lys Arg
145                 150                 155                 160
```

-continued

```
Lys Val Glu Pro Pro Thr Pro Gln Glu Pro Gly Pro Ala Lys Val Ala
                165                 170                 175

Val Thr Ser Ser Ser Ser Ser Ser Ser Ser Ser Ile Pro Ser
            180                 185                 190

Ala Glu Lys Val Pro Thr Thr Lys Ser Thr Leu Trp Gln Glu Glu Met
        195                 200                 205

Arg Thr Lys Asp Gln Pro Asp Gly Ser Ser Leu Ser Pro Ala Gln Ser
    210                 215                 220

Pro Ser Gln Ser Gln Pro Pro Ala Ala Ser Ser Leu Arg Glu Pro Gly
225                 230                 235                 240

Leu Glu Ser Lys Glu Glu Glu Ser Ala Met Ser Ser Asp Arg Met Asp
                245                 250                 255

Cys Gly Arg Lys Val Arg Val Glu Ser Gly Tyr Phe Ser Leu Glu Lys
                260                 265                 270

Thr Lys Gln Asp Leu Lys Ala Glu Glu Gln Gln Leu Pro Pro Pro Leu
        275                 280                 285

Ser Pro Pro Ser Pro Ser Thr Pro Asn His Arg Arg Ser Gln Val Ile
        290                 295                 300

Glu Lys Phe Glu Ala Leu Asp Ile Glu Lys Ala Glu His Met Glu Thr
305                 310                 315                 320

Asn Ala Val Gly Pro Ser Pro Ser Ser Asp Thr Arg Gln Gly Arg Ser
                325                 330                 335

Glu Lys Arg Ala Phe Pro Arg Lys Arg Asp Phe Thr Asn Glu Ala Pro
                340                 345                 350

Pro Ala Pro Leu Pro Asp Ala Ser Ala Ser Pro Leu Ser Pro His Arg
            355                 360                 365

Arg Ala Lys Ser Leu Asp Arg Arg Ser Thr Glu Pro Ser Val Thr Pro
    370                 375                 380

Asp Leu Leu Asn Phe Lys Lys Gly Trp Leu Thr Lys Gln Tyr Glu Asp
385                 390                 395                 400

Gly Gln Trp Lys Lys His Trp Phe Val Leu Ala Asp Gln Ser Leu Arg
                405                 410                 415

Tyr Tyr Arg Asp Ser Val Ala Glu Glu Ala Ala Asp Leu Asp Gly Glu
            420                 425                 430

Ile Asp Leu Ser Ala Cys Tyr Asp Val Thr Glu Tyr Pro Val Gln Arg
        435                 440                 445

Asn Tyr Gly Phe Gln Ile His Thr Lys Glu Gly Glu Phe Thr Leu Ser
    450                 455                 460

Ala Met Thr Ser Gly Ile Arg Arg Asn Trp Ile Gln Thr Ile Met Lys
465                 470                 475                 480

His Val His Pro Thr Thr Ala Pro Asp Val Thr Ser Ser Leu Pro Glu
                485                 490                 495

Glu Lys Asn Lys Ser Ser Cys Ser Phe Glu Thr Cys Pro Arg Pro Thr
            500                 505                 510

Glu Lys Gln Glu Ala Glu Leu Gly Glu Pro Asp Pro Gln Lys Arg
        515                 520                 525

Ser Arg Ala Arg Glu Arg Arg Glu Gly Arg Ser Lys Thr Phe Asp
    530                 535                 540

Trp Ala Glu Phe Arg Pro Ile Gln Gln Ala Leu Ala Gln Glu Arg Val
545                 550                 555                 560

Gly Gly Val Gly Pro Ala Asp Thr His Glu Pro Leu Arg Pro Glu Ala
                565                 570                 575
```

```
Glu Pro Gly Glu Leu Glu Arg Glu Ala Arg Arg Glu Arg
            580                 585                 590

Arg Lys Arg Phe Gly Met Leu Asp Ala Thr Asp Gly Pro Gly Thr Glu
        595                 600                 605

Asp Ala Ala Leu Arg Met Glu Val Asp Arg Ser Pro Gly Leu Pro Met
        610                 615                 620

Ser Asp Leu Lys Thr His Asn Val His Val Glu Ile Glu Gln Arg Trp
625                 630                 635                 640

His Gln Val Glu Thr Thr Pro Leu Arg Glu Lys Gln Val Pro Ile
            645                 650                 655

Ala Pro Val His Leu Ser Ser Glu Asp Gly Asp Arg Leu Ser Thr
            660                 665                 670

His Glu Leu Thr Ser Leu Leu Glu Lys Glu Leu Glu Gln Ser Gln Lys
        675                 680                 685

Glu Ala Ser Asp Leu Leu Glu Gln Asn Arg Leu Leu Gln Asp Gln Leu
        690                 695                 700

Arg Val Ala Leu Gly Arg Glu Gln Ser Ala Arg Glu Gly Tyr Val Leu
705                 710                 715                 720

Gln Ala Thr Cys Glu Arg Gly Phe Ala Ala Met Glu Glu Thr His Gln
            725                 730                 735

Lys Lys Ile Glu Asp Leu Gln Arg Gln His Gln Arg Glu Leu Glu Lys
            740                 745                 750

Leu Arg Glu Glu Lys Asp Arg Leu Leu Ala Glu Thr Ala Ala Thr
        755                 760                 765

Ile Ser Ala Ile Glu Ala Met Lys Asn Ala His Arg Glu Glu Met Glu
770                 775                 780

Arg Glu Leu Glu Lys Ser Gln Arg Ser Gln Ile Ser Ser Val Asn Ser
785                 790                 795                 800

Asp Val Glu Ala Leu Arg Arg Gln Tyr Leu Glu Glu Leu Gln Ser Val
            805                 810                 815

Gln Arg Glu Leu Glu Val Leu Ser Glu Gln Tyr Ser Gln Lys Cys Leu
        820                 825                 830

Glu Asn Ala His Leu Ala Gln Ala Leu Glu Ala Glu Arg Gln Ala Leu
        835                 840                 845

Arg Gln Cys Gln Arg Glu Asn Gln Glu Leu Asn Ala His Asn Gln Glu
850                 855                 860

Leu Asn Asn Arg Leu Ala Ala Glu Ile Thr Arg Leu Arg Thr Leu Leu
865                 870                 875                 880

Thr Gly Asp Gly Gly Glu Ala Thr Gly Ser Pro Leu Ala Gln Gly
            885                 890                 895

Lys Asp Ala Tyr Glu Leu Glu Val Leu Leu Arg Val Lys Glu Ser Glu
        900                 905                 910

Ile Gln Tyr Leu Lys Gln Glu Ile Ser Ser Leu Lys Asp Glu Leu Gln
            915                 920                 925

Thr Ala Leu Arg Asp Lys Lys Tyr Ala Ser Asp Lys Tyr Lys Asp Ile
        930                 935                 940

Tyr Thr Glu Leu Ser Ile Ala Lys Ala Lys Ala Asp Cys Asp Ile Ser
945                 950                 955                 960

Arg Leu Lys Glu Gln Leu Lys Ala Ala Thr Glu Ala Leu Gly Glu Lys
            965                 970                 975

Ser Pro Asp Ser Ala Thr Val Ser Gly Tyr Asp Ile Met Lys Ser Lys
            980                 985                 990
```

Ser Asn Pro Asp Phe Leu Lys Lys Asp Arg Ser Cys Val Thr Arg Gln
        995                 1000                    1005

Leu Arg Asn Ile Arg Ser Lys Ser Leu Lys Glu Gly Leu Thr Val
    1010                1015                1020

Gln Glu Arg Leu Lys Leu Phe Glu Ser Arg Asp Leu Lys Lys Asp
1025                1030                1035

<210> SEQ ID NO 5
<211> LENGTH: 4301
<212> TYPE: DNA
<213> ORGANISM: Artificial Sequence
<220> FEATURE:
<223> OTHER INFORMATION: Synthetic polynucleotide

<400> SEQUENCE: 5

| | | | | | |
|---|---|---|---|---|---|
| gcggccgcgc | tgagccccta | gcccgccggg | agcgccaggc | cggccaggcc | tgcgccgccg | 60 |
| ccgccgccgc | cgtcgccgcc | gcgccgacca | tgtcggcagc | caaggagaac | ccgtgcagga | 120 |
| aattccaggc | caacatcttc | aacaagagca | agtgtcagaa | ctgcttcaag | ccccgcgagt | 180 |
| cgcatctgct | caacgacgag | gacctgacgc | aggcaaaacc | catttatggc | ggttggctgc | 240 |
| tcctggctcc | agatgggacc | gactttgaca | acccagtgca | ccgtctcgg | aaatggcagc | 300 |
| gacggttctt | catcctttac | gagcacggcc | tcttgcgcta | cgccctggat | gagatgccca | 360 |
| cgacccttcc | tcagggcacc | atcaacatga | ccagtgcac | agatgtggtg | gatggggagg | 420 |
| gccgcacggg | ccagaagttc | tccctgtgta | ttctgacgcc | tgagaaggag | catttcatcc | 480 |
| gggcggagac | caaggagatc | gtcagtgggt | ggctggagat | gctcatggtc | tatccccgga | 540 |
| ccaacaagca | gaatcagaag | aagaaacgga | agtggagcc | cccacacca | caggagcctg | 600 |
| ggcctgccaa | ggtggctgtt | accagcagca | gcagcagcag | cagcagcagc | agcagcatcc | 660 |
| ccagtgctga | gaaagtcccc | accaccaagt | ccacactctg | gcaggaagaa | atgaggacca | 720 |
| aggaccagcc | agatggcagc | agcctgagtc | cagctcagag | tcccagccag | agccagcctc | 780 |
| ctgctgccag | ctccctgcgg | gaacctgggc | tagagagcaa | agaagaggag | agcgccatga | 840 |
| gtagcgaccg | catggactgt | ggccgcaaag | tccgggtgga | gagcggctac | ttctctctgg | 900 |
| agaagaccaa | acaggacttg | aaggctgaag | aacagcagct | gccccgccg | ctctcccctc | 960 |
| ccagccccag | caccccaac | acaggaggt | cccaggtgat | tgaaaagttt | gaggccttgg | 1020 |
| acattgagaa | ggcagagcac | atggagacca | atgcagtggg | gccctcacca | tccagcgaca | 1080 |
| cacgccaggg | ccgcagcgag | aagagggcgt | tccctaggaa | gcgggacttc | accaatgaag | 1140 |
| cccccccagc | tcctctccca | gacgcctcgg | cttccccct | gtctccacac | cgaagagcca | 1200 |
| agtcactgga | caggaggtcc | acggagccct | ccgtgacgcc | cgacctgctg | aatttcaaga | 1260 |
| aaggctggct | gactaagcag | tatgaggacg | gccagtggaa | gaaacactgg | tttgtcctcg | 1320 |
| ccgatcaaag | cctgagatac | tacagggatt | cagtggctga | ggaggcagcc | gacttggatg | 1380 |
| gagaaattga | cttgtccgca | tgttacgatg | tcacagagta | tccagttcag | agaaactatg | 1440 |
| gcttccagat | acatacaaag | gagggcgagt | ttaccctgtc | ggccatgaca | tctgggattc | 1500 |
| ggcggaactg | gatccagacc | atcatgaagc | acgtgcaccc | gaccactgcc | ccggatgtga | 1560 |
| ccagctcgtt | gccagaggaa | aaaacaaga | gcagctgctc | ttttgagacc | tgcccgaggc | 1620 |
| ctactgagaa | gcaagaggca | gagctggggg | agcggaccc | tgagcagaag | aggagccgcg | 1680 |
| cacgggagcg | gaggcgagag | ggccgctcca | agacctttga | ctgggctgag | ttccgtccca | 1740 |
| tccagcaggc | cctggctcag | gagcgggtgg | gcggcgtggg | gcctgctgac | acccacgagc | 1800 |

```
ccctgcgccc tgaggcggag cctggggagc tggagcggga gcgtgcacgg aggcgggagg    1860
agcgccgcaa gcgcttcggg atgctcgacg ccacagacgg gccaggcact gaggatgcag    1920
ccctgcgcat ggaggtggac cggagcccag ggctgcctat gagcgacctc aaaacgcata    1980
acgtccacgt ggagattgag cagcggtggc atcaggtgga gaccacacct ctccgggaag    2040
agaagcaggt gcccatcgcc cccgtccacc tgtcttctga agatgggggt gaccggctct    2100
ccacacacga gctgacctct ctgctcgaga aggagctgga gcagagccag aaggaggcct    2160
cagaccttct ggagcagaac cggctcctgc aggaccagct gagggtggcc ctgggccggg    2220
agcagagcgc ccgtgagggc tacgtgctgc aggccacgtg cgagcgaggg tttgcagcaa    2280
tggaagaaac gcaccagaag aagattgaag atctccagag gcagcaccag cgggagctag    2340
agaaacttcg agaagagaaa gaccgcctcc tagccgagga gacagcggcc accatctcag    2400
ccatcgaagc catgaagaac gcccaccggg aggaaatgga gcgggagctg gagaagagcc    2460
agcggtccca gatcagcagc gtcaactcgg atgttgaggc cctgcggcgc cagtacctgg    2520
aggagctgca gtcggtgcag cgggaactgg aggtcctctc ggagcagtac tcgcagaagt    2580
gcctggagaa tgcccatctg gcccaggcgc tggaggccga gcggcaggcc ctgcggcagt    2640
gccagcgtga gaaccaggag ctcaatgccc acaaccagga gctgaacaac cgcctggctg    2700
cagagatcac acggttgcgg acgctgctga ctggggacgg cggtggggag gccactgggt    2760
caccccttgc acagggcaag gatgcctatg aactagaggt cttattgcgg gtaaaggaat    2820
cggaaataca gtacctgaaa caggagatta gctccctcaa ggatgagctg cagacggcac    2880
tgcgggacaa gaagtacgca agtgacaagt acaaagacat ctacacagag ctcagcatcg    2940
cgaaggctaa ggctgactgt gacatcagca ggttgaagga gcagctcaag gctgcaacgg    3000
aagcactggg ggagaagtcc cctgacagtg ccacggtgtc cggatatggc ccggctgtgc    3060
tggctccaga ggatgggctg gccatgtccc tgcatttcat gacattgggt ggcagctccc    3120
tgtcccccac cgagggcaaa ggctctgggc tccaaggcca catcatcgag aacccacaat    3180
acttcagtga tgcctgtgtt caccacatca gcgccgggga catcgtgctc aagtgggagc    3240
tgggggaggg cgcctttggg aaggtcttcc ttgctgagtg ccacaacctc ctgcctgagc    3300
aggacaagat gctggtggct gtcaaggcac tgaaggaggc gtccgagagt gctcggcagg    3360
acttccagcg tgaggctgag ctgctcacca tgctgcagca ccagcacatc gtgcgcttct    3420
tcggcgtctg caccgagggc cgcccccctgc tcatggtctt tgagtatatg cggcacgggg    3480
acctcaaccg cttcctccga tcccatggac ctgatgccaa gctgctggct ggtgggagg    3540 atgtggctcc aggccccctg ggtctggggc agctgctggc cgtggctagc caggtcgctg    3600
cggggatggt gtacctggcg ggtctgcatt ttgtgcaccg ggacctggcc acacgcaact    3660
gtctagtggg ccagggactg gtggtcaaga ttggtgattt tggcatgagc agggatatct    3720
acagcaccga ctattaccgt gtgggaggcc gcaccatgct gcccattcgc tggatgccgc    3780
ccgagagcat cctgtaccgt aagttcacca ccgagagcga cgtgtggagc ttcggcgtgg    3840
tgctctggga gatcttcacc tacggcaagc agccctggta ccagctctcc aacacggagg    3900
caatcgactg catcacgcag ggacgtgagt tggagcggcc acgtgcctgc ccaccagagg    3960
tctacgccat catgcgggc tgctggcagc gggagcccca gcaacgccac agcatcaagg    4020
atgtgcacgc ccggctgcaa gccctggccc aggcacctcc tgtctacctg gatgtcctgg    4080 gctaggggc cggcccaggg gctggagtg gttagccgga atactggggc ctgccctcag    4140
```

| | |
|---|---|
| catccccat agctcccagc agcccaggg tgatctcaaa gtatctaatt caccctcagc | 4200 |
| atgtgggaag ggacaggtgg gggctgggag tagaggatgt tcctgcttct ctaggcaagg | 4260 |
| tcccgtcata gcaattatat ttattatccc ttgaaaaaaa a | 4301 |

<210> SEQ ID NO 6
<211> LENGTH: 4301
<212> TYPE: DNA
<213> ORGANISM: Artificial Sequence
<220> FEATURE:
<223> OTHER INFORMATION: Synthetic polynucleotide

<400> SEQUENCE: 6

| | |
|---|---|
| gcggccgcgc tgagccccta gcccgccggg agcgccaggc cggccaggcc tgcgccgccg | 60 |
| ccgccgccgc cgtcgccgcc gcgccgacca tgtcggcagc caaggagaac ccgtgcagga | 120 |
| aattccaggc caacatcttc aacaagagca agtgtcagaa ctgcttcaag ccccgcgagt | 180 |
| cgcatctgct caacgacgag gacctgacgc aggcaaaacc catttatggc ggttggctgc | 240 |
| tcctggctcc agatgggacc gactttgaca acccagtgca ccggtctcgg aaatggcagc | 300 |
| gacggttctt catcctttac gagcacggcc tcttgcgcta cgccctggat gagatgccca | 360 |
| cgacccttcc tcagggcacc atcaacatga accagtgcac agatgtggtg gatggggagg | 420 |
| gccgcacggg ccagaagttc tccctgtgta ttctgacgcc tgagaaggag catttcatcc | 480 |
| gggcggagac caaggagatc gtcagtgggt ggctggagat gctcatggtc tatccccgga | 540 |
| ccaacaagca gaatcagaag aagaaacgga agtggagcc cccacacca caggagcctg | 600 |
| ggcctgccaa ggtggctgtt accagcagca gcagcagcag cagcagcagc agcagcatcc | 660 |
| ccagtgctga gaaagtcccc accaccaagt ccacactctg gcaggaagaa atgaggacca | 720 |
| aggaccagcc agatggcagc agcctgagtc cagctcagag tcccagccag agccagcctc | 780 |
| ctgctgccag ctccctgcgg gaacctgggc tagagagcaa agaagaggag agcgccatga | 840 |
| gtagcgaccg catggactgt ggccgcaaag tccgggtgga gagcggctac ttctctctgg | 900 |
| agaagaccaa acaggacttg aaggctgaag aacagcagct gccccgccg ctctcccctc | 960 |
| ccagccccag caccccaac cacaggaggt cccaggtgat tgaaaagttt gaggccttgg | 1020 |
| acattgagaa ggcagagcac atggagacca atgcagtggg gccctcacca tccagcgaca | 1080 |
| cacgccaggg ccgcagcgag aagagggcgt tccctaggaa gcgggacttc accaatgaag | 1140 |
| ccccccagc tcctctccca gacgcctcgg cttcccccct gtctccacac cgaagagcca | 1200 |
| agtcactgga caggaggtcc acggagccct ccgtgacgcc cgacctgctg aatttcaaga | 1260 |
| aaggctggct gactaagcag tatgaggacg gccagtggaa gaaacactgg tttgtcctcg | 1320 |
| ccgatcaaag cctgagatac tacagggatt cagtggctga ggaggcagcc gacttggatg | 1380 |
| gagaaattga cttgtccgca tgttacgatg tcacagagta tccagttcag agaaactatg | 1440 |
| gcttccagat acatacaaag gagggcgagt ttacccctgtc ggccatgaca tctgggattc | 1500 |
| ggcggaactg gatccagacc atcatgaagc acgtgcaccc gaccactgcc ccggatgtga | 1560 |
| ccagctcgtt gccagaggaa aaaacaaga gcagctgctc ttttgagacc tgcccgaggc | 1620 |
| ctactgagaa gcaagaggca gagctggggg agccggaccc tgagcagaag aggagccgcg | 1680 |
| cacgggagcg gaggcgagag ggccgctcca agacctttga ctgggctgag ttccgtccca | 1740 |
| tccagcaggc cctggctcag gagcgggtgg gcggcgtggg gcctgctgac acccacgagc | 1800 |
| ccctgcgccc tgaggcggag cctggggagc tggagcggga gcgtgacgg aggcgggagg | 1860 |
| agcgccgcaa gcgcttcggg atgctcgacg ccacagacgg gccaggcact gaggatgcag | 1920 |

```
ccctgcgcat ggaggtggac cggagcccag ggctgcctat gagcgacctc aaaacgcata   1980
acgtccacgt ggagattgag cagcggtggc atcaggtgga gaccacacct ctccgggaag   2040
agaagcaggt gcccatcgcc cccgtccacc tgtcttctga agatgggggt gaccggctct   2100
ccacacacga gctgacctct ctgctcgaga aggagctgga gcagagccag aaggaggcct   2160
cagaccttct ggagcagaac cggctcctgc aggaccagct gagggtggcc ctgggccggg   2220
agcagagcgc ccgtgagggc tacgtgctgc aggccacgtg cgagcgaggg tttgcagcaa   2280
tggaagaaac gcaccagaag aagattgaag atctccagag gcagcaccag cgggagctag   2340
agaaacttcg agaagagaaa gaccgcctcc tagccgagga gacagcggcc accatctcag   2400
ccatcgaagc catgaagaac gcccaccggg aggaaatgga gcgggagctg gagaagagcc   2460
agcggtccca gatcagcagc gtcaactcgg atgttgaggc cctgcggcgc cagtacctgg   2520
aggagctgca gtcggtgcag cgggaactgg aggtcctctc ggagcagtac tcgcagaagt   2580
gcctggagaa tgcccatctg gcccaggcgc tggaggccga gcggcaggcc ctgcggcagt   2640
gccagcgtga gaaccaggag ctcaatgccc acaaccagga gctgaacaac cgcctggctg   2700
cagagatcac acggttgcgg acgctgctga ctggggacgg cggtggggag gccactgggt   2760
caccccttgc acagggcaag gatgcctatg aactagaggt cttattgcgg gtaaaggaat   2820
cggaaataca gtacctgaaa caggagatta gctccctcaa ggatgagctg cagacggcac   2880
tgcgggacaa gaagtacgca agtgacaagt acaaagacat ctacacagag ctcagcatcg   2940
cgaaggctaa ggctgactgt gacatcagca ggttgaagga gcagctcaag gctgcaacgg   3000
aagcactggg ggagaagtcc cctgacagtg ccacggtgtc cggatatggc ccggctgtgc   3060
tggctccaga ggatgggctg gccatgtccc tgcatttcat gacattgggt ggcagctccc   3120
tgtcccccac cgagggcaaa ggctctgggc tccaaggcca catcatcgag aacccacaat   3180
acttcagtga tgcctgtgtt caccacatca gcgccggga catcgtgctc aagtgggagc   3240
tgggggaggg cgcctttggg aaggtcttcc ttgctgagtg ccacaacctc ctgcctgagc   3300
aggacaagat gctggtggct gtcaaggcac tgaaggaggc gtccgagagt gctcggcagg   3360
acttccagcg tgaggctgag ctgctcacca tgctgcagca ccagcacatc gtgcgcttct   3420
tcggcgtctg caccgagggc cgcccccctgc tcatggtctt tgagtatatg cggcacgggg   3480
acctcaaccg cttcctccga tcccatggac ctgatgccaa gctgctggct ggtgggagg    3540 atgtggctcc aggcccccctg ggtctggggc agctgctggc cgtggctagc caggtcgctg   3600
cggggatggt gtacctggcg ggtctgcatt ttgtgcaccg ggacctggcc acacgcaact   3660
gtctagtggg ccagggactg gtggtcaaga ttggtgattt tggcatgagc agggatatct   3720
acagcaccga ctattaccgt gtgggaggcc gcaccatgct gcccattcgc tggatgccgc   3780
ccgagagcat cctgtaccgt aagttcacca ccgagagcga cgtgtggagc ttcggcgtgg   3840
tgctctggga gatcttcacc tacggcaagc agccctggta ccagctctcc aacacggagg   3900
caatcgactg catcacgcag ggacgtgagt tggagcggcc acgtgcctgc ccaccagagg   3960
tctacgccat catgcggggc tgctggcagc gggagcccca gcaacgccac agcatcaagg   4020
atgtgcacgc ccggctgcaa gccctggccc aggcacctcc tgtctacctg gatgtcctgg   4080 gctaggggc cggcccaggg gctggagtg gttagccgga atactgggc ctgccctcag     4140 catccccat agctcccagc agccccaggg tgatctcaaa gtatctaatt caccctcagc    4200
```

```
atgtgggaag ggacaggtgg gggctgggag tagaggatgt tcctgcttct ctaggcaagg    4260
tcccgtcata gcaattatat ttattatccc ttgaaaaaaa a                         4301
```

<210> SEQ ID NO 7
<211> LENGTH: 1331
<212> TYPE: PRT
<213> ORGANISM: Artificial Sequence
<220> FEATURE:
<223> OTHER INFORMATION: Synthetic polypeptide

<400> SEQUENCE: 7

```
Met Ser Ala Ala Lys Glu Asn Pro Cys Arg Lys Phe Gln Ala Asn Ile
1               5                   10                  15

Phe Asn Lys Ser Lys Cys Gln Asn Cys Phe Lys Pro Arg Glu Ser His
                20                  25                  30

Leu Leu Asn Asp Glu Asp Leu Thr Gln Ala Lys Pro Ile Tyr Gly Gly
            35                  40                  45

Trp Leu Leu Leu Ala Pro Asp Gly Thr Asp Phe Asp Asn Pro Val His
        50                  55                  60

Arg Ser Arg Lys Trp Gln Arg Phe Phe Ile Leu Tyr Glu His Gly
65                  70                  75                  80

Leu Leu Arg Tyr Ala Leu Asp Glu Met Pro Thr Thr Leu Pro Gln Gly
                85                  90                  95

Thr Ile Asn Met Asn Gln Cys Thr Asp Val Val Asp Gly Glu Gly Arg
            100                 105                 110

Thr Gly Gln Lys Phe Ser Leu Cys Ile Leu Thr Pro Glu Lys Glu His
        115                 120                 125

Phe Ile Arg Ala Glu Thr Lys Glu Ile Val Ser Gly Trp Leu Glu Met
    130                 135                 140

Leu Met Val Tyr Pro Arg Thr Asn Lys Gln Asn Gln Lys Lys Lys Arg
145                 150                 155                 160

Lys Val Glu Pro Pro Thr Pro Gln Glu Pro Gly Pro Ala Lys Val Ala
                165                 170                 175

Val Thr Ser Ser Ser Ser Ser Ser Ser Ser Ser Ile Pro Ser
            180                 185                 190

Ala Glu Lys Val Pro Thr Thr Lys Ser Thr Leu Trp Gln Glu Glu Met
        195                 200                 205

Arg Thr Lys Asp Gln Pro Asp Gly Ser Ser Leu Ser Pro Ala Gln Ser
    210                 215                 220

Pro Ser Gln Ser Gln Pro Pro Ala Ala Ser Ser Leu Arg Glu Pro Gly
225                 230                 235                 240

Leu Glu Ser Lys Glu Glu Ser Ala Met Ser Ser Asp Arg Met Asp
                245                 250                 255

Cys Gly Arg Lys Val Arg Val Glu Ser Gly Tyr Phe Ser Leu Glu Lys
            260                 265                 270

Thr Lys Gln Asp Leu Lys Ala Glu Glu Gln Gln Leu Pro Pro Pro Leu
        275                 280                 285

Ser Pro Pro Ser Pro Ser Thr Pro Asn His Arg Arg Ser Gln Val Ile
    290                 295                 300

Glu Lys Phe Glu Ala Leu Asp Ile Glu Lys Ala Glu His Met Glu Thr
305                 310                 315                 320

Asn Ala Val Gly Pro Ser Pro Ser Ser Asp Thr Arg Gln Gly Arg Ser
                325                 330                 335
```

```
Glu Lys Arg Ala Phe Pro Arg Lys Arg Asp Phe Thr Asn Glu Ala Pro
            340                 345                 350

Pro Ala Pro Leu Pro Asp Ala Ser Ala Ser Pro Leu Ser Pro His Arg
            355                 360                 365

Arg Ala Lys Ser Leu Asp Arg Arg Ser Thr Glu Pro Ser Val Thr Pro
            370                 375                 380

Asp Leu Leu Asn Phe Lys Lys Gly Trp Leu Thr Lys Gln Tyr Glu Asp
385                 390                 395                 400

Gly Gln Trp Lys Lys His Trp Phe Val Leu Ala Asp Gln Ser Leu Arg
                405                 410                 415

Tyr Tyr Arg Asp Ser Val Ala Glu Glu Ala Ala Asp Leu Asp Gly Glu
            420                 425                 430

Ile Asp Leu Ser Ala Cys Tyr Asp Val Thr Glu Tyr Pro Val Gln Arg
            435                 440                 445

Asn Tyr Gly Phe Gln Ile His Thr Lys Glu Gly Glu Phe Thr Leu Ser
            450                 455                 460

Ala Met Thr Ser Gly Ile Arg Arg Asn Trp Ile Gln Thr Ile Met Lys
465                 470                 475                 480

His Val His Pro Thr Thr Ala Pro Asp Val Thr Ser Ser Leu Pro Glu
                485                 490                 495

Glu Lys Asn Lys Ser Ser Cys Ser Phe Glu Thr Cys Pro Arg Pro Thr
            500                 505                 510

Glu Lys Gln Glu Ala Glu Leu Gly Glu Pro Asp Pro Glu Gln Lys Arg
            515                 520                 525

Ser Arg Ala Arg Glu Arg Arg Glu Gly Arg Ser Lys Thr Phe Asp
            530                 535                 540

Trp Ala Glu Phe Arg Pro Ile Gln Gln Ala Leu Ala Gln Glu Arg Val
545                 550                 555                 560

Gly Gly Val Gly Pro Ala Asp Thr His Glu Pro Leu Arg Pro Glu Ala
                565                 570                 575

Glu Pro Gly Glu Leu Glu Arg Glu Arg Ala Arg Arg Glu Glu Arg
            580                 585                 590

Arg Lys Arg Phe Gly Met Leu Asp Ala Thr Asp Gly Pro Gly Thr Glu
            595                 600                 605

Asp Ala Ala Leu Arg Met Glu Val Asp Arg Ser Pro Gly Leu Pro Met
            610                 615                 620

Ser Asp Leu Lys Thr His Asn Val His Val Glu Ile Glu Gln Arg Trp
625                 630                 635                 640

His Gln Val Glu Thr Thr Pro Leu Arg Glu Glu Lys Gln Val Pro Ile
                645                 650                 655

Ala Pro Val His Leu Ser Ser Glu Asp Gly Gly Asp Arg Leu Ser Thr
            660                 665                 670

His Glu Leu Thr Ser Leu Leu Glu Lys Glu Leu Glu Gln Ser Gln Lys
            675                 680                 685

Glu Ala Ser Asp Leu Leu Glu Gln Asn Arg Leu Leu Gln Asp Gln Leu
            690                 695                 700

Arg Val Ala Leu Gly Arg Glu Gln Ser Ala Arg Glu Gly Tyr Val Leu
705                 710                 715                 720

Gln Ala Thr Cys Glu Arg Gly Phe Ala Ala Met Glu Glu Thr His Gln
            725                 730                 735

Lys Lys Ile Glu Asp Leu Gln Arg Gln His Gln Arg Glu Leu Glu Lys
            740                 745                 750
```

```
Leu Arg Glu Glu Lys Asp Arg Leu Leu Ala Glu Glu Thr Ala Ala Thr
            755                 760                 765

Ile Ser Ala Ile Glu Ala Met Lys Asn Ala His Arg Glu Glu Met Glu
770                 775                 780

Arg Glu Leu Glu Lys Ser Gln Arg Ser Gln Ile Ser Ser Val Asn Ser
785                 790                 795                 800

Asp Val Glu Ala Leu Arg Arg Gln Tyr Leu Glu Glu Leu Gln Ser Val
            805                 810                 815

Gln Arg Glu Leu Glu Val Leu Ser Glu Gln Tyr Ser Gln Lys Cys Leu
            820                 825                 830

Glu Asn Ala His Leu Ala Gln Ala Leu Glu Ala Glu Arg Gln Ala Leu
            835                 840                 845

Arg Gln Cys Gln Arg Glu Asn Gln Glu Leu Asn Ala His Asn Gln Glu
850                 855                 860

Leu Asn Asn Arg Leu Ala Ala Glu Ile Thr Arg Leu Arg Thr Leu Leu
865                 870                 875                 880

Thr Gly Asp Gly Gly Gly Glu Ala Thr Gly Ser Pro Leu Ala Gln Gly
                885                 890                 895

Lys Asp Ala Tyr Glu Leu Glu Val Leu Leu Arg Val Lys Glu Ser Glu
            900                 905                 910

Ile Gln Tyr Leu Lys Gln Glu Ile Ser Ser Leu Lys Asp Glu Leu Gln
            915                 920                 925

Thr Ala Leu Arg Asp Lys Lys Tyr Ala Ser Asp Lys Tyr Lys Asp Ile
            930                 935                 940

Tyr Thr Glu Leu Ser Ile Ala Lys Ala Lys Ala Asp Cys Asp Ile Ser
945                 950                 955                 960

Arg Leu Lys Glu Gln Leu Lys Ala Ala Thr Glu Ala Leu Gly Glu Lys
                965                 970                 975

Ser Pro Asp Ser Ala Thr Val Ser Gly Tyr Gly Pro Ala Val Leu Ala
            980                 985                 990

Pro Glu Asp Gly Leu Ala Met Ser Leu His Phe Met Thr Leu Gly Gly
            995                1000                1005

Ser Ser Leu Ser Pro Thr Glu Gly Lys Gly Ser Gly Leu Gln Gly
       1010                1015                1020

His Ile Ile Glu Asn Pro Gln Tyr Phe Ser Asp Ala Cys Val His
       1025                1030                1035

His Ile Lys Arg Arg Asp Ile Val Leu Lys Trp Glu Leu Gly Glu
       1040                1045                1050

Gly Ala Phe Gly Lys Val Phe Leu Ala Glu Cys His Asn Leu Leu
       1055                1060                1065

Pro Glu Gln Asp Lys Met Leu Val Ala Val Lys Ala Leu Lys Glu
       1070                1075                1080

Ala Ser Glu Ser Ala Arg Gln Asp Phe Gln Arg Glu Ala Glu Leu
       1085                1090                1095

Leu Thr Met Leu Gln His Gln His Ile Val Arg Phe Phe Gly Val
       1100                1105                1110

Cys Thr Glu Gly Arg Pro Leu Leu Met Val Phe Glu Tyr Met Arg
       1115                1120                1125

His Gly Asp Leu Asn Arg Phe Leu Arg Ser His Gly Pro Asp Ala
       1130                1135                1140

Lys Leu Leu Ala Gly Gly Glu Asp Val Ala Pro Gly Pro Leu Gly
       1145                1150                1155
```

Leu Gly Gln Leu Leu Ala Val Ala Ser Gln Val Ala Ala Gly Met
    1160                1165                1170

Val Tyr Leu Ala Gly Leu His Phe Val His Arg Asp Leu Ala Thr
    1175                1180                1185

Arg Asn Cys Leu Val Gly Gln Gly Leu Val Val Lys Ile Gly Asp
    1190                1195                1200

Phe Gly Met Ser Arg Asp Ile Tyr Ser Thr Asp Tyr Tyr Arg Val
    1205                1210                1215

Gly Gly Arg Thr Met Leu Pro Ile Arg Trp Met Pro Pro Glu Ser
    1220                1225                1230

Ile Leu Tyr Arg Lys Phe Thr Thr Glu Ser Asp Val Trp Ser Phe
    1235                1240                1245

Gly Val Val Leu Trp Glu Ile Phe Thr Tyr Gly Lys Gln Pro Trp
    1250                1255                1260

Tyr Gln Leu Ser Asn Thr Glu Ala Ile Asp Cys Ile Thr Gln Gly
    1265                1270                1275

Arg Glu Leu Glu Arg Pro Arg Ala Cys Pro Pro Glu Val Tyr Ala
    1280                1285                1290

Ile Met Arg Gly Cys Trp Gln Arg Glu Pro Gln Gln Arg His Ser
    1295                1300                1305

Ile Lys Asp Val His Ala Arg Leu Gln Ala Leu Ala Gln Ala Pro
    1310                1315                1320

Pro Val Tyr Leu Asp Val Leu Gly
    1325                1330

<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 8
acggtgtccg gatatggccc ggctgtgctg gc                                   32

<210> SEQ ID NO 9
<211> LENGTH: 30
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(30)
<223> OTHER INFORMATION: /note="Description of Artificial Sequence:
      Synthetic primer"

<400> SEQUENCE: 9
accatgtcgg cagccaagga gaacccgtgc                                      30

<210> SEQ ID NO 10
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(22)
<223> OTHER INFORMATION: /note="Description of Artificial Sequence:
      Synthetic primer"

<400> SEQUENCE: 10
acacacgagc tgacctctct gc                                             22

<210> SEQ ID NO 11
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(22)
<223> OTHER INFORMATION: /note="Description of Artificial Sequence:
      Synthetic primer"

<400> SEQUENCE: 11
gcgaaggcta aggctgactg tg                                             22

<210> SEQ ID NO 12
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(22)
<223> OTHER INFORMATION: /note="Description of Artificial Sequence:
      Synthetic primer"

<400> SEQUENCE: 12
ccattgctgc aaaccctcgc tc                                             22

<210> SEQ ID NO 13
<211> LENGTH: 28
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(28)
<223> OTHER INFORMATION: /note="Description of Artificial Sequence:
      Synthetic primer"

<400> SEQUENCE: 13
gaattcgccg ccgcgccgac catgtcgg                                       28

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(20)
<223> OTHER INFORMATION: /note="Description of Artificial Sequence:
      Synthetic primer"

<400> SEQUENCE: 14
cggcgcttga tgtggtgaac                                                20

<210> SEQ ID NO 15
<211> LENGTH: 22
<212> TYPE: DNA
<213> ORGANISM: Artificial Sequence
<220> FEATURE:
<223> OTHER INFORMATION: Synthetic oligonucleotide

```
<220> FEATURE:
<221> NAME/KEY: source
<222> LOCATION: (1)..(22)
<223> OTHER INFORMATION: /note="Description of Artificial Sequence:
      Synthetic primer"

<400> SEQUENCE: 15
tattccggct aaccactccc ag                                              22

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: 1source
<222> LOCATION: (1)..(20)
<223> OTHER INFORMATION: /note="Description of Artificial Sequence:
      Synthetic primer"

<400> SEQUENCE: 16
cctagcccag gacatccagg                                                 20

<210> SEQ ID NO 17
<211> LENGTH: 55
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: source
<222> LOCATION: (1)..(55)
<223> OTHER INFORMATION: /note="Description of Artificial Sequence:
      Synthetic primer"

<400> SEQUENCE: 17
cgcggccgct taagcgtagt ctgggacgtc gtatgggtag cccaggacat ccagg          55
```